(12) United States Patent
Carroll et al.

(10) Patent No.: US 8,445,287 B2
(45) Date of Patent: May 21, 2013

(54) METHOD AND APPARATUS FOR DETERMINING ANTICOAGULANT THERAPY FACTORS

(75) Inventors: Wallace E. Carroll, Santa Barbara, CA (US); R. David Jackson, Alexandria, IN (US)

(73) Assignee: WADA, Inc., Santa Barbara, CA (US)

( * ) Notice: Subject to any disclaimer, the term of this patent is extended or adjusted under 35 U.S.C. 154(b) by 156 days.

(21) Appl. No.: 12/932,822

(22) Filed: Mar. 7, 2011

(65) Prior Publication Data

US 2011/0224292 A1 Sep. 15, 2011

Related U.S. Application Data

(63) Continuation-in-part of application No. 12/378,456, filed on Feb. 14, 2009, now Pat. No. 7,901,694.

(51) Int. Cl.
*G01N 33/86* (2006.01)
*G01N 33/48* (2006.01)
*A61K 45/00* (2006.01)
*A61P 7/02* (2006.01)
*G06F 19/00* (2011.01)

(52) U.S. Cl.
USPC ............ 436/69; 436/34; 436/63; 436/164; 422/73; 422/82.05; 422/82.09; 424/278.1; 514/802; 73/64.41; 73/64.43; 600/369; 702/19

(58) Field of Classification Search
USPC ........... 436/34, 63, 69, 164; 422/73, 82.05, 422/82.09; 424/278.1; 514/802; 73/64.41, 73/64.43; 600/369; 702/19
See application file for complete search history.

(56) References Cited

U.S. PATENT DOCUMENTS

| | | | | |
|---|---|---|---|---|
| 3,905,769 A * | 9/1975 | Carroll et al. | ................... | 436/69 |
| 4,217,107 A * | 8/1980 | Saito et al. | ....................... | 436/69 |
| 4,252,536 A * | 2/1981 | Kishimoto et al. | ............. | 356/36 |
| 4,720,787 A * | 1/1988 | Lipscomb | ..................... | 600/369 |
| 5,197,017 A * | 3/1993 | Carroll et al. | ................... | 702/19 |
| 5,502,651 A * | 3/1996 | Jackson et al. | ................ | 702/108 |
| 5,981,285 A * | 11/1999 | Carroll et al. | ................... | 436/69 |
| 6,706,536 B1 * | 3/2004 | Carroll et al. | ................. | 436/164 |
| 7,276,377 B2 * | 10/2007 | Carroll et al. | ................... | 436/69 |
| 7,901,694 B2 * | 3/2011 | Carroll et al. | ............. | 424/278.1 |

* cited by examiner

*Primary Examiner* — Maureen Wallenhorst
(74) *Attorney, Agent, or Firm* — John F. A. Earley, III; Frank J. Bonini, Jr.; Harding, Earley, Follmer & Frailey, P.C.

(57) ABSTRACT

Methods and apparatus are disclosed for determining new anticoagulant therapy factors for monitoring oral anticoagulant therapy to help prevent excessive bleeding or deleterious blood clots that might otherwise occur before, during or after surgery. The inventive methods and apparatus provide an International Normalization Ratio (INR) based on a coagulation reaction with a blood sample of a living being. Embodiments include methods and apparatus for determining an anticoagulant therapy factor without requiring use of a mean normal prothrombin time determination or an ISI, and may be carried out with the patient sample and a coagulation reagent, where the coagulation reagent may be selected from a number of coagulation reagents. One embodiment provides an INRs value which is determined from a prothrombin time (PT or T1) of a patient blood sample and a theoretical end of test time (TEOT), where a theoretical clotting area is used to determine the INRs value according to the expression, INRs=T1*TEOT*MUL, where MUL is a multiplier that takes into account pixel parity and sampling times. The INRs may be used to determine a course of treatment for a patient or other living being without regard to the specific coagulation regent used to generate the coagulation data (e.g., time and optical activity values).

45 Claims, 10 Drawing Sheets

METHOD AND APPARATUS FOR DETERMINING ANTICOAGULANT THERAPY FACTORS

CROSS-REFERENCE TO RELATED APPLICATION

This application is a continuation-in-part of U.S. application Ser. No. 12/378,456 filed on Feb. 14, 2009 now U.S. Pat. No. 7,901,694, issued on Mar. 8, 2011, the complete disclosures of which are herein incorporated by reference.

BACKGROUND OF THE INVENTION

1. Field of the Invention

This invention relates to analyzing blood for carrying out coagulation studies and other chemistry procedures, including monitoring oral anticoagulant therapy to take into account the platelet count in determining prothrombin times (PT), and providing new Anticoagulant Therapy Factors that are useful in diagnosing and treating individuals in relation to blood conditions.

2. Brief Description of the Related Art

Testing of blood and other body fluids is commonly done in hospitals, labs, clinics and other medical facilities. For example, to prevent excessive bleeding or deleterious blood clots, a patient may receive oral anticoagulant therapy before, during and after surgery. Oral anticoagulant therapy generally involves the use of oral anticoagulants—a class of drugs which inhibit blood clotting. To assure that the oral anticoagulant therapy is properly administered, strict monitoring is accomplished and is more fully described in various medical technical literature, such as the articles entitled "PTs, PR, ISIs and INRs: A Primer on Prothrombin Time Reporting Parts I and II" respectively published November, 1993 and December, 1993 issues of *Clinical Hemostasis Review*, and herein incorporated by reference.

These technical articles disclose anticoagulant therapy monitoring that takes into account three parameters which are: International Normalized Ratio (INR), International Sensitivity Index (ISI) and prothrombin time (PT), reported in seconds. The prothrombin time (PT) indicates the level of prothrombin and blood factors V, VII, and X in a plasma sample and is a measure of the coagulation response of a patient. Also affecting this response may be plasma coagulation inhibitors, such as, for example, protein C and protein S. Some individuals have deficiencies of protein C and protein S. The INR and ISI parameters are needed so as to take into account various differences in instrumentation, methodologies and in thromboplastins' (Tps) sensitivities used in anticoagulant therapy. In general, thromboplastins (Tps) used in North America are derived from rabbit brain, those previously used in Great Britain from human brain, and those used in Europe from either rabbit brain or bovine brain. The INR and ISI parameters take into account all of these various factors, such as the differences in thromboplastins (Tps), to provide a standardized system for monitoring oral anticoagulant therapy to reduce serious problems related to prior, during and after surgery, such as excessive bleeding or the formation of blood clots.

The ISI itself according to the WHO 1999 guidelines, Publication no. 889-1999, have coefficients of variation ranging from 1.7% to 8.1%. Therefore, if the ISI is used exponentially to determine the INR of a patient, then the coefficients of variation for the INR's must be even greater than those for the ISI range.

As reported in Part I (Calibration of Thromboplastin Reagents and Principles of Prothrombin Time Report) of the above technical article of the *Clinical Hemostasis Review*, the determination of the INR and ISI parameters are quite involved, and as reported in Part II (Limitation of INR Reporting) of the above technical article of the *Clinical Hemostasis Review*, the error yielded by the INR and ISI parameters is quite high, such as about up to 10%. The complexity of the interrelationship between the International Normalized Ratio (INR), the International Sensitivity Index (ISI) and the patient's prothrombin time (PT) may be given by the below expression (A),
wherein the quantity $$\left[\frac{\text{Patient's } PT}{\text{Mean of } PT \text{ Normal Range}}\right] \quad (A)$$

is commonly referred to as prothrombin ratio (PR):

$$INR = \left[\frac{\text{Patient's } PT}{\text{Mean of } PT \text{ Normal Range}}\right]^{ISI} \quad (B)$$

The possible error involved with the use of International Normalized Ratio (INR) is also discussed in the technical article entitled "Reliability and Clinical Impact of the Normalization of the Prothrombin Times in Oral Anticoagulant Control" of E. A. Loeliger et al., published in *Thrombosis and Hemostasis* 1985; 53: 148-154, and herein incorporated by reference. As can be seen in the above expression (B), ISI is an exponent of INR which leads to the possible error involved in the use of INR to be about 10% or possibly even more. A procedure related to the calibration of the ISI is described in a technical article entitled "Failure of the International Normalized Ratio to Generate Consistent Results within a Local Medical Community" of V. L. Ng et al., published in Am. J. Clin. Pathol. 1993; 99: 689-694, and herein incorporated by reference.

The unwanted INR deviations are further discussed in the technical article entitled "Minimum Lyophilized Plasma Requirement for ISI Calibration" of L. Poller et al. published in *Am. J. Clin. Pathol.* February 1998, Vol. 109, No. 2, 196-204, and herein incorporated by reference. As discussed in this article, the INR deviations became prominent when the number of abnormal samples being tested therein was reduced to fewer than 20 which leads to keeping the population of the samples to at least 20. The paper of L. Poller et al. also discusses the usage of 20 high lyophilized INR plasmas and 7 normal lyophilized plasmas to calibrate the INR. Further, in this article, a deviation of +/−10% from means was discussed as being an acceptable limit of INR deviation. Further still, this article discusses the evaluation techniques of taking into account the prothrombin ratio (PR) and the mean normal prothrombin time (MNPT), i.e., the geometric mean of normal plasma samples.

The discrepancies related to the use of the INR are further studied and described in the technical article of V.L. NG et al. entitled, "Highly Sensitive Thromboplastins Do Not Improve INR Precision," published in *Am. J. Clin. Pathol.*, 1998; 109, No. 3, 338-346 and herein incorporated by reference. In this article, the clinical significance of INR discordance is examined with the results being tabulated in Table 4 therein and which are analyzed to conclude that the level of discordance for paired values of individual specimens tested with different thromboplastins disadvantageously range from 17% to 29%.

U.S. Pat. No. 5,981,285 issued on Nov. 9, 1999 to Wallace E. Carroll et al., which discloses a "Method and Apparatus for Determining Anticoagulant Therapy Factors" provides an accurate method for taking into account varying prothrombin times (PT) caused by different sensitivities of various thromboplastin formed from rabbit brain, bovine brain or other sources used for anticoagulant therapy. This method does not suffer from the relatively high (10%) error sometimes occurring because of the use of the INR and ISI parameters with the exponents used in their determination.

The lack of existing methods to provide reliable results for physicians to utilize in treatment of patients has been discussed, including in a paper by Davis, Kent D., Danielson, Constance F. M., May, Lawrence S., and Han, Zi-Qin, "Use of Different Thromboplastin Reagents Causes Greater Variability in International Normalized Ratio Results Than Prolonged Room Temperature Storage of Specimens," *Archives of Pathol. and Lab. Medicine*, November 1998. The authors observed that a change in the thromboplastin reagent can result in statistically and clinically significant differences in the INR. Considering the current methods for determining anticoagulant therapy factors, there are numerous opportunities for error. For example, it has been reported that patient deaths have occurred at St. Agnes Hospital in Philadelphia, Pa. There the problem did not appear to be the thromboplastin reagent, but rather, was apparently due to a failure to enter the correct ISI in the instrument used to carry out the prothrombin times when the reagent was changed. This resulted in the incorrect INR's being reported. Doses of coumadin were given to already overanticoagulated patients based on the faulty INR error, and it is apparent that patient deaths were caused by excessive bleeding due to coumadin overdoses. In the St. Agnes Hospital, Philadelphia 2001 INR disaster, an incorrect ISI of 1.01 was used instead of 2.028. As has been recommended by Poller, INR studies should be performed at the INR 2.0 and 3.0 levels. 2.0 to 3.0 is the Therapeutic INR Range recommended for most clotting/thrombotic conditions. These two levels will be used in the following calculations:

The PRs at INR 2.0 calculation are:

$$INR=PR^{ISI}; \log INR=(ISI)(\log PR);$$

$$\log PR=\log INR/ISI;$$

$$\log PR=\log 2.0=0.301; \log PR/ISI=0.301/1.01=0.298$$

$$PR=1.986$$

$$INR=PR^{ISI}1.986^{1.01}=2.00$$

$$INR=PR^{ISI}=1.986^{2.028}=4.02$$

An INR of 2.00 would have been reported, not the actual 4.02. Warfarin at a reported INR 2.0 level would likely have been administered to an already overanticoagulated patient, but serious consequences may not necessarily have occurred here. Using the erroneous 1.01 ISI with an INR of 3.0 for calculations is drastically different:

$$\log PR=\log INR/ISI=0.477/1.01=0.472$$

$$PR=2.968$$

$$INR=PR^{ISI}=2.968^{1.01}=3.00$$

$$INR^{ISI}=2.968 2.028=9.08$$

This incorrectly reported INR of 3.0 would actually have been 9.08. 9.08 is well above INR=6.0 where excessive bleeding is considered to occur. In addition, the five fatal St. Agnes cases, even at INR=9.08, could have even been administered a routine warfarin dose, since it would have been believed it was intended for patients with an INR of 3.0, not 9.08.

But even in addition to errors where a value is not input correctly, the known methods for determining anticoagulant therapy factors still may be prone to errors, even when the procedure is carried out in accordance with the reagent manufacturer's ISI data. One can see this in that current methods have reported that reagents used to calculate prothrombin times, may, for healthy (i.e., presumed normal) subjects, give rise to results ranging from 9.7 to 12.3 seconds at the 95th % reference interval for a particular reagent, and 10.6 to 12.4 for another. The wide ranges for normal patients illustrates the mean normal prothrombin time differences. When the manufacturer reference data ranges are considered, if indeed 20 presumed normal patients' data may be reported within a broad range, then there is the potential for introduction of this range into the current anticoagulation therapy factor determinations, since they rely on the data for 20 presumed normal patients. Considering the reagent manufacturer expected ranges for expected normal prothrombin times, INR units may vary up to 30%. This error is apparently what physicians must work with when treating patients. A way to remove the potential for this type of error is needed.

This invention relates to the inventions disclosed in U.S. Pat. Nos. 3,905,769 ('769) of Sep. 16, 1975; 5,197,017 ('017) dated Mar. 23, 1993; and 5,502,651 ('651) dated Mar. 26, 1996, all issued to Wallace E. Carroll and R. David Jackson, and all of which are incorporated herein by reference. The present invention provides apparatus and methods for monitoring anticoagulant therapy.

SUMMARY OF THE INVENTION

Methods and apparatus useful for processing coagulation studies, and other chemistry procedures involving blood and blood components. The apparatus and methods may be used to determine anticoagulant therapy factors which are designated herein, in particular, to determine new Anticoagulant Therapy Factors (nATF's) which preferably may replace International Normalized Ratio (INR) in anticoagulation therapy management. Previously, anticoagulation therapy involved the use of International Normalized Ratios (INR's). The International Normalized Ratio (INR) was utilized in order to arrive at an anticoagulant therapy factor (ATF). The INR based ATF was dependent on the prothrombin time (PT), the prothrombin ratio (PR), a fibrinogen transformation rate (FTR), and a maximum acceleration point (MAP) having an associated time to maximum acceleration (TMA).

Methods and apparatus are disclosed for determining a new anticoagulant therapy factor (nATF) for monitoring oral anticoagulant therapy to help prevent excessive bleeding or deleterious blood clots that might otherwise occur before, during or after surgery. In one embodiment, a new anticoagulant therapy factor (nATF) is based upon a determination of the fibrinogen transformation rate (FTR) which, in turn, is dependent on a maximum acceleration point (MAP) for fibrinogen (FBG) conversion. The nATF quantity is also based upon the time to maximum acceleration from the time of reagent injection (TX) into a plasma sample, but does not require the difficulty of obtaining prior art International Normalized Ratio (INR) and International Sensitivity Index (ISI) parameters. The International Normalized Ratio (INR) was created to relate all species' clotting material to human clotting material, and nATF can replace INR in anticoagulant therapy management.

In accordance with other embodiments, methods and apparatus are provided for determining an anticoagulation therapy factor, which do not require the use of a mean normal prothrombin time (MNPT) and ISI data. In other words, the need to obtain and calculate the prothrombin time of 20 presumed normal patients, is not required to determine an anticoagulant therapy factor.

In accordance with the present invention, there is provided apparatus and methods for carrying out coagulation studies and other chemical procedures and analyses.

Another embodiment provides methods and apparatus for determining an anticoagulant therapy factor or INR, such as INRn, from the derivation of clotting curve values in connection with a designated area defined by clotting curve data. One preferred embodiment relates to an area defined by clotting curve data that corresponds with the area of a trapezoid formed along the clotting curve.

Another embodiment provides methods and apparatus for determining an anticoagulant therapy factor or INR, such as INRs, from the derivation of clotting curve values in connection with a designated area defined by clotting curve data that may be utilized to determine an anticoagulant therapy factor. One preferred embodiment relates to an area defined by clotting curve data that corresponds with a clotting area that is derived derived from values represented by the optical activity (such as absorbance values) and time intervals at which that activity occurs. Embodiments used for determining an INRs also may apply a multiplier to an area value to adjust the area, for example, to account for pixel parity and sampling time.

It is another object of the invention to provide a method and apparatus for determining an INR, such as INRs/ATFs, where a transformed INR, INRs, is obtained using various clotting reagents to carry out a clotting reaction of a blood sample where clear fibrinogen in the sample is converted into turbid fibrin to give an optical activity (or absorbance) curve. The traditional INR, an empirically-derived INR, was conceived by Kirkwood in 1983 to standardize the Quick prothrombin time (PT) for oral anticoagulant therapy management, and has two major sources of error: 1. its common denominator, the mean normal prothrombin time (MNPT), and 2. the exponentially-derived ISI exponent. The present methods and devices provide improved alternative INR determinations. According to one embodiment, an INR value, INRs, is determined using a standard curve that is created with fibrinogen standards, such as, for example, using FDA-cleared high and low fibrinogen standards and three fibrinogen/INR controls of levels 1, 2 and 3. The INR (standard) value is obtained for the standards and a hypothetical or theoretical clotting AREA value (A) is calculated for each of the tested thromboplastin standards. The resultant Area and INR values are related to determine a power regression, in which the determination of patient samples using the same thromboplastin reagent as that used for the standards may be carried out by determining the clotting area for the sample, and applying the power regression expression to derive an INRs value for the sample based on the sample's clotting area (A).

The method and apparatus may provide INRs/ATFs coagulation values that may be used to determine a course of treatment for a patient.

These and other advantages are provided by the invention.

DETAILED DESCRIPTION OF THE PREFERRED EMBODIMENTS

Figure 1:
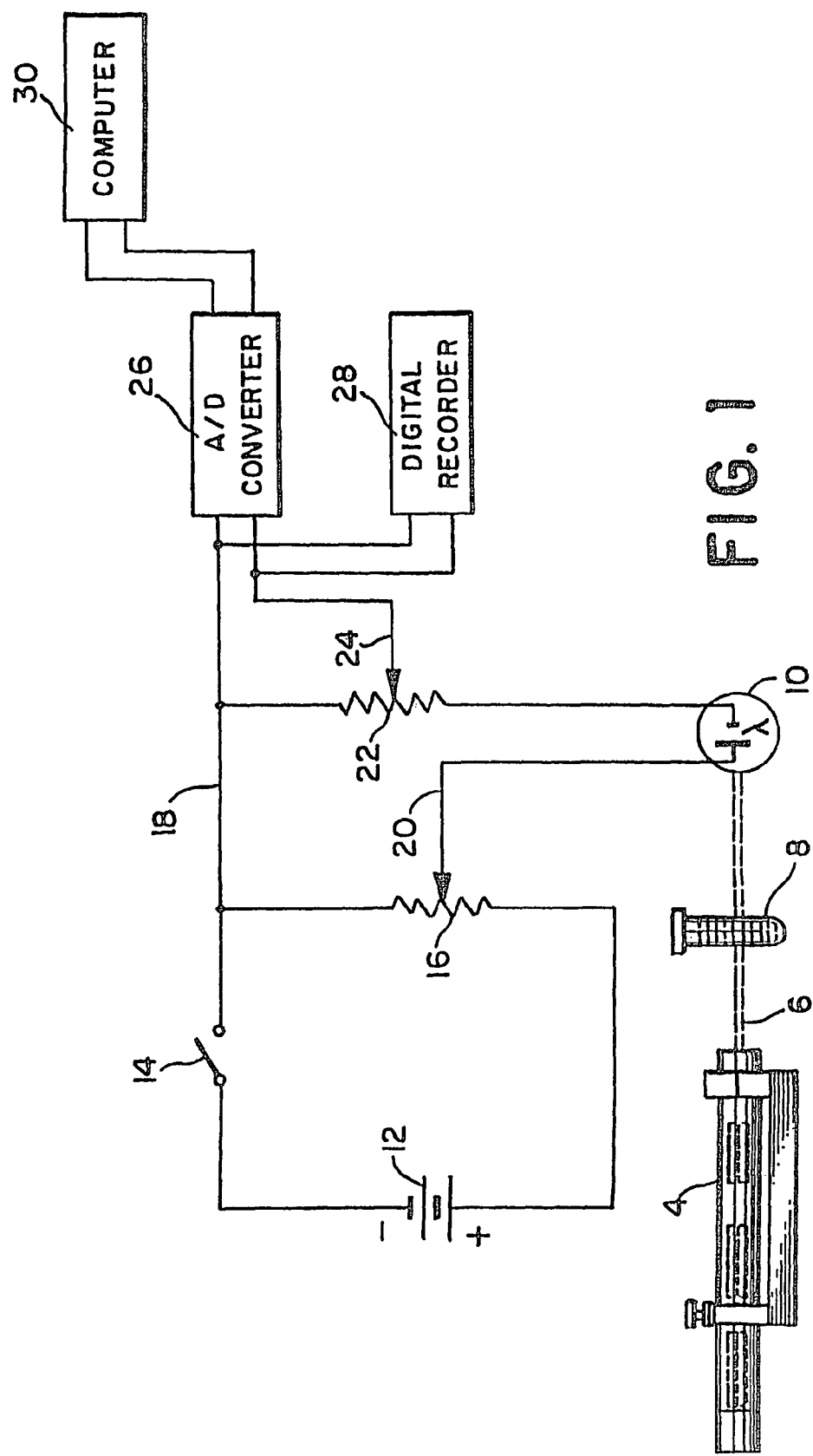
FIG. 1 is a diagram of potentiophotometric apparatus constructed in accordance with one embodiment of the present invention for determining blood chemistry analyses such as coagulation studies, including determination of the new anticoagulant therapy factor (nATF), where the output of the analog/digital (A/D) converter is applied to a computer.

Referring to the drawings, wherein the same reference numbers indicate the same elements throughout, there is shown in FIG. 1 a light source 4 which may be a low power gas laser, or other light producing device, producing a beam of light 6 which passes through a sample test tube, such as the container 8, and is received by detection means which is preferably a silicon or selenium generating photocell 10 (photovoltaic cell). Battery 12 acts as a constant voltage DC source. Its negative terminal is connected through switch 14 to one end of variable resistor 16 and its positive terminal is connected directly to the opposite end of variable resistor 16. The combination of battery 12 and variable resistor 16 provides a variable DC voltage source, the variable voltage being derivable between line 18 at the upper terminal of resistor 16 and wiper 20. This variable DC voltage source is connected in series with detection means photocell 10, the positive output of detection means photocell 10 being connected to the wiper 20 of variable resistor 16 so that the voltage produced by the variable voltage DC source opposes the voltage produced by the detection means photocell 10. The negative output of detection means photocell 10 is connected through variable resistor 22 to line 18. Thus, the voltage across variable resistor 22 is the difference between the voltage produced by the variable voltage DC source and the voltage produced by the photovoltaic cell 10. The output of the electrical network is taken between line 18 and wiper 24 of variable resistor 22. Thus, variable resistor 22 acts as a multiplier, multiplying the voltage produced as a result of the aforesaid subtraction by a selective variable depending on the setting of variable resistor 22. The potentiophotometer just described embodies the electrical-analog solution to Beer's Law and its output is expressed directly in the concentration of the substance being measured.

Wiper 24 is illustrated placed at a position to give a suitable output and is not varied during the running of the test. The output between line 18 and wiper 24 is delivered to an A/D converter 26 and digital recorder 28. As is known, the A/D converter 26 and the digital recorder 28 may be combined into one piece of equipment and may, for example, be a device sold commercially by National Instrument of Austin, Tex. as their type Lab-PC+. The signal across variable resistor 22 is an analog signal and hence the portion of the signal between leads 18 and wiper 24, which is applied to the A/D converter 26 and digital recorder 28, is also analog. A computer 30 is connected to the output of the A/D converter 26, is preferably IBM compatible, and is programmed in a manner described hereinafter.

For example, preferably, the detector cell 10 is positioned adjacent an opposite wall of the sample container 8, and the emitter light source 4 positioned adjacent on opposite wall, so the light 6 emitted from the light source 4 passes through the container 8. The light source 4 is preferably selected to produce light 6 which can be absorbed by one or more components which are to be measured.

The apparatus can be used to carry out coagulation studies in accordance with the invention. In accordance with a preferred embodiment of the present invention, the light source 4 may, for example, comprise a light emitting diode (LED) emitting a predetermined wavelength, such as for example, a wavelength of 660 nm, and the detector cell 10 may, for example, comprise a silicon photovoltaic cell detector. Optionally, though not shown, a bar code reader may also be provided to read bar code labels placed on the sample container 8. The bar code reader may produce a signal which can be read by the computer 30 to associate a set of data with a particular sample container 8.

To carry out a coagulation study on blood plasma, the citrated blood is separated from the red blood cell component of the blood. Conventional methods of separation, which include centrifugation, may be employed. Also, the use of a container device such as that disclosed in our issued U.S. Pat. No. 6,706,536, may also be used, and the method disclosed therein for reading the plasma volume relative to the sample volume may also be employed.

Illustrative of an apparatus and method according to one embodiment is a coagulation study which can be carried out therewith. A reagent, such as, for example, Thromboplastin-Calcium (Tp-Ca), is added to the plasma sample which is maintained at about 37° C. by any suitable temperature control device, such as a heated sleeve or compartment (not shown). The reagent addition is done by dispensing an appropriate amount of the reagent into the plasma portion of the blood. The plasma portion may be obtained by any suitable separation technique, such as for example, centrifugation. In one embodiment illustrated herein, the container 8 is vented when reagent is added. The reagent for example, may comprise thromboplastin, which is added in an amount equal to twice the volume of the plasma. The reagent is mixed with the plasma. It is preferable to minimize air bubbles so as not to interfere with the results. The plasma sample to which the reagent has been added is heated to maintain a 37° C. temperature, which, for example, may be done by placing the container holding the plasma and reagent in a heating chamber (not shown).

Readings are taken of the optical activity of the components in the sample container 8.

Reaction kinematics may be studied by observing changes in the optical density of the plasma layer. For example, an amount of reagent, such as Thromboplastin-Calcium (Tp-Ca), may be added to the plasma sample in the container. The plasma sample in the container may comprise a known amount of volume. Alternately, the plasma volume may be ascertained through the method and apparatus described in our U.S. Pat. No. 6,706,536. A controlled amount of Tp-Ca reagent is added to the plasma sample. The amount of reagent added corresponds to the amount of plasma volume. The detector cell 10 and emitter light source 4 are preferably positioned so the absorbance of the plasma sample may be read, including when the reagent is added and the sample volume is thereby increased.

Figure 2:
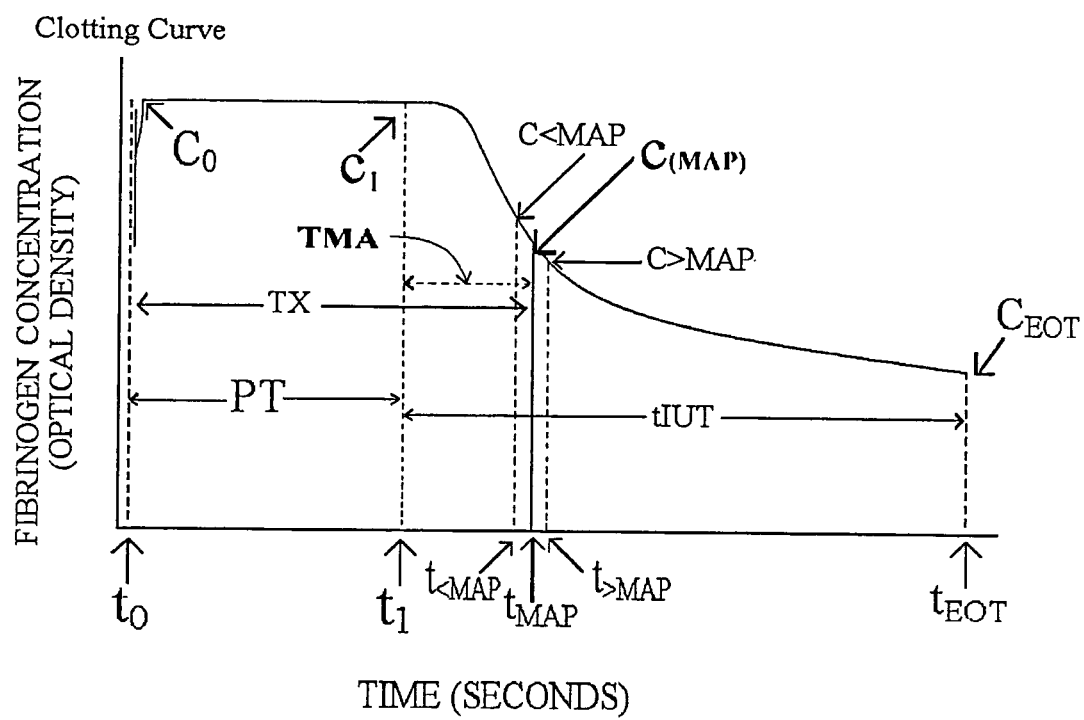
FIG. 2 is a plot of the various phases of the fibrinogen concentration occurring in a typical plasma clotting process.

With the detection elements, such as the cell 10 and emitter 4, positioned to read the plasma sample and the reagents added thereto, the reaction analysis of the extended prothrombin time curve can be followed. FIG. 2 shows a graph of a plot of the various phases of the fibrinogen concentration occurring in a typical plasma clotting process. The change in optical density of the plasma level occurs after reagents have been added. The optical density of the plasma sample is monitored, as optically clear fibrinogen converts to turbid fibrin.

The coagulation study of the type described above is used to ascertain the results shown in the graph plotted on FIG. 2. The description of the analysis makes reference to terms, and symbols thereof, having a general description as used herein, all to be further described and all of which are given in Table 1.

TABLE 1

| SYMBOL | TERM | GENERAL DESCRIPTION |
| --- | --- | --- |
| PT | Prothrombin Time | A period of time calculated from the addition of the reagent (e.g., thromboplastin-calcium) to a point where the conversion of fibrinogen to fibrin begins (i.e. the formation of the first clot). |
| TMA | Time to Maximum Acceleration | The time from PT to a point where the rate of conversion of fibrinogen to fibrin has reached maximum and begins to slow. |
| MAP | Maximum Acceleration Point | A point where the fibrinogen conversion achieves maximum acceleration and begins to decelerate. |
| EOT | End of Test | Point where there is no appreciable change in the polymerization of fibrin. |
| TEOT | Theoretical End Of Test | The time to convert all fibrinogen based on the time to convert the fibrinogen during the simulated Zero Order Kinetic rate. |
| TX (or $T_2$) | Time to Map | Time to reach the Maximum Acceleration Point (MAP) from point of injection. |
| MNTX | Mean Normal Time to Map | The mean of the times of at least 20 normal people to reach then Maximum Acceleration Point (MAP). |

TABLE 1-continued

| SYMBOL | TERM | GENERAL DESCRIPTION |
|---|---|---|
| FTR | Fibrinogen Transformation Ratio | The amount of fibrinogen converted during a particular time period. This is a percentage of the total Fibrinogen. |
| ATF | Anticoagulation Therapy Factor | The calculated value used to monitor the uses of an anticoagulant without a need for an International Sensitivity Index (ISI) of a thromboplastin. |
| nATF | new Anticoagulation Therapy Factor | A replacement for the INR to provide a standardized system for monitoring oral anticoagulant therapy. (Also expressed as ATFt and ATFz) |
| PR | Prothrombin Ratio | A value computed by dividing a sample PT by the geometric mean of at least 20 normal people (MNPT). |
| INR | International Normalized Ratio | A parameter which takes into account the various factors involved in anticoagulation therapy monitoring to provide a standardized system for monitoring oral anticoagulant therapy. |
| ATFt | Anticoagulation Therapy Factor Theoretical | Utilizing a calculated Theoretical End Of Test value and the Natural Log "e" to removed the need for an MNPT. |
| XR | Time to MAP Ratio | The value computed by dividing a sample "TX" by the geometric mean of at least 20 normal people "MNTX". |

Prior patents for obtaining an anticoagulant therapy factor (ATF) relied on the International Normalized Ratio (INR) system which was derived in order to improve the consistency of results from one laboratory to another. The INR system utilized the calculation of INR from the equation:

$$INR = PT_{patient}/PT_{geometric\ mean})^{ISI}$$

wherein the $PT_{patient}$ is the prothrombin time (PT) as an absolute value in seconds for a patient, $PT_{geometric\ mean}$ is the mean, a presumed number of normal patients. The International Sensitivity Index (ISI) is an equalizing number which a reagent manufacturer of thromboplastin specifies. The ISI is a value which is obtained through calibration against a World Health Organization primary reference thromboplastin standard. Local ISI (LSI) values have also been used to provide a further refinement of the manufacturer-assigned ISI of the referenced thromboplastin in order to provide local calibration of the ISI value.

For illustration, the present invention can be employed for accurate determination of a new Anticoagulant Therapy Factor (nATF) from a human blood sample, for use during the monitoring of oral anticoagulant therapy, without the need for an ISI or LSI value, and without the need for an INR value as traditionally determined from the above equation (using a patient's prothrombin time and the prothrombin time from a geometric mean of individuals). As is known in the art, blood clotting Factors I, II, V, VII, VIII, IX and X are associated with platelets (Bounameaux, 1957); and, among these, Factors II, VII, IX and X are less firmly attached, since they are readily removed from the platelets by washing (Betterle, Fabris et al, 1977). The role of these platelet-involved clotting factors in blood coagulation is not, however, defined. The present invention provides a method and apparatus for a new Anticoagulant Therapy Factor (nATF) which may be used for anticoagulant therapy monitoring without the need for INR.

The International Normalized Ratio (INR) is previously discussed in already incorporated reference technical articles entitled "PTs, PRs, ISIS and INRs: A Primer on Prothrombin Time Reporting Part I and II respectively," published in November, 1993 and December, 1993 issues of *Clinical Hemostasis Review*. The illustrative example of an analysis which is carried out employing the present invention relies upon the maximum acceleration point (MAP) at which fibrinogen conversion achieves a maximum and from there decelerates, the time to reach the MAP (TX), and the mean normal time to MAP (MNTX), and a fibrinogen transformation rate (FTR), that is, the thrombin activity in which fibrinogen (FBG) is converted to fibrin to cause clotting in blood plasma.

More particularly, during the clotting steps used to determine the clotting process of a plasma specimen of a patient under observation, a thromboplastin (Tp) activates factor VII which, activates factor X, which, in turn, under catalytic action of factor V, activates factor II (sometimes referred to as prothrombin) to cause factor IIa (sometimes referred to as thrombin) that converts fibrinogen (FBG) to fibrin with resultant turbidity activity which is measured, in a manner as to be described hereinafter, when the reaction is undergoing simulated zero-order kinetics.

From the above, it should be noted that the thromboplastin (Tp) does not take part in the reaction where factor IIa (thrombin) converts fibrinogen (FBG) to fibrin which is deterministic of the clotting of the plasma of the patient under consideration. The thromboplastin (Tp) only acts to activate factor VII to start the whole cascade rolling. Note also that differing thromboplastins (Tps) have differing rates of effect on factor VII, so the rates of enzyme factor reactions up to II-IIa (the PT) will vary.

Therefore, the prothrombin times (PTs) vary with the different thromboplastins (Tps) which may have been a factor that mislead authorities to the need of taking into account the International Normalized Ratio (INR) and the International Sensitivity Index (ISI) to compensate for the use of different types of thromboplastins (Tps) during the monitoring of oral anticoagulant therapy. It is further noted, that thromboplastins (Tps) have nothing directly to do with factor IIa converting fibrinogen (FBG) to fibrin, so it does not matter which thromboplastin is used when the fibrinogen transformation is a primary factor.

The thromboplastin (Tp) is needed therefore only to start the reactions that give factor IIa. Once the factor IIa is obtained, fibrinogen (FBG) to fibrin conversion goes on its own independent of the thromboplastin (Tp) used.

In one embodiment, the present method and apparatus has use, for example, in coagulation studies where fibrinogen (FBG) standard solutions and a control solution are employed, wherein the fibrinogen standard solutions act as dormant references to which solutions analyzed with the present invention are compared, whereas the control solution acts as a reagent that is used to control a reaction. The fibrinogen standards include both high and low solutions, whereas the control solution is particularly used to control clotting times and fibrinogens of blood samples. It is only necessary to use fibrinogen standards when PT-derived fibrinogens (FBG's) are determined. In connection with other embodiments of the invention, fibrinogen (FBG) standards are not necessary for the INR determination (such as for example INRz described herein).

Another embodiment provides a method and apparatus for determining an anticoagulation therapy factor which does not require the use of fibrinogen standard solutions. In this embodiment, the apparatus and method may be carried out without the need to ascertain the mean normal prothrombin time (MNPT) of 20 presumed normal patients.

Where a fibrinogen standard solution is utilized, a fibrinogen (FBG) solution of about 10 g/l may be prepared from a cryoprecipitate. The cryoprecipitate may be prepared by freezing plasma, letting the plasma thaw in a refrigerator and then, as known in the art, expressing off the plasma so as to leave behind the residue cryoprecipitate. The gathered cryoprecipitate should contain a substantial amount of both desired fibrinogen (FBG) and factor VIII (antihemophilic globulin), along with other elements that are not of particular concern to the present invention. The 10 g/l fibrinogen (FBG) solution, after further treatment, serves as the source for the high fibrinogen (FBG) standard. A 0.5 g/l fibrinogen (FBG) solution may then be prepared by a 1:20 (10 g/l/20=0.5 g/l) dilution of some of the gathered cryoprecipitate to which may be added an Owren's Veronal Buffer (pH 7.35) (known in the art) or normal saline solution and which, after further treatment, may serve as a source of the low fibrinogen (FBG) standard.

The fibrinogen standard can be created by adding fibrinogen to normal plasma in an empty container. Preferably, the fibrinogen standard is formed from a 1:1 fibrinogen to normal plasma solution. For example, 0.5 ml of fibrinogen and 0.5 ml of plasma can be added together in an empty container. Thromboplastin calcium is then added to the fibrinogen standard. Preferably, twice the amount by volume of thromboplastin is added into the container per volume amount of fibrinogen standard which is present in the container. The reaction is watched with the apparatus 10.

Then, 1 ml of each of the high (10 g/l) and low (0.5 g/l) sources of the fibrinogen standards may be added to 1 ml of normal human plasma (so the cryoprecipitate plasma solution can clot). Through analysis, high and low fibrinogen (FBG) standards are obtained. Preferably, a chemical method to determine fibrinogen (FBG) is used, such as, the Ware method to clot, collect and wash the fibrin clot and the Ratnoff method to dissolve the clot and measure the fibrinogen (FBG) by its tyrosine content. The Ware method is used to obtain the clot and generally involves collecting blood using citrate, oxalate or disodium ethylenediaminetetraacetate as anticoagulant, typically adding 1.0 ml to about 30 ml 0.85% or 0.90% sodium chloride (NaCl) in a flask containing 1 ml M/5 phosphate buffer and 0.5 ml 1% calcium chloride $CaCl_2$, and then adding 0.2 ml (100 units) of a thrombin solution. Preferably, the solution is mixed and allowed to stand at room temperature for fifteen minutes, the fibrin forming in less than one minute forming a solid gel if the fibrinogen concentration is normal. A glass rod may be introduced into the solution and the clot wound around the rod. See Richard J. Henry, M.D., et al., Clinical Chemistry: Principals and Techniques ($2^{nd}$ Edition) 1974, Harper and Row, pp. 458-459, the disclosure of which is incorporated herein by reference. Once the clot is obtained, preferably the Ratnoff method may be utilized to dissolve the clot and measure the fibrinogen (FBG) by its tyrosine content. See "A New Method for the Determination of Fibrinogen in Small Samples of Plasma", Oscar D. Ratnoff, M. D. et al., J. Lab. Clin. Med., 1951: V. 37 pp. 316-320, the complete disclosure of which is incorporated herein by reference. The Ratnoff method relies on the optical density of the developed color being proportional to the concentration of fibrinogen or tyrosine and sets forth a calibration curve for determining the relationship between optical density and concentration of fibrinogen. The addition of a fibrinogen standard preferably is added to the plasma sample based on the volume of the plasma.

As is known, the addition of the reagent Thromboplastin C serves as a coagulant to cause clotting to occur within a sample of citrated blood under test which may be contained in a container 8. As clotting occurs, the A/D converter 26 of FIG. 1 will count and produce a digital value of voltage at a predetermined period, such as once every 0.05 or 0.01 seconds. As more fully described in the previously incorporated by reference U.S. Pat. No. 5,197,017 ('017), these voltage values are stored and then printed by the recorder as an array of numbers, the printing being from left to right and line by line, top to bottom. There are typically one hundred numbers in the five groups representing voltage values every second and hence, one line represents one-fifth of a second in time (20× 0.01 seconds). Individual numbers in the same column are twenty sequential numbers apart. Hence, the time difference between two adjacent numbers in a column is one-fifth of a second. The significance of these recorded values may be more readily appreciated after a general review of the operating principles illustrated in FIG. 2 having a Y axis identified as Fibrinogen Concentration (Optical Density) and an X axis identified in time (seconds).

FIG. 2 illustrates the data point locations of a clotting curve related to a coagulation study which illustrates the activation and conversion of fibrinogen to fibrin. In general, FIG. 2 illustrates a "clot slope" method that may be used in a blood coagulation study carried out for determining a new anticoagulant therapy factor (nATFa). The ATFa represents an anticoagulation therapy factor represented by the expression $ATFa=XR^{(2-nFTR)}$ wherein a maximum acceleration point is obtained, and nFTR=IUX/IUT, where IUX is the change in optical density from a time prior to the MAP time ($t_{<MAP}$ which is $t_{MAP}$ minus some time from MAP) to the optical density at a time after the MAP time ($t_{>MAP}$ which is $t_{MAP}$ plus some time from MAP); and wherein IUT=the change in optical density at the time $t_1$ to the optical density measured at time $t_{EOT}$, where time $t_{EOT}$ is the end of the test (EOT). The first delta (IUX) represents the fibrinogen (FBG) for MAP (−a number of seconds) to MAP (+a number of seconds) (that is the fibrinogen (FBG) converted from $t_{<MAP}$ to $t_{>MAP}$ on FIG. 2). The (IUT) represents fibrinogen converted from $c_1$ to $c_{EOT}$ (that is the fibrinogen converted from $t_1$ to $t_{EOT}$, see FIG. 2). The XR for the ATFa expression is XR=TX/MNTX, which is the ratio of time to map (TX) by the mean normal time to map of 20 presumed "normal" patients.

The study which measures the concentration of the fibrinogen (FBG) in the plasma that contributes, to the clotting of the plasma and uses an instrument, such as, for example, the potentiophotometer apparatus illustrated in FIG. 1, to provide an output voltage signal that is directly indicative of the fibrinogen (FBG) concentration in the plasma sample under test, is more fully discussed in the previously incorporated by reference U.S. Pat. No. 5,502,651. The quantities given along the Y-axis of FIG. 2 are values (+ and −) that may be displayed by the digital recorder 28. The "clot slope" method comprises detection of the rate or the slope of the curve associated with the formation of fibrin from fibrinogen. The "clot slope" method takes into account the time to maximum acceleration (TX) which is the point at which fibrinogen conversion achieves a maximum and from there decelerates.

As seen in FIG. 2, at time $t_0$, corresponding to a concentration $c_0$, the thromboplastin/calcium ion reagent is introduced into the blood plasma which causes a disturbance to the composition of the plasma sample which, in turn, causes the optical density of the plasma sample to increase momentarily. After the injection of the reagent (the time of which is known, as to be described, by the computer 30), the digital quantity of the recorder 28 of FIG. 1 rapidly increases and then levels off in a relatively smooth manner and then continues along until the quantity $c_1$ is reached at a time $t_1$. The time which elapses between the injection of thromboplastin at $t_0$ and the instant time $t_1$ of the quantity $c_1$ is the prothrombin time (PT) and is indicated in FIG. 2 by the symbol PT. As shown in FIG. 2, the baseline that develops after the thromboplastin (TP) is introduced or injected into the sample generally is thought to represent the "lag phase" of all of the enzymes preceding prothrombin converting to fibrin. The enzymes types and amounts may vary from person to person, and thus, this would demonstrate the potential for prothrombin times to vary between individuals.

An anticoagulant therapy factor (nATF) is determined. The optical density of a quantity $c_1$ directly corresponds to a specified minimum amount of fibrinogen (FBG) that must be present for a measuring system, such as the circuit arrangement of FIG. 1, to detect in the plasma sample that a clot is being formed, i.e., through the transformation of fibrinogen to fibrin. The quantities shown in FIG. 2 are of optical densities, which may be measured in instrument units, that are directly correlatable to fibrinogen concentration values. The quantity $c_1$, may vary from one clot detection system to another, but for the potentiophotometer system of FIG. 1, this minimum is defined by units of mass having a value of about 0.05 grams/liter (g/l).

Figure 3:
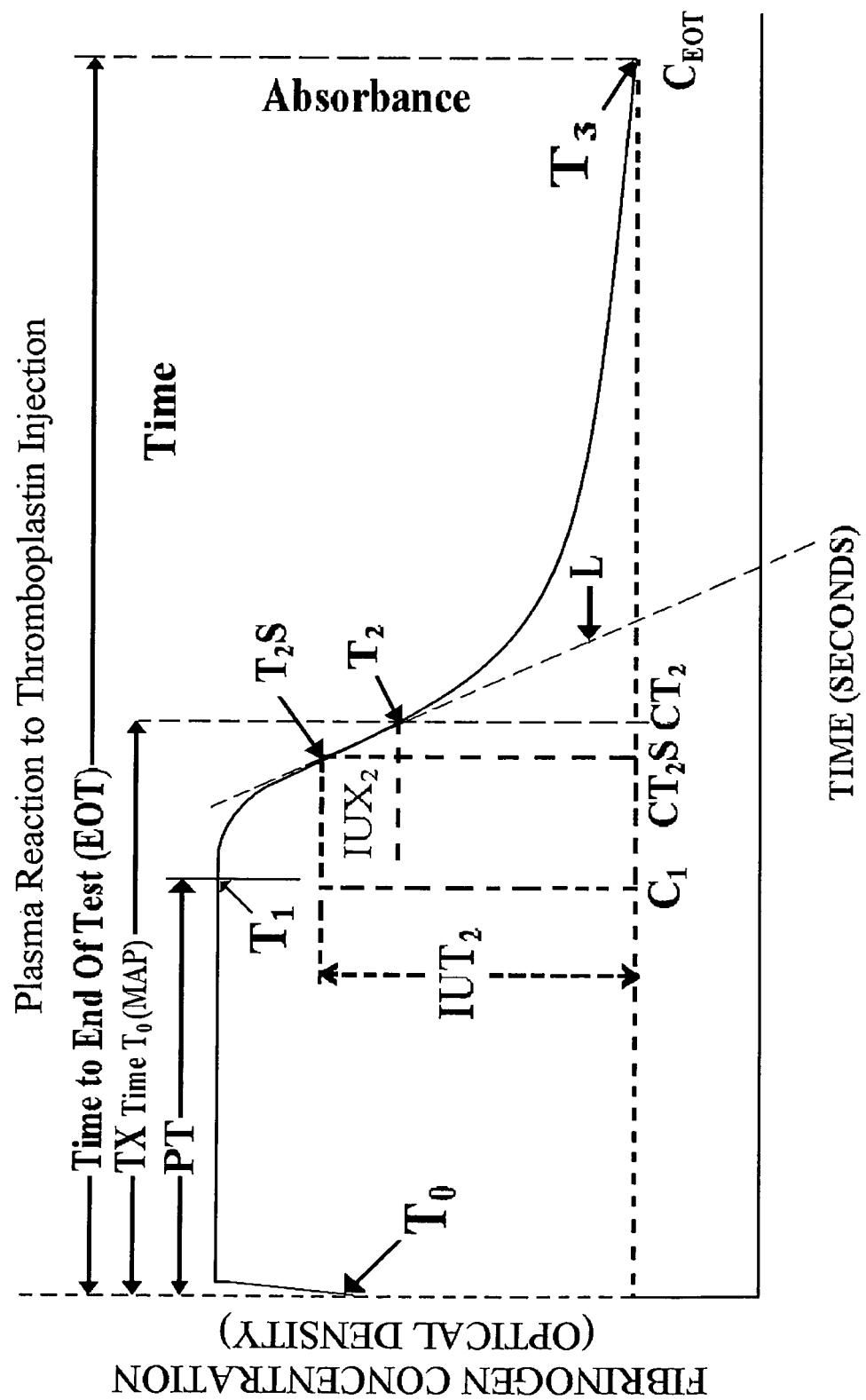
FIG. 3 is another plot of the various phases of the fibrinogen concentration occurring in a typical plasma clotting process.

Considering the clotting curve of FIG. 2, detection of a first predetermined quantity $c_1$ is illustrated occurring at a corresponding time $t_1$, which is the start of the clotting process. In accordance with one or more embodiments, this process may be monitored with the apparatus of FIG. 1 for determining a new anticoagulant therapy factor (nATF). The time $t_1$ is the beginning point of the fibrinogen formation, that is, it is the point that corresponds to the beginning of the acceleration of the fibrinogen conversion that lasts for a predetermined time, The acceleration of the fibrinogen conversion proceeds from time ($t_1$) and continues until a time $t_{MAP}$, having a corresponding quantity $c_{MAP}$. The time $t_{MAP}$, as well as the quantity $c_{MAP}$, is of primary importance because it is the point of maximum acceleration of the fibrinogen (FBG) to fibrin conversion and is also the point where deceleration of fibrinogen (FBG) to fibrin conversion begins. Further, the elapsed time from $t_0$ to $t_{MAP}$ is a time to maximum acceleration from reagent injection (TX), shown in FIG. 2. Preferably, the conversion of fibrinogen to fibrin is quantified every 0.1 seconds. The time to maximum acceleration from reagent injection (TX) is defined as the point on the clotting curve time line where this conversion has reached its maximum value for the last time, simulating a zero-order kinetic rate. To facilitate ascertainment of the location point of the last maximum value, the delta value of two points at a fixed interval may be measured until this value begins to decrease. This value is tracked for a period of time, such as for example five seconds, after the first decreasing value has been determined. This facilitates ascertainment of the last point of what may be referred to as a simulated zero-order kinetic rate. Referring to FIG. 3, a zero order kinetic rate is illustrated by the line (L).

As shown in FIG. 2, a quantity $c_{MAP}$ and a corresponding time $t_{MAP}$ define a maximum acceleration point (MAP). Fibrin formation, after a short lag phase before the MAP, occurs for a period of time, in a linear manner. Fibrinogen (FBG) is in excess during this lag phase, and fibrin formation appears linear up to the MAP.

The deceleration of fibrinogen (FBG) to fibrin conversion continues until a quantity $c_{EOT}$ is reached at a time $t_{EOT}$. The time $t_{EOT}$ is the point where the deceleration of the fibrinogen (FBG) to fibrin conversion corresponds to a value which is less than the required amount of fibrinogen (FBG) that was present in order to start the fibrinogen (FBG) to fibrin conversion process. Thus, because the desired fibrinogen (FBG) to fibrin conversion is no longer in existence, the time $t_{EOT}$ represents the ending point of the fibrinogen (FBG) to fibrin conversion in accordance with the coagulation study exemplified herein, which may be referred to as the end of the test (EOT). The fibrinogen (FBG) to fibrin conversion has a starting point of $t_1$ and an ending point of $t_{EOT}$. The differential of these times, $t_1$ and $t_{EOT}$, define a second delta (IUT).

The "clot slope" method that gathers typical data as shown in FIG. 2 has four critical parameters. The first is that the initial delta optical density of substance being analyzed should be greater than about 0.05 g/l in order for the circuit arrangement of FIG. 1 to operate effectively. Second, the acceleration fibrinogen (FBG) to fibrin conversion should be increasing for a minimum period of about 1.5 seconds so as to overcome any false reactions created by bubbles. Third, the total delta optical density (defined by the difference in quantities $c_1$ and $c_{EOT}$) should be at least three (3) times the instrument value in order to perform a valid test, i.e., (3)*(0.05 g/l)=0.15 g/l. Fourth, the fibrinogen (FBG) to fibrin conversion is defined, in part, by the point ($t_{EOT}$) where the deceleration of conversion becomes less than the instrument value of about 0.05 g/l that is used to detect the clot point ($t_1$). As with most clot detection systems, a specific amount of fibrinogen needs to be present in order to detect a clot forming. Adhering to the four given critical parameters is an example of how the present apparatus and method may be used to carry out a coagulation study to determine a specific quantity of fibrinogen. In order for that specific amount of fibrinogen to be determined, it is first necessary to detect a clot point ($t_1$). After that clot point ($t_1$) is detected, it logically follows that when the fibrinogen conversion becomes less than the specific amount (about 0.05 g/l for the circuit arrangement of FIG. 1), the end point ($t_{EOT}$) of the fibrinogen conversion has been reached.

One embodiment of the method and apparatus is illustrated in accordance with the clotting curve shown in FIG. 3. The clotting curve of FIG. 3 illustrates the values ascertained in arriving at a new anticoagulation therapy factor (nATFz). The embodiment illustrates the determination of a new anticoagulation therapy factor (nATFz), expressed by the following formula:

$$nATFz = XR^{(2-nFTR)} \tag{1}$$

This embodiment utilizes a zero order line (L) to obtain a first delta, in particular IUXz, which is a first differential taken along the simulated zero order kinetic line (L), and preferably along the segment between the start of the simulated zero order kinetic ($T_2S$) to the last highest absorbance value ($T_2$) (i.e., preferably, the last highest absorbance value of a simulated zero order kinetic). As previously discussed, the acceleration of the fibrinogen conversion proceeds from a first time, here time ($T_1$) and continues, eventually reaching a time where the last highest delta absorbance value or maximum acceleration point ($T_2$) having a corresponding quantity $c_{T2}$ is reached. The values for "T" correspond with times, and the values for "c" correspond with quantity, which may be measured in instrument units based on optical density readings (also referred to as optical density or o.d.). The time $T_2$, as well as the quantity $c_{T2}$, is the point of maximum acceleration of the fibrinogen (FBG) to fibrin conversion and is also the point where deceleration of fibrinogen (FBG) to fibrin conversion begins. In this embodiment, IUXz is the change in optical density preferably from the beginning of the at the time $T_2S$ at which the simulated zero order kinetic begins to the optical density at time $T_2$ which is the maximum acceleration point or the last highest delta absorbance value of a simulated zero order kinetic. FIG. 3 shows the differential IUXz taken between a preferred segment of the zero order line. The second delta in particular (IUTz) is the change in optical density at the time $T_2S$ to the optical density measured at time $T_3$, where time $T_3$ is the end of the test (EOT).

The (IUXz) represents the fibrinogen (FBG) converted between time $T_2S$ and $T_2$. The (IUTz) represents fibrinogen converted from the time $T_2S$ to the end of the test or $T_3$.

The maximum acceleration ratio (XR) for this embodiment is calculated to arrive at the new alternate anticoagulation therapy factor (nATFz). The maximum acceleration ratio (XR) is defined as the time to maximum acceleration from reagent injection (TX) divided by the mean normal TX value of a number of presumed normal specimens (MNTX). For example, the mean normal TX value may be derived based on the value of 20 or more presumed normal specimens. The maximum acceleration ratio (XR) may be expressed through the following formula:

$$XR = TX/MNTX \quad (2)$$

The clotting curve of FIG. 3 illustrates the values ascertained in arriving at the new alternate anticoagulation therapy factor (nATFz). The new alternate anticoagulation therapy factor (nATFz) is preferably expressed by the following formula:

$$nATFz = XR^{(2-nFTR)} \quad (3)$$

with FTR being IUXz/IUTz.

The preferred IBM-compatible computer 30 of FIG. 1 stores and manipulates these digital values corresponding to related data of FIG. 3 and is preferably programmed as follows:

(a) a sample of blood where the plasma is available, such as, for example, a sample of citrated blood, is obtained and placed in an appropriate container, the computer 30, as well as the recorder 28, sequentially records voltage values for a few seconds before injection of thromboplastin. As previously discussed, thromboplastin (tissue factor) is one of the factors in the human body that causes blood to clot. Prothrombin is another. Fibrinogen is yet another. Before injection of the thromboplastin, the output from the A/D converter 26 is relatively constant. When thromboplastin is injected into the plasma sample in the container, a significant and abrupt change occurs in the recorded voltage values of both the computer 30 and the recorder 28. This abrupt change is recognized by both the recorder 28 and, more importantly, by the computer 30 which uses such recognition to establish $T_o$. The computer 30 may be programmed so as to correlate the digital quantities of the A/D converter 26 to the analog output of the detector means photocell 10 which, in turn, is directly correlatable to the fibrinogen (FBG) concentration g/l of the sample of blood discussed with reference to FIG. 3;

(b) the computer 30 may be programmed to look for a digital quantity representative of a critical quantity $c_1$, and when such occurs, record its instant time $T_1$. (The time span between $T_o$ and $T_1$ is the prothrombin time (PT), and has an normal duration of about 12 seconds, but may be greater than 30 seconds);

(c) following the detection of the quantity $c_1$, the computer 30 may be programmed to detect for the acceleration of fibrinogen (FBG) to fibrin conversion. The computer 30 is programmed to detect the maximum acceleration quantity $c_{MAP}$ or $C_{T2}$ as illustrated in FIG. 3, and its corresponding time of occurrence $t_{MAP}$, which is $T_2$ in FIG. 3.

(d) the computer detects a quantity $c_{EOT}$ occurring at time $t_{EOT}$. Typically, it is important that the rate of fibrin formation increase for at least 1.5 seconds following the occurrence of ($T_1$);

(e) The computer 30 is programmed to ascertain the value for the time to start ($T_2S$) which corresponds with the time at which the simulated zero order kinetic rate begins.

(f) following the detection of the acceleration of fibrinogen conversion to detect the start time $T_2S$, the computer 30 is programmed to detect for a deceleration of the fibrinogen conversion, wherein the fibrinogen concentration decreases from a predetermined quantity $c_{MAP}$ to a predetermined quantity $c_{EOT}$ having a value which is about equal but less than the first quantity $c_1$. The computer is programmed to ascertain a first delta (IUTz), by determining the difference between the quantity $c_{T2S}$ and the quantity $c_{EOT}$; and a second delta (IUXz) by determining the difference between the quantity $c_{T2S}$ and the quantity $c_2$ (or $c_{MAP}$).

(g) the computer 30 manipulates the collected data of (a); (b); (c); (d); (e) and (f) above, to determine the new fibrinogen transfer rate (nFTR). The nFTR may be arrived at based on the principle that if a required amount (e.g., 0.05 g/l) of fibrinogen concentration $c_1$ is first necessary to detect a clot point ($T_1$); then when the fibrinogen concentration ($c_{EOT}$) becomes less than the required amount $c_1$, which occurs at time ($T_{EOT}$), the fibrinogen end point has been reached. More particularly, the required fibrinogen concentration $c_1$ is the starting point of fibrinogen conversion of the clotting process and the less than required fibrinogen concentration $c_{EOT}$ is the end point of the fibrinogen conversion of the clotting process.

(h) The computer now has the information needed to determine the new fibrinogen transfer rate (nFTRz) which is expressed by the following formula:

$$nFTRz = IUXz/IUTz \quad (4)$$

(i) data collected is manipulated by the computer 30 to calculate the maximum acceleration ratio (XR), which is expressed as TX divided by the mean normal TX value of at least 20 presumed normal specimens (MNTX):

$$XR = TX/MNTX \quad (2)$$

The MNTX value may be ascertained and stored in the computer for reference.

(j) the computer 30 now has the information needed to determine the nATFz, (also referred to as INRz) which typically is expressed as:

$$nATFz \text{ or } INRz = XR^{(2-nFTR)} \quad (3)$$

where, in the exponent, the value 2 is the logarithm of the total fibrinogen, which, as expressed in terms of the optical density, is 100% transmittance, the log of 100 being 2.

The new anticoagulation therapy factor (nATFz) does not require an ISI value, as was previously used to determine anticoagulation therapy factors. The new anticoagulation therapy factor (nATFz) uses for its ascertainment the values extracted from the clotting curve (see FIG. 3), in particular (nFTRz) (determined based on IUXz and IUTz), and (TX). In carrying out coagulation studies, the new anticoagulant therapy factor (nATFz) may replace INR in anticoagulant therapy management.

The apparatus and method for obtaining a new anticoagulant therapy factor, (nATFz), may be accomplished without encountering the complications involved with obtaining the prior art quantities International Normalized Ratio (INR) and International Sensitivity Index (ISI).

The new anticoagulant therapy factor (nATFz or ATF) preferably is a replacement for the International Normalized Ratio (INR), hence it may be referred to as INRz. Existing medical literature, instrumentation, and methodologies are closely linked to the International Normalized Ratio (INR). The nATFz was compared for correlation with the INR by comparative testing, to INR quantities, even with the understanding that the INR determination may have an error of about ten (10) % which needs to be taken into account to explain certain inconsistencies.

Table 2, below, includes anticoagulant therapy factors obtained from patients at two different hospitals. The ATFz values were obtained, with GATFz representing one geographic location where patients were located and MATFz being another location. The ATFz was obtained as the new anticoagulant therapy factor, and as illustrated in Tables 4 and 5, below, compares favorably to results obtained for INR determinations.

Figure 4:
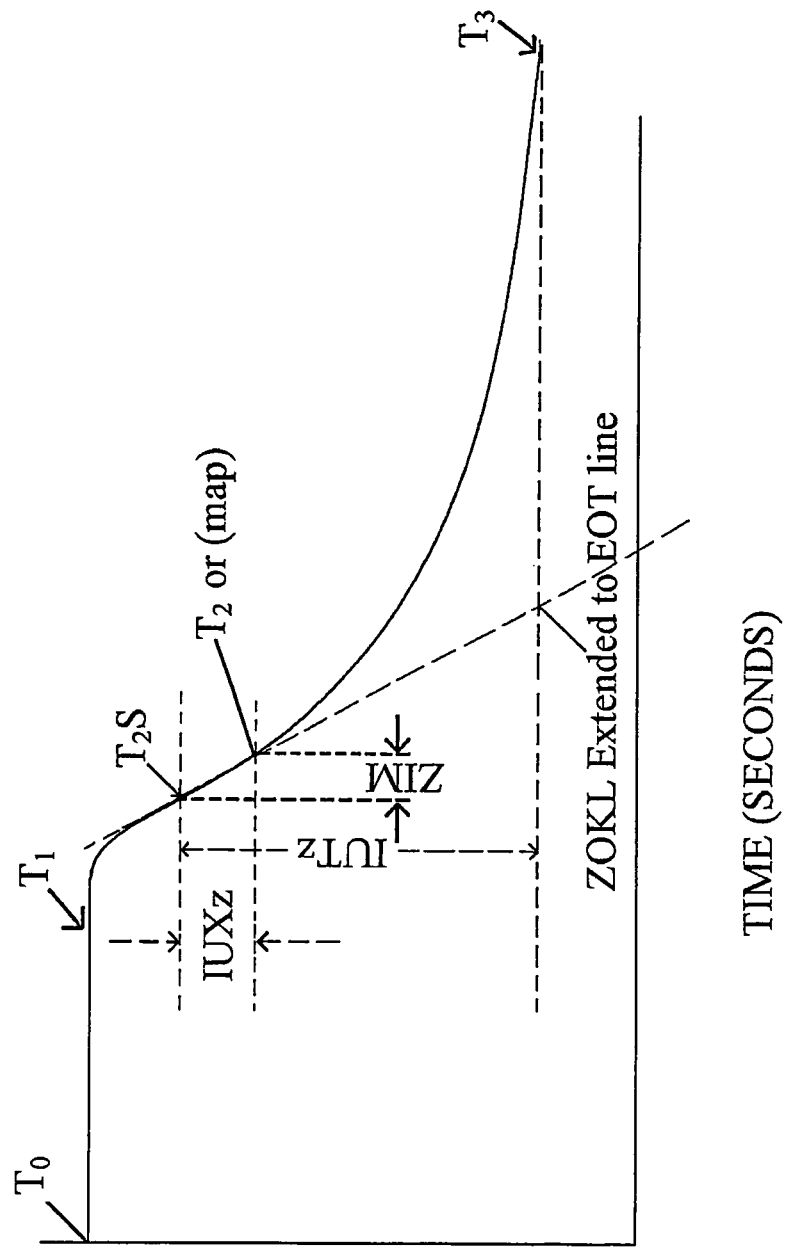
FIG. 4 is another plot of the various phases of the fibrinogen concentration occurring in a typical plasma clotting process.

Another alternate embodiment for determining a new anticoagulant therapy factor (ATFt) is provided. The alternate embodiment for determining ATFt eliminates the need for determining a mean normal prothrombin time (MNPT) (or MNXT) and ISI, saving considerable time and costs, and removing potential sources of error, as the MNPT (the expected value of MNPT's depending on the varying 20 presumed normals population) and ISI (generally provided by the manufacturer of the reagent—such as, for example, the thromboplastin, etc.) are not required for the determination of the ATFt. An alternate embodiment for determining ATFt is illustrated in accordance with the clotting curve shown in FIG. 4. The clotting curve of FIG. 4 illustrates values ascertained in arriving at the alternate new anticoagulation therapy factor (nATFt). The alternate new anticoagulation therapy factor (nATFt) is preferably expressed by the following formula:

$$\text{nATFt} = \text{Value 1} * \text{Value 2} \quad (4)$$

The alternate embodiment utilizes the zero order line (L) to obtain a first delta, in particular IUXz, which is a first differential taken along the simulated zero order kinetic line (L), and preferably along the segment between the start of the simulated zero order kinetic ($T_2S$) to the last highest absorbance value ($T_2$) (i.e., preferably, the last highest absorbance value of a simulated zero order kinetic). As previously discussed, the acceleration of the fibrinogen conversion proceeds from a first time, here time ($T_1$) and continues, eventually reaching a time where the last highest delta absorbance value or maximum acceleration point ($T_2$) having a corresponding quantity $c_{T2}$ is reached. The time $T_2$, as well as the quantity $c_{T2}$, is the point of maximum acceleration of the fibrinogen (FBG) to fibrin conversion and also is the point where deceleration of fibrinogen (FBG) to fibrin conversion begins. As illustrated on the clotting chart in FIG. 4, IUXz represents a change in optical density (o.d.) preferably from the beginning of the at the time $T_2S$ at which the simulated zero order kinetic begins to the optical density at time $T_2$ which is the maximum acceleration point or the last highest delta absorbance value of a simulated zero order kinetic. The value IUXz is generally expressed in instrument units (corresponding to absorbance or percent transmittance) and may generally be referred to as optical density or o.d. FIG. 4 shows the differential IUXz taken between a preferred segment of the zero order line. The second delta in particular (IUTz) represents a change in optical density at a time $T_2S$ to the optical density measured at a time $T_3$, where time $T_3$ is the end of the test (EOT).

The (IUXz) represents the fibrinogen (FBG) converted between time $T_2S$ and $T_2$. The (IUTz) represents fibrinogen converted from the time $T_2S$ to the end of the test or $T_3$.

The first value V1 corresponds to the value determined for the theoretical end of test (TEOT), which, as illustrated in the clotting curve representation in FIG. 4, is where the zero order kinetic line (L) crosses the line $y=T_3$. The value TEOT is the elapsed time to convert the total instrument units (TIU) at the zero order kinetic rate, which is representative of the fibrinogen in the sample undergoing the conversion to fibrin. In other words, the expression for the first value (V1), or TEOT, is:

$$V1 = \text{TEOT} = \text{ZTM}/\text{IUXz} * \text{IUTz} \quad (5)$$

where ZTM is the time between Tmap (i.e., $T_2$ shown on FIG. 4) and T2S. ZTM may be generally represented by the following expression:

$$\text{ZTM} = T_2 - T_2S \quad (6)$$

A second value, V2, also referred to as a multiplier, is determined based on the value $T_2S$. In the expression for the ATFt, the second value, V2, may be obtained by taking the value of the time ($T_2S$) corresponding to a second time (t2) or the maximum acceleration point (Tmap), and scaling this value. It is illustrated in this embodiment that the multiplier is derived from the natural log base "e", which is 2.71828, scaled to provide an appropriately decimaled value. The scaling number used in the example set forth for this embodiment is 100. The second value (V2) may be expressed by the following relationship:

$$V2 = T_2S/100e \quad (7)$$

where $T_2S$ is the maximum acceleration point for the sample, and 100e is the value 100 multiplied by the natural log base "e" (2.71828) or 271.828. The new anticoagulation therapy factor according to the alternate embodiment may be expressed as follows:

$$\text{nATFt} = [(T_2 - T_2S)/\text{IUXz} * \text{IUTz}] * [T_2S/M] \quad (8)$$

where M represents a multiplier. In the present example, the multiplier M, corresponds to the value 271.828 (which is 100 times the natural log base "e").

Figure 5:
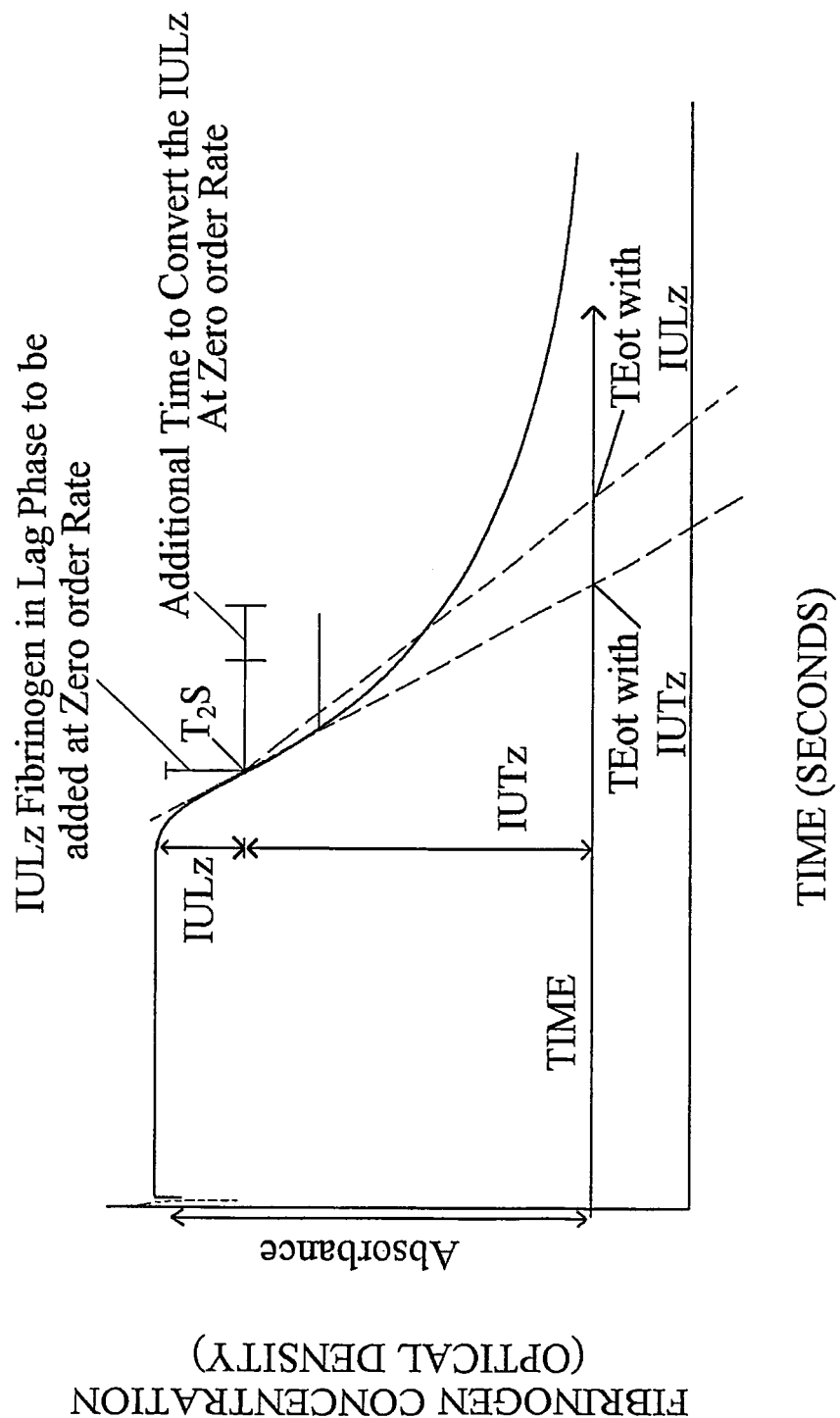
FIG. 5 is another plot of the various phases of the fibrinogen concentration occurring in a typical plasma clotting process illustrating the fibrinogen lag phase.

An alternate embodiment of an anticoagulant therapy factor, ATFt2, which does not require the ascertainment of a mean normal prothrombin time (MNPT) or use of an ISI value, is derived using the expression (5), wherein the IUTz is replaced by the expression (IUTz+IULz). In this alternate expression the method is carried out to ascertain the values for Value1 and Value2, in the manner described herein, with Value 1 being obtained through expression (5.1):

$$V1 = \text{TEOT} = \text{ZTM}/\text{IUXz} * (\text{IUTz} + \text{IULz}) \quad (5.1)$$

where IULz is time to convert the lag phase fibrinogen (FBG) measured along the ordinate between T1 and T2S. In expression 5.1, the theoretical end of test (TEOT) is set to include the time to convert the fibrinogen (FBG) in the lag phase of the clotting curve. FIG. 5 illustrates the fibrinogen lag phase and the TEOT obtained from the line L2, and shows the IULz. ATFt2 is expressed by the following:

$$nATFt2=[(T_2-T_2S)/IUXz*(IUTz+IULz)]*[T_2S/M] \quad (8.1)$$

The apparatus may comprise a computer which is programmed to record, store and process data. The zero order rate may be determined by ascertaining data from analyzing the sample, and optical density properties. One example of how this may be accomplished is using two arrays, a data array and a sub array. A data array may be ascertained by collecting data over a time interval. In one embodiment, for example, the data array may comprise a sequential list of optical densities, taken of a sample by an optical analytical instrument, such as, for example, a spectrophotometer, for a frequency of time. In the example, the frequency of sample data is taken every $100^{th}$ of a second. In this embodiment, a computer is programmed to record the optical density of the sample, every $100^{th}$ of a second. Two values, NOW and THEN, for the data array are provided for ascertaining the Prothrombin Time (PT) (which is the time point $T_1$), maximum acceleration point (MAP), and end of test point (EOT). Two time definitions may be specified, one being the interval between NOW and THEN on the clotting curve, which may be 2.72 seconds ($^{272}/_{100}{}^{th}$ of a second), the second being the size of the filter used for signal averaging. NOW is the sum of the last 20 optical densities and THEN is the sum of the 10 prior data points 2.72 seconds prior to NOW. A graphical illustration is provided in FIG. 5. As illustrated in FIG. 5, four values are defined: SUM(NOW), SUM(THEN), AVERAGE (NOW) and AVERAGE(THEN). The average is the sum divided by the filter value.

The sub array may be defined as a sequential list of delta absorbance units. This may begin at $T_1$, the prothrombin time (PT), and continue until the last highest delta absorbance (delta A) has been detected, then continues an additional five (5) seconds to insure the last delta A has been found. A determination of $T_2S$ may be accomplished by locating within the sub array, the first occurrence of when the sub array delta value is greater than or equal to 80% of the highest delta absorbance units. The first derivative is ascertained by computing the difference between (NOW) and (THEN). The PT is ascertained by determining the point prior to the positive difference between AVERAGE(THEN) and AVERAGE (NOW) for a period of 2.72 seconds or 272 ticks. The MAP is the point where the last highest difference between SUM (THEN) and SUM(NOW) has occurred. The computer may be programmed to store this delta A value in the sub array. The EOT may be ascertained by determining the point prior to where the difference between SUM(THEN) and SUM (NOW) is less than one.

Table 2 illustrates examples of samples, identified by ID numbers, along with corresponding data which compares the ATF values obtained for an ATF determined through the prior method, using ISI and INR values (represented as ATFa), an ATF determined through the use of a zero order kinetic reaction using the MNTX (nATFz), and an ATF determined without using the MNXT or ISI (nATFt). The data in table 2 represents universal laboratory data from combined locations for the patients listed. The data is based on analysis of absorbance data, storage of the data by the computer, such as, for example, with a storage device, like a hard drive, and retrieving the data and processing the data. The data, in the example represented in Table 2 was processed using the definitions and NOW and THEN intervals.

TABLE 2

| ID | AINR | GINR | GatfA | GatfZ | GatfT | MINR | MatfA | MatfZ | MatfT |
|---|---|---|---|---|---|---|---|---|---|
| U0047 | 2.10 | 1.70 | 1.76 | 1.74 | 1.62 | 2.00 | 2.08 | 1.78 | 1.68 |
| U0048 | 1.80 | 1.80 | 1.84 | 1.83 | 1.72 | 1.90 | 1.96 | 1.85 | 1.82 |
| U0050 | 1.80 | 1.70 | 1.77 | 1.80 | 1.68 | 1.90 | 2.00 | 1.80 | 1.70 |
| U0056 | 1.60 | 1.50 | 1.54 | 1.54 | 1.40 | 1.80 | 1.83 | 1.61 | 1.48 |
| U0058 | 3.20 | 2.80 | 2.93 | 2.92 | 2.93 | 3.30 | 3.38 | 3.10 | 3.29 |
| U0060 | 2.20 | 2.10 | 2.15 | 2.17 | 2.11 | 2.20 | 2.21 | 2.26 | 2.27 |
| U0062 | 2.80 | 2.60 | 2.69 | 2.72 | 2.69 | 3.00 | 3.19 | 2.86 | 2.91 |
| U0415 | 0.90 | 0.90 | 0.88 | 0.94 | 0.74 | 0.90 | 0.95 | 0.97 | 0.83 |
| U0432 | 1.80 | 1.50 | 1.53 | 1.42 | 1.24 | 1.40 | 1.39 | 1.46 | 1.33 |
| U0436 | 2.40 | 2.40 | 2.57 | 2.24 | 1.99 | 2.40 | 2.41 | 2.28 | 2.17 |
| U0438 | 3.90 | 3.70 | 4.25 | 3.26 | 3.21 | 3.80 | 4.22 | 3.40 | 3.55 |
| U0439 | 2.30 | 2.20 | 2.27 | 1.94 | 1.75 | 2.30 | 2.32 | 2.07 | 2.02 |
| U0440 | 5.80 | 4.80 | 5.41 | 4.33 | 4.50 | 4.60 | 4.84 | 4.55 | 5.18 |
| U0441 | 4.50 | 4.90 | 5.58 | 5.01 | 4.86 | 4.40 | 4.71 | 4.64 | 5.35 |
| U0442 | 1.80 | 1.70 | 1.79 | 1.65 | 1.48 | 1.80 | 1.84 | 1.64 | 1.52 |
| U0800 | 2.00 | 2.00 | 2.02 | 1.78 | 1.64 | 2.10 | 2.11 | 2.12 | 2.09 |
| U0843 | 1.40 | 1.40 | 1.43 | 1.42 | 1.22 | 1.40 | 1.47 | 1.44 | 1.31 |
| U0848 | 1.30 | 1.40 | 1.41 | 1.31 | 1.13 | 1.30 | 1.37 | 1.34 | 1.23 |
| U0849 | 2.40 | 2.30 | 2.44 | 1.94 | 1.77 | 2.30 | 2.38 | 1.98 | 1.93 |
| U0855 | 1.30 | 1.30 | 1.29 | 1.35 | 1.17 | 1.20 | 1.24 | 1.36 | 1.22 |
| U0860 | 1.00 | 1.00 | 0.99 | 1.00 | 0.77 | 1.00 | 0.97 | 1.00 | 0.85 |
| U0861 | 2.80 | 2.90 | 2.98 | 2.70 | 2.58 | 3.00 | 2.99 | 2.88 | 3.00 |
| U0863 | 1.70 | 1.70 | 1.70 | 1.76 | 1.65 | 1.70 | 1.77 | 1.83 | 1.79 |
| U0867 | 3.20 | 2.90 | 3.19 | 2.64 | 2.38 | 3.00 | 3.10 | 2.85 | 2.83 |
| U0875 | 2.20 | 2.00 | 2.16 | 1.80 | 1.60 | 2.00 | 2.02 | 1.81 | 1.71 |
| U1198 | 2.20 | 2.10 | 2.17 | 2.07 | 1.91 | 2.00 | 1.98 | 2.22 | 2.22 |
| U1199 | 2.80 | 3.30 | 3.57 | 2.79 | 2.76 | 3.20 | 3.21 | 2.99 | 3.28 |
| U1201 | 1.90 | 1.90 | 1.95 | 1.76 | 1.62 | 1.80 | 1.84 | 1.82 | 1.80 |
| U1202 | 1.30 | 1.30 | 1.35 | 1.31 | 1.16 | 1.40 | 1.39 | 1.35 | 1.20 |
| U1205 | 1.60 | 1.80 | 1.90 | 1.71 | 1.53 | 1.90 | 1.90 | 1.80 | 1.67 |
| U1207 | 1.90 | 1.90 | 1.96 | 1.68 | 1.49 | 1.90 | 1.87 | 1.78 | 1.61 |
| U1218 | 3.00 | 2.60 | 2.86 | 2.57 | 2.56 | 2.80 | 3.07 | 2.90 | 3.08 |
| U1225 | 2.20 | 2.30 | 2.34 | 2.01 | 1.83 | 2.60 | 2.40 | 2.21 | 2.16 |
| U1230 | 1.30 | 1.40 | 1.45 | 1.47 | 1.32 | 1.40 | 1.45 | 1.50 | 1.45 |
| U1575 | 1.40 | 1.30 | 1.30 | 1.53 | 1.41 | 1.40 | 1.44 | 1.49 | 1.35 |
| U1576 | 2.20 | 2.10 | 2.11 | 2.10 | 2.02 | 2.30 | 2.32 | 2.19 | 2.17 |

TABLE 2-continued

| ID | AINR | GINR | GatfA | GatfZ | GatfT | MINR | MatfA | MatfZ | MatfT |
|---|---|---|---|---|---|---|---|---|---|
| U1579 | 1.50 | 1.70 | 1.72 | 1.64 | 1.49 | 1.80 | 1.81 | 1.61 | 1.44 |
| U1581 | 1.70 | 1.70 | 1.74 | 1.85 | 1.81 | 1.70 | 1.77 | 1.74 | 1.73 |
| U1599 | 2.00 | 1.70 | 1.78 | 2.01 | 1.96 | 2.00 | 2.14 | 2.04 | 1.93 |
| U1600 | 3.50 | 3.30 | 3.39 | 3.58 | 3.63 | 3.90 | 4.21 | 3.37 | 3.64 |
| U1649 | 0.90 | 0.80 | 0.80 | 0.94 | 0.76 | 0.90 | 0.89 | 0.89 | 0.74 |
| U3050 | 2.70 | 2.80 | 3.08 | 2.34 | 2.17 | 2.30 | 2.34 | 2.05 | 2.02 |
| U3077 | 1.30 | 1.40 | 1.44 | 1.34 | 1.17 | 1.30 | 1.28 | 1.31 | 1.16 |
| U3083 | 1.60 | 1.60 | 1.58 | 1.47 | 1.31 | 1.60 | 1.68 | 1.48 | 1.37 |
| U3395 | 2.70 | 3.20 | 3.51 | 2.80 | 2.70 | 2.80 | 2.90 | 2.38 | 2.32 |
| U3398 | 1.50 | 1.70 | 1.77 | 1.60 | 1.47 | 1.60 | 1.65 | 1.61 | 1.47 |
| U3408 | 1.10 | 1.20 | 1.18 | 1.13 | 0.92 | 1.10 | 1.03 | 1.09 | 0.94 |
| U3453 | 1.10 | 1.20 | 1.24 | 1.19 | 0.97 | 1.20 | 1.18 | 1.11 | 1.00 |
| U3456 | 1.10 | 1.00 | 0.96 | 0.99 | 0.81 | 1.00 | 0.98 | 1.04 | 0.90 |
| U3457 | 2.20 | 2.30 | 2.38 | 2.03 | 1.94 | 2.10 | 2.28 | 1.94 | 1.86 |
| U3459 | 2.90 | 2.60 | 2.81 | 2.40 | 2.22 | 2.40 | 2.53 | 2.11 | 2.04 |
| U3724 | 2.70 | 2.40 | 2.47 | 2.16 | 1.95 | 2.60 | 2.72 | 2.31 | 2.25 |
| U4471 | 1.50 | 1.60 | 1.67 | 1.63 | 1.43 | 1.70 | 1.71 | 1.71 | 1.62 |
| U4737 | 2.90 | 2.60 | 2.79 | 2.42 | 2.26 | 2.70 | 2.87 | 2.51 | 2.42 |
| U4752 | 1.40 | 1.50 | 1.55 | 1.47 | 1.26 | 1.50 | 1.48 | 1.46 | 1.33 |
| U4757 | 2.00 | 2.10 | 2.09 | 1.95 | 1.77 | 2.00 | 2.02 | 2.00 | 1.92 |
| U4767 | 2.60 | 2.40 | 2.52 | 2.16 | 1.95 | 2.60 | 2.56 | 2.33 | 2.27 |
| U4772 | 2.50 | 2.70 | 2.78 | 2.59 | 2.58 | 2.80 | 2.84 | 2.55 | 2.56 |
| U4801 | 1.30 | 1.40 | 1.41 | 1.33 | 1.13 | 1.50 | 1.49 | 1.41 | 1.22 |
| U5133 | 0.90 | 0.90 | 0.91 | 0.92 | 0.74 | 1.00 | 0.97 | 0.97 | 0.78 |
| U5158 | 5.50 | 5.10 | 5.90 | 5.34 | 5.64 | 6.00 | 6.57 | 6.50 | 7.00 |
| U5169 | 2.60 | 2.90 | 3.16 | 3.14 | 3.09 | 3.20 | 3.35 | 3.35 | 3.67 |
| U5173 | 1.10 | 1.20 | 1.17 | 1.19 | 1.02 | 1.20 | 1.21 | 1.16 | 1.03 |
| U5175 | 1.70 | 1.80 | 1.86 | 1.85 | 1.67 | 1.90 | 1.92 | 1.82 | 1.70 |
| U5178 | 2.30 | 2.20 | 2.28 | 2.02 | 1.79 | 2.60 | 2.85 | 2.03 | 2.01 |
| U5183 | 2.90 | 2.60 | 2.83 | 2.43 | 2.23 | 3.60 | 3.86 | 2.88 | 3.01 |
| U5190 | 2.80 | 2.70 | 2.82 | 2.85 | 2.70 | 3.20 | 3.36 | 3.00 | 3.15 |
| U5193 | 3.10 | 3.00 | 3.13 | 2.93 | 2.81 | 3.60 | 3.73 | 3.33 | 3.30 |
| U5565 | 2.70 | 3.20 | 3.34 | 3.16 | 3.04 | 3.50 | 3.48 | 3.31 | 3.50 |
| U5589 | 1.60 | 1.80 | 1.86 | 1.69 | 1.52 | 1.90 | 1.96 | 1.64 | 1.44 |
| U5591 | 2.00 | 2.20 | 2.33 | 2.16 | 1.98 | 2.30 | 2.28 | 2.19 | 2.24 |
| U5592 | 1.10 | 1.20 | 1.23 | 1.26 | 1.09 | 1.40 | 1.35 | 1.49 | 1.37 |
| U5593 | 1.70 | 1.80 | 1.89 | 1.76 | 1.55 | 1.80 | 1.85 | 1.76 | 1.70 |
| U5594 | 2.30 | 2.60 | 2.79 | 2.84 | 2:81 | 2.80 | 2.84 | 2.85 | 2.96 |
| U5597 | 3.30 | 3.30 | 3.64 | 3.25 | 2.96 | 4.10 | 4.03 | 3.85 | 4.08 |
| U5992 | 1.40 | 1.40 | 1.42 | 1.45 | 1.29 | 1.30 | 1.37 | 1.37 | 1.30 |
| U5993 | 1.00 | 0.90 | 0.94 | 1.03 | 0.84 | 1.00 | 0.98 | 1.03 | 0.84 |
| U6017 | 1.00 | 0.90 | 0.95 | 0.99 | 0.77 | 0.90 | 0.89 | 0.97 | 0.79 |
| U6047 | 2.30 | 2.30 | 2.36 | 2.17 | 1.97 | 2.20 | 2.28 | 2.23 | 2.22 |
| U6056 | 1.00 | 1.00 | 1.01 | 1.03 | 0.87 | 1.00 | 1.01 | 1.02 | 0.85 |
| U6060 | 1.90 | 2.10 | 2.17 | 2.10 | 1.94 | 2.30 | 2.00 | 2.16 | 2.12 |
| U6065 | 3.10 | 2.80 | 2.93 | 2.77 | 2.60 | 3.00 | 3.13 | 2.74 | 2.76 |
| U6928 | 1.20 | 1.20 | 1.17 | 1.34 | 1.17 | 1.20 | 1.24 | 1.22 | 1.05 |
| U6929 | 1.20 | 1.20 | 1.20 | 1.23 | 1.06 | 1.20 | 1.19 | 1.15 | 0.98 |
| U6936 | 2.40 | 2.50 | 2.45 | 3.02 | 3.15 | 2.60 | 2.61 | 2.51 | 2.60 |
| U6938 | 2.10 | 2.10 | 2.12 | 2.30 | 2.22 | 2.30 | 2.26 | 2.25 | 2.21 |
| U6951 | 1.50 | 1.50 | 1.51 | 1.59 | 1.42 | 1.60 | 1.66 | 1.49 | 1.36 |
| U6972 | 2.40 | 2.40 | 2.47 | 2.57 | 2.49 | 2.80 | 2.84 | 2.54 | 2.51 |
| U6977 | 1.30 | 1.30 | 1.34 | 1.35 | 1.19 | 1.30 | 1.37 | 1.23 | 1.08 |
| U6987 | 5.10 | 4.50 | 4.43 | 5.29 | 5.42 | 5.70 | 5.44 | 6.16 | 6.82 |
| U7316 | 1.20 | 1.10 | 1.15 | 1.28 | 1.14 | 1.30 | 1.28 | 1.26 | 1.11 |
| U7317 | 2.00 | 1.60 | 1.68 | 1.66 | 1.56 | 1.90 | 1.90 | 1.68 | 1.56 |
| U7318 | 2.80 | 2.70 | 2.86 | 2.71 | 2.57 | 3.30 | 3.40 | 2.70 | 2.72 |
| U7320 | 2.00 | 1.90 | 1.92 | 2.17 | 2.13 | 2.00 | 2.06 | 2.12 | 2.13 |
| U7321 | 1.50 | 1.40 | 1.38 | 1.59 | 1.50 | 1.60 | 1.60 | 1.61 | 1.51 |
| U7322 | 1.80 | 1.70 | 1.72 | 1.63 | 1.46 | 1.70 | 1.76 | 1.55 | 1.42 |
| U7324 | 1.30 | 1.20 | 1.25 | 1.33 | 1.17 | 1.40 | 1.40 | 1.30 | 1.13 |
| U7440 | 2.60 | 3.00 | 2.98 | 2.90 | 2.89 | 3.00 | 3.01 | 3.05 | 3.37 |
| U7443 | 2.00 | 2.00 | 2.03 | 1.87 | 1.73 | 2.10 | 2.17 | 1.90 | 1.79 |
| U7458 | 1.40 | 1.40 | 1.43 | 1.38 | 1.20 | 1.40 | 1.40 | 1.40 | 1.26 |
| U7465 | 9.70 | 7.40 | 8.12 | 6.47 | 7.80 | 7.10 | 7.54 | 7.06 | 7.63 |
| U7469 | 1.10 | 1.10 | 1.11 | 1.11 | 0.86 | 1.20 | 1.14 | 1.10 | 0.90 |
| U7470 | 3.20 | 3.40 | 3.65 | 3.27 | 3.12 | 3.60 | 3.67 | 3.62 | 3.70 |
| U7707 | 2.20 | 2.20 | 2.27 | 2.34 | 2.28 | 2.30 | 2.29 | 2.23 | 2.22 |
| U7708 | 1.60 | 1.60 | 1.60 | 1.73 | 1.61 | 1.70 | 1.73 | 1.71 | 1.62 |
| U7710 | 2.30 | 2.50 | 2.64 | 2.71 | 2.73 | 2.70 | 2.85 | 2.75 | 2.96 |
| U7713 | 1.40 | 1.60 | 1.59 | 1.57 | 1.50 | 1.60 | 1.64 | 1.58 | 1.48 |
| U7724 | 2.40 | 2.40 | 2.47 | 2.62 | 2.65 | 2.70 | 2.73 | 2.75 | 2.84 |
| U7727 | 1.70 | 1.70 | 1.73 | 1.78 | 1.68 | 1.90 | 1.90 | 1.91 | 1.86 |
| U7738 | 2.40 | 2.30 | 2.45 | 2.27 | 2.21 | 2.40 | 2.54 | 2.29 | 2.32 |
| U7794 | 1.90 | 1.80 | 1.91 | 1.72 | 1.58 | 1.70 | 1.78 | 1.71 | 1.55 |
| U8080 | 3.10 | 3.60 | 3.63 | 3.41 | 3.54 | 3.30 | 3.33 | 3.18 | 3.34 |
| U8087 | 1.90 | 1.90 | 1.95 | 1.80 | 1.62 | 1.90 | 1.91 | 1.79 | 1.74 |
| U8092 | 1.70 | 1.70 | 1.76 | 1.67 | 1.49 | 1.90 | 1.93 | 1.67 | 1.57 |

TABLE 2-continued

| ID | AINR | GINR | GatfA | GatfZ | GatfT | MINR | MatfA | MatfZ | MatfT |
|---|---|---|---|---|---|---|---|---|---|
| U8210 | 2.60 | 2.90 | 3.04 | 2.72 | 2.63 | 2.70 | 2.77 | 2.54 | 2.56 |
| U8221 | 3.20 | 3.70 | 3.99 | 3.42 | 3.35 | 3.50 | 3.47 | 3.24 | 3.46 |
| U8555 | 2.60 | 2.40 | 2.54 | 2.56 | 2.52 | 2.90 | 3.09 | 2.57 | 2.56 |
| U8558 | 2.30 | 2.20 | 2.26 | 2.16 | 2.15 | 2.30 | 2.33 | 2.31 | 2.35 |
| U8559 | 1.60 | 1.40 | 1.45 | 1.42 | 1.24 | 1.60 | 1.65 | 1.45 | 1.28 |
| U8563 | 2.20 | 2.30 | 2.30 | 2.32 | 2.30 | 2.40 | 2.43 | 2.34 | 2.42 |
| U8570 | 1.20 | 1.20 | 1.20 | 1.34 | 1.23 | 1.20 | 1.21 | 1.35 | 1.25 |
| U8575 | 0.90 | 0.80 | 0.84 | 0.96 | 0.80 | 0.90 | 0.89 | 0.95 | 0.78 |
| U9031 | 2.10 | 2.40 | 2.33 | 2.42 | 2.42 | 2.60 | 2.38 | 2.34 | 2.35 |
| U9032 | 1.70 | 1.70 | 1.75 | 1.78 | 1.58 | 1.90 | 1.93 | 1.68 | 1.53 |
| U9034 | 3.00 | 2.90 | 2.82 | 3.79 | 3.97 | 3.40 | 3.37 | 3.49 | 3.80 |
| U9039 | 2.70 | 3.00 | 3.17 | 2.99 | 3.03 | 3.20 | 3.20 | 3.12 | 3.27 |
| U9040 | 1.40 | 1.40 | 1.44 | 1.36 | 1.20 | 1.40 | 1.39 | 1.33 | 1.15 |
| U9049 | 3.50 | 3.30 | 3.46 | 3.33 | 3.45 | 3.60 | 3.77 | 3.33 | 3.72 |
| U9055 | 2.40 | 2.10 | 2.14 | 2.15 | 2.04 | 2.40 | 2.39 | 2.15 | 2.13 |

A statistical comparison of the above data from Table 2 is presented below in Tables 4 and 5. The value AINR in Table 2 represents the INR value obtained pursuant to the World Health Organization (WHO), using expressions (A) and (B) above. GINR and MINR correspond to INR values used to determine the comparison data set forth in Tables 4 and 5.

The determination of the new anticoagulant therapy factor (ATFt) may be carried out with a computer. According to one example, the gathering, storing, and manipulation of the data generally illustrated in FIG. 4, may be accomplished by computer 30 of FIG. 1 that receives digital voltage values converted, by the A/D converter 26, from analog voltage quantities of the photocell 10 detection means.

In accordance with one embodiment, the IBM-compatible computer 30 of FIG. 1 stores and manipulates these digital values corresponding to related data of FIG. 4 and may be programmed as follows:

(a) a sample of blood where the plasma is available, such as, for example, a sample of citrated blood, is obtained and placed in an appropriate container, the computer 30, as well as the recorder 28, sequentially records voltage values for a few seconds before injection of thromboplastin. As previously discussed, thromboplastin (tissue factor) is one of the factors in the human body that causes blood to clot. Prothrombin is another. Fibrinogen is yet another. Before injection of the thromboplastin, the output from the A/D converter 26 is relatively constant. When thromboplastin is injected into the plasma sample in the container, a significant and abrupt change occurs in the recorded voltage values of both the computer 30 and the recorder 28. This abrupt change is recognized by both the recorder 28 and, more importantly, by the computer 30 which uses such recognition to establish $T_o$. The computer 30 may be programmed so as to correlate the digital quantities of the A/D converter 26 to the analog output of the detector means photocell 10 which, in turn, is directly correlatable to the fibrinogen (FBG) concentration g/l of the sample of blood discussed with reference to FIG. 3;

(b) the computer 30 may be programmed to look for a digital quantity representative of a critical quantity $c_1$, and when such occurs, record its instant time $T_1$. (The time span between $T_o$ and $T_1$ is the prothrombin time (PT), and has an normal duration of about 12 seconds, but may be greater than 30 seconds);

(c) following the detection of the quantity $c_1$, the computer 30 may be programmed to detect for the acceleration of fibrinogen (FBG) to fibrin conversion. The computer 30 is programmed to detect the maximum acceleration quantity $c_{MAP}$ or $c_{T2}$ as illustrated in FIG. 3, and its corresponding time of occurrence $t_{MAP}$, which is $T_2$ in FIG. 3.

(d) the computer detects a quantity $c_{EOT}$ occurring at time $t_{EOT}$. Typically, it is important that the rate of fibrin formation increase for at least 1.5 seconds following the occurrence of ($T_1$); the computer determines a theoretical end of test (TEOT) based on the determination of the zero order kinetic rate. The computer may be programmed to determine the zero order rate, which is expressed as a Line (L) in FIG. 4. The TEOT may be determined by the corresponding time value (TEOT) along the line L which corresponds with the quantity $c_{EOT}$ (i.e., that quantity corresponding to the time, $T_3$).

(e) following the detection of the maximum acceleration quantity $c_{T2}$ (also representing $c_{MAP}$) and the time $T_2$ (also representing $t_{MAP}$) both of which define the maximum acceleration point (MAP), and the TEOT, the computer is programmed to determine a new fibrinogen transformation rate (nFTR) covering a predetermined range starting prior to the maximum acceleration point (MAP) and ending after the maximum acceleration point (MAP). The elapsed time from $T_0$ to $T_2$ (which is $t_{MAP}$) is the time to maximum acceleration (TMA), shown in FIG. 4, and is represented by TX (i.e., time to MAP);

The new fibrinogen transformation rate (nFTR) has an upwardly rising (increasing quantities) slope prior to the maximum acceleration point (MAP) and, conversely, has a downwardly falling (decreasing quantities) slope after the maximum acceleration point (MAP).

The computer 30 is programmed to ascertain the value for the time to start ($T_2S$) which corresponds with the time at which the simulated zero order kinetic rate begins.

(f) following the detection of the acceleration of fibrinogen conversion to detect the start time $T_2S$, the computer 30 is programmed to detect for a deceleration of the fibrinogen conversion, wherein the fibrinogen concentration decreases from a predetermined quantity $c_{MAP}$ to a predetermined quantity $c_{EOT}$ having a value which is about equal but less than the first quantity $c_1$. The computer is programmed to ascertain a first delta (IUTz), by determining the difference between the quantity $c_{T2S}$ and the quantity $c_{EOT}$; and a second delta (IUXz) by determining the difference between the quantity $c_{T2S}$ and the quantity $c_{2(or\ CMAP)}$; the computer also determines the value ZTM by determining the difference between the time $T_2$ (which is Tmap) and the time $T_2S$;

(g) the computer 30 manipulates the collected data of (a); (b); (c); (d), (e) and (f) above, to determine the new fibrinogen transfer rate (nFTR). The nFTR may be arrived at based on the principle that if a required amount (e.g., 0.05 g/l) of fibrinogen concentration $c_1$ is first necessary to detect a clot point $(t_1)$; then when the fibrinogen concentration $(c_{EOT})$ becomes less than the required amount $c_1$, which occurs at time $(t_{EOT})$, the fibrinogen end point has been reached. More particularly, the required fibrinogen concentration $c_1$ is the starting point of fibrinogen conversion of the clotting process and the less than required fibrinogen concentration $c_{EOT}$ is the end point of the fibrinogen conversion of the clotting process.

(h) the duration of the fibrinogen conversion of the clotting process of the present invention is defined by the zero order time period between TEOT and $T_2S$ and is generally indicated in FIG. 3 as IUTz. The difference between the corresponding concentrations $c_{T2S}$ and cT2 is used to define a delta IUXz. The computer now has the information needed to determine the TEOT, which is expressed by the following formula:

$$TEOT = ZTM/IUXz * IUTz \quad (5)$$

The value TEOT may be assigned VALUE 1;

(i) data collected is manipulated by the computer 30 to calculate a second value, VALUE 2, using $T_2S$ and a multiplier M (which in this example, in expression 7 below, is a fraction). The computer may be programmed to use as a multiplier a value based on the natural log base "e" (which is 2.71828), scaled by a scaling value. Here, the scaling value is 100, and the multiplier may be expressed as follows:

$$M = 100e \quad (9)$$

VALUE 2 is determined using the information which the computer has ascertained and stored, by the following expression:

$$VALUE\ 2 = T2S/100e \quad (7)$$

The data may be ascertained and stored in the computer for reference.

(j) the computer 30 now has the information needed to determine the nATFt, which typically is expressed as:

$$nATFt = VALUE\ 1 * VALUE\ 2 \quad (4)$$

The computer 30 may be used to manipulate and derive the quantities of expression (4) to determine a new anticoagulant therapy factor nATFt utilizing known programming routines and techniques. The data collected by a computer 30 may be used to manipulate and derive the new anticoagulant therapy factor (nATFt) of expression (4). Similarly, one skilled in the art, using known mathematical techniques may derive the theoretical end of test TEOT of expression (5) and the second value VALUE 2 of expression (7) which, in turn, are used to determine the new anticoagulant therapy (nATFt) of expression (4). In the nATFt determination, the determination is based on the patient's own sample, and does not rely on the determination of normal prothrombin times for the reagent used (e.g., thromboplastin, innovin or the like). With the nATFt, no longer does the accuracy of the quantities determined depend, in whole or part, on the number of specimens used, that is, the number of stable (or presumed stable) patients.

The new anticoagulation therapy factor (nATFt) does not require an ISI value, as was previously used to determine anticoagulation therapy factors. The new anticoagulation therapy factor (nATFt) uses for its ascertainment the values extracted from the clotting curve (see FIG. 4), in particular $T_2S$, Tmap, TEOT, $c_{T2S}$, cmap and ceot. In determining the new anticoagulant therapy factor (nATFt), the ISI is not required, nor is the MNPT, or the need to obtain and calculate the prothrombin times (PT's) for 20 presumed normal patients. In carrying out coagulation studies, the new anticoagulant therapy factor (nATFt) may replace INR in anticoagulant therapy management. In addition, using the sample from the patient, the computer 30 has knowledge of the values obtained for the fibrinogen reaction, to ascertain the (nATFt).

It should now be appreciated that the present invention provides an apparatus and method for obtaining a new anticoagulant therapy factor (nATF) without encountering the complications involved with obtaining the prior art quantities International Normalized Ratio (INR) and International Sensitivity Index (ISI).

The new anticoagulant therapy factor (nATFt) preferably is a replacement for the International Normalized Ratio (INR). Existing medical literature, instrumentation, and methodologies are closely linked to the International Normalized Ratio (INR). The nATFt was compared for correlation with the INR by comparative testing, to INR quantities, even with the understanding that the INR determination may have an error of about +/−15%, at a 95% confidence interval, which needs to be taken into account to explain certain inconsistencies.

The hereinbefore description of the new anticoagulant therapy factor (nATFt) does correlate at least as well as, and preferably better than, studies carried out using the International Normalized Ratio (INR). For some comparisons, see the tables below, and in particular Table 4 and Table 5.

Table 3 (Part A) and Table 3 (Part B) provide corresponding data for a coagulation study. In Table 3 (Part A and B), the following references are used:

| Column | Label | Definition |
|---|---|---|
| A | ID | Sample ID |
| B | OD@$T_2$S | OD at the start of Zero Order Kinetic |
| C | OD@Map | OD at the Maximum Acceleration Point (MAP) |
| D | OD@Eot | OD at the END OF TEST (Eot) |
| E | $\Delta T_2$SMap | Delta of Column B and C creating the IUXz |
| F | $\Delta T_2$SEot | Delta of Column B and D creating the IUTz |
| G | FTR od | Ratio of Column E divided by F |
|   |   | The FTR od is subtracted from 2 creating the Exponent that replaces the ISI |
| H | Time@$T_2$S | Time at the start of Zero Order Kinetics |
| I | Time@Map | Time at the Maximum Acceleration Point (MAP) |
| J | Time@TEot | Time at the Theoretical End of Test (TEOT) |
| K | $\Delta T_2$SMap | Delta of Column H and I creating the IUXz (and ZTM) |
| L | $\Delta T_2$STEot | Delta of Column H and J creating the IUTz |
| M | FTR Time | Ration of Column K divided by L |

TABLE 3

(Part A)

| ID | OD@T2S | OD@Map | OD@Eot | ΔT2SMap | ΔT2SEot |
|---|---|---|---|---|---|
| A001 | 3719 | 3707 | 3664 | 12 | 55 |
| A002 | 3713 | 3704 | 3686 | 9 | 27 |
| A003 | 3729 | 3720 | 3705 | 9 | 24 |
| A004 | 3708 | 3696 | 3663 | 12 | 45 |
| A005 | 3727 | 3715 | 3700 | 12 | 27 |
| A007 | 3725 | 3718 | 3698 | 7 | 27 |
| A008 | 3714 | 3693 | 3646 | 21 | 68 |
| A009 | 3727 | 3716 | 3697 | 11 | 30 |
| A010 | 3727 | 3714 | 3701 | 13 | 26 |
| A011 | 3690 | 3676 | 3647 | 14 | 43 |
| A012 | 3728 | 3716 | 3695 | 12 | 33 |

TABLE 3-continued (Part A)

| ID | OD@T2S | OD@Map | OD@Eot | ΔT2SMap | ΔT2SEot |
|---|---|---|---|---|---|
| A013 | 3715 | 3690 | 3641 | 25 | 74 |
| A014 | 3717 | 3708 | 3694 | 9 | 23 |
| A015 | 3726 | 3718 | 3706 | 8 | 20 |
| A016 | 3722 | 3715 | 3678 | 7 | 44 |
| A017 | 3720 | 3707 | 3681 | 13 | 39 |
| A018 | 3723 | 3709 | 3697 | 14 | 26 |
| A019 | 3716 | 3695 | 3653 | 21 | 63 |
| A020 | 3727 | 3716 | 3698 | 11 | 29 |
| A021 | 3727 | 3720 | 3694 | 7 | 33 |
| A022 | 3717 | 3700 | 3667 | 17 | 50 |
| A023 | 3719 | 3706 | 3663 | 13 | 56 |
| A024 | 3717 | 3702 | 3661 | 15 | 56 |
| A025 | 3731 | 3727 | 3716 | 4 | 15 |
| A026 | 3717 | 3705 | 3673 | 12 | 44 |
| A027 | 3714 | 3698 | 3667 | 16 | 47 |
| A028 | 3713 | 3696 | 3651 | 17 | 62 |
| A029 | 3712 | 3691 | 3647 | 21 | 65 |
| A030 | 3716 | 3695 | 3635 | 21 | 81 |
| A031 | 3715 | 3704 | 3687 | 11 | 28 |
| A032 | 3716 | 3710 | 3675 | 6 | 41 |
| A033 | 3718 | 3704 | 3671 | 14 | 47 |
| A034 | 3721 | 3705 | 3674 | 16 | 47 |
| A035 | 3723 | 3715 | 3699 | 8 | 24 |
| A036 | 3722 | 3710 | 3681 | 12 | 41 |
| A037 | 3715 | 3700 | 3669 | 15 | 46 |
| A038 | 3722 | 3707 | 3686 | 15 | 36 |
| A039 | 3721 | 3712 | 3698 | 9 | 23 |
| A040 | 3720 | 3706 | 3664 | 14 | 56 |
| A041 | 3711 | 3695 | 3638 | 16 | 73 |
| A042 | 3722 | 3709 | 3687 | 13 | 35 |
| A044 | 3723 | 3709 | 3683 | 14 | 40 |
| A045 | 3712 | 3697 | 3647 | 15 | 65 |
| A047 | 3716 | 3697 | 3668 | 19 | 48 |
| A048 | 3720 | 3708 | 3682 | 12 | 38 |
| A049 | 3725 | 3711 | 3690 | 14 | 35 |
| A050 | 3724 | 3712 | 3685 | 12 | 39 |
| A051 | 3705 | 3688 | 3634 | 17 | 71 |
| A052 | 3725 | 3714 | 3687 | 11 | 38 |
| A053 | 3724 | 3717 | 3696 | 7 | 28 |
| A054 | 3715 | 3701 | 3679 | 14 | 36 |
| A055 | 3718 | 3684 | 3627 | 34 | 91 |
| A056 | 3710 | 3689 | 3624 | 21 | 86 |
| A057 | 3709 | 3701 | 3683 | 8 | 26 |
| A058 | 3725 | 3710 | 3669 | 15 | 56 |
| A059 | 3722 | 3712 | 3696 | 10 | 26 |
| A060 | 3719 | 3712 | 3698 | 7 | 21 |
| A061 | 3720 | 3708 | 3680 | 12 | 40 |
| A062 | 3719 | 3701 | 3651 | 18 | 68 |
| A063 | 3728 | 3715 | 3697 | 13 | 31 |
| A064 | 3718 | 3707 | 3685 | 11 | 33 |
| A065 | 3721 | 3704 | 3680 | 17 | 41 |
| A066 | 3727 | 3717 | 3707 | 10 | 20 |
| A067 | 3708 | 3689 | 3641 | 19 | 67 |
| A068 | 3726 | 3712 | 3686 | 14 | 40 |
| A069 | 3719 | 3715 | 3695 | 4 | 24 |
| A070 | 3716 | 3705 | 3671 | 11 | 45 |
| A071 | 3714 | 3696 | 3660 | 18 | 54 |
| A072 | 3713 | 3693 | 3646 | 20 | 67 |
| A073 | 3707 | 3686 | 3639 | 21 | 68 |
| A074 | 3699 | 3684 | 3665 | 15 | 34 |
| A075 | 3734 | 3730 | 3726 | 4 | 8 |
| A076 | 3719 | 3704 | 3665 | 15 | 54 |
| A077 | 3718 | 3694 | 3634 | 24 | 84 |
| A078 | 3723 | 3707 | 3684 | 16 | 39 |
| A080 | 3729 | 3712 | 3637 | 17 | 92 |
| A081 | 3710 | 3694 | 3626 | 16 | 84 |
| A082 | 3716 | 3703 | 3654 | 13 | 62 |
| A083 | 3720 | 3710 | 3686 | 10 | 34 |
| A084 | 3731 | 3721 | 3667 | 10 | 64 |
| A085 | 3727 | 3704 | 3675 | 23 | 52 |
| A086 | 3717 | 3699 | 3650 | 18 | 67 |
| A087 | 3715 | 3694 | 3654 | 21 | 61 |
| A088 | 3704 | 3681 | 3630 | 23 | 74 |
| A089 | 3723 | 3714 | 3687 | 9 | 36 |
| A090 | 3714 | 3685 | 3588 | 29 | 126 |
| A091 | 3724 | 3710 | 3659 | 14 | 65 |
| A092 | 3696 | 3657 | 3582 | 39 | 114 |
| A093 | 3730 | 3716 | 3693 | 14 | 37 |
| A094 | 3720 | 3708 | 3676 | 12 | 44 |
| A095 | 3710 | 3689 | 3638 | 21 | 72 |
| A096 | 3725 | 3717 | 3700 | 8 | 25 |
| A097 | 3721 | 3713 | 3692 | 8 | 29 |
| A098 | 3716 | 3696 | 3659 | 20 | 57 |
| A099 | 3720 | 3712 | 3685 | 8 | 35 |
| A100 | 3709 | 3685 | 3625 | 24 | 84 |
| A101 | 3727 | 3715 | 3690 | 12 | 37 |
| A102 | 3722 | 3708 | 3661 | 14 | 61 |
| A103 | 3714 | 3693 | 3640 | 21 | 74 |
| A104 | 3719 | 3705 | 3682 | 14 | 37 |
| A105 | 3725 | 3706 | 3660 | 19 | 65 |
| A107 | 3720 | 3707 | 3660 | 13 | 60 |
| A108 | 3731 | 3723 | 3709 | 8 | 22 |
| A109 | 3727 | 3711 | 3689 | 16 | 38 |
| A110 | 3719 | 3693 | 3635 | 26 | 84 |
| A111 | 3723 | 3701 | 3667 | 22 | 56 |
| A112 | 3714 | 3695 | 3614 | 19 | 100 |
| A113 | 3717 | 3702 | 3664 | 15 | 53 |
| A114 | 3711 | 3687 | 3655 | 24 | 56 |
| A115 | 3716 | 3697 | 3652 | 19 | 64 |
| A116 | 3726 | 3717 | 3698 | 9 | 28 |
| A117 | 3710 | 3688 | 3630 | 22 | 80 |
| A118 | 3729 | 3721 | 3699 | 8 | 30 |
| A119 | 3729 | 3716 | 3679 | 13 | 50 |
| A120 | 3722 | 3713 | 3688 | 9 | 34 |
| A121 | 3730 | 3722 | 3704 | 8 | 26 |
| A122 | 3713 | 3688 | 3650 | 25 | 63 |
| A123 | 3729 | 3721 | 3704 | 8 | 25 |
| A124 | 3721 | 3712 | 3696 | 9 | 25 |
| A125 | 3683 | 3668 | 3600 | 15 | 83 |
| A126 | 3736 | 3723 | 3714 | 13 | 22 |
| A127 | 3715 | 3703 | 3640 | 12 | 75 |
| A128 | 3723 | 3714 | 3682 | 9 | 41 |
| A129 | 3728 | 3715 | 3677 | 13 | 51 |
| A130 | 3715 | 3700 | 3656 | 15 | 59 |
| A131 | 3723 | 3711 | 3690 | 12 | 33 |
| A132 | 3720 | 3700 | 3665 | 20 | 55 |
| A133 | 3728 | 3706 | 3673 | 22 | 55 |
| A134 | 3725 | 3696 | 3667 | 29 | 58 |
| A135 | 3717 | 3703 | 3676 | 14 | 41 |
| A136 | 3725 | 3712 | 3659 | 13 | 66 |
| A137 | 3712 | 3691 | 3662 | 21 | 50 |
| A138 | 3714 | 3691 | 3641 | 23 | 73 |
| A139 | 3717 | 3700 | 3642 | 17 | 75 |
| A140 | 3710 | 3690 | 3642 | 20 | 68 |
| A141 | 3715 | 3698 | 3661 | 17 | 54 |
| A142 | 3729 | 3719 | 3706 | 10 | 23 |
| A143 | 3726 | 3709 | 3693 | 17 | 33 |
| A144 | 3709 | 3693 | 3641 | 16 | 68 |
| A145 | 3704 | 3688 | 3639 | 16 | 65 |
| A146 | 3718 | 3706 | 3664 | 12 | 54 |
| A147 | 3713 | 3698 | 3661 | 15 | 52 |
| A148 | 3714 | 3701 | 3646 | 13 | 68 |
| A149 | 3711 | 3692 | 3653 | 19 | 58 |
| A150 | 3701 | 3678 | 3608 | 23 | 93 |
| A151 | 3701 | 3668 | 3587 | 33 | 114 |
| A152 | 3717 | 3706 | 3683 | 11 | 34 |
| A153 | 3691 | 3669 | 3596 | 22 | 95 |
| A154 | 3706 | 3690 | 3645 | 16 | 61 |
| A155 | 3724 | 3703 | 3667 | 21 | 57 |
| A156 | 3717 | 3711 | 3688 | 6 | 29 |
| A157 | 3717 | 3702 | 3678 | 15 | 39 |
| A158 | 3723 | 3715 | 3689 | 8 | 34 |
| A159 | 3714 | 3696 | 3652 | 18 | 62 |
| A160 | 3717 | 3690 | 3655 | 27 | 62 |
| A161 | 3720 | 3713 | 3676 | 7 | 44 |
| A162 | 3722 | 3706 | 3653 | 16 | 69 |
| A163 | 3725 | 3715 | 3683 | 10 | 42 |
| A164 | 3721 | 3712 | 3685 | 9 | 36 |
| A165 | 3707 | 3693 | 3636 | 14 | 71 |
| A166 | 3704 | 3683 | 3631 | 21 | 73 |
| A167 | 3718 | 3712 | 3690 | 6 | 28 |
| A168 | 3722 | 3700 | 3669 | 22 | 53 |

TABLE 3-continued (Part A)

| ID | OD@T2S | OD@Map | OD@Eot | ΔT2SMap | ΔT2SEot |
|---|---|---|---|---|---|
| A169 | 3705 | 3694 | 3624 | 11 | 81 |
| A170 | 3717 | 3704 | 3680 | 13 | 37 |
| A171 | 3721 | 3699 | 3666 | 22 | 55 |
| A172 | 3726 | 3719 | 3691 | 7 | 35 |
| A173 | 3718 | 3708 | 3680 | 10 | 38 |
| A174 | 3707 | 3692 | 3648 | 15 | 59 |
| A175 | 3689 | 3671 | 3642 | 18 | 47 |
| A176 | 3724 | 3711 | 3671 | 13 | 53 |
| A177 | 3721 | 3710 | 3689 | 11 | 32 |
| A178 | 3716 | 3700 | 3655 | 16 | 61 |
| A179 | 3717 | 3707 | 3672 | 10 | 45 |
| A180 | 3718 | 3706 | 3686 | 12 | 32 |
| A181 | 3722 | 3703 | 3676 | 19 | 46 |
| A182 | 3716 | 3706 | 3667 | 10 | 49 |
| A183 | 3711 | 3703 | 3689 | 8 | 22 |
| A184 | 3717 | 3705 | 3661 | 12 | 56 |
| A185 | 3711 | 3694 | 3639 | 17 | 72 |
| A186 | 3721 | 3675 | 3620 | 46 | 101 |
| A187 | 3715 | 3704 | 3668 | 11 | 47 |
| A188 | 3717 | 3703 | 3672 | 14 | 45 |
| A189 | 3709 | 3689 | 3658 | 20 | 51 |
| A190 | 3718 | 3709 | 3688 | 9 | 30 |
| A191 | 3725 | 3717 | 3696 | 8 | 29 |
| A192 | 3722 | 3714 | 3691 | 8 | 31 |
| A193 | 3727 | 3718 | 3685 | 9 | 42 |
| A194 | 3720 | 3710 | 3688 | 10 | 32 |
| A195 | 3691 | 3667 | 3589 | 24 | 102 |
| A196 | 3718 | 3707 | 3673 | 11 | 45 |
| A197 | 3706 | 3692 | 3637 | 14 | 69 |
| A198 | 3717 | 3707 | 3692 | 10 | 25 |
| A199 | 3720 | 3705 | 3684 | 15 | 36 |
| A200 | 3718 | 3709 | 3686 | 9 | 32 |
| A201 | 3725 | 3713 | 3681 | 12 | 44 |
| A202 | 3723 | 3713 | 3694 | 10 | 29 |
| A203 | 3715 | 3704 | 3670 | 11 | 45 |
| A204 | 3723 | 3713 | 3697 | 10 | 26 |
| A205 | 3717 | 3706 | 3674 | 11 | 43 |
| A207 | 3710 | 3702 | 3668 | 8 | 42 |
| A208 | 3722 | 3708 | 3680 | 14 | 42 |
| A209 | 3725 | 3709 | 3682 | 16 | 43 |
| A210 | 3724 | 3714 | 3688 | 10 | 36 |
| A211 | 3712 | 3694 | 3637 | 18 | 75 |
| A212 | 3727 | 3711 | 3689 | 16 | 38 |
| A213 | 3724 | 3705 | 3652 | 19 | 72 |
| A214 | 3727 | 3715 | 3687 | 12 | 40 |
| A215 | 3715 | 3703 | 3668 | 12 | 47 |
| A216 | 3722 | 3707 | 3667 | 15 | 55 |
| A217 | 3716 | 3695 | 3630 | 21 | 86 |
| A218 | 3699 | 3665 | 3583 | 34 | 116 |
| A219 | 3727 | 3716 | 3699 | 11 | 28 |
| A220 | 3717 | 3704 | 3674 | 13 | 43 |
| A222 | 3713 | 3704 | 3684 | 9 | 29 |
| A223 | 3724 | 3715 | 3695 | 9 | 29 |
| A224 | 3718 | 3703 | 3676 | 15 | 42 |
| A225 | 3721 | 3707 | 3683 | 14 | 38 |

TABLE 3

(Part B)

| ID | FTR od | Time@T2S | Time@Map | Time@TEot | ΔT2SMap | ΔT2STEot | FTR time | FTR od |
|---|---|---|---|---|---|---|---|---|
| A001 | 0.218 | 2211 | 2366 | 2921 | 155 | 710 | 0.218 | 0.218 |
| A002 | 0.333 | 2279 | 2464 | 2834 | 185 | 555 | 0.333 | 0.333 |
| A003 | 0.375 | 2329 | 2523 | 2846 | 194 | 517 | 0.375 | 0.375 |
| A004 | 0.267 | 1975 | 2107 | 2470 | 132 | 495 | 0.267 | 0.267 |
| A005 | 0.444 | 2166 | 2387 | 2663 | 221 | 497 | 0.444 | 0.444 |
| A007 | 0.259 | 1838 | 1931 | 2197 | 93 | 359 | 0.259 | 0.259 |
| A008 | 0.309 | 2160 | 2369 | 2837 | 209 | 677 | 0.309 | 0.309 |
| A009 | 0.367 | 2391 | 2598 | 2956 | 207 | 565 | 0.367 | 0.367 |
| A010 | 0.500 | 1716 | 1925 | 2134 | 209 | 418 | 0.500 | 0.500 |
| A011 | 0.326 | 1788 | 1935 | 2240 | 147 | 452 | 0.326 | 0.326 |
| A012 | 0.364 | 2233 | 2428 | 2769 | 195 | 536 | 0.364 | 0.364 |
| A013 | 0.338 | 2409 | 2667 | 3173 | 258 | 764 | 0.338 | 0.338 |
| A014 | 0.391 | 1701 | 1836 | 2046 | 135 | 345 | 0.391 | 0.391 |
| A015 | 0.400 | 1715 | 1877 | 2120 | 162 | 405 | 0.400 | 0.400 |
| A016 | 0.159 | 2233 | 2336 | 2880 | 103 | 647 | 0.159 | 0.159 |
| A017 | 0.333 | 1728 | 1882 | 2190 | 154 | 462 | 0.333 | 0.333 |
| A018 | 0.538 | 1862 | 2175 | 2443 | 313 | 581 | 0.538 | 0.538 |
| A019 | 0.333 | 1756 | 1927 | 2269 | 171 | 513 | 0.333 | 0.333 |
| A020 | 0.379 | 2535 | 2761 | 3131 | 226 | 596 | 0.379 | 0.379 |
| A021 | 0.212 | 2151 | 2283 | 2773 | 132 | 622 | 0.212 | 0.212 |
| A022 | 0.340 | 1900 | 2089 | 2456 | 189 | 556 | 0.340 | 0.340 |
| A023 | 0.232 | 2251 | 2384 | 2824 | 133 | 573 | 0.232 | 0.232 |
| A024 | 0.268 | 2522 | 2676 | 3097 | 154 | 575 | 0.268 | 0.268 |
| A025 | 0.267 | 1708 | 1775 | 1959 | 67 | 251 | 0.267 | 0.267 |
| A026 | 0.273 | 1611 | 1730 | 2047 | 119 | 436 | 0.273 | 0.273 |
| A027 | 0.340 | 1537 | 1689 | 1984 | 152 | 447 | 0.340 | 0.340 |
| A028 | 0.274 | 1780 | 1927 | 2316 | 147 | 536 | 0.274 | 0.274 |
| A029 | 0.323 | 1839 | 2023 | 2409 | 184 | 570 | 0.323 | 0.323 |
| A030 | 0.259 | 2051 | 2245 | 2799 | 194 | 748 | 0.259 | 0.259 |
| A031 | 0.393 | 2107 | 2321 | 2652 | 214 | 545 | 0.393 | 0.393 |
| A032 | 0.146 | 2584 | 2678 | 3226 | 94 | 642 | 0.146 | 0.146 |
| A033 | 0.298 | 2251 | 2426 | 2839 | 175 | 588 | 0.298 | 0.298 |
| A034 | 0.340 | 1909 | 2107 | 2491 | 198 | 582 | 0.340 | 0.340 |
| A035 | 0.333 | 3037 | 3305 | 3841 | 268 | 804 | 0.333 | 0.333 |
| A036 | 0.293 | 2211 | 2417 | 2915 | 206 | 704 | 0.293 | 0.293 |
| A037 | 0.326 | 2173 | 2335 | 2670 | 162 | 497 | 0.326 | 0.326 |
| A038 | 0.417 | 1543 | 1713 | 1951 | 170 | 408 | 0.417 | 0.417 |
| A039 | 0.391 | 1572 | 1721 | 1953 | 149 | 381 | 0.391 | 0.391 |
| A040 | 0.250 | 1959 | 2119 | 2599 | 160 | 640 | 0.250 | 0.250 |

TABLE 3-continued (Part B)

| ID | FTR od | Time@T2S | Time@Map | Time@TEot | ΔT2SMap | ΔT2STEot | FTR time | FTR od |
|---|---|---|---|---|---|---|---|---|
| A041 | 0.219 | 1993 | 2144 | 2682 | 151 | 689 | 0.219 | 0.219 |
| A042 | 0.371 | 2660 | 2929 | 3384 | 269 | 724 | 0.371 | 0.371 |
| A044 | 0.350 | 2657 | 2858 | 3231 | 201 | 574 | 0.350 | 0.350 |
| A045 | 0.231 | 2175 | 2325 | 2825 | 150 | 650 | 0.231 | 0.231 |
| A047 | 0.396 | 2197 | 2458 | 2856 | 261 | 659 | 0.396 | 0.396 |
| A048 | 0.316 | 2535 | 2783 | 3320 | 248 | 785 | 0.316 | 0.316 |
| A049 | 0.400 | 2004 | 2256 | 2634 | 252 | 630 | 0.400 | 0.400 |
| A050 | 0.308 | 2193 | 2403 | 2876 | 210 | 683 | 0.308 | 0.308 |
| A051 | 0.239 | 1745 | 1867 | 2255 | 122 | 510 | 0.239 | 0.239 |
| A052 | 0.289 | 2073 | 2247 | 2674 | 174 | 601 | 0.289 | 0.289 |
| A053 | 0.250 | 2239 | 2353 | 2695 | 114 | 456 | 0.250 | 0.250 |
| A054 | 0.389 | 1816 | 2005 | 2302 | 189 | 486 | 0.389 | 0.389 |
| A055 | 0.374 | 3127 | 3668 | 4575 | 541 | 1448 | 0.374 | 0.374 |
| A056 | 0.244 | 2538 | 2728 | 3316 | 190 | 778 | 0.244 | 0.244 |
| A057 | 0.308 | 2125 | 2263 | 2574 | 138 | 449 | 0.308 | 0.308 |
| A058 | 0.268 | 4120 | 4529 | 5647 | 409 | 1527 | 0.268 | 0.268 |
| A059 | 0.385 | 2164 | 2358 | 2668 | 194 | 504 | 0.385 | 0.385 |
| A060 | 0.333 | 2325 | 2494 | 2832 | 169 | 507 | 0.333 | 0.333 |
| A061 | 0.300 | 2006 | 2205 | 2669 | 199 | 663 | 0.300 | 0.300 |
| A062 | 0.265 | 3718 | 4058 | 5002 | 340 | 1284 | 0.265 | 0.265 |
| A063 | 0.419 | 2231 | 2584 | 3073 | 353 | 842 | 0.419 | 0.419 |
| A064 | 0.333 | 1926 | 2076 | 2376 | 150 | 450 | 0.333 | 0.333 |
| A065 | 0.415 | 2225 | 2494 | 2874 | 269 | 649 | 0.415 | 0.415 |
| A066 | 0.500 | 1761 | 1968 | 2175 | 207 | 414 | 0.500 | 0.500 |
| A067 | 0.284 | 1701 | 1852 | 2233 | 151 | 532 | 0.284 | 0.284 |
| A068 | 0.350 | 1979 | 2215 | 2653 | 236 | 674 | 0.350 | 0.350 |
| A069 | 0.167 | 1935 | 1998 | 2313 | 63 | 378 | 0.167 | 0.167 |
| A070 | 0.244 | 1939 | 2063 | 2446 | 124 | 507 | 0.244 | 0.244 |
| A071 | 0.333 | 1762 | 1950 | 2326 | 188 | 564 | 0.333 | 0.333 |
| A072 | 0.299 | 1723 | 1912 | 2356 | 189 | 633 | 0.299 | 0.299 |
| A073 | 0.309 | 1614 | 1774 | 2132 | 160 | 518 | 0.309 | 0.309 |
| A074 | 0.441 | 1698 | 1884 | 2120 | 186 | 422 | 0.441 | 0.441 |
| A075 | 0.500 | 1489 | 1620 | 1751 | 131 | 262 | 0.500 | 0.500 |
| A076 | 0.278 | 1529 | 1684 | 2087 | 155 | 558 | 0.278 | 0.278 |
| A077 | 0.286 | 2845 | 3154 | 3927 | 309 | 1082 | 0.286 | 0.286 |
| A078 | 0.410 | 1867 | 2081 | 2389 | 214 | 522 | 0.410 | 0.410 |
| A080 | 0.185 | 3548 | 3924 | 5583 | 376 | 2035 | 0.185 | 0.185 |
| A081 | 0.190 | 2698 | 2853 | 3512 | 155 | 814 | 0.190 | 0.190 |
| A082 | 0.210 | 1625 | 1744 | 2193 | 119 | 568 | 0.210 | 0.210 |
| A083 | 0.294 | 1583 | 1692 | 1954 | 109 | 371 | 0.294 | 0.294 |
| A084 | 0.156 | 3394 | 3647 | 5013 | 253 | 1619 | 0.156 | 0.156 |
| A085 | 0.442 | 2416 | 2867 | 3436 | 451 | 1020 | 0.442 | 0.442 |
| A086 | 0.269 | 2111 | 2293 | 2788 | 182 | 677 | 0.269 | 0.269 |
| A087 | 0.344 | 1740 | 1924 | 2274 | 184 | 534 | 0.344 | 0.344 |
| A088 | 0.311 | 1715 | 1881 | 2249 | 166 | 534 | 0.311 | 0.311 |
| A089 | 0.250 | 1876 | 1981 | 2296 | 105 | 420 | 0.250 | 0.250 |
| A090 | 0.230 | 3411 | 3775 | 4993 | 364 | 1582 | 0.230 | 0.230 |
| A091 | 0.215 | 3897 | 4201 | 5308 | 304 | 1411 | 0.215 | 0.215 |
| A092 | 0.342 | 1906 | 2151 | 2622 | 245 | 716 | 0.342 | 0.342 |
| A093 | 0.378 | 2821 | 3197 | 3815 | 376 | 994 | 0.378 | 0.378 |
| A094 | 0.273 | 2447 | 2600 | 3008 | 153 | 561 | 0.273 | 0.273 |
| A095 | 0.292 | 1573 | 1726 | 2098 | 153 | 525 | 0.292 | 0.292 |
| A096 | 0.320 | 1784 | 1913 | 2187 | 129 | 403 | 0.320 | 0.320 |
| A097 | 0.276 | 1374 | 1479 | 1755 | 105 | 381 | 0.276 | 0.276 |
| A098 | 0.351 | 1480 | 1655 | 1979 | 175 | 499 | 0.351 | 0.351 |
| A099 | 0.229 | 1679 | 1770 | 2077 | 91 | 398 | 0.229 | 0.229 |
| A100 | 0.286 | 1538 | 1705 | 2123 | 167 | 585 | 0.286 | 0.286 |
| A101 | 0.324 | 2137 | 2344 | 2775 | 207 | 638 | 0.324 | 0.324 |
| A102 | 0.230 | 2473 | 2657 | 3275 | 184 | 802 | 0.230 | 0.230 |
| A103 | 0.284 | 1868 | 2069 | 2576 | 201 | 708 | 0.284 | 0.284 |
| A104 | 0.378 | 2344 | 2732 | 3369 | 388 | 1025 | 0.378 | 0.378 |
| A105 | 0.292 | 2427 | 2750 | 3532 | 323 | 1105 | 0.292 | 0.292 |
| A107 | 0.217 | 2140 | 2305 | 2902 | 165 | 762 | 0.217 | 0.217 |
| A108 | 0.364 | 1876 | 2034 | 2311 | 158 | 435 | 0.364 | 0.364 |
| A109 | 0.421 | 1900 | 2206 | 2627 | 306 | 727 | 0.421 | 0.421 |
| A110 | 0.310 | 2621 | 3048 | 4001 | 427 | 1380 | 0.310 | 0.310 |
| A111 | 0.393 | 2064 | 2409 | 2942 | 345 | 878 | 0.393 | 0.393 |
| A112 | 0.190 | 2000 | 2165 | 2868 | 165 | 868 | 0.190 | 0.190 |
| A113 | 0.283 | 1699 | 1872 | 2310 | 173 | 611 | 0.283 | 0.283 |
| A114 | 0.429 | 1838 | 2101 | 2452 | 263 | 614 | 0.429 | 0.429 |
| A115 | 0.297 | 2091 | 2281 | 2731 | 190 | 640 | 0.297 | 0.297 |
| A116 | 0.321 | 1571 | 1707 | 1994 | 136 | 423 | 0.321 | 0.321 |
| A117 | 0.275 | 1691 | 1874 | 2356 | 183 | 665 | 0.275 | 0.275 |
| A118 | 0.267 | 1835 | 1969 | 2338 | 134 | 503 | 0.267 | 0.267 |
| A119 | 0.260 | 2118 | 2320 | 2895 | 202 | 777 | 0.260 | 0.260 |
| A120 | 0.265 | 1833 | 1960 | 2313 | 127 | 480 | 0.265 | 0.265 |

TABLE 3-continued (Part B)

| ID | FTR od | Time@T2S | Time@Map | Time@TEot | ΔT2SMap | ΔT2STEot | FTR time | FTR od |
|---|---|---|---|---|---|---|---|---|
| A121 | 0.308 | 1825 | 1992 | 2368 | 167 | 543 | 0.308 | 0.308 |
| A122 | 0.397 | 1674 | 1931 | 2322 | 257 | 648 | 0.397 | 0.397 |
| A123 | 0.320 | 1669 | 1824 | 2153 | 155 | 484 | 0.320 | 0.320 |
| A124 | 0.360 | 1627 | 1766 | 2013 | 139 | 386 | 0.360 | 0.360 |
| A125 | 0.181 | 1485 | 1591 | 2072 | 106 | 587 | 0.181 | 0.181 |
| A126 | 0.591 | 2476 | 2969 | 3310 | 493 | 834 | 0.591 | 0.591 |
| A127 | 0.160 | 1935 | 2040 | 2591 | 105 | 656 | 0.160 | 0.160 |
| A128 | 0.220 | 2485 | 2627 | 3132 | 142 | 647 | 0.220 | 0.220 |
| A129 | 0.255 | 3083 | 3385 | 4268 | 302 | 1185 | 0.255 | 0.255 |
| A130 | 0.254 | 3137 | 3330 | 3896 | 193 | 759 | 0.254 | 0.254 |
| A131 | 0.364 | 1729 | 1930 | 2282 | 201 | 553 | 0.364 | 0.364 |
| A132 | 0.364 | 2288 | 2601 | 3149 | 313 | 861 | 0.364 | 0.364 |
| A133 | 0.400 | 2132 | 2531 | 3130 | 399 | 998 | 0.400 | 0.400 |
| A134 | 0.500 | 3654 | 4285 | 4916 | 631 | 1262 | 0.500 | 0.500 |
| A135 | 0.341 | 1511 | 1652 | 1924 | 141 | 413 | 0.341 | 0.341 |
| A136 | 0.197 | 2697 | 2874 | 3596 | 177 | 899 | 0.197 | 0.197 |
| A137 | 0.420 | 1797 | 1980 | 2233 | 183 | 436 | 0.420 | 0.420 |
| A138 | 0.315 | 1931 | 2137 | 2585 | 206 | 654 | 0.315 | 0.315 |
| A139 | 0.227 | 1905 | 2069 | 2629 | 164 | 724 | 0.227 | 0.227 |
| A140 | 0.294 | 1483 | 1623 | 1959 | 140 | 476 | 0.294 | 0.294 |
| A141 | 0.315 | 1872 | 2044 | 2418 | 172 | 546 | 0.315 | 0.315 |
| A142 | 0.435 | 2390 | 2573 | 2811 | 183 | 421 | 0.435 | 0.435 |
| A143 | 0.515 | 2047 | 2421 | 2773 | 374 | 726 | 0.515 | 0.515 |
| A144 | 0.235 | 2017 | 2143 | 2553 | 126 | 536 | 0.235 | 0.235 |
| A145 | 0.246 | 1492 | 1602 | 1939 | 110 | 447 | 0.246 | 0.246 |
| A146 | 0.222 | 1899 | 2068 | 2660 | 169 | 761 | 0.222 | 0.222 |
| A147 | 0.288 | 1608 | 1738 | 2059 | 130 | 451 | 0.288 | 0.288 |
| A148 | 0.191 | 1967 | 2090 | 2610 | 123 | 643 | 0.191 | 0.191 |
| A149 | 0.328 | 1581 | 1718 | 1999 | 137 | 418 | 0.328 | 0.328 |
| A150 | 0.247 | 1558 | 1690 | 2092 | 132 | 534 | 0.247 | 0.247 |
| A151 | 0.289 | 2177 | 2402 | 2954 | 225 | 777 | 0.289 | 0.289 |
| A152 | 0.324 | 1876 | 2006 | 2278 | 130 | 402 | 0.324 | 0.324 |
| A153 | 0.232 | 1713 | 1859 | 2343 | 146 | 630 | 0.232 | 0.232 |
| A154 | 0.262 | 1887 | 2053 | 2520 | 166 | 633 | 0.262 | 0.262 |
| A155 | 0.368 | 2906 | 3327 | 4049 | 421 | 1143 | 0.368 | 0.368 |
| A156 | 0.207 | 2191 | 2291 | 2674 | 100 | 483 | 0.207 | 0.207 |
| A157 | 0.385 | 1886 | 2065 | 2351 | 179 | 465 | 0.385 | 0.385 |
| A158 | 0.235 | 2424 | 2551 | 2964 | 127 | 540 | 0.235 | 0.235 |
| A159 | 0.290 | 2678 | 2973 | 3694 | 295 | 1016 | 0.290 | 0.290 |
| A160 | 0.435 | 2160 | 2489 | 2915 | 329 | 755 | 0.435 | 0.435 |
| A161 | 0.159 | 1674 | 1762 | 2227 | 88 | 553 | 0.159 | 0.159 |
| A162 | 0.232 | 3480 | 3835 | 5011 | 355 | 1531 | 0.232 | 0.232 |
| A163 | 0.238 | 2505 | 2697 | 3311 | 192 | 806 | 0.238 | 0.238 |
| A164 | 0.250 | 2535 | 2718 | 3267 | 183 | 732 | 0.250 | 0.250 |
| A165 | 0.197 | 2072 | 2189 | 2665 | 117 | 593 | 0.197 | 0.197 |
| A166 | 0.288 | 1883 | 2051 | 2467 | 168 | 584 | 0.288 | 0.288 |
| A167 | 0.214 | 2228 | 2321 | 2662 | 93 | 434 | 0.214 | 0.214 |
| A168 | 0.415 | 2366 | 2847 | 3525 | 481 | 1159 | 0.415 | 0.415 |
| A169 | 0.136 | 2543 | 2661 | 3412 | 118 | 869 | 0.136 | 0.136 |
| A170 | 0.351 | 1456 | 1589 | 1835 | 133 | 379 | 0.351 | 0.351 |
| A171 | 0.400 | 2463 | 2761 | 3208 | 298 | 745 | 0.400 | 0.400 |
| A172 | 0.200 | 1944 | 2070 | 2574 | 126 | 630 | 0.200 | 0.200 |
| A173 | 0.263 | 1505 | 1600 | 1866 | 95 | 361 | 0.263 | 0.263 |
| A174 | 0.254 | 1687 | 1816 | 2194 | 129 | 507 | 0.254 | 0.254 |
| A175 | 0.383 | 1681 | 1821 | 2047 | 140 | 366 | 0.383 | 0.383 |
| A176 | 0.245 | 2344 | 2544 | 3159 | 200 | 815 | 0.245 | 0.245 |
| A177 | 0.344 | 1596 | 1733 | 1995 | 137 | 399 | 0.344 | 0.344 |
| A178 | 0.262 | 2019 | 2183 | 2644 | 164 | 625 | 0.262 | 0.262 |
| A179 | 0.222 | 2056 | 2181 | 2619 | 125 | 563 | 0.222 | 0.222 |
| A180 | 0.375 | 1891 | 2096 | 2438 | 205 | 547 | 0.375 | 0.375 |
| A181 | 0.413 | 2575 | 2959 | 3505 | 384 | 930 | 0.413 | 0.413 |
| A182 | 0.204 | 1828 | 1930 | 2328 | 102 | 500 | 0.204 | 0.204 |
| A183 | 0.364 | 1523 | 1644 | 1856 | 121 | 333 | 0.364 | 0.364 |
| A184 | 0.214 | 2049 | 2187 | 2693 | 138 | 644 | 0.214 | 0.214 |
| A185 | 0.236 | 2417 | 2606 | 3217 | 189 | 800 | 0.236 | 0.236 |
| A186 | 0.455 | 2223 | 2909 | 3729 | 686 | 1506 | 0.455 | 0.455 |
| A187 | 0.234 | 1654 | 1755 | 2086 | 101 | 432 | 0.234 | 0.234 |
| A188 | 0.311 | 2229 | 2460 | 2972 | 231 | 743 | 0.311 | 0.311 |
| A189 | 0.392 | 2320 | 2588 | 3003 | 268 | 683 | 0.392 | 0.392 |
| A190 | 0.300 | 2473 | 2670 | 3130 | 197 | 657 | 0.300 | 0.300 |
| A191 | 0.276 | 1782 | 1907 | 2235 | 125 | 453 | 0.276 | 0.276 |
| A192 | 0.258 | 2127 | 2255 | 2623 | 128 | 496 | 0.258 | 0.258 |
| A193 | 0.214 | 1788 | 1920 | 2404 | 132 | 616 | 0.214 | 0.214 |
| A194 | 0.313 | 1930 | 2107 | 2496 | 177 | 566 | 0.313 | 0.313 |
| A195 | 0.235 | 1581 | 1710 | 2129 | 129 | 548 | 0.235 | 0.235 |
| A196 | 0.244 | 1821 | 1958 | 2381 | 137 | 560 | 0.244 | 0.244 |

TABLE 3-continued (Part B)

| ID | FTR od | Time@T2S | Time@Map | Time@TEot | ΔT2SMap | ΔT2STEot | FTR time | FTR od |
|---|---|---|---|---|---|---|---|---|
| A197 | 0.203 | 1743 | 1835 | 2196 | 92 | 453 | 0.203 | 0.203 |
| A198 | 0.400 | 1696 | 1912 | 2236 | 216 | 540 | 0.400 | 0.400 |
| A199 | 0.417 | 1498 | 1665 | 1899 | 167 | 401 | 0.417 | 0.417 |
| A200 | 0.281 | 1441 | 1554 | 1843 | 113 | 402 | 0.281 | 0.281 |
| A201 | 0.273 | 2036 | 2205 | 2656 | 169 | 620 | 0.273 | 0.273 |
| A202 | 0.345 | 1898 | 2080 | 2426 | 182 | 528 | 0.345 | 0.345 |
| A203 | 0.244 | 1768 | 1880 | 2226 | 112 | 458 | 0.244 | 0.244 |
| A204 | 0.385 | 1642 | 1820 | 2105 | 178 | 463 | 0.385 | 0.385 |
| A205 | 0.256 | 1851 | 1983 | 2367 | 132 | 516 | 0.256 | 0.256 |
| A207 | 0.190 | 2173 | 2299 | 2835 | 126 | 662 | 0.190 | 0.190 |
| A208 | 0.333 | 2277 | 2531 | 3039 | 254 | 762 | 0.333 | 0.333 |
| A209 | 0.372 | 1721 | 1937 | 2302 | 216 | 581 | 0.372 | 0.372 |
| A210 | 0.278 | 1907 | 2066 | 2479 | 159 | 572 | 0.278 | 0.278 |
| A211 | 0.240 | 2153 | 2306 | 2791 | 153 | 638 | 0.240 | 0.240 |
| A212 | 0.421 | 2143 | 2458 | 2891 | 315 | 748 | 0.421 | 0.421 |
| A213 | 0.264 | 2057 | 2332 | 3099 | 275 | 1042 | 0.264 | 0.264 |
| A214 | 0.300 | 2116 | 2363 | 2939 | 247 | 823 | 0.300 | 0.300 |
| A215 | 0.255 | 1982 | 2118 | 2515 | 136 | 533 | 0.255 | 0.255 |
| A216 | 0.273 | 2799 | 3061 | 3760 | 262 | 961 | 0.273 | 0.273 |
| A217 | 0.244 | 2021 | 2237 | 2906 | 216 | 885 | 0.244 | 0.244 |
| A218 | 0.293 | 2319 | 2571 | 3179 | 252 | 860 | 0.293 | 0.293 |
| A219 | 0.393 | 2098 | 2309 | 2635 | 211 | 537 | 0.393 | 0.393 |
| A220 | 0.302 | 1803 | 1943 | 2266 | 140 | 463 | 0.302 | 0.302 |
| A222 | 0.310 | 1705 | 1876 | 2256 | 171 | 551 | 0.310 | 0.310 |
| A223 | 0.310 | 1593 | 1732 | 2041 | 139 | 448 | 0.310 | 0.310 |
| A224 | 0.357 | 1649 | 1811 | 2103 | 162 | 454 | 0.357 | 0.357 |
| A225 | 0.368 | 1655 | 1824 | 2114 | 169 | 459 | 0.368 | 0.368 |

Comparative Results of nATFt's and nATFz's

Results between patients in two different geographic locations (i.e., two different hospitals) were compared for correlation with each other. This comparison is expressed in Table 4 below, and includes a comparison of INR values calculated by the WHO method for each respective location, with GInr representing one location for these traditionally WHO determined values, and MInr representing values based on data obtained at the other location. The values identified as ATFz and ATFt, such as, GATFt and MATFt, and GATFz and MATFz, represent anticoagulant therapy factors derived from the expressions (1) through (9) above.

The ATFa represents an anticoagulation therapy factor derived from our method and apparatus for the expression ATFa=XR$^{(2-nFTR)}$ wherein a maximum acceleration point is obtained, and nFTR=IUX/IUT, where IUX is the change in optical density from a time prior to the MAP time ($t_{<MAP}$ which is $t_{MAP}$ minus some time from MAP) to the optical density at a time after the MAP time ($t_{>MAP}$ which is $t_{MAP}$ plus some time from MAP); and wherein IUT=the change in optical density at the time $t_1$ to the optical density measured at time $t_{EOT}$, where time $t_{EOT}$ is the end of the test (EOT). The (IUX) represents the fibrinogen (FBG) for MAP (−a number of seconds) to MAP (+a number of seconds) (that is the fibrinogen (FBG) converted from $t_{<MAP}$ to $t_{>MAP}$ on FIG. 2) The (IUT) represents fibrinogen converted from $c_1$ to $c_{EOT}$ (that is the fibrinogen converted from $t_1$ to $t_{EOT}$, see FIG. 2). The XR for the ATFa expression is XR=TX/MNTX, which is the ratio of time to map (TX) by the mean normal time to map of 20 presumed "normal" patients.

TABLE 4

COMPARATIVE RESULTS FOR ATFt and ATFz

| Comparison | n | r | m | b | Std. Error | Ng | Lassen |
|---|---|---|---|---|---|---|---|
| GInr vs. GATFa | 129 | 0.996 | 0.891 | 0.148 | 0.082 | 6/129 = 4.7% mismatches | delta <= 0.4 5@96.1% delta <= 0.7 2@98.4% |
| GInr vs. GATFz | 129 | 0.975 | 1.014 | −0.016 | 0.215 | 15/129 = 11.6% mismatches | delta <= 0.4 9@93% delta <= 0.7 3@97.7% |
| GInr vs. GATFt | 129 | 0.971 | 0.895 | 0.332 | 0.232 | 26/129 = 20.2% mismatches | delta <= 0.4 18@86.0% delta <= 0.7 2@98.4% |
| MInr vs. MATFa | 129 | 0.996 | 0.943 | 0.082 | 0.094 | 18/129 = 14.0% mismatches | delta <= 0.4 15@88.4% delta <= 0.7 5@96.1% |
| MInr vs. MATFz | 129 | 0.985 | 0.993 | −0.058 | 0.177 | 2/129 = 1.6% mismatches | delta <= 0.4 0@100% delta <= 0.7 0@100% |
| MInr vs. MATFt | 129 | 0.981 | 0.851 | 0.420 | 0.200 | 8/129 = 6.2% mismatches | delta <= 0.4 6@95.3 delta <= 0.7 2@98.4% |

A comparison of combined location data is shown in Table 5, below. The sample size was 217.

TABLE 5

STATISTICAL SUMMARY OF MHTL DATA

| Comparison | n | r | m | b | Std. Error | Ng | Lassen |
|---|---|---|---|---|---|---|---|
| Inr vs ATFa | 217 | 0.984 | 1.006 | 0.011 | 0.215 | 30/217 = 13.8% mismatches | delta <= 0.4 16@92.6% delta <= 0.7 1@99.5% |
| Inr vs. ATFz | 217 | 0.984 | 1.002 | 0.120 | 0.214 | 26/217 = 12.0% mismatched | delta <= 0.4 18@91.7% delta <= 0.7 3@98.6% |
| Inr vs. ATFt | 217 | 0.984 | 0.900 | 0.482 | 1.218 | 45/217 = 20.7% mismatches | delta <= 0.4 43@80.2% delta <= 0.7 6@97.2% |

Comparative results were also calculated for the ATFt which includes the lag phase fibrinogen, in accordance with the IULz, using the expression (5.1) for the TEOT value. Table 6 below provides the values for the ATFz, ATFt, and the ATFt2 (which is obtained from expression 5.1 using the IULz).

TABLE 6

| ID | INR | INRz | ATFt | ATFt2 |
|---|---|---|---|---|
| A001 | 3.1 | 2.9 | 2.4 | 2.6 |
| A002 | 3.3 | 2.9 | 2.4 | 2.6 |
| A003 | 3.3 | 2.9 | 2.4 | 2.6 |
| A004 | 2.1 | 2.3 | 1.8 | 2.0 |
| A005 | 2.9 | 2.6 | 2.1 | 2.3 |
| A007 | 2.1 | 2.0 | 1.5 | 1.6 |
| A008 | 2.8 | 2.8 | 2.3 | 2.5 |
| A009 | 3.4 | 3.1 | 2.6 | 2.8 |
| A010 | 1.9 | 1.8 | 1.3 | 1.5 |
| A011 | 2.1 | 1.9 | 1.5 | 1.6 |
| A012 | 3.2 | 2.8 | 2.3 | 2.5 |
| A013 | 3.5 | 3.3 | 2.8 | 3.0 |
| A014 | 1.8 | 1.7 | 1.3 | 1.4 |
| A015 | 1.9 | 1.8 | 1.3 | 1.5 |
| A016 | 3.2 | 2.9 | 2.4 | 2.6 |
| A017 | 1.8 | 1.9 | 1.4 | 1.6 |
| A018 | 2.2 | 2.1 | 1.7 | 1.8 |
| A019 | 1.8 | 1.9 | 1.5 | 1.6 |
| A020 | 3.5 | 3.4 | 2.9 | 3.2 |
| A021 | 2.8 | 2.7 | 2.2 | 2.4 |
| A022 | 2.2 | 2.2 | 1.7 | 1.9 |
| A023 | 3.2 | 2.9 | 2.3 | 2.5 |
| A024 | 3.7 | 3.5 | 2.9 | 3.1 |
| A025 | 1.8 | 1.7 | 1.2 | 1.4 |
| A026 | 1.6 | 1.6 | 1.2 | 1.4 |
| A027 | 1.5 | 1.5 | 1.1 | 1.3 |
| A028 | 1.9 | 2.0 | 1.5 | 1.7 |
| A029 | 2.1 | 2.1 | 1.6 | 1.8 |
| A030 | 2.6 | 2.6 | 2.1 | 2.3 |
| A031 | 2.7 | 2.5 | 2.1 | 2.3 |
| A032 | 4.1 | 3.8 | 3.1 | 3.3 |
| A033 | 2.9 | 2.9 | 2.4 | 2.6 |
| A034 | 2.2 | 2.2 | 1.7 | 1.9 |
| A035 | 4.9 | 4.7 | 4.3 | 4.7 |
| A036 | 3.2 | 2.9 | 2.4 | 2.6 |
| A037 | 2.5 | 2.7 | 2.1 | 2.4 |
| A038 | 1.6 | 1.6 | 1.1 | 1.2 |
| A039 | 1.4 | 1.6 | 1.1 | 1.3 |
| A040 | 2.4 | 2.4 | 1.9 | 2.1 |
| A041 | 2.3 | 2.4 | 2.0 | 2.2 |
| A042 | 4.1 | 3.8 | 3.3 | 3.6 |
| A044 | 4.2 | 3.7 | 3.2 | 3.4 |
| A045 | 2.7 | 2.8 | 2.3 | 2.5 |
| A047 | 2.8 | 2.8 | 2.3 | 2.5 |
| A048 | 3.9 | 3.6 | 3.1 | 3.3 |
| A049 | 2.6 | 2.4 | 1.9 | 2.1 |
| A050 | 2.8 | 2.8 | 2.3 | 2.5 |
| A051 | 1.9 | 1.9 | 1.4 | 1.6 |
| A052 | 2.8 | 2.6 | 2.0 | 2.2 |
| A053 | 3.0 | 2.8 | 2.2 | 2.4 |
| A054 | 2.1 | 2.0 | 1.5 | 1.7 |

TABLE 6-continued

| ID | INR | INRz | ATFt | ATFt2 |
|---|---|---|---|---|
| A055 | 5.6 | 5.4 | 5.3 | 5.6 |
| A056 | 3.6 | 3.7 | 3.1 | 3.4 |
| A057 | 2.8 | 2.6 | 2.0 | 2.2 |
| A058 | 8.5 | 8.7 | 8.6 | 9.1 |
| A059 | 2.9 | 2.6 | 2.1 | 2.3 |
| A060 | 3.5 | 3.0 | 2.4 | 2.6 |
| A061 | 2.4 | 2.5 | 2.0 | 2.1 |
| A062 | 7.0 | 7.2 | 6.8 | 7.3 |
| A063 | 3.0 | 3.0 | 2.5 | 2.7 |
| A064 | 2.2 | 2.2 | 1.7 | 1.9 |
| A065 | 2.6 | 2.8 | 2.4 | 2.6 |
| A066 | 2.0 | 1.9 | 1.4 | 1.6 |
| A067 | 1.8 | 1.8 | 1.4 | 1.6 |
| A068 | 2.6 | 2.4 | 1.9 | 2.1 |
| A069 | 2.4 | 2.2 | 1.6 | 1.8 |
| A070 | 2.4 | 2.3 | 1.7 | 1.9 |
| A071 | 1.9 | 2.0 | 1.5 | 1.7 |
| A072 | 1.8 | 1.9 | 1.5 | 1.6 |
| A073 | 1.5 | 1.7 | 1.3 | 1.4 |
| A074 | 1.7 | 1.8 | 1.3 | 1.5 |
| A075 | 1.6 | 1.4 | 1.0 | 1.1 |
| A076 | 1.4 | 1.6 | 1.2 | 1.3 |
| A077 | 4.5 | 4.6 | 4.1 | 4.4 |
| A078 | 2.2 | 2.1 | 1.6 | 1.8 |
| A080 | 7.3 | 7.4 | 7.3 | 7.6 |
| A081 | 3.8 | 4.2 | 3.5 | 3.8 |
| A082 | 1.6 | 1.7 | 1.3 | 1.5 |
| A083 | 1.6 | 1.6 | 1.1 | 1.3 |
| A084 | 6.7 | 6.7 | 6.3 | 6.6 |
| A085 | 3.3 | 3.4 | 3.1 | 3.3 |
| A086 | 2.8 | 2.7 | 2.2 | 2.4 |
| A087 | 1.8 | 1.9 | 1.5 | 1.6 |
| A088 | 1.7 | 1.9 | 1.4 | 1.6 |
| A089 | 2.3 | 2.1 | 1.6 | 1.7 |
| A090 | 6.3 | 6.6 | 6.3 | 6.7 |
| A091 | 7.6 | 8.1 | 7.6 | 8.1 |
| A092 | 1.9 | 2.3 | 1.8 | 2.0 |
| A093 | 4.9 | 4.3 | 4.0 | 4.2 |
| A094 | 3.2 | 3.3 | 2.7 | 2.9 |
| A095 | 1.5 | 1.6 | 1.2 | 1.4 |
| A096 | 2.3 | 1.9 | 1.4 | 1.6 |
| A097 | 1.3 | 1.3 | 0.9 | 1.0 |
| A098 | 1.4 | 1.5 | 1.1 | 1.2 |
| A099 | 1.8 | 1.7 | 1.3 | 1.4 |
| A100 | 1.4 | 1.6 | 1.2 | 1.3 |
| A101 | 2.7 | 2.7 | 2.2 | 2.4 |
| A102 | 3.8 | 3.6 | 3.0 | 3.2 |
| A103 | 2.0 | 2.2 | 1.8 | 1.9 |
| A104 | 3.2 | 3.3 | 2.9 | 3.2 |
| A105 | 3.7 | 3.6 | 3.2 | 3.4 |
| A107 | 2.9 | 2.8 | 2.3 | 2.5 |
| A108 | 2.1 | 2.1 | 1.6 | 1.8 |
| A109 | 2.2 | 2.3 | 1.8 | 2.0 |
| A110 | 3.9 | 4.2 | 3.9 | 4.1 |
| A111 | 2.5 | 2.7 | 2.2 | 2.4 |
| A112 | 2.5 | 2.5 | 2.1 | 2.3 |
| A113 | 1.9 | 1.9 | 1.4 | 1.6 |
| A114 | 2.1 | 2.1 | 1.7 | 1.8 |
| A115 | 2.4 | 2.6 | 2.1 | 2.3 |

TABLE 6-continued

| ID | INR | INRz | ATFt | ATFt2 |
|---|---|---|---|---|
| A116 | 1.7 | 1.6 | 1.2 | 1.3 |
| A117 | 1.6 | 1.9 | 1.5 | 1.6 |
| A118 | 2.1 | 2.1 | 1.6 | 1.7 |
| A119 | 3.0 | 2.7 | 2.3 | 2.4 |
| A120 | 2.1 | 2.0 | 1.6 | 1.7 |
| A121 | 2.2 | 2.1 | 1.6 | 1.7 |
| A122 | 1.7 | 1.9 | 1.4 | 1.6 |
| A123 | 1.8 | 1.8 | 1.3 | 1.5 |
| A124 | 1.8 | 1.7 | 1.2 | 1.3 |
| A125 | 1.4 | 1.4 | 1.1 | 1.3 |
| A126 | 3.7 | 3.2 | 3.0 | 3.3 |
| A127 | 2.4 | 2.3 | 1.8 | 2.0 |
| A128 | 3.8 | 3.5 | 2.9 | 3.1 |
| A129 | 5.3 | 5.3 | 4.8 | 5.3 |
| A130 | 4.7 | 5.2 | 4.5 | 4.9 |
| A131 | 1.7 | 1.9 | 1.5 | 1.6 |
| A132 | 2.8 | 3.1 | 2.7 | 2.9 |
| A133 | 2.6 | 2.9 | 2.5 | 2.7 |
| A134 | 6.6 | 6.0 | 6.6 | 7.1 |
| A135 | 1.5 | 1.5 | 1.1 | 1.2 |
| A136 | 4.3 | 4.2 | 3.6 | 3.8 |
| A137 | 1.9 | 1.9 | 1.5 | 1.6 |
| A138 | 2.0 | 2.3 | 1.8 | 2.0 |
| A139 | 2.1 | 2.3 | 1.8 | 2.0 |
| A140 | 1.3 | 1.5 | 1.1 | 1.2 |
| A141 | 2.2 | 2.1 | 1.7 | 1.8 |
| A142 | 3.4 | 2.9 | 2.5 | 2.7 |
| A143 | 2.5 | 2.5 | 2.1 | 2.3 |
| A144 | 2.5 | 2.4 | 1.9 | 2.1 |
| A145 | 1.4 | 1.4 | 1.1 | 1.2 |
| A146 | 2.3 | 2.3 | 1.9 | 2.0 |
| A147 | 1.7 | 1.6 | 1.2 | 1.4 |
| A148 | 2.3 | 2.4 | 1.9 | 2.1 |
| A149 | 1.6 | 1.6 | 1.2 | 1.3 |
| A150 | 1.6 | 1.6 | 1.2 | 1.3 |
| A151 | 2.8 | 2.9 | 2.4 | 2.6 |
| A152 | 2.2 | 2.1 | 1.6 | 1.7 |
| A153 | 1.8 | 1.9 | 1.5 | 1.6 |
| A154 | 2.2 | 2.2 | 1.7 | 1.9 |
| A155 | 4.8 | 4.6 | 4.3 | 4.7 |
| A156 | 2.9 | 2.8 | 2.2 | 2.4 |
| A157 | 2.1 | 2.1 | 1.6 | 1.8 |
| A158 | 3.6 | 3.3 | 2.6 | 2.8 |
| A159 | 3.9 | 4.1 | 3.6 | 3.9 |
| A160 | 2.7 | 2.8 | 2.3 | 2.5 |
| A161 | 1.7 | 1.8 | 1.4 | 1.5 |
| A162 | 6.6 | 6.8 | 6.4 | 6.9 |
| A163 | 3.9 | 3.6 | 3.1 | 3.3 |
| A164 | 4.0 | 3.6 | 3.0 | 3.3 |
| A165 | 2.7 | 2.6 | 2.0 | 2.2 |
| A166 | 2.2 | 2.2 | 1.7 | 1.9 |
| A167 | 2.9 | 2.8 | 2.2 | 2.4 |
| A168 | 3.6 | 3.5 | 3.1 | 3.3 |
| A169 | 4.1 | 3.8 | 3.2 | 3.4 |
| A170 | 1.4 | 1.4 | 1.0 | 1.1 |
| A171 | 3.4 | 3.3 | 2.9 | 3.1 |
| A172 | 2.5 | 2.3 | 1.8 | 2.0 |
| A173 | 1.6 | 1.4 | 1.0 | 1.1 |
| A174 | 1.8 | 1.8 | 1.4 | 1.5 |
| A175 | 1.8 | 1.7 | 1.3 | 1.4 |
| A176 | 3.4 | 3.3 | 2.7 | 2.9 |
| A177 | 1.7 | 1.6 | 1.2 | 1.3 |
| A178 | 2.3 | 2.5 | 2.0 | 2.1 |
| A179 | 2.6 | 2.5 | 2.0 | 2.2 |
| A180 | 2.3 | 2.2 | 1.7 | 1.9 |
| A181 | 3.5 | 3.7 | 3.3 | 3.6 |
| A182 | 2.1 | 2.0 | 1.6 | 1.7 |
| A183 | 1.5 | 1.5 | 1.0 | 1.2 |
| A184 | 2.6 | 2.5 | 2.0 | 2.2 |
| A185 | 3.3 | 3.4 | 2.9 | 3.1 |
| A186 | 3.1 | 3.5 | 3.1 | 3.3 |
| A187 | 1.8 | 1.7 | 1.3 | 1.4 |
| A188 | 3.1 | 2.9 | 2.4 | 2.6 |
| A189 | 3.0 | 3.0 | 2.6 | 2.8 |
| A190 | 3.6 | 3.4 | 2.8 | 3.1 |
| A191 | 2.0 | 1.9 | 1.5 | 1.6 |
| A192 | 2.7 | 2.6 | 2.1 | 2.3 |
| A193 | 2.1 | 2.0 | 1.6 | 1.7 |
| A194 | 2.2 | 2.3 | 1.8 | 2.0 |
| A195 | 1.4 | 1.6 | 1.2 | 1.4 |
| A196 | 2.0 | 2.1 | 1.6 | 1.8 |
| A197 | 1.8 | 1.9 | 1.4 | 1.5 |
| A198 | 2.0 | 1.9 | 1.4 | 1.5 |
| A199 | 1.5 | 1.5 | 1.0 | 1.2 |
| A200 | 1.4 | 1.4 | 1.0 | 1.1 |
| A201 | 2.6 | 2.5 | 2.0 | 2.2 |
| A202 | 2.5 | 2.2 | 1.7 | 1.9 |
| A203 | 2.0 | 1.9 | 1.4 | 1.6 |
| A204 | 1.8 | 1.7 | 1.3 | 1.4 |
| A205 | 1.9 | 2.1 | 1.6 | 1.8 |
| A207 | 2.7 | 2.8 | 2.3 | 2.5 |
| A208 | 3.0 | 3.0 | 2.5 | 2.8 |
| A209 | 1.9 | 1.9 | 1.5 | 1.6 |
| A210 | 2.4 | 2.2 | 1.7 | 1.9 |
| A211 | 2.9 | 2.7 | 2.2 | 2.4 |
| A212 | 2.8 | 2.7 | 2.3 | 2.5 |
| A213 | 2.7 | 2.8 | 2.3 | 2.5 |
| A214 | 2.8 | 2.8 | 2.3 | 2.5 |
| A215 | 2.5 | 2.3 | 1.8 | 2.0 |
| A216 | 4.1 | 4.4 | 3.9 | 4.2 |
| A217 | 2.3 | 2.6 | 2.2 | 2.3 |
| A218 | 2.9 | 3.2 | 2.7 | 3.0 |
| A219 | 2.7 | 2.5 | 2.0 | 2.2 |
| A220 | 2.0 | 2.0 | 1.5 | 1.7 |
| A222 | 2.0 | 1.9 | 1.4 | 1.6 |
| A223 | 1.7 | 1.6 | 1.2 | 1.4 |
| A224 | 1.6 | 1.7 | 1.3 | 1.4 |
| A225 | 1.8 | 1.7 | 1.3 | 1.4 |

Table 7 represents a comparison of the data from Table 6.

TABLE 7

| | | "r" | "m" | "b" | StdErr | StdDev |
|---|---|---|---|---|---|---|
| INR | | | | | | |
| vs | INRz | 0.988 | 0.988 | 0.059 | 0.190 | 1.201 |
| | ATFt | 0.984 | 0.966 | 0.568 | 0.215 | 1.238 |
| | ATFt2 | 0.983 | 0.913 | 0.504 | 0.219 | 1.257 |
| ATFt | | | | | | |
| vs | ATFt2 | 1.000 | 0.946 | −0.068 | 0.022 | 1.264 |

Table 8 provides comparative data for the anticoagulant therapy factors, similar to Table 2, but using the ATFt2 method from expressions (4) and (5.1) for corresponding GINRt2 and MINRt2 values.

TABLE 8

| ID | AINR | GINR | GINRa | GINRz | GINRt2 | MINR | MINRa | MINRz | MINRt2 |
|---|---|---|---|---|---|---|---|---|---|
| U0800 | 2.0 | 2.0 | 2.0 | 2.0 | 1.7 | 2.1 | 2.1 | 2.2 | 2.1 |
| U7440 | 2.6 | 3.0 | 3.0 | 2.9 | 2.9 | 3.0 | 3.0 | 2.8 | 3.4 |
| U7443 | 2.0 | 2.0 | 2.0 | 2.0 | 1.8 | 2.1 | 2.2 | 2.1 | 1.8 |
| U7458 | 1.4 | 1.4 | 1.4 | 1.4 | 1.2 | 1.4 | 1.4 | 1.3 | 1.3 |
| U7465 | 9.7 | 7.4 | 8.1 | 6.6 | 7.9 | 7.1 | 7.5 | 8.1 | 7.8 |
| U7469 | 1.1 | 1.1 | 1.1 | 1.1 | 0.9 | 1.2 | 1.1 | 1.1 | 1.0 |

TABLE 8-continued

| ID | AINR | GINR | GINRa | GINRz | GINRt2 | MINR | MINRa | MINRz | MINRt2 |
|---|---|---|---|---|---|---|---|---|---|
| U7470 | 3.2 | 3.4 | 3.6 | 3.4 | 3.2 | 3.6 | 3.7 | 3.8 | 3.8 |
| U8080 | 3.1 | 3.6 | 3.6 | 3.3 | 3.6 | 3.3 | 3.3 | 3.5 | 3.4 |
| U8087 | 1.9 | 1.9 | 1.9 | 1.8 | 1.6 | 1.9 | 1.9 | 1.9 | 1.7 |
| U8092 | 1.7 | 1.7 | 1.8 | 1.7 | 1.6 | 1.9 | 1.9 | 1.9 | 1.6 |
| U3050 | 2.7 | 2.8 | 3.1 | 2.6 | 2.2 | 2.3 | 2.3 | 2.3 | 2.0 |
| U3077 | 1.3 | 1.4 | 1.4 | 1.4 | 1.1 | 1.3 | 1.3 | 1.3 | 1.2 |
| U3083 | 1.6 | 1.6 | 1.6 | 1.6 | 1.3 | 1.6 | 1.7 | 1.6 | 1.4 |
| U8210 | 2.6 | 2.9 | 3.0 | 2.8 | 2.7 | 2.7 | 2.8 | 2.8 | 2.6 |
| U8221 | 3.2 | 3.7 | 4.0 | 3.7 | 3.4 | 3.5 | 3.5 | 3.3 | 3.6 |
| U3408 | 1.1 | 1.2 | 1.2 | 1.2 | 0.9 | 1.1 | 1.0 | 1.0 | 0.9 |
| U3453 | 1.1 | 1.2 | 1.2 | 1.2 | 1.0 | 1.2 | 1.2 | 1.2 | 1.0 |
| U3457 | 2.2 | 2.3 | 2.4 | 2.2 | 1.9 | 2.1 | 2.3 | 2.2 | 1.8 |
| U3395 | 2.7 | 3.2 | 3.5 | 3.2 | 2.7 | 2.8 | 2.9 | 2.5 | 2.3 |
| U3398 | 1.5 | 1.7 | 1.8 | 1.8 | 1.5 | 1.6 | 1.6 | 1.6 | 1.5 |
| U3456 | 1.1 | 1.0 | 1.0 | 1.0 | 0.8 | 1.0 | 1.0 | 1.0 | 0.9 |
| U3459 | 2.9 | 2.6 | 2.8 | 2.6 | 2.2 | 2.4 | 2.5 | 2.5 | 2.0 |
| U0415 | 0.9 | 0.9 | 0.9 | 0.9 | 0.8 | 0.9 | 1.0 | 1.0 | 0.8 |
| U0432 | 1.8 | 1.5 | 1.5 | 1.5 | 1.3 | 1.4 | 1.4 | 1.4 | 1.3 |
| U0436 | 2.4 | 2.4 | 2.6 | 2.3 | 2.1 | 2.4 | 2.4 | 2.4 | 2.2 |
| U0438 | 3.9 | 3.7 | 4.2 | 3.7 | 3.2 | 3.8 | 4.2 | 3.9 | 3.6 |
| U0439 | 2.3 | 2.2 | 2.3 | 2.1 | 1.8 | 2.3 | 2.3 | 2.2 | 2.0 |
| U0440 | 5.8 | 4.8 | 5.4 | 5.2 | 4.4 | 4.6 | 4.8 | 4.3 | 5.2 |
| U0441 | 4.5 | 4.9 | 5.6 | 6.0 | 5.0 | 4.4 | 4.7 | 4.7 | 5.4 |
| U0442 | 1.8 | 1.7 | 1.8 | 1.7 | 1.5 | 1.8 | 1.8 | 1.8 | 1.6 |
| U3724 | 2.7 | 2.4 | 2.5 | 2.4 | 2.0 | 2.6 | 2.7 | 2.6 | 2.3 |
| U0849 | 2.4 | 2.3 | 2.4 | 2.1 | 1.8 | 2.3 | 2.4 | 2.2 | 2.0 |
| U0860 | 1.0 | 1.0 | 1.0 | 1.0 | 0.8 | 1.0 | 1.0 | 1.0 | 0.9 |
| U0861 | 2.8 | 2.9 | 3.0 | 2.8 | 2.6 | 3.0 | 3.0 | 2.9 | 3.0 |
| U0863 | 1.7 | 1.7 | 1.7 | 1.7 | 1.7 | 1.7 | 1.8 | 1.8 | 1.8 |
| U0875 | 2.2 | 2.0 | 2.2 | 2.1 | 1.6 | 2.0 | 2.0 | 2.0 | 1.7 |
| U0843 | 1.4 | 1.4 | 1.4 | 1.4 | 1.2 | 1.4 | 1.5 | 1.5 | 1.3 |
| U0848 | 1.3 | 1.4 | 1.4 | 1.4 | 1.2 | 1.3 | 1.4 | 1.4 | 1.2 |
| U0855 | 1.3 | 1.3 | 1.3 | 1.3 | 1.2 | 1.2 | 1.2 | 1.2 | 1.3 |
| U0867 | 3.2 | 2.9 | 3.2 | 2.8 | 2.5 | 3.0 | 3.1 | 3.0 | 2.9 |
| U1201 | 1.9 | 1.9 | 2.0 | 1.9 | 1.7 | 1.8 | 1.8 | 1.9 | 1.8 |
| U1202 | 1.3 | 1.3 | 1.3 | 1.3 | 1.2 | 1.4 | 1.4 | 1.4 | 1.2 |
| U1205 | 1.6 | 1.8 | 1.9 | 1.8 | 1.6 | 1.9 | 1.9 | 1.8 | 1.7 |
| U1207 | 1.9 | 1.9 | 2.0 | 1.8 | 1.5 | 1.9 | 1.9 | 1.7 | 1.7 |
| U1230 | 1.3 | 1.4 | 1.5 | 1.4 | 1.3 | 1.4 | 1.5 | 1.5 | 1.5 |
| U1198 | 2.2 | 2.1 | 2.2 | 2.1 | 1.9 | 2.0 | 2.0 | 2.0 | 2.3 |
| U1199 | 2.8 | 3.3 | 3.6 | 3.1 | 2.8 | 3.2 | 3.2 | 2.8 | 3.3 |
| U1218 | 3.0 | 2.6 | 2.9 | 2.9 | 2.7 | 2.8 | 3.1 | 3.1 | 3.2 |
| U1225 | 2.2 | 2.3 | 2.3 | 2.1 | 1.9 | 2.6 | 2.4 | 2.2 | 2.2 |
| U1575 | 1.4 | 1.3 | 1.3 | 1.3 | 1.4 | 1.4 | 1.4 | 1.4 | 1.4 |
| U1579 | 1.5 | 1.7 | 1.7 | 1.7 | 1.5 | 1.8 | 1.8 | 1.7 | 1.5 |
| U1649 | 0.9 | 0.8 | 0.8 | 0.8 | 0.8 | 0.9 | 0.9 | 0.9 | 0.8 |
| U1576 | 2.2 | 2.1 | 2.1 | 2.1 | 2.1 | 2.3 | 2.3 | 2.3 | 2.2 |
| U1581 | 1.7 | 1.7 | 1.7 | 1.8 | 1.9 | 1.7 | 1.8 | 1.8 | 1.7 |
| U1599 | 2.0 | 1.7 | 1.8 | 1.8 | 2.0 | 2.0 | 2.1 | 2.1 | 2.0 |
| U1600 | 3.5 | 3.2 | 3.4 | 3.4 | 3.7 | 3.9 | 4.2 | 3.5 | 3.7 |
| U4471 | 1.5 | 1.6 | 1.7 | 1.6 | 1.5 | 1.7 | 1.7 | 1.7 | 1.7 |
| U4757 | 2.0 | 2.1 | 2.1 | 2.0 | 1.8 | 2.0 | 2.0 | 2.1 | 2.0 |
| U4767 | 2.6 | 2.4 | 2.5 | 2.6 | 2.0 | 2.6 | 2.6 | 2.5 | 2.3 |
| U4772 | 2.5 | 2.7 | 2.8 | 2.5 | 2.6 | 2.8 | 2.8 | 2.9 | 2.5 |
| U4801 | 1.3 | 1.4 | 1.4 | 1.4 | 1.2 | 1.5 | 1.5 | 1.4 | 1.2 |
| U4737 | 2.9 | 2.6 | 2.8 | 2.7 | 2.3 | 2.7 | 2.9 | 2.8 | 2.5 |
| U4752 | 1.4 | 1.5 | 1.6 | 1.5 | 1.3 | 1.5 | 1.5 | 1.5 | 1.4 |
| U5133 | 0.9 | 0.9 | 0.9 | 0.9 | 0.7 | 1.0 | 1.0 | 1.0 | 0.8 |
| U5173 | 1.1 | 1.2 | 1.2 | 1.2 | 1.1 | 1.2 | 1.2 | 1.2 | 1.0 |
| U5175 | 1.7 | 1.8 | 1.9 | 1.8 | 1.7 | 1.9 | 1.9 | 1.9 | 1.7 |
| U5178 | 2.3 | 2.2 | 2.3 | 2.1 | 1.9 | 2.6 | 2.9 | 2.8 | 2.0 |
| U5183 | 2.9 | 2.6 | 2.8 | 2.6 | 2.3 | 3.6 | 3.9 | 3.7 | 3.0 |
| U5158 | 5.5 | 5.1 | 5.9 | 5.7 | 5.8 | 6.0 | 6.6 | 7.1 | 7.0 |
| U5169 | 2.6 | 2.9 | 3.2 | 3.2 | 3.2 | 3.2 | 3.4 | 3.6 | 3.7 |
| U5190 | 2.8 | 2.7 | 2.8 | 2.9 | 2.8 | 3.2 | 3.4 | 3.5 | 3.2 |
| U5193 | 3.1 | 3.0 | 3.1 | 3.0 | 2.9 | 3.6 | 3.7 | 3.7 | 3.4 |
| U5589 | 1.6 | 1.8 | 1.9 | 1.8 | 1.6 | 1.9 | 2.0 | 1.8 | 1.5 |
| U5592 | 1.1 | 1.2 | 1.2 | 1.2 | 1.1 | 1.4 | 1.3 | 1.3 | 1.4 |
| U5593 | 1.7 | 1.8 | 1.9 | 1.8 | 1.6 | 1.8 | 1.9 | 1.8 | 1.7 |
| U5565 | 2.7 | 3.2 | 3.3 | 3.3 | 3.1 | 3.5 | 3.5 | 3.6 | 3.5 |
| U5591 | 2.0 | 2.2 | 2.3 | 2.3 | 2.1 | 2.3 | 2.3 | 2.1 | 2.3 |
| U5594 | 2.3 | 2.6 | 2.8 | 2.8 | 2.8 | 2.8 | 2.8 | 3.0 | 3.0 |
| U5597 | 3.3 | 3.3 | 3.6 | 3.6 | 3.1 | 4.1 | 4.0 | 4.3 | 4.0 |
| U5993 | 1.0 | 0.9 | 0.9 | 0.9 | 0.8 | 1.0 | 1.0 | 1.0 | 0.8 |
| U6017 | 1.0 | 0.9 | 1.0 | 1.0 | 0.8 | 0.9 | 0.9 | 0.9 | 0.8 |
| U6056 | 1.0 | 1.0 | 1.0 | 1.0 | 0.9 | 1.0 | 1.0 | 1.0 | 0.9 |
| U5992 | 1.4 | 1.4 | 1.4 | 1.4 | 1.3 | 1.3 | 1.4 | 1.4 | 1.3 |
| U6047 | 2.3 | 2.3 | 2.4 | 2.3 | 2.0 | 2.2 | 2.3 | 2.3 | 2.2 |

TABLE 8-continued

| ID | AINR | GINR | GINRa | GINRz | GINRt2 | MINR | MINRa | MINRz | MINRt2 |
|---|---|---|---|---|---|---|---|---|---|
| U6060 | 1.9 | 2.1 | 2.2 | 2.2 | 2.0 | 2.3 | 2.0 | 2.0 | 2.1 |
| U6065 | 3.1 | 2.8 | 2.9 | 2.8 | 2.7 | 3.0 | 3.1 | 2.9 | 2.8 |
| U6928 | 1.2 | 1.2 | 1.2 | 1.2 | 1.2 | 1.2 | 1.2 | 1.2 | 1.1 |
| U6929 | 1.2 | 1.2 | 1.2 | 1.2 | 1.1 | 1.2 | 1.2 | 1.2 | 1.0 |
| U6951 | 1.5 | 1.5 | 1.5 | 1.5 | 1.5 | 1.6 | 1.7 | 1.6 | 1.4 |
| U6977 | 1.3 | 1.3 | 1.3 | 1.3 | 1.2 | 1.3 | 1.4 | 1.4 | 1.1 |
| U6936 | 2.4 | 2.5 | 2.4 | 2.6 | 3.2 | 2.6 | 2.6 | 2.7 | 2.6 |
| U6938 | 2.1 | 2.1 | 2.1 | 2.2 | 2.3 | 2.3 | 2.3 | 2.3 | 2.3 |
| U6972 | 2.4 | 2.4 | 2.5 | 2.4 | 2.5 | 2.8 | 2.8 | 2.8 | 2.5 |
| U6987 | 5.1 | 4.5 | 4.4 | 5.0 | 5.5 | 5.7 | 5.4 | 5.7 | 7.0 |
| U7316 | 1.2 | 1.1 | 1.1 | 1.1 | 1.1 | 1.3 | 1.3 | 1.3 | 1.1 |
| U7321 | 1.5 | 1.4 | 1.4 | 1.4 | 1.5 | 1.6 | 1.6 | 1.6 | 1.5 |
| U7324 | 1.3 | 1.2 | 1.3 | 1.2 | 1.2 | 1.4 | 1.4 | 1.4 | 1.2 |
| U7317 | 2.0 | 1.6 | 1.7 | 1.7 | 1.6 | 1.9 | 1.9 | 1.8 | 1.6 |
| U7318 | 2.8 | 2.7 | 2.9 | 2.9 | 2.6 | 3.3 | 3.4 | 3.3 | 2.7 |
| U7320 | 2.0 | 1.9 | 1.9 | 1.9 | 2.2 | 2.0 | 2.1 | 2.1 | 2.2 |
| U7322 | 1.8 | 1.7 | 1.7 | 1.7 | 1.5 | 1.7 | 1.8 | 1.7 | 1.4 |
| U7708 | 1.6 | 1.6 | 1.6 | 1.6 | 1.6 | 1.7 | 1.7 | 1.7 | 1.7 |
| U7713 | 1.4 | 1.6 | 1.6 | 1.6 | 1.5 | 1.6 | 1.6 | 1.6 | 1.5 |
| U7727 | 1.7 | 1.7 | 1.7 | 1.8 | 1.7 | 1.9 | 1.9 | 1.9 | 1.9 |
| U7794 | 1.9 | 1.8 | 1.9 | 1.8 | 1.6 | 1.7 | 1.8 | 1.7 | 1.6 |
| U7707 | 2.2 | 2.2 | 2.3 | 2.3 | 2.3 | 2.3 | 2.3 | 2.3 | 2.2 |
| U7710 | 2.3 | 2.5 | 2.6 | 2.7 | 2.8 | 2.7 | 2.9 | 3.0 | 3.0 |
| U7724 | 2.4 | 2.4 | 2.5 | 2.6 | 2.7 | 2.7 | 2.7 | 2.8 | 2.9 |
| U7738 | 2.4 | 2.3 | 2.4 | 2.5 | 2.2 | 2.4 | 2.5 | 2.6 | 2.3 |
| U8559 | 1.6 | 1.4 | 1.4 | 1.4 | 1.3 | 1.6 | 1.7 | 1.6 | 1.3 |
| U8570 | 1.2 | 1.2 | 1.2 | 1.2 | 1.3 | 1.2 | 1.2 | 1.2 | 1.3 |
| U8575 | 0.9 | 0.8 | 0.8 | 0.8 | 0.8 | 0.9 | 0.9 | 0.9 | 0.8 |
| U8555 | 2.6 | 2.4 | 2.5 | 2.6 | 2.6 | 2.9 | 3.1 | 3.0 | 2.6 |
| U8558 | 2.3 | 2.2 | 2.3 | 2.3 | 2.2 | 2.3 | 2.3 | 2.4 | 2.4 |
| U8563 | 2.2 | 2.3 | 2.3 | 2.4 | 2.3 | 2.4 | 2.4 | 2.5 | 2.5 |
| U9031 | 2.1 | 2.4 | 2.3 | 2.3 | 2.5 | 2.6 | 2.4 | 2.3 | 2.4 |
| U9032 | 1.7 | 1.7 | 1.7 | 1.7 | 1.6 | 1.9 | 1.9 | 1.7 | 1.5 |
| U9040 | 1.4 | 1.4 | 1.4 | 1.4 | 1.2 | 1.4 | 1.4 | 1.3 | 1.1 |
| U9034 | 3.0 | 2.9 | 2.8 | 3.0 | 4.0 | 3.4 | 3.4 | 3.5 | 3.8 |
| U9039 | 2.7 | 3.0 | 3.2 | 3.1 | 3.1 | 3.2 | 3.2 | 3.2 | 3.3 |
| U9049 | 3.5 | 3.3 | 3.5 | 3.5 | 3.5 | 3.6 | 3.8 | 3.6 | 3.7 |
| U9055 | 2.4 | 2.1 | 2.1 | 2.2 | 2.1 | 2.4 | 2.4 | 2.4 | 2.1 |
| U0048 | 1.8 | 1.8 | 1.8 | 1.8 | 1.7 | 1.9 | 2.0 | 2.0 | 1.8 |
| U0050 | 1.8 | 1.7 | 1.8 | 1.8 | 1.7 | 1.9 | 2.0 | 2.0 | 1.7 |
| U0056 | 1.6 | 1.5 | 1.5 | 1.5 | 1.4 | 1.8 | 1.8 | 1.7 | 1.5 |
| U0047 | 2.1 | 1.7 | 1.8 | 1.8 | 1.6 | 2.0 | 2.1 | 2.0 | 1.7 |
| U0058 | 3.2 | 2.8 | 2.9 | 3.0 | 3.0 | 3.3 | 3.4 | 3.2 | 3.3 |
| U0060 | 2.2 | 2.1 | 2.1 | 2.2 | 2.1 | 2.2 | 2.2 | 2.2 | 2.3 |
| U0062 | 2.8 | 2.6 | 2.7 | 2.8 | 2.7 | 3.0 | 3.2 | 3.2 | 2.9 |

TABLE 9

COMPARATIVE RESULTS

| Comparison on | n | r | m | b | Std. Error | Ng | Lassen |
|---|---|---|---|---|---|---|---|
| GInr vs GATFa | 129 | 0.997 | 0.879 | 0.163 | 0.079 | 7/129 = 5.4% | Delta <= 0.4 \| 5 @ 96.1%<br>Delta <= 0.7 \| 2 @ 98.4% |
| GInr vs GATFz | 129 | 0.986 | 0.948 | 0.078 | 0.162 | 3/129 = 2.3% | Delta <= 0.4 \| 4 @ 96.9%<br>Delta <= 0.7 \| 2 @ 98.4% |
| GInr vs GATFt2 | 129 | 0.974 | 0.935 | 0.413 | 0.221 | 20/129 = 15.5% | Delta <= 0.4 \| 16 @ 87.6%<br>Delta <= 0.7 \| 4 @ 96.9% |
| MInr vs MATFa | 129 | 0.996 | 0.921 | 0.122 | 0.092 | 9/129 = 7.0% | Delta <= 0.4 \| 2 @ 98.4%<br>Delta <= 0.7 \| 0 @ 100.0% |
| MInr vs MATFz | 129 | 0.989 | 0.908 | 0.190 | 0.155 | 7/129 = 5.4% | Delta <= 0.4 \| 4 @ 96.9%<br>Delta <= 0.7 \| 2 @ 98.4% |
| MInr vs MATFt2 | 129 | 0.983 | 0.893 | 0.491 | 0.193 | 8/129 = 6.2% | Delta <= 0.4 \| 13 @ 89.9%<br>Delta <= 0.7 \| 4 @ 96.9% |

Table 9 provides comparative data for the ATFa, ATFz and ATFt2 and INR values calculated by the WHO method for each respective location, with GInr representing one location for these traditionally WHO determined values, and MInr representing values based on data obtained at the other location. The values identified as ATFz and ATFt2, such as, GATFt2 and MATFt2, and GATFz and MATFz, represent anticoagulant therapy factors derived from the expressions (1) through (9) above, inclusive of expressions (5.1) and (8.1).

Further comparative results are provided in Table 10 to illustrate the effect of prothrombin time (PT) on INR values. Table 10 provides a comparison based on data from Table 3, and provides INR values for PT's of PT=PT (under the heading "INR"), PT=PT+0.5 (under the heading "+0.5"), PT=PT+

1.0 (under the heading "+1.0"), PT=PT+1.5 (under the heading "+1.5"), and PT=+2.0 (under the heading "+2.0"). The new anticoagulation therapy factor (ATFt2) was compared with the WHO method for determining ATF. The WHO method utilizes the mean prothrombin time of 20 presumed normal patients. The thromboplastin reagents list MNPT "expected ranges" listed in the accompanying thromboplastin-reagent (Tp) brochures. These brochures acknowledge that MNPT differences are inevitable because of variations in the 20 "normal donor" populations. Geometric, rather than arithmetic mean calculation limits MNPT variation somewhat, but simulated 0.5 second incremented increases over a total 2.5 second range, show ever-increasing INR differences notably at higher INR levels. To exemplify this, Table 10 shows these changes with Thromboplastin C Plus (which has a manufacturer's reported ISI=1.74 and MNPT=9.89 seconds) in POTENS+.

TABLE 10

| ID | PT | INR | +0.5 | +1.0 | +1.5 | +2.0 |
|---|---|---|---|---|---|---|
| WEC | 9.8 | 1.0 | 0.9 | 0.8 | 0.8 | 0.7 |
| A095 | 12.5 | 1.5 | 1.4 | 1.3 | 1.2 | 1.1 |
| A191 | 14.8 | 2.0 | 1.9 | 1.7 | 1.6 | 1.5 |
| A112 | 16.9 | 2.5 | 2.3 | 2.2 | 2.0 | 1.8 |
| A208 | 18.6 | 3.0 | 2.8 | 2.5 | 2.3 | 2.2 |
| A020 | 20.3 | 3.5 | 3.2 | 3.0 | 2.7 | 2.5 |
| A164 | 21.9 | 4.0 | 3.7 | 3.4 | 3.1 | 2.9 |

TABLE 10-continued

| ID | PT | INR | +0.5 | +1.0 | +1.5 | +2.0 |
|---|---|---|---|---|---|---|
| A093 | 24.5 | 4.9 | 4.5 | 4.1 | 3.8 | 3.5 |
| A055 | 26.5 | 5.6 | 5.1 | 4.7 | 4.4 | 4.0 |
| A090 | 28.5 | 6.3 | 5.8 | 5.3 | 4.9 | 4.6 |
| R091 | 32.2 | 7.8 | 7.2 | 6.6 | 6.1 | 5.7 |
| A058 | 33.8 | 8.5 | 7.8 | 7.2 | 6.6 | 6.2 |

Since the in-house determined MNPT would continue with that Tp lot, intralaboratory results would be relatively unaffected. However, between laboratory INR agreements, or interlab results, are compromised. As a denominator, considering the expression used to derive the MNPT, such as expression (B), above, MNPT is, of course, less problematic for INRs than the exponent, ISI. Comparative results, showing interlab results, are provided in Table 11. ATFt is seen to be numerically equal to WHO/INRs determined in both analytical instruments, namely, the MDA-Electra 9000C and the POTENS+. Identical computer bits derived in POTENS+ from the absorbances creating the thrombin-fibrinogen-fibrin clotting curve are used for the POTENS+WHO/INR and ATFt (NO ISI, NO MNPT) determinations. MNPT is, of course, still necessary for the WHO method. For ATFt, Zero Order Kinetics Line's slope is extended in both directions to intersect with the Tp-plasma baseline and the absorbance at total fibrin formation. The sum of this interval and the time from the Tp injection to the beginning of Zero Order Kinetics ($T_2S$) is Value 1. Value 2 is $T_2S/100e$. "e" is the Natural Logarithm, base 2.71828. ATFt=(Value 1)*(Value 2), in accordance with expression (4) herein (and the expression (8.1) for ATFt2).

Table 11 provides statistical comparisons for results obtained using two POTENS+ coagulometers (one designated as GINR and another designated as MINR), and using a Bio Merieux MDA-180 coagulometer (designated as AINR). The POTENS+, WHO/INRs, INRzs, and ATFts and the MDA-180 (AINR) WHO/INRs are compared. Statistical data and Bland-Altman plot data demonstrate that the new anticoagulant therapy factor ATFt may replace WHO/INR and provide results which are within the parameters of traditional therapeutic or reference ranges.

TABLE 11

|  |  | "r" | "m" | "b" | StdErr | StdDev | mY | mX | My/mX |
|---|---|---|---|---|---|---|---|---|---|
| AINR |  |  |  |  |  |  |  |  |  |
| vs | GINR | 0.937 | 0.872 | 0.290 | 0.388 | 1.148 | 2.169 | 2.155 | 1.007 |
|  | GATFz | 0.941 | 1.119 | −0.208 | 0.378 | 1.022 | 2.169 | 2.124 | 1.021 |
|  | GATFt2 | 0.951 | 1.003 | 0.146 | 0.343 | 1.081 | 2.169 | 2.016 | 1.076 |
|  | MINR | 0.950 | 1.018 | −0.126 | 0.349 | 1.070 | 2.169 | 2.253 | 0.963 |
|  | MATFz | 0.943 | 1.020 | −0.040 | 0.371 | 1.065 | 2.169 | 2.167 | 1.001 |
|  | MATFt2 | 0.937 | 0.872 | 0.290 | 0.388 | 1.148 | 2.169 | 2.155 | 1.007 |
| MINR |  |  |  |  |  |  |  |  |  |
| vs MINRz | GINR | 0.971 | 1.036 | 0.039 | 0.247 | 1.001 | 2.253 | 2.136 | 1.055 |
| vs MINRt2 | GINRz | 0.984 | 1.082 | −0.132 | 0.186 | 0.978 | 2.167 | 2.124 | 1.020 |
| vs | GINRt2 | 0.979 | 1.110 | −0.083 | 0.242 | 1.123 | 2.155 | 2.016 | 1.069 |

The linear regression analysis expression y=mx+b, when solved for the slope, m, is expressed as (y−b)/x. This is biased, so the expression is y/x is when b is equal to zero. The comparison in Table 11, above, provides comparative data for mean y (mY) and mean x (mX) values, including the slope mY/mX. The use of mY/mX is used to provide comparative results.

In another embodiment, an article may be provided to derive an anticoagulant therapy factor (ATF). The article may comprise stored instructions on a storage media which can be read and processed with a processor. For example, the computer may be provided with a stored set of instructions, or chip, which is programmed to determine a new ATF for the spectral data obtained from the coagulation activity of a sample. For example, the computer chip may be preprogrammed with a set of instructions for cooperating with the output of a photodetection device, such as, the device shown and described in FIG. 1, which provides electrical data to said computer processor and/or storage device as a function of the optical density for a sample being analyzed. The chip may be employed in, or used with, an apparatus having input means and storage means for storing data. The set of instructions on the chip includes instructions for carrying out the steps of determining one or more anticoagulant therapy factors based on the expressions (1) through (9), inclusive of expressions (5.1) and (8.1).

According to alternate embodiments, methods for determining an anticoagulant therapy factor are provided to derive an INR. The customary classical INR (also referred to herein as $INR_m$) has been the laboratory standard of care for monitoring oral anticoagulant therapies, such as, for example, coumarin therapy, for 25 years. However, the classical INR (INRm) which is discussed in the background, above, is cumbersome, and suffers from exponential inaccuracies. According to an alternate embodiment, the exponent-derived $INR_m$ (that is, the manufacturer's INR) may be supplantable by carrying out a clotting reaction and recording absorbance values over time intervals. The alternate INR (INRn) may be determined by computing the representative area of a trapezoid formed within the clotting curve absorbance, as determined by the absorbance values for the clotting reaction of a patient sample. According to preferred embodiments, the trapezoidal area is provided to approximate area under the clotting curve. According to this embodiment, the ISI and MNPT are eliminated. The sample of a person's blood or blood component is obtained and reacted with the coagulant, such as thromboplastin C, and the corresponding time and absorbance values for the clotting reaction of the sample are recorded.

The INRn may be used to determine and regulate treatment for a patient, including administration of anticoagulant therapy, and other blood therapy applications. According to one embodiment of the method, obtaining values for an area in connection with a blood clotting analysis is used to derive a corresponding INR value (INRn) (e.g., a value that may be used as the INR value is used). For example, according to a preferred embodiment, an Area T, which may be made up of two sides S1 and S2, an upper base S3 and a lower base S4, may be derived to generate an INR value, INRn. An INRn value may be derived from clotting curve data, wherein one or more locations along the clotting curve may be used to determine values corresponding to a designated area, as in accordance with preferred embodiments, may be represented by a trapezoidal area, such as that area represented by Area T. According to a preferred embodiment, the area is a two dimensional planar location, and, for example, may comprise a designated area located in a quadrant of an ordinate and abscissa corresponding with clotting curve time and absorbance values. The clotting curve and absorbance values, preferably, may be obtained with the use of a photodetection apparatus, and a computer that records the electrical output of the detection components. For example, a linear-output photo-optical coagulometer may be used to obtain optically responsive signal data from the sample, as the clotting reaction takes place. This reaction and absorbance data collection may be conducted as described herein in conjunction with the use of a coagulometer, such as the instrument illustrated in FIG. 1, or other suitable absorbance measuring device. Preferred devices are described herein and may be configured with the instructions to provide the INRn.

As illustrated in connection with FIG. 6, a clotting curve is shown. An Area T is identified in the first quadrant where the clotting curve of a coagulation reaction is illustrated. The Area T derivation may be used to derive a corresponding INRn value for the patient sample that generated the information represented by the clotting curve. The INRn values obtained by the method and apparatus are useful in determining the treatment course for an individual, based on the INRn value.

According to a preferred embodiment, the INRn may be expressed with the following formulae:

$$INRn = (\text{Area } T) * MUL \quad (10)$$

The MUL is a multiplier that is based on two relationships that are addressed by the multiplier. MUL relates the sampling rate of the instrument and the pixel parity of the x-y axis. The instrument used to measure the optical changes in the sample generates values, and preferably, the values, or signals are taken at a particular frequency. For example, a preferred sampling rate for the clotting curve reaction of a patient blood or blood component sample may be a number of optical absorbance values in a particular time interval. A preferred rate, for example, may be 100 optical absorbance values (or samples) per second, expressed 100/second. The sample rate preferably is used to derive a multiplier component, MUL. Also used to derive the multiplier component is the parity value, which is a multiplier utilized to create x-y pixel parity for the clotting curve information (that is shown expressed on the clotting curve graph, see FIG. 6). According to the example illustrated, the sampling rate used was 100 values per second. The pixel parity multiplier was 0.535. The multiplier, according to this example, is 0.535 (pixel parity value)/100 (the number of samples reflected in a second). The multiplier, or MUL, according to a preferred embodiment, was 0.00535.

In order to derive the INRn, the clotting curve is considered, and the theoretical or hypothetical zero order kinetic line, or line L as it is referred to and appears on the Figures, provides an (x,y) coordinate of (TEOT, 0), where the time value at which the clotting reaction, if theorized from the slope or line taken between the point where the maximum acceleration of the conversion rate of fibrinogen transformation begins (T2S) and the end of the maximum conversion (which is the last highest delta value of conversion rate), which is T2 or Tmap. The value, TEOT, is a time value, and generally, for example, may be expressed in seconds. As illustrated, the right side S2, may be designated to correspond with the line formed between the point (t1, c1) and TEOT. According to an alternate embodiment, the slope of the line L may corresponds with the slope of the side S2 of trapezoidal Area T. For example, according to some embodiments, the line L may form the side S2 of the trapezoid whose area is illustrated as Area T.

Figure 6:
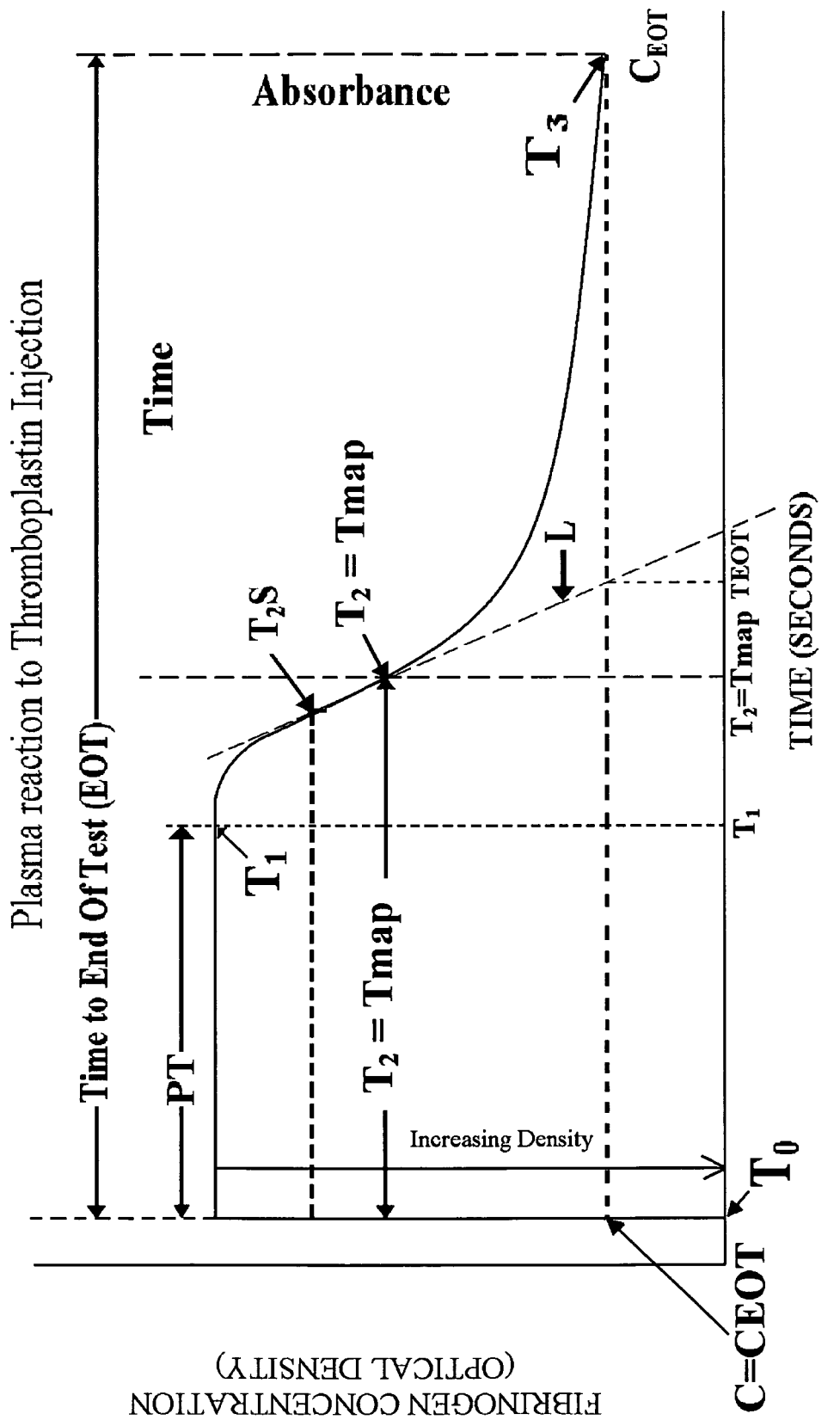
FIG. 6 is another plot of the various phases of the fibrinogen concentration occurring in a typical plasma clotting process.
Figure 7:
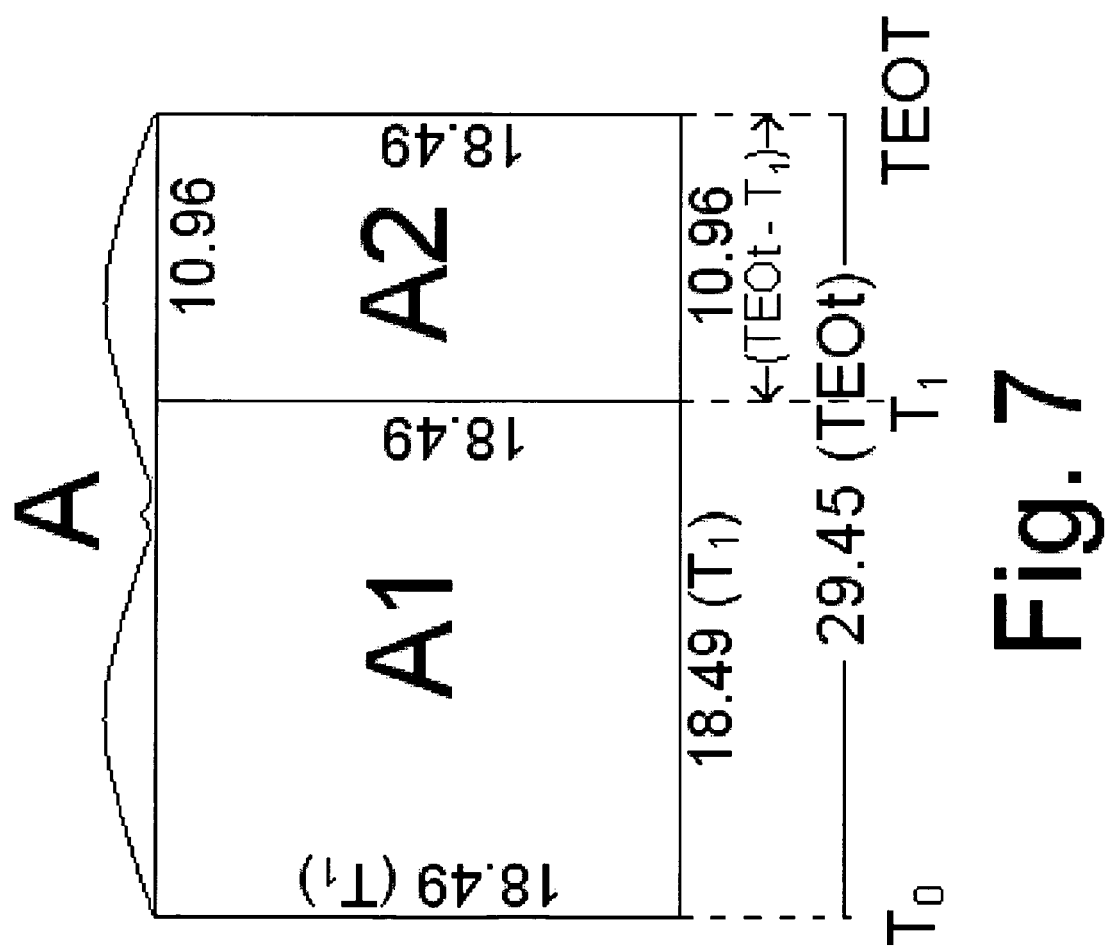
FIG. 7 is an illustration showing a preferred embodiment of the area determination and representational clotting area formed based on data from the clotting curve reaction shown in FIG. 6.

As shown in the preferred embodiments illustrated in FIGS. 6 and 7, a segment of the line from TEOT and the point on the clotting curve T1, forms the trapezoid side S2.

With the multiplier MUL, the INRn may be derived according to the following expression:

$$INRn = ((T1 + TEOT)/2) * 0.00535 * T2 \quad (11)$$

As illustrated in FIG. 7, the lower base, S4, of the trapezoid TP, is the time value of the theoretical or hypothetical end of the coagulation test, TEOT. The time value component TEOT includes the time value of T2 plus the time value (Tiut) to convert the remainder of the fibrinogen in the sample that is considered to provide active optical activity (by the theoretical time value of the end of the test, TEOT). Both the Teot and TSot are values that are determined from the absorbance readings for a sample in a coagulation reaction. Dividing the difference in Instrument Units (IU) @ T2S to IU @ T2 (which is IUX) by the time it takes this conversion T2S to T2 (which may be represented by the time interval, Tiux) gives the maximum transformation rate for a specific sample. Using this specific test rate (IUX/Tiux), it is determined how long it would take to convert the fibrinogen from T2S to T3 (end of test) and add this value to T2S. This gives the TEot. Another value listed in the data Table 14 is the TSot which is the hypothetical start of test. The TSot is similar to the TEot, the hypothetical end of test. (The TEot, according to some embodiments, also may be referred to herein as a theoretical end of test.) The time that it takes to convert the IU@T1 to IU@T2S (which may be expressed as the difference between T1 and T2S (the value Tcon)) may be determined using the same rate of change. The TSot is determined by subtracting the time (Tcon) from T2S to give the TSot. The TSot may come before or after T1 and the TEot will always come before T3.

Referring again to FIG. 7, an upper base, S3, is indicated to correspond with the time of the start of the clot formation when the coagulation reaction is carried out. The start time of the clotting is represented by the time, T1, as shown in FIG. 6. With the upper and lower bases, S3 and S4, respectively, being ascertained through the clotting reaction times, they may be averaged (e.g., divided by 2). The S3,S4 average may be used to derive a trapezoidal area, such as, for example, Area T, represented by the clotting absorbance signal data. The altitude S1 (or height) of the trapezoidal area, Area T, is derived by the value of the point of time (T1) where the beginning of the conversion of fibrinogen to fibrin for the patient sample is determined. That point is represented as time value T1 on FIGS. 6 and 7. The height component of the trapezoid represented by Area T is designated to correspond with the side S1. The height component is assigned the value T1*MUL (T1 multiplied by the multiplier).

The INRn may be determined for a patient sample by determining (i) when the clot formation begins, which is represented by the time value T1, (ii) when the clotting commences a maximum conversion rate (of conversion of fibrinogen to fibrin in the patient sample), which is represented by the time value T2, and (iii) the end of the maximum conversion rate, represented by the time value T3 (the end of the maximum conversion rate). Therefore, according to embodiments of the present method and apparatus, a new INR determination that, through the transformation of information (e.g., signals corresponding to optical activity of a clotting reaction), may be derived by (i) determining the start of the clotting when a reagent (such as, for example, thromboplastin C) is reacted with a blood or blood component sample of a person (by determining the length of time from the introduction of the reagent and sample to the time clotting begins, which is T1), (ii) determining the start of the maximum acceleration rate of conversion for the clotting reaction that began at time T1) which is represented by the time T2, and (ii) determining the value of the end of the maximum conversion rate for the clotting reaction, which is represented by the value T3.

The present method and apparatus may be used to derive an INR, INRn, which does not utilize exponential components, and therefore, is not subject to exponential inaccuracies that have previously been experienced in connection with traditional INR determinations. The INRn value may be used to monitor a patient's blood or blood components for administration of oral anticoagulant therapy, such as, for example, coumarin, and other treatment agents, including those discussed herein. The present method and apparatus preferably, according to a preferred embodiment, where INRn is derived (and may be used for treatment administration of anticoagulant therapy).

The clotting curve illustrates a representation of absorbance values for a clotting reaction where substantially optically clear fibrinogen converts to turbid fibrin, hence reducing the absorbance unit values, as indicated on the abscissa. The point of intersection of the line L with the x-axis, or the time axis, preferably, may be derived using the value T2S and adding to that time value, the time required to convert additional fibrinogen in the sample, which is the time value corresponding with the absorbance value IUT (in instrument units). The TEOT value may be derived from the intercept that the slope of the line L defined by T2S and T2 makes with the x-axis. However, as described herein, the x axis would, in theory, be where y=0, and accordingly, since some signal may be detected (and hence not zero), the trapezoidal lower base S4 (FIGS. 6 and 7) may be represented along y=Ceot, between times T0 and TEot. According to a preferred embodiment, the TEOT value may be derived by the following determination:

$$TEOT = T2S + (ZTM/IUX * IUT) \quad (12)$$

where ZTM is the time (in seconds) to convert the fibrinogen corresponding to the time interval between T2S and T2, or in other words, the time to convert the IUX absorbance value (the IUX being the difference between instrument units (or IU) at T2S (IU@T2S) and instrument units at T2 (IU@T2)). The IUT value is the difference between instrument units (or IU) at T2S (IU@T2S) and instrument units at T3 (IU@T3).

A method was carried out using the Dade Behring Thromboplastin C Plus (Dade TPC+) as the reagent. The number of patient samples that were reacted and used to obtain the following data was 218. The WHO INR (the World Health Organization INR is the average of INR values from five different thromboplastins. The INRm is the manufacturer's INR. INRz is the INR that is derived using the exponent (2-FTR) instead of the ISI (as described herein (see formulae (1), (2), (3), (3.1), above). INRn (uses no ISI and no MNPT values for its determination) and is the calculation for the INR in accordance with the alternate embodiment described herein and represented by the formula INRn=((T1+TEOT)/2)*0.00535*T2, which is formula (II), above.

Coagulation reactions were carried out for a number of individuals, using the blood samples from the individuals, prepared as indicated herein in connection with clotting reactions, where a clotting reagent is added to the blood sample, and preferably a blood plasma sample. The absorbance values (measured in instrument units) were obtained for the sample throughout the coagulation reaction using a linear-output photo-optical coagulometer, POTENS+. The clotting agent used was thromboplastin reagent (Tp) which was injected into citrated human blood plasma. The clotting curve absorbance values were tracked as optically-clear fibrinogen (Fg) (also referred to as FBG herein) converts into turbid fibrin. The table below provides the values of the absorbance and time data that was obtained. By extending the slope L derived by the slope of the curve where the maximum conversion rate of fibrinogen occurs, a trapezoid is formed whose area may be derived and used to provide a value, INRn, which is essentially equal to the traditionally obtained INR values.

TABLE 12

Comparative Summary

| INK WHO (INRw) Versus | NG Discordant | LASSEN Agreement | | Poller Diff >10% | Highest Percent |
|---|---|---|---|---|---|
| | | <=0.4 | <=0.7 | | |
| vs. $INR_M$ | 13.8% | 85.3% | 95.9% | 9/218 4.1% | 18.3% |
| vs. $INR_Z$ | 10.1% | 89.4% | 96.3% | 7/218 3.2% | 15.2% |
| vs. $INR_N$ | 9.2% | 88.5% | 96.3% | 12/218 5.5% | 14.8% |

Table 12 provides comparative data for INRm, INRz and INRn values compared with INR values calculated by the INR WHO method (which is also represented as INRw). The INR obtained using the WHO method (INRw) was compared with each of the alternate INR determinations, including INRm (using the manufacturer's INR), INRz, using the expressions of the above formulae (1), (2), (3), (3.1), as discussed herein, and INRn, using the expressions of the above formulae (10), (11), (12).

Further details of the comparative data are provided in Table 13 to illustrate values for each of the INR WHO comparisons.

TABLE 13

COMPARATIVE SUMMARY DETAILS using
DADE TPC + Thromboplastin

WHO INR vs INRm Specimens
Using NG algorithm
Number of mismatches 30/218 = 13.8%

| Range | <2.0 | 13(13, 0)/79 | 16.5% |
|---|---|---|---|
| Range | 2.0 to 3.0 | 12(10, 2)/91 | 13.2% |
| Range | >3.0 to 4.5 | 5(4, 1)/37 | 13.5% |
| Range | >4.5 | 0(0, 0)/11 | 0.0% |

Lassen values
Samples: 218 delta <= 0.4 32@ 85.3% delta <= 0.7 9@ 95.9%

WHO INR vs INRz Specimens
Using NG algorithm
Number of mismatches 22/218 = 10.1%

| Range | <2.0 | 11(11, 0)/79 | 13.9% |
|---|---|---|---|
| Range | 2.0 to 3.0 | 5(4, 1)/91 | 5.5% |
| Range | >3.0 to 4.5 | 5(2, 3)/37 | 13.5% |
| Range | >4.5 | 1(0, 1)/11 | 9.1% |

LASSEN values
Samples: 218 delta <= 0.4 23@ 89.4% delta <= 0.7 8@ 96.3%

INRw vs. INRn Specimens
Using NG algorithm
Number of mismatches 20/218 = 9.2%

| Range | <2.0 | 1(1, 0)/79 | 1.3% |
|---|---|---|---|
| Range | 2.0 to 3.0 | 13(4, 9)/91 | 14.3% |
| Range | >3.0 to 4.5 | 6(4, 2)/37 | 16.2% |
| Range | >4.5 | 0(0, 0)/11 | 0.0% |

TABLE 13-continued

COMPARATIVE SUMMARY DETAILS using
DADE TPC + Thromboplastin

LASSEN values
Samples: 218 delta <= 0.4 25@ 88.5% delta <= 0.7 8@ 96.3%

The sample data upon which the above data summaries were based, is provided in Table 14. Table 14 provides corresponding data for a coagulation study. In Tables 14 and 15, the following references are used, and may be further identified by reference to FIG. 8:

ID—Sample ID

T0—Time of thromboplastin reagent injection

T1—Start of the clot formation

T2S—Start of maximum conversion rate

T2—End of maximum conversion rate. (Last highest delta value of conversion rate.)

T3—$(T_4-T_{2s})$

T4—Hypothetical End Of Test (HEOT)

IU—Instrument unit

IUT—Delta IU between IU@T2S and IU@T3

RTX—Delta IU between IU@T2S and IU@T2

IUA—Altitude component value of the trapezoidal area (in instrument units) (c1-ceot)

IUL—Length component value of the trapezoidal area (in instrument units)

ZTM—Time in seconds to convert the IUX (T2-T2S)

TEOT—Hypothetical End Of Test. (Time at T2S plus the time to convert IUT.)

TSot—Hypothetical Start Of Test

Fg—Fibrinogen concentration of the blood sample (in g/l)

c1—Absorbance value (in instrument units) at time of the start of the clot formation (T1)

cT2S—Absorbance value (in instrument units) at the time of the start of maximum conversion rate (T2S)

c2—Absorbance value (in instrument units) at time of the end of maximum conversion rate (T2). (Last highest delta value of conversion rate.)

ceot—Absorbance value (in instrument units) at time TEOT

TABLE 14

| ID | WHO | INRm | INRz | INRn | T1 | T2S | T2 | T3 | TSot | TEot |
|---|---|---|---|---|---|---|---|---|---|---|
| A001 | 3.00 | 3.08 | 2.55 | 2.38 | 18.89 | 22.04 | 23.89 | 49.55 | 19.66 | 29.44 |
| A002 | 2.88 | 3.32 | 2.56 | 2.19 | 19.71 | 23.00 | 24.42 | 37.75 | 20.87 | 27.61 |
| A003 | 2.78 | 3.33 | 2.55 | 2.41 | 19.75 | 23.10 | 25.48 | 37.55 | 20.94 | 28.51 |
| A004 | 2.08 | 2.03 | 2.03 | 1.66 | 14.85 | 19.66 | 21.62 | 37.55 | 16.89 | 24.96 |
| A005 | 2.30 | 2.87 | 2.31 | 2.04 | 18.11 | 21.69 | 23.83 | 37.55 | 19.36 | 26.75 |
| A007 | 1.85 | 2.03 | 1.78 | 1.45 | 14.86 | 18.19 | 20.18 | 33.95 | 15.87 | 22.83 |
| A008 | 2.83 | 2.62 | 2.42 | 2.17 | 17.22 | 21.59 | 23.63 | 41.95 | 18.97 | 28.20 |
| A009 | 2.70 | 3.38 | 2.65 | 2.47 | 19.91 | 23.91 | 26.43 | 37.87 | 21.39 | 29.31 |
| A010 | 1.65 | 1.88 | 1.61 | 1.24 | 14.22 | 17.16 | 19.27 | 30.15 | 14.73 | 21.38 |
| A011 | 1.83 | 2.09 | 1.71 | 1.34 | 15.10 | 17.90 | 19.32 | 33.75 | 15.57 | 22.26 |
| A012 | 2.68 | 3.17 | 2.47 | 2.03 | 19.21 | 22.40 | 23.94 | 36.95 | 19.78 | 27.33 |
| A013 | 3.30 | 3.44 | 2.92 | 2.86 | 20.13 | 24.09 | 26.68 | 50.15 | 21.60 | 31.76 |
| A014 | 1.60 | 1.78 | 1.55 | 1.12 | 13.76 | 17.01 | 18.35 | 30.15 | 14.78 | 20.43 |
| A015 | 1.70 | 1.88 | 1.60 | 1.20 | 14.23 | 17.15 | 18.96 | 28.30 | 14.74 | 21.17 |

TABLE 14-continued

| ID | WHO | INRm | INRz | INRn | T1 | T2S | T2 | T3 | TSot | TEot |
|---|---|---|---|---|---|---|---|---|---|---|
| A016 | 2.73 | 3.02 | 2.53 | 2.14 | 18.68 | 22.33 | 23.35 | 45.75 | 19.91 | 27.94 |
| A017 | 1.70 | 1.78 | 1.63 | 1.24 | 13.76 | 17.29 | 18.86 | 31.35 | 14.82 | 21.66 |
| A018 | 2.18 | 2.17 | 1.91 | 1.60 | 15.44 | 18.77 | 21.23 | 34.55 | 16.09 | 24.36 |
| A019 | 1.85 | 1.82 | 1.71 | 1.41 | 13.97 | 17.58 | 19.30 | 36.75 | 15.29 | 22.74 |
| A020 | 3.80 | 3.52 | 2.93 | 2.75 | 20.40 | 25.35 | 28.02 | 42.75 | 22.47 | 31.31 |
| A021 | 2.63 | 2.83 | 2.39 | 2.08 | 17.98 | 21.51 | 23.37 | 37.35 | 18.91 | 27.65 |
| A022 | 2.08 | 2.18 | 1.92 | 1.59 | 15.46 | 19.01 | 20.55 | 36.75 | 16.65 | 24.14 |
| A023 | 3.20 | 3.11 | 2.55 | 2.20 | 18.98 | 22.51 | 23.92 | 43.35 | 20.09 | 28.15 |
| A024 | 3.03 | 3.39 | 3.05 | 2.81 | 19.94 | 25.22 | 27.22 | 45.28 | 22.66 | 31.44 |
| A025 | 1.73 | 1.84 | 1.51 | 1.06 | 14.03 | 16.98 | 18.01 | 27.40 | 15.09 | 19.73 |
| A026 | 1.45 | 1.60 | 1.45 | 1.11 | 12.94 | 15.96 | 17.58 | 31.69 | 13.53 | 20.52 |
| A027 | 1.45 | 1.48 | 1.36 | 1.05 | 12.41 | 15.34 | 16.91 | 33.35 | 13.12 | 19.77 |
| A028 | 1.90 | 1.93 | 1.73 | 1.41 | 14.41 | 17.80 | 19.22 | 39.15 | 15.38 | 22.98 |
| A029 | 2.20 | 2.06 | 1.85 | 1.59 | 14.99 | 18.36 | 20.31 | 40.55 | 16.07 | 23.96 |
| A030 | 2.50 | 2.61 | 2.25 | 2.05 | 17.17 | 20.52 | 22.08 | 48.75 | 18.18 | 27.54 |
| A031 | 2.43 | 2.75 | 2.25 | 1.95 | 17.69 | 21.07 | 23.20 | 35.84 | 18.55 | 26.49 |
| A032 | 3.63 | 3.83 | 3.33 | 2.88 | 21.40 | 25.84 | 26.78 | 48.15 | 23.33 | 32.26 |
| A033 | 2.65 | 2.94 | 2.52 | 2.22 | 18.39 | 22.44 | 24.46 | 41.95 | 19.79 | 28.37 |
| A034 | 2.08 | 2.24 | 1.96 | 1.69 | 15.71 | 19.14 | 20.89 | 38.95 | 16.92 | 24.62 |
| A035 | 4.00 | 4.87 | 3.71 | 4.36 | 24.58 | 29.96 | 34.33 | 47.75 | 27.15 | 38.08 |
| A036 | 2.98 | 3.19 | 2.51 | 2.47 | 19.26 | 21.94 | 24.50 | 43.55 | 19.89 | 29.11 |
| A037 | 2.20 | 2.50 | 2.32 | 1.97 | 16.73 | 21.61 | 23.71 | 36.95 | 18.96 | 26.80 |
| A038 | 1.45 | 1.57 | 1.35 | 0.99 | 12.82 | 15.48 | 16.81 | 29.69 | 13.15 | 19.36 |
| A039 | 1.50 | 1.46 | 1.39 | 0.99 | 12.27 | 15.70 | 17.37 | 28.67 | 13.27 | 19.34 |
| A040 | 2.28 | 2.39 | 2.06 | 1.79 | 16.33 | 19.59 | 21.24 | 39.75 | 17.17 | 25.75 |
| A041 | 2.18 | 2.30 | 2.14 | 1.88 | 15.95 | 19.93 | 21.44 | 45.15 | 17.29 | 26.82 |
| A042 | 3.40 | 4.07 | 3.36 | 3.15 | 22.16 | 26.65 | 29.21 | 49.35 | 23.45 | 33.90 |
| A044 | 3.38 | 4.31 | 3.31 | 2.90 | 22.90 | 26.85 | 28.41 | 41.15 | 24.38 | 31.92 |
| A045 | 2.60 | 2.70 | 2.44 | 2.26 | 17.52 | 21.56 | 24.20 | 45.75 | 18.92 | 28.64 |
| A047 | 2.45 | 2.81 | 2.46 | 2.24 | 17.90 | 21.99 | 24.21 | 41.55 | 19.51 | 28.26 |
| A048 | 3.38 | 3.82 | 3.13 | 3.15 | 21.35 | 25.34 | 28.49 | 46.15 | 22.61 | 33.32 |
| A049 | 2.28 | 2.68 | 2.15 | 1.99 | 17.42 | 20.04 | 22.56 | 39.55 | 17.88 | 26.34 |
| A050 | 2.70 | 2.80 | 2.49 | 2.17 | 17.86 | 22.06 | 24.08 | 40.75 | 19.20 | 28.46 |
| A051 | 1.88 | 1.91 | 1.64 | 1.32 | 14.35 | 17.45 | 18.41 | 35.55 | 15.19 | 22.32 |
| A052 | 2.55 | 2.82 | 2.31 | 2.05 | 17.94 | 20.98 | 22.93 | 40.35 | 18.50 | 27.36 |
| A053 | 2.88 | 3.06 | 2.48 | 2.09 | 18.82 | 22.39 | 24.07 | 38.75 | 19.78 | 27.62 |
| A054 | 1.90 | 2.07 | 1.78 | 1.48 | 15.04 | 18.09 | 20.21 | 33.15 | 15.84 | 22.99 |
| A055 | 6.58 | 5.56 | 4.81 | 5.66 | 26.51 | 31.27 | 36.08 | 70.15 | 28.32 | 45.39 |
| A056 | 3.48 | 3.58 | 3.19 | 3.09 | 20.60 | 25.34 | 27.68 | 53.15 | 22.73 | 33.17 |
| A057 | 2.58 | 2.85 | 2.23 | 1.87 | 18.05 | 21.05 | 22.66 | 35.15 | 18.72 | 25.88 |
| A058 | 7.40 | 8.47 | 7.73 | 8.65 | 33.76 | 41.78 | 45.33 | 79.97 | 37.98 | 55.47 |
| A059 | 2.25 | 2.93 | 2.27 | 1.99 | 18.34 | 21.38 | 23.74 | 34.15 | 18.82 | 26.69 |
| A060 | 2.43 | 3.15 | 2.54 | 2.21 | 19.12 | 23.19 | 25.32 | 36.55 | 20.59 | 28.16 |
| A061 | 2.25 | 2.49 | 2.17 | 1.97 | 16.70 | 20.05 | 22.25 | 38.35 | 17.68 | 26.82 |
| A062 | 6.35 | 6.20 | 6.43 | 6.80 | 28.21 | 37.32 | 40.28 | 78.95 | 33.62 | 49.72 |
| A063 | 2.65 | 3.04 | 2.63 | 2.61 | 18.75 | 22.31 | 25.84 | 42.15 | 19.59 | 30.73 |
| A064 | 2.05 | 2.21 | 1.92 | 1.55 | 15.59 | 19.19 | 21.08 | 32.55 | 16.76 | 23.78 |
| A065 | 2.28 | 2.65 | 2.47 | 2.22 | 17.32 | 22.25 | 24.96 | 39.75 | 19.39 | 28.42 |
| A066 | 1.83 | 1.99 | 1.67 | 1.24 | 14.69 | 17.83 | 19.19 | 30.15 | 15.50 | 21.52 |
| A067 | 1.78 | 1.75 | 1.62 | 1.30 | 13.63 | 17.02 | 18.52 | 36.75 | 14.49 | 22.31 |
| A068 | 2.68 | 2.65 | 2.13 | 1.90 | 17.30 | 19.97 | 21.86 | 37.35 | 17.76 | 26.11 |
| A069 | 2.10 | 2.41 | 1.92 | 1.41 | 16.41 | 19.35 | 20.15 | 31.95 | 16.95 | 23.19 |
| A070 | 1.65 | 2.38 | 1.97 | 1.58 | 16.29 | 19.40 | 20.80 | 37.55 | 16.92 | 24.25 |
| A071 | 1.73 | 1.89 | 1.73 | 1.44 | 14.25 | 17.63 | 19.53 | 39.50 | 15.23 | 23.03 |
| A072 | 1.60 | 1.82 | 1.69 | 1.45 | 13.97 | 17.27 | 18.98 | 43.55 | 14.80 | 23.54 |
| A073 | 1.48 | 1.49 | 1.50 | 1.21 | 12.46 | 16.14 | 17.82 | 37.75 | 13.77 | 21.33 |
| A074 | 1.65 | 1.71 | 1.59 | 1.26 | 13.44 | 16.86 | 19.03 | 33.35 | 14.56 | 21.33 |
| A075 | 1.58 | 1.57 | 1.21 | 0.75 | 12.80 | 14.89 | 15.87 | 23.28 | 13.18 | 16.85 |
| A076 | 1.45 | 1.44 | 1.37 | 1.11 | 12.18 | 15.39 | 16.78 | 37.55 | 13.01 | 20.65 |
| A077 | 4.63 | 4.64 | 4.03 | 4.26 | 23.88 | 28.45 | 31.55 | 64.71 | 25.61 | 39.30 |
| A078 | 2.05 | 2.16 | 1.88 | 1.64 | 15.41 | 18.55 | 20.89 | 35.71 | 16.35 | 24.06 |
| A080 | 6.13 | 7.35 | 6.42 | 8.00 | 31.12 | 35.48 | 40.50 | 86.95 | 32.86 | 55.56 |
| A081 | 3.55 | 3.76 | 3.63 | 3.30 | 21.18 | 26.98 | 28.55 | 57.95 | 23.84 | 35.22 |
| A082 | 1.53 | 1.54 | 1.55 | 1.29 | 12.69 | 16.24 | 18.15 | 43.55 | 13.76 | 22.16 |
| A083 | 1.60 | 1.60 | 1.38 | 0.98 | 12.97 | 15.82 | 16.98 | 28.23 | 13.50 | 19.41 |
| A084 | 6.98 | 6.67 | 5.72 | 6.91 | 29.43 | 33.64 | 38.19 | 76.55 | 30.96 | 51.04 |
| A085 | 3.10 | 3.27 | 3.01 | 3.29 | 19.55 | 24.14 | 29.21 | 48.15 | 21.22 | 34.28 |
| A086 | 2.45 | 2.85 | 2.35 | 2.11 | 18.07 | 21.11 | 22.84 | 46.95 | 18.57 | 27.93 |
| A087 | 1.93 | 1.84 | 1.69 | 1.40 | 14.06 | 17.40 | 19.24 | 37.00 | 15.03 | 22.74 |
| A088 | 1.78 | 1.71 | 1.64 | 1.35 | 13.44 | 17.15 | 18.79 | 37.95 | 14.80 | 22.43 |
| A089 | 2.18 | 2.28 | 1.83 | 1.44 | 15.90 | 18.76 | 20.00 | 33.95 | 16.62 | 22.82 |
| A090 | 5.93 | 6.31 | 5.59 | 6.68 | 28.51 | 33.63 | 38.36 | 84.35 | 30.64 | 49.81 |
| A091 | 8.23 | 7.68 | 6.96 | 7.83 | 31.91 | 38.95 | 42.75 | 74.75 | 35.15 | 53.48 |
| A092 | 2.00 | 1.91 | 2.03 | 1.81 | 14.36 | 19.10 | 21.48 | 50.15 | 16.41 | 26.06 |
| A093 | 4.30 | 4.86 | 3.81 | 4.26 | 24.53 | 28.21 | 31.94 | 53.15 | 25.81 | 38.07 |
| A094 | 2.53 | 3.17 | 2.94 | 2.41 | 19.18 | 24.61 | 25.77 | 42.95 | 22.06 | 29.60 |
| A095 | 1.43 | 1.50 | 1.43 | 1.15 | 12.48 | 15.73 | 17.24 | 37.76 | 13.36 | 20.91 |
| A096 | 1.80 | 2.12 | 1.69 | 1.29 | 15.22 | 17.85 | 19.14 | 30.95 | 15.59 | 21.88 |

TABLE 14-continued

| ID | WHO | INRm | INRz | INRn | T1 | T2S | T2 | T3 | TSot | TEot |
|---|---|---|---|---|---|---|---|---|---|---|
| A097 | 1.40 | 1.32 | 1.11 | 0.76 | 11.59 | 13.74 | 14.88 | 27.05 | 11.21 | 17.41 |
| A098 | 1.45 | 1.40 | 1.32 | 1.04 | 11.98 | 14.78 | 16.59 | 34.95 | 12.54 | 19.69 |
| A099 | 1.53 | 1.81 | 1.52 | 1.17 | 13.93 | 16.63 | 18.24 | 30.15 | 14.48 | 20.60 |
| A100 | 1.40 | 1.41 | 1.40 | 1.18 | 12.06 | 15.39 | 17.01 | 39.15 | 13.23 | 21.06 |
| A101 | 2.45 | 2.76 | 2.39 | 2.26 | 17.71 | 21.22 | 24.16 | 42.97 | 18.67 | 28.47 |
| A102 | 3.83 | 3.79 | 3.13 | 2.90 | 21.28 | 24.77 | 25.93 | 56.17 | 22.32 | 32.50 |
| A103 | 2.15 | 2.03 | 1.94 | 1.74 | 14.84 | 18.67 | 20.63 | 45.75 | 16.35 | 25.35 |
| A104 | 3.10 | 3.21 | 2.96 | 3.01 | 19.32 | 23.44 | 27.32 | 50.53 | 20.39 | 33.69 |
| A105 | 3.85 | 3.69 | 3.15 | 3.34 | 20.93 | 24.28 | 26.92 | 63.15 | 22.14 | 35.01 |
| A107 | 2.53 | 2.84 | 2.42 | 2.36 | 18.01 | 21.27 | 23.85 | 50.16 | 19.06 | 28.89 |
| A108 | 1.95 | 2.08 | 1.85 | 1.55 | 15.06 | 18.37 | 20.98 | 32.12 | 15.76 | 23.83 |
| A109 | 2.28 | 2.27 | 2.06 | 1.85 | 15.86 | 19.19 | 22.04 | 38.31 | 16.53 | 26.22 |
| A110 | 3.83 | 3.91 | 3.72 | 4.05 | 21.65 | 26.20 | 29.96 | 67.75 | 23.26 | 39.93 |
| A111 | 2.90 | 2.52 | 2.39 | 2.35 | 16.84 | 20.64 | 24.09 | 45.11 | 18.13 | 29.42 |
| A112 | 2.30 | 2.39 | 2.22 | 2.13 | 16.33 | 20.00 | 22.03 | 56.41 | 17.63 | 28.46 |
| A113 | 1.80 | 1.87 | 1.65 | 1.41 | 14.17 | 16.98 | 18.78 | 38.35 | 14.73 | 22.94 |
| A114 | 1.90 | 2.10 | 1.87 | 1.65 | 15.13 | 18.38 | 20.51 | 43.35 | 16.14 | 24.34 |
| A115 | 2.10 | 2.38 | 2.30 | 2.03 | 16.26 | 20.91 | 22.84 | 47.35 | 18.27 | 27.41 |
| A116 | 1.78 | 1.73 | 1.40 | 1.07 | 13.53 | 15.66 | 17.28 | 29.70 | 13.64 | 19.58 |
| A117 | 1.65 | 1.62 | 1.65 | 1.45 | 13.04 | 16.91 | 18.76 | 49.15 | 14.58 | 23.34 |
| A118 | 1.98 | 2.18 | 1.80 | 1.46 | 15.46 | 18.36 | 19.65 | 35.35 | 16.10 | 23.20 |
| A119 | 2.65 | 2.98 | 2.43 | 2.32 | 18.53 | 21.29 | 23.20 | 48.14 | 19.06 | 29.09 |
| A120 | 1.85 | 2.11 | 1.79 | 1.48 | 15.18 | 18.33 | 19.61 | 34.35 | 16.20 | 23.17 |
| A121 | 2.05 | 2.21 | 1.82 | 1.58 | 15.60 | 18.24 | 20.28 | 36.04 | 16.20 | 23.54 |
| A122 | 1.55 | 1.76 | 1.64 | 1.42 | 13.70 | 16.76 | 18.82 | 42.35 | 14.50 | 22.94 |
| A123 | 1.70 | 1.81 | 1.55 | 1.25 | 13.91 | 16.51 | 18.38 | 31.51 | 14.27 | 21.37 |
| A124 | 1.63 | 1.80 | 1.46 | 1.08 | 13.85 | 16.27 | 17.67 | 29.01 | 13.94 | 20.16 |
| A125 | 1.50 | 1.39 | 1.26 | 1.04 | 11.93 | 14.86 | 15.88 | 37.95 | 12.41 | 20.50 |
| A126 | 3.25 | 3.70 | 2.97 | 3.02 | 20.99 | 25.08 | 28.61 | 41.35 | 22.26 | 32.49 |
| A127 | 2.20 | 2.38 | 2.05 | 1.83 | 16.28 | 19.39 | 20.92 | 51.15 | 16.81 | 26.47 |
| A128 | 3.38 | 3.89 | 3.06 | 2.64 | 21.58 | 24.88 | 26.01 | 47.86 | 22.48 | 30.67 |
| A129 | 4.35 | 5.25 | 4.67 | 4.77 | 25.65 | 30.83 | 33.84 | 60.80 | 27.13 | 42.64 |
| A130 | 4.05 | 4.66 | 4.55 | 4.16 | 23.94 | 31.39 | 33.06 | 58.52 | 28.41 | 38.43 |
| A131 | 1.63 | 1.72 | 1.68 | 1.42 | 13.49 | 17.05 | 19.42 | 34.86 | 14.68 | 22.81 |
| A132 | 2.43 | 2.65 | 2.75 | 2.62 | 17.33 | 22.89 | 26.55 | 47.95 | 19.39 | 31.64 |
| A133 | 2.65 | 2.64 | 2.56 | 2.63 | 17.27 | 21.32 | 25.37 | 48.11 | 18.85 | 31.00 |
| A134 | 6.33 | 6.48 | 6.27 | 6.27 | 28.95 | 36.89 | 39.54 | 62.23 | 32.81 | 48.31 |
| A135 | 1.40 | 1.49 | 1.32 | 0.97 | 12.42 | 15.07 | 16.62 | 30.63 | 12.59 | 19.31 |
| A136 | 4.38 | 4.33 | 3.63 | 3.63 | 22.96 | 26.93 | 29.17 | 62.05 | 24.27 | 36.17 |
| A137 | 1.58 | 1.96 | 1.73 | 1.33 | 14.56 | 18.09 | 19.56 | 35.32 | 15.80 | 22.09 |
| A138 | 2.18 | 1.99 | 2.04 | 1.74 | 14.69 | 19.49 | 21.15 | 46.15 | 16.78 | 25.69 |
| A139 | 2.05 | 2.12 | 1.97 | 1.78 | 15.24 | 19.05 | 20.42 | 48.75 | 16.77 | 25.90 |
| A140 | 1.35 | 1.34 | 1.28 | 1.01 | 11.72 | 14.83 | 16.21 | 38.35 | 12.55 | 19.52 |
| A141 | 2.05 | 2.22 | 1.87 | 1.52 | 15.65 | 18.77 | 20.00 | 34.32 | 16.40 | 23.78 |
| A142 | 3.10 | 3.36 | 2.60 | 2.24 | 19.86 | 23.90 | 25.80 | 37.58 | 21.43 | 28.27 |
| A143 | 2.08 | 2.56 | 2.23 | 2.08 | 16.97 | 20.55 | 23.80 | 37.75 | 17.91 | 27.25 |
| A144 | 2.20 | 2.44 | 2.12 | 1.76 | 16.53 | 20.17 | 21.49 | 41.68 | 17.76 | 25.45 |
| A145 | 1.28 | 1.38 | 1.28 | 0.99 | 11.91 | 14.81 | 16.17 | 36.48 | 12.38 | 19.53 |
| A146 | 2.48 | 2.26 | 1.98 | 1.80 | 15.81 | 18.99 | 20.67 | 49.55 | 16.66 | 25.97 |
| A147 | 1.48 | 1.64 | 1.45 | 1.10 | 13.14 | 16.08 | 17.38 | 34.14 | 13.57 | 20.59 |
| A148 | 2.18 | 2.38 | 2.07 | 1.79 | 16.28 | 19.67 | 21.10 | 46.95 | 17.00 | 26.15 |
| A149 | 1.33 | 1.52 | 1.41 | 1.05 | 12.57 | 15.82 | 17.19 | 34.20 | 13.23 | 20.16 |
| A150 | 1.45 | 1.55 | 1.40 | 1.14 | 12.72 | 15.57 | 16.97 | 39.21 | 13.27 | 20.78 |
| A151 | 2.83 | 2.80 | 2.52 | 2.42 | 17.89 | 21.77 | 24.31 | 56.93 | 19.30 | 29.60 |
| A152 | 1.85 | 2.19 | 1.82 | 1.34 | 15.50 | 18.79 | 20.08 | 33.19 | 16.21 | 22.66 |
| A153 | 1.73 | 1.77 | 1.64 | 1.41 | 13.75 | 17.14 | 18.49 | 46.91 | 14.70 | 23.25 |
| A154 | 2.30 | 2.29 | 1.97 | 1.75 | 15.94 | 18.86 | 20.90 | 41.84 | 16.50 | 25.41 |
| A155 | 4.98 | 4.80 | 3.87 | 4.77 | 24.37 | 29.06 | 35.08 | 53.55 | 26.05 | 40.50 |
| A156 | 2.80 | 2.77 | 2.40 | 1.89 | 17.76 | 21.91 | 23.03 | 40.00 | 19.35 | 26.55 |
| A157 | 2.03 | 2.22 | 1.87 | 1.52 | 15.64 | 18.86 | 20.65 | 36.62 | 16.47 | 23.51 |
| A158 | 3.43 | 3.64 | 2.84 | 2.55 | 20.79 | 24.24 | 25.84 | 44.53 | 22.00 | 29.68 |
| A159 | 3.78 | 3.94 | 3.60 | 3.72 | 21.74 | 26.43 | 29.76 | 61.35 | 23.28 | 37.47 |
| A160 | 2.58 | 2.74 | 2.47 | 2.40 | 17.64 | 21.60 | 24.95 | 44.35 | 18.99 | 29.29 |
| A161 | 1.68 | 1.66 | 1.60 | 1.31 | 13.24 | 16.74 | 18.54 | 35.95 | 14.17 | 22.40 |
| A162 | 7.33 | 6.56 | 5.90 | 6.52 | 29.16 | 34.82 | 38.19 | 74.78 | 31.45 | 49.35 |
| A163 | 3.90 | 3.90 | 3.15 | 3.04 | 21.62 | 25.10 | 27.09 | 49.55 | 22.75 | 32.70 |
| A164 | 3.45 | 3.79 | 3.19 | 2.83 | 21.28 | 25.53 | 26.93 | 47.44 | 23.08 | 31.66 |
| A165 | 2.63 | 2.60 | 2.25 | 1.96 | 17.13 | 20.69 | 22.34 | 43.75 | 18.17 | 26.86 |
| A166 | 2.05 | 2.19 | 1.91 | 1.62 | 15.52 | 18.84 | 20.12 | 42.98 | 16.44 | 24.60 |
| A167 | 2.65 | 3.00 | 2.45 | 1.91 | 18.61 | 22.28 | 23.38 | 36.00 | 19.77 | 26.68 |
| A168 | 3.60 | 3.61 | 3.03 | 3.20 | 20.68 | 23.69 | 25.98 | 51.55 | 21.61 | 34.72 |
| A169 | 3.78 | 4.13 | 3.34 | 3.14 | 22.35 | 25.61 | 26.64 | 60.89 | 23.24 | 33.75 |
| A170 | 1.30 | 1.37 | 1.24 | 0.88 | 11.84 | 14.56 | 16.01 | 30.00 | 12.18 | 18.39 |
| A171 | 3.18 | 3.41 | 2.94 | 3.02 | 20.01 | 24.48 | 27.83 | 47.95 | 21.97 | 32.30 |
| A172 | 2.58 | 2.58 | 1.99 | 1.71 | 17.06 | 19.43 | 20.73 | 39.75 | 17.41 | 24.63 |
| A173 | 1.48 | 1.51 | 1.30 | 0.95 | 12.55 | 15.03 | 16.46 | 28.97 | 12.78 | 18.91 |
| A174 | 1.88 | 1.84 | 1.60 | 1.31 | 14.04 | 16.86 | 18.51 | 36.75 | 14.60 | 21.98 |
| A175 | 1.60 | 1.84 | 1.52 | 1.13 | 14.02 | 16.78 | 18.20 | 29.70 | 14.61 | 20.37 |

TABLE 14-continued

| ID | WHO | INRm | INRz | INRn | T1 | T2S | T2 | T3 | TSot | TEot |
|---|---|---|---|---|---|---|---|---|---|---|
| A176 | 3.08 | 3.33 | 2.82 | 2.72 | 19.75 | 23.45 | 25.14 | 50.35 | 21.34 | 30.91 |
| A177 | 1.58 | 1.73 | 1.42 | 1.05 | 13.56 | 15.96 | 17.33 | 31.35 | 13.59 | 19.95 |
| A178 | 2.53 | 2.34 | 2.16 | 1.89 | 16.13 | 20.20 | 21.83 | 43.07 | 17.75 | 26.41 |
| A179 | 2.33 | 2.51 | 2.18 | 1.86 | 16.78 | 20.38 | 22.02 | 39.95 | 17.86 | 26.18 |
| A180 | 2.18 | 2.26 | 1.88 | 1.59 | 15.79 | 18.80 | 20.33 | 36.32 | 16.66 | 23.85 |
| A181 | 3.68 | 3.49 | 3.21 | 3.44 | 20.29 | 25.17 | 29.85 | 51.67 | 21.98 | 35.38 |
| A182 | 2.05 | 2.10 | 1.78 | 1.44 | 15.15 | 18.28 | 19.30 | 39.14 | 15.93 | 23.28 |
| A183 | 1.53 | 1.55 | 1.30 | 0.91 | 12.70 | 15.24 | 16.46 | 28.49 | 12.95 | 18.59 |
| A184 | 2.48 | 2.58 | 2.22 | 1.96 | 17.06 | 20.49 | 21.89 | 47.65 | 18.04 | 27.02 |
| A185 | 3.05 | 3.28 | 2.96 | 2.87 | 19.59 | 24.06 | 26.64 | 54.15 | 21.37 | 32.25 |
| A186 | 3.10 | 3.12 | 3.09 | 3.58 | 19.01 | 22.19 | 29.51 | 65.55 | 19.65 | 37.28 |
| A187 | 1.75 | 1.83 | 1.51 | 1.18 | 13.99 | 16.52 | 17.86 | 34.85 | 14.22 | 21.02 |
| A188 | 2.93 | 3.12 | 2.56 | 2.46 | 19.01 | 22.29 | 24.63 | 36.67 | 20.11 | 29.31 |
| A189 | 2.93 | 2.98 | 2.68 | 2.47 | 18.52 | 23.20 | 25.87 | 44.13 | 20.26 | 30.01 |
| A190 | 3.25 | 3.59 | 3.00 | 2.75 | 20.62 | 24.60 | 26.72 | 44.63 | 21.77 | 31.67 |
| A191 | 2.05 | 2.04 | 1.71 | 1.39 | 14.91 | 17.82 | 19.08 | 34.18 | 15.77 | 22.39 |
| A192 | 2.28 | 2.49 | 2.25 | 1.81 | 16.69 | 21.28 | 22.69 | 39.02 | 18.88 | 25.65 |
| A193 | 1.95 | 2.11 | 1.84 | 1.64 | 15.20 | 17.86 | 20.52 | 39.35 | 15.51 | 24.43 |
| A194 | 2.18 | 2.27 | 1.98 | 1.72 | 15.83 | 19.27 | 21.44 | 36.83 | 16.93 | 24.78 |
| A195 | 1.45 | 1.37 | 1.46 | 1.17 | 11.86 | 15.76 | 17.48 | 34.90 | 13.23 | 21.30 |
| A196 | 1.95 | 1.99 | 1.82 | 1.56 | 14.68 | 18.04 | 20.23 | 42.94 | 15.59 | 23.97 |
| A197 | 1.63 | 1.78 | 1.62 | 1.28 | 13.76 | 17.46 | 18.33 | 41.41 | 15.35 | 21.69 |
| A198 | 1.85 | 1.92 | 1.66 | 1.43 | 14.39 | 16.92 | 19.77 | 31.95 | 14.88 | 22.21 |
| A199 | 1.40 | 1.49 | 1.32 | 0.94 | 12.42 | 15.08 | 16.68 | 28.38 | 12.57 | 19.08 |
| A200 | 1.35 | 1.38 | 1.21 | 0.88 | 11.92 | 14.39 | 15.64 | 30.32 | 12.02 | 18.39 |
| A201 | 2.40 | 2.56 | 2.19 | 1.96 | 16.97 | 20.37 | 22.05 | 42.55 | 18.13 | 26.53 |
| A202 | 2.20 | 2.39 | 1.93 | 1.59 | 16.31 | 18.99 | 20.82 | 37.23 | 16.43 | 24.30 |
| A203 | 1.80 | 2.07 | 1.67 | 1.28 | 15.04 | 17.69 | 18.76 | 36.37 | 15.26 | 22.07 |
| A204 | 1.73 | 1.80 | 1.50 | 1.14 | 13.85 | 16.41 | 17.97 | 30.75 | 14.07 | 20.62 |
| A205 | 1.85 | 1.87 | 1.84 | 1.46 | 14.19 | 18.51 | 20.05 | 39.13 | 15.79 | 23.60 |
| A207 | 2.65 | 2.75 | 2.42 | 2.11 | 17.69 | 21.70 | 23.07 | 45.74 | 19.37 | 27.59 |
| A208 | 3.05 | 3.04 | 2.63 | 2.62 | 18.75 | 22.27 | 25.50 | 45.50 | 19.80 | 30.63 |
| A209 | 1.70 | 1.84 | 1.69 | 1.44 | 14.06 | 17.22 | 19.31 | 37.35 | 15.00 | 22.84 |
| A210 | 2.35 | 2.37 | 1.95 | 1.58 | 16.23 | 19.23 | 20.54 | 39.33 | 16.76 | 24.32 |
| A211 | 2.50 | 2.68 | 2.40 | 2.12 | 17.44 | 21.54 | 23.03 | 47.55 | 19.14 | 27.75 |
| A212 | 2.88 | 2.77 | 2.44 | 2.18 | 17.78 | 21.82 | 23.45 | 43.47 | 19.54 | 27.85 |
| A213 | 2.53 | 2.74 | 2.40 | 2.41 | 17.65 | 20.57 | 23.19 | 56.75 | 18.23 | 30.50 |
| A214 | 2.60 | 2.80 | 2.44 | 2.38 | 17.86 | 21.07 | 24.24 | 44.75 | 18.53 | 29.52 |
| A215 | 2.40 | 2.47 | 2.06 | 1.70 | 16.63 | 19.82 | 21.16 | 41.43 | 17.36 | 25.07 |
| A216 | 4.48 | 4.13 | 3.86 | 3.78 | 22.33 | 27.99 | 30.59 | 58.40 | 24.70 | 37.52 |
| A217 | 2.23 | 2.33 | 2.26 | 2.19 | 16.10 | 20.21 | 22.30 | 63.13 | 17.82 | 28.77 |
| A218 | 2.95 | 2.94 | 2.82 | 2.70 | 18.38 | 23.22 | 25.69 | 59.95 | 20.39 | 31.65 |
| A219 | 2.38 | 2.71 | 2.17 | 2.01 | 17.55 | 20.69 | 23.43 | 36.97 | 18.50 | 26.17 |
| A220 | 1.90 | 2.05 | 1.74 | 1.34 | 14.92 | 18.06 | 19.41 | 34.75 | 15.57 | 22.53 |
| A222 | 1.83 | 1.89 | 1.63 | 1.36 | 14.27 | 17.07 | 18.81 | 33.95 | 14.98 | 22.12 |
| A223 | 1.73 | 1.74 | 1.41 | 1.05 | 13.60 | 16.00 | 17.00 | 31.79 | 13.57 | 20.14 |
| A224 | 1.73 | 1.62 | 1.52 | 1.15 | 13.03 | 16.52 | 18.07 | 31.77 | 14.04 | 20.86 |
| A225 | 1.68 | 1.81 | 1.52 | 1.18 | 13.93 | 16.59 | 17.97 | 32.58 | 14.29 | 20.96 |

TABLE 15

Table 15 provides additional data for the coagulation study of the samples in Table 14.

| ID | Fg | c1 | ct2s | C2 | Ceot | IUL | IUX | IUT | IUA | Ztm |
|---|---|---|---|---|---|---|---|---|---|---|
| A001 | 388 | 3738 | 3720 | 3706 | 3664 | 18 | 14 | 56 | 74 | 1.85 |
| A002 | 226 | 3724 | 3712 | 3704 | 3686 | 12 | 8 | 26 | 38 | 1.42 |
| A003 | 213 | 3740 | 3730 | 3719 | 3705 | 10 | 11 | 25 | 35 | 2.38 |
| A004 | 370 | 3733 | 3709 | 3692 | 3663 | 24 | 17 | 46 | 70 | 1.96 |
| A005 | 226 | 3738 | 3726 | 3715 | 3700 | 12 | 11 | 26 | 38 | 2.14 |
| A007 | 244 | 3740 | 3726 | 3714 | 3698 | 14 | 12 | 28 | 42 | 1.99 |
| A008 | 482 | 3741 | 3714 | 3693 | 3646 | 27 | 21 | 68 | 95 | 2.04 |
| A009 | 253 | 3741 | 3727 | 3713 | 3697 | 14 | 14 | 30 | 44 | 2.52 |
| A010 | 240 | 3742 | 3727 | 3714 | 3701 | 15 | 13 | 26 | 41 | 2.11 |
| A011 | 352 | 3713 | 3690 | 3676 | 3647 | 23 | 14 | 43 | 66 | 1.42 |
| A012 | 276 | 3744 | 3727 | 3717 | 3695 | 17 | 10 | 32 | 49 | 1.54 |
| A013 | 496 | 3739 | 3715 | 3690 | 3641 | 24 | 25 | 74 | 98 | 2.59 |
| A014 | 226 | 3732 | 3717 | 3708 | 3694 | 15 | 9 | 23 | 38 | 1.34 |
| A015 | 199 | 3738 | 3726 | 3717 | 3706 | 12 | 9 | 20 | 32 | 1.81 |
| A016 | 340 | 3741 | 3722 | 3714 | 3678 | 19 | 8 | 44 | 63 | 1.02 |
| A017 | 331 | 3742 | 3720 | 3706 | 3681 | 22 | 14 | 39 | 61 | 1.57 |
| A018 | 218 | 3734 | 3722 | 3711 | 3697 | 12 | 11 | 25 | 37 | 2.46 |
| A019 | 472 | 3744 | 3716 | 3695 | 3653 | 28 | 21 | 63 | 91 | 1.72 |
| A020 | 246 | 3741 | 3727 | 3714 | 3698 | 14 | 13 | 29 | 43 | 2.67 |
| A021 | 265 | 3741 | 3727 | 3717 | 3694 | 14 | 10 | 33 | 47 | 1.86 |

TABLE 15-continued

Table 15 provides additional data for the coagulation study of the samples in Table 14.

| ID | Fg | c1 | ct2s | C2 | Ceot | IUL | IUX | IUT | IUA | Ztm |
|---|---|---|---|---|---|---|---|---|---|---|
| A022 | 387 | 3740 | 3717 | 3702 | 3667 | 23 | 15 | 50 | 73 | 1.54 |
| A023 | 420 | 3743 | 3719 | 3705 | 3663 | 24 | 14 | 56 | 80 | 1.41 |
| A024 | 415 | 3740 | 3717 | 3699 | 3661 | 23 | 18 | 56 | 79 | 2.00 |
| A025 | 171 | 3743 | 3732 | 3726 | 3716 | 11 | 6 | 16 | 27 | 1.03 |
| A026 | 363 | 3742 | 3718 | 3702 | 3673 | 24 | 16 | 45 | 69 | 1.62 |
| A027 | 377 | 3739 | 3715 | 3698 | 3667 | 24 | 17 | 48 | 72 | 1.57 |
| A028 | 463 | 3742 | 3713 | 3696 | 3651 | 29 | 17 | 62 | 91 | 1.42 |
| A029 | 472 | 3740 | 3713 | 3690 | 3647 | 27 | 23 | 66 | 93 | 1.95 |
| A030 | 540 | 3743 | 3716 | 3698 | 3635 | 27 | 18 | 81 | 108 | 1.56 |
| A031 | 236 | 3728 | 3715 | 3704 | 3687 | 13 | 11 | 28 | 41 | 2.13 |
| A032 | 309 | 3732 | 3716 | 3710 | 3675 | 16 | 6 | 41 | 57 | 0.94 |
| A033 | 358 | 3739 | 3718 | 3702 | 3671 | 21 | 16 | 47 | 68 | 2.02 |
| A034 | 349 | 3740 | 3721 | 3706 | 3674 | 19 | 15 | 47 | 66 | 1.75 |
| A035 | 209 | 3734 | 3725 | 3711 | 3699 | 9 | 14 | 26 | 35 | 4.37 |
| A036 | 295 | 3735 | 3723 | 3708 | 3681 | 12 | 15 | 42 | 54 | 2.56 |
| A037 | 372 | 3740 | 3716 | 3697 | 3669 | 24 | 19 | 47 | 71 | 2.10 |
| A038 | 304 | 3742 | 3721 | 3709 | 3686 | 21 | 12 | 35 | 56 | 1.33 |
| A039 | 232 | 3738 | 3722 | 3711 | 3698 | 16 | 11 | 24 | 40 | 1.67 |
| A040 | 404 | 3742 | 3720 | 3705 | 3664 | 22 | 15 | 56 | 78 | 1.65 |
| A041 | 493 | 3739 | 3711 | 3695 | 3638 | 28 | 16 | 73 | 101 | 1.51 |
| A042 | 261 | 3736 | 3721 | 3709 | 3687 | 15 | 12 | 34 | 49 | 2.56 |
| A044 | 301 | 3741 | 3722 | 3710 | 3683 | 19 | 12 | 39 | 58 | 1.56 |
| A045 | 453 | 3739 | 3714 | 3689 | 3647 | 25 | 25 | 67 | 92 | 2.64 |
| A047 | 341 | 3735 | 3716 | 3699 | 3668 | 19 | 17 | 48 | 67 | 2.22 |
| A048 | 270 | 3733 | 3720 | 3705 | 3682 | 13 | 15 | 38 | 51 | 3.15 |
| A049 | 252 | 3737 | 3725 | 3711 | 3690 | 12 | 14 | 35 | 47 | 2.52 |
| A050 | 288 | 3740 | 3723 | 3711 | 3685 | 17 | 12 | 38 | 55 | 2.02 |
| A051 | 514 | 3738 | 3705 | 3691 | 3634 | 33 | 14 | 71 | 104 | 0.96 |
| A052 | 276 | 3737 | 3723 | 3712 | 3687 | 14 | 11 | 36 | 50 | 1.95 |
| A053 | 241 | 3738 | 3724 | 3715 | 3696 | 14 | 9 | 28 | 42 | 1.68 |
| A054 | 294 | 3733 | 3716 | 3700 | 3679 | 17 | 16 | 37 | 54 | 2.12 |
| A055 | 540 | 3737 | 3718 | 3687 | 3627 | 19 | 31 | 91 | 110 | 4.81 |
| A056 | 566 | 3740 | 3711 | 3685 | 3624 | 29 | 26 | 87 | 116 | 2.34 |
| A057 | 232 | 3723 | 3710 | 3701 | 3683 | 13 | 9 | 27 | 40 | 1.61 |
| A058 | 360 | 3738 | 3723 | 3709 | 3669 | 15 | 14 | 54 | 69 | 3.55 |
| A059 | 232 | 3736 | 3723 | 3711 | 3696 | 13 | 12 | 27 | 40 | 2.36 |
| A060 | 197 | 3730 | 3719 | 3710 | 3698 | 11 | 9 | 21 | 32 | 2.13 |
| A061 | 294 | 3734 | 3720 | 3707 | 3680 | 14 | 13 | 40 | 54 | 2.20 |
| A062 | 439 | 3738 | 3718 | 3702 | 3651 | 20 | 16 | 67 | 87 | 2.96 |
| A063 | 237 | 3738 | 3728 | 3715 | 3697 | 10 | 13 | 31 | 41 | 3.53 |
| A064 | 285 | 3737 | 3719 | 3705 | 3685 | 18 | 14 | 34 | 52 | 1.89 |
| A065 | 320 | 3740 | 3721 | 3703 | 3680 | 19 | 18 | 41 | 60 | 2.71 |
| A066 | 186 | 3738 | 3726 | 3719 | 3707 | 12 | 7 | 19 | 31 | 1.36 |
| A067 | 494 | 3740 | 3708 | 3689 | 3641 | 32 | 19 | 67 | 99 | 1.50 |
| A068 | 286 | 3739 | 3725 | 3713 | 3686 | 14 | 12 | 39 | 53 | 1.89 |
| A069 | 223 | 3734 | 3719 | 3714 | 3695 | 15 | 5 | 24 | 39 | 0.80 |
| A070 | 354 | 3739 | 3716 | 3703 | 3671 | 23 | 13 | 45 | 68 | 1.40 |
| A071 | 399 | 3738 | 3714 | 3695 | 3660 | 24 | 19 | 54 | 78 | 1.90 |
| A072 | 463 | 3738 | 3712 | 3694 | 3646 | 26 | 18 | 66 | 92 | 1.71 |
| A073 | 494 | 3738 | 3707 | 3685 | 3639 | 31 | 22 | 68 | 99 | 1.68 |
| A074 | 286 | 3718 | 3700 | 3683 | 3665 | 18 | 17 | 35 | 53 | 2.17 |
| A075 | 114 | 3741 | 3734 | 3730 | 3726 | 7 | 4 | 8 | 15 | 0.98 |
| A076 | 385 | 3742 | 3718 | 3704 | 3665 | 24 | 14 | 53 | 77 | 1.39 |
| A077 | 508 | 3740 | 3718 | 3694 | 3634 | 22 | 24 | 84 | 106 | 3.10 |
| A078 | 296 | 3740 | 3724 | 3707 | 3684 | 16 | 17 | 40 | 56 | 2.34 |
| A080 | 499 | 3741 | 3729 | 3706 | 3637 | 12 | 23 | 92 | 104 | 5.02 |
| A081 | 550 | 3742 | 3710 | 3694 | 3626 | 32 | 16 | 84 | 116 | 1.57 |
| A082 | 431 | 3742 | 3716 | 3696 | 3654 | 26 | 20 | 62 | 88 | 1.91 |
| A083 | 296 | 3742 | 3720 | 3709 | 3686 | 22 | 11 | 34 | 56 | 1.16 |
| A084 | 376 | 3742 | 3732 | 3715 | 3667 | 10 | 17 | 65 | 75 | 4.55 |
| A085 | 342 | 3742 | 3727 | 3701 | 3675 | 15 | 26 | 52 | 67 | 5.07 |
| A086 | 448 | 3742 | 3717 | 3700 | 3650 | 25 | 17 | 67 | 92 | 1.73 |
| A087 | 431 | 3742 | 3715 | 3694 | 3654 | 27 | 21 | 61 | 88 | 1.84 |
| A088 | 512 | 3737 | 3704 | 3681 | 3630 | 33 | 23 | 74 | 107 | 1.64 |
| A089 | 292 | 3742 | 3723 | 3712 | 3687 | 19 | 11 | 36 | 55 | 1.24 |
| A090 | 711 | 3742 | 3718 | 3680 | 3588 | 24 | 38 | 130 | 154 | 4.73 |
| A091 | 393 | 3741 | 3724 | 3707 | 3659 | 17 | 17 | 65 | 82 | 3.80 |
| A092 | 711 | 3740 | 3696 | 3657 | 3582 | 44 | 39 | 114 | 158 | 2.38 |
| A093 | 243 | 3739 | 3730 | 3716 | 3693 | 9 | 14 | 37 | 46 | 3.73 |
| A094 | 322 | 3741 | 3719 | 3709 | 3676 | 22 | 10 | 43 | 65 | 1.16 |
| A095 | 490 | 3743 | 3710 | 3689 | 3638 | 33 | 21 | 72 | 105 | 1.51 |
| A096 | 214 | 3739 | 3725 | 3717 | 3700 | 14 | 8 | 25 | 39 | 1.29 |
| A097 | 256 | 3741 | 3721 | 3712 | 3692 | 20 | 9 | 29 | 49 | 1.14 |
| A098 | 398 | 3742 | 3716 | 3695 | 3659 | 26 | 21 | 57 | 83 | 1.81 |
| A099 | 289 | 3742 | 3722 | 3707 | 3685 | 20 | 15 | 37 | 57 | 1.61 |
| A100 | 536 | 3741 | 3709 | 3685 | 3625 | 32 | 24 | 84 | 116 | 1.62 |

TABLE 15-continued

Table 15 provides additional data for the coagulation study of the samples in Table 14.

| ID | Fg | c1 | ct2s | C2 | Ceot | IUL | IUX | IUT | IUA | Ztm |
|---|---|---|---|---|---|---|---|---|---|---|
| A101 | 269 | 3740 | 3727 | 3712 | 3690 | 13 | 15 | 37 | 50 | 2.94 |
| A102 | 397 | 3740 | 3721 | 3712 | 3661 | 19 | 9 | 60 | 79 | 1.16 |
| A103 | 495 | 3741 | 3715 | 3693 | 3640 | 26 | 22 | 75 | 101 | 1.96 |
| A104 | 260 | 3730 | 3719 | 3705 | 3682 | 11 | 14 | 37 | 48 | 3.88 |
| A105 | 393 | 3738 | 3725 | 3709 | 3660 | 13 | 16 | 65 | 78 | 2.64 |
| A107 | 402 | 3740 | 3722 | 3701 | 3660 | 18 | 21 | 62 | 80 | 2.58 |
| A108 | 198 | 3743 | 3732 | 3721 | 3709 | 11 | 11 | 23 | 34 | 2.61 |
| A109 | 273 | 3740 | 3726 | 3711 | 3689 | 14 | 15 | 37 | 51 | 2.85 |
| A110 | 499 | 3737 | 3719 | 3696 | 3635 | 18 | 23 | 84 | 102 | 3.76 |
| A111 | 366 | 3739 | 3723 | 3701 | 3667 | 16 | 22 | 56 | 72 | 3.45 |
| A112 | 614 | 3742 | 3714 | 3690 | 3614 | 28 | 24 | 100 | 128 | 2.03 |
| A113 | 371 | 3737 | 3717 | 3701 | 3664 | 20 | 16 | 53 | 73 | 1.80 |
| A114 | 388 | 3732 | 3711 | 3691 | 3655 | 21 | 20 | 56 | 77 | 2.13 |
| A115 | 446 | 3742 | 3716 | 3697 | 3652 | 26 | 19 | 64 | 90 | 1.93 |
| A116 | 230 | 3742 | 3727 | 3715 | 3698 | 15 | 12 | 29 | 44 | 1.62 |
| A117 | 499 | 3739 | 3710 | 3687 | 3630 | 29 | 23 | 80 | 109 | 1.85 |
| A118 | 230 | 3743 | 3729 | 3721 | 3699 | 14 | 8 | 30 | 44 | 1.29 |
| A119 | 308 | 3742 | 3728 | 3716 | 3679 | 14 | 12 | 49 | 63 | 1.91 |
| A120 | 250 | 3737 | 3722 | 3713 | 3688 | 15 | 9 | 34 | 49 | 1.28 |
| A121 | 196 | 3740 | 3730 | 3720 | 3704 | 10 | 10 | 26 | 36 | 2.04 |
| A122 | 404 | 3736 | 3713 | 3692 | 3650 | 23 | 21 | 63 | 86 | 2.06 |
| A123 | 205 | 3742 | 3730 | 3720 | 3704 | 12 | 10 | 26 | 38 | 1.87 |
| A124 | 213 | 3736 | 3721 | 3712 | 3696 | 15 | 9 | 25 | 40 | 1.40 |
| A125 | 541 | 3719 | 3683 | 3668 | 3600 | 36 | 15 | 83 | 119 | 1.02 |
| A126 | 177 | 3743 | 3735 | 3725 | 3714 | 8 | 10 | 21 | 29 | 3.53 |
| A127 | 482 | 3741 | 3714 | 3698 | 3640 | 27 | 16 | 74 | 101 | 1.53 |
| A128 | 300 | 3740 | 3723 | 3715 | 3682 | 17 | 8 | 41 | 58 | 1.13 |
| A129 | 338 | 3744 | 3728 | 3715 | 3677 | 16 | 13 | 51 | 67 | 3.01 |
| A130 | 410 | 3740 | 3715 | 3701 | 3656 | 25 | 14 | 59 | 84 | 1.67 |
| A131 | 258 | 3738 | 3724 | 3710 | 3690 | 14 | 14 | 34 | 48 | 2.37 |
| A132 | 381 | 3742 | 3720 | 3697 | 3665 | 22 | 23 | 55 | 77 | 3.66 |
| A133 | 347 | 3742 | 3728 | 3705 | 3673 | 14 | 23 | 55 | 69 | 4.05 |
| A134 | 376 | 3743 | 3723 | 3710 | 3667 | 20 | 13 | 56 | 76 | 2.65 |
| A135 | 330 | 3741 | 3717 | 3702 | 3676 | 24 | 15 | 41 | 65 | 1.55 |
| A136 | 414 | 3744 | 3725 | 3709 | 3659 | 19 | 16 | 66 | 85 | 2.24 |
| A137 | 381 | 3739 | 3711 | 3693 | 3662 | 28 | 18 | 49 | 77 | 1.47 |
| A138 | 487 | 3743 | 3712 | 3693 | 3641 | 31 | 19 | 71 | 102 | 1.66 |
| A139 | 478 | 3742 | 3717 | 3702 | 3642 | 25 | 15 | 75 | 100 | 1.37 |
| A140 | 482 | 3743 | 3710 | 3690 | 3642 | 33 | 20 | 68 | 101 | 1.38 |
| A141 | 373 | 3739 | 3714 | 3701 | 3661 | 25 | 13 | 53 | 78 | 1.23 |
| A142 | 197 | 3742 | 3729 | 3719 | 3706 | 13 | 10 | 23 | 36 | 1.90 |
| A143 | 239 | 3739 | 3726 | 3710 | 3693 | 13 | 16 | 33 | 46 | 3.25 |
| A144 | 460 | 3740 | 3709 | 3692 | 3641 | 31 | 17 | 68 | 99 | 1.32 |
| A145 | 465 | 3739 | 3705 | 3686 | 3639 | 34 | 19 | 66 | 100 | 1.36 |
| A146 | 347 | 3736 | 3718 | 3705 | 3664 | 18 | 13 | 54 | 72 | 1.68 |
| A147 | 385 | 3742 | 3713 | 3698 | 3661 | 29 | 15 | 52 | 81 | 1.30 |
| A148 | 448 | 3742 | 3714 | 3699 | 3646 | 28 | 15 | 68 | 96 | 1.43 |
| A149 | 427 | 3744 | 3710 | 3692 | 3653 | 34 | 18 | 57 | 91 | 1.37 |
| A150 | 607 | 3742 | 3701 | 3676 | 3608 | 41 | 25 | 93 | 134 | 1.40 |
| A151 | 698 | 3737 | 3701 | 3664 | 3587 | 36 | 37 | 114 | 150 | 2.54 |
| A152 | 293 | 3738 | 3716 | 3705 | 3683 | 22 | 11 | 33 | 55 | 1.29 |
| A153 | 626 | 3729 | 3691 | 3670 | 3596 | 38 | 21 | 95 | 133 | 1.35 |
| A154 | 412 | 3728 | 3706 | 3687 | 3645 | 22 | 19 | 61 | 83 | 2.04 |
| A155 | 365 | 3739 | 3724 | 3694 | 3667 | 15 | 30 | 57 | 72 | 6.02 |
| A156 | 250 | 3733 | 3717 | 3710 | 3688 | 16 | 7 | 29 | 45 | 1.12 |
| A157 | 310 | 3737 | 3717 | 3702 | 3678 | 20 | 15 | 39 | 59 | 1.79 |
| A158 | 263 | 3737 | 3723 | 3713 | 3689 | 14 | 10 | 34 | 48 | 1.60 |
| A159 | 404 | 3733 | 3715 | 3696 | 3652 | 18 | 19 | 63 | 81 | 3.33 |
| A160 | 412 | 3738 | 3717 | 3690 | 3655 | 21 | 27 | 62 | 83 | 3.35 |
| A161 | 331 | 3740 | 3720 | 3706 | 3676 | 20 | 14 | 44 | 64 | 1.80 |
| A162 | 421 | 3738 | 3722 | 3706 | 3653 | 16 | 16 | 69 | 85 | 3.37 |
| A163 | 293 | 3738 | 3725 | 3714 | 3683 | 13 | 11 | 42 | 55 | 1.99 |
| A164 | 267 | 3734 | 3720 | 3712 | 3685 | 14 | 8 | 35 | 49 | 1.40 |
| A165 | 485 | 3736 | 3707 | 3688 | 3636 | 29 | 19 | 71 | 100 | 1.65 |
| A166 | 486 | 3733 | 3703 | 3687 | 3631 | 30 | 16 | 72 | 102 | 1.28 |
| A167 | 235 | 3734 | 3718 | 3711 | 3690 | 16 | 7 | 28 | 44 | 1.10 |
| A168 | 317 | 3732 | 3722 | 3711 | 3669 | 10 | 11 | 53 | 63 | 2.29 |
| A169 | 486 | 3726 | 3703 | 3693 | 3624 | 23 | 10 | 79 | 102 | 1.03 |
| A170 | 304 | 3740 | 3717 | 3703 | 3680 | 23 | 14 | 37 | 60 | 1.45 |
| A171 | 365 | 3740 | 3722 | 3698 | 3666 | 18 | 24 | 56 | 74 | 3.35 |
| A172 | 261 | 3741 | 3727 | 3718 | 3691 | 14 | 9 | 36 | 50 | 1.30 |
| A173 | 304 | 3740 | 3718 | 3704 | 3680 | 22 | 14 | 38 | 60 | 1.43 |
| A174 | 412 | 3733 | 3707 | 3688 | 3648 | 26 | 19 | 59 | 85 | 1.65 |
| A175 | 378 | 3719 | 3690 | 3671 | 3642 | 29 | 19 | 48 | 77 | 1.42 |
| A176 | 337 | 3739 | 3724 | 3712 | 3671 | 15 | 12 | 53 | 68 | 1.69 |
| A177 | 267 | 3740 | 3721 | 3710 | 3689 | 19 | 11 | 32 | 51 | 1.37 |

TABLE 15-continued

Table 15 provides additional data for the coagulation study of the samples in Table 14.

| ID | Fg | c1 | ct2s | C2 | Ceot | IUL | IUX | IUT | IUA | Ztm |
|---|---|---|---|---|---|---|---|---|---|---|
| A178 | 408 | 3740 | 3716 | 3700 | 3655 | 24 | 16 | 61 | 85 | 1.63 |
| A179 | 329 | 3738 | 3718 | 3705 | 3672 | 20 | 13 | 46 | 66 | 1.64 |
| A180 | 250 | 3733 | 3719 | 3709 | 3686 | 14 | 10 | 33 | 47 | 1.53 |
| A181 | 317 | 3739 | 3724 | 3702 | 3676 | 15 | 22 | 48 | 63 | 4.68 |
| A182 | 354 | 3739 | 3716 | 3706 | 3667 | 23 | 10 | 49 | 72 | 1.02 |
| A183 | 209 | 3726 | 3711 | 3703 | 3689 | 15 | 8 | 22 | 37 | 1.22 |
| A184 | 375 | 3738 | 3717 | 3705 | 3661 | 21 | 12 | 56 | 77 | 1.40 |
| A185 | 458 | 3736 | 3712 | 3689 | 3639 | 24 | 23 | 73 | 97 | 2.58 |
| A186 | 545 | 3738 | 3721 | 3672 | 3620 | 17 | 49 | 101 | 118 | 7.32 |
| A187 | 350 | 3739 | 3715 | 3701 | 3668 | 24 | 14 | 47 | 71 | 1.34 |
| A188 | 300 | 3731 | 3717 | 3702 | 3672 | 14 | 15 | 45 | 59 | 2.34 |
| A189 | 358 | 3731 | 3709 | 3689 | 3658 | 22 | 20 | 51 | 73 | 2.67 |
| A190 | 230 | 3730 | 3718 | 3709 | 3688 | 12 | 9 | 30 | 42 | 2.12 |
| A191 | 234 | 3738 | 3725 | 3717 | 3696 | 13 | 8 | 29 | 42 | 1.26 |
| A192 | 261 | 3739 | 3722 | 3712 | 3691 | 17 | 10 | 31 | 48 | 1.41 |
| A193 | 301 | 3742 | 3727 | 3710 | 3685 | 15 | 17 | 42 | 57 | 2.66 |
| A194 | 257 | 3735 | 3721 | 3708 | 3688 | 14 | 13 | 33 | 47 | 2.17 |
| A195 | 716 | 3739 | 3692 | 3660 | 3589 | 47 | 32 | 103 | 150 | 1.72 |
| A196 | 337 | 3738 | 3719 | 3702 | 3673 | 19 | 17 | 46 | 65 | 2.19 |
| A197 | 502 | 3739 | 3705 | 3691 | 3637 | 34 | 14 | 68 | 102 | 0.87 |
| A198 | 208 | 3728 | 3718 | 3704 | 3692 | 10 | 14 | 26 | 36 | 2.85 |
| A199 | 301 | 3741 | 3719 | 3705 | 3684 | 22 | 14 | 35 | 57 | 1.60 |
| A200 | 274 | 3737 | 3718 | 3708 | 3686 | 19 | 10 | 32 | 51 | 1.25 |
| A201 | 319 | 3741 | 3725 | 3713 | 3681 | 16 | 12 | 44 | 60 | 1.68 |
| A202 | 243 | 3737 | 3723 | 3713 | 3694 | 14 | 10 | 29 | 43 | 1.83 |
| A203 | 364 | 3740 | 3715 | 3704 | 3670 | 25 | 11 | 45 | 70 | 1.07 |
| A204 | 239 | 3739 | 3724 | 3714 | 3697 | 15 | 10 | 27 | 42 | 1.56 |
| A205 | 346 | 3740 | 3717 | 3704 | 3674 | 23 | 13 | 43 | 66 | 1.54 |
| A207 | 319 | 3728 | 3711 | 3701 | 3668 | 17 | 10 | 43 | 60 | 1.37 |
| A208 | 306 | 3737 | 3724 | 3707 | 3680 | 13 | 17 | 44 | 57 | 3.23 |
| A209 | 319 | 3742 | 3725 | 3709 | 3682 | 17 | 16 | 43 | 60 | 2.09 |
| A210 | 283 | 3740 | 3723 | 3714 | 3688 | 17 | 9 | 35 | 52 | 1.31 |
| A211 | 515 | 3741 | 3712 | 3694 | 3637 | 29 | 18 | 75 | 104 | 1.49 |
| A212 | 279 | 3740 | 3726 | 3716 | 3689 | 14 | 10 | 37 | 51 | 1.63 |
| A213 | 448 | 3741 | 3724 | 3705 | 3652 | 17 | 19 | 72 | 89 | 2.62 |
| A214 | 283 | 3739 | 3727 | 3712 | 3687 | 12 | 15 | 40 | 52 | 3.17 |
| A215 | 359 | 3737 | 3715 | 3703 | 3668 | 22 | 12 | 47 | 69 | 1.34 |
| A216 | 389 | 3741 | 3722 | 3707 | 3667 | 19 | 15 | 55 | 74 | 2.60 |
| A217 | 560 | 3740 | 3716 | 3695 | 3630 | 24 | 21 | 86 | 110 | 2.09 |
| A218 | 773 | 3738 | 3699 | 3665 | 3583 | 39 | 34 | 116 | 155 | 2.47 |
| A219 | 238 | 3741 | 3729 | 3714 | 3699 | 12 | 15 | 30 | 42 | 2.74 |
| A220 | 356 | 3741 | 3717 | 3704 | 3674 | 24 | 13 | 43 | 67 | 1.35 |
| A222 | 233 | 3725 | 3713 | 3703 | 3684 | 12 | 10 | 29 | 41 | 1.74 |
| A223 | 257 | 3741 | 3724 | 3717 | 3695 | 17 | 7 | 29 | 46 | 1.00 |
| A224 | 351 | 3742 | 3718 | 3703 | 3676 | 24 | 15 | 42 | 66 | 1.55 |
| A225 | 314 | 3741 | 3721 | 3709 | 3683 | 20 | 12 | 38 | 58 | 1.38 |

Though the sample ID's in Tables 14 and 15 range from A001 to A225, gaps in sample numbers indicate occurrences where a sample was not able to be tested because it was beyond three standard deviations.

TABLE 16

| | | $R^2$ | mY |
|---|---|---|---|
| INRw | | | |
| vs | TPC INRm | 0.9482 | 1.0506x |
| | TPC INRz | 0.9482 | 1.0389x |
| | TPC INRn | 0.9401 | 1.048x |
| INRw | | | |
| vs | INRm | −0.0908 | −0.0186x |
| | INRz | −0.0966 | −0.0144X |
| | INRn | 0.0327 | −0.0065x |

The linear regression analysis expression $y = mx + b$, when solved for the slope, m, is expressed as $(y-b)/x$. This is biased, so the expression is $y/x$ is when b is equal to zero. Statistical data and plots demonstrate that the INRn may replace prior WHO INR and provide results which are within the parameters of traditional therapeutic or reference ranges.

In accordance with one embodiment, the IBM-compatible computer 30 of FIG. 1 stores and manipulates these digital values corresponding to the clotting curve represented in FIG. 6 and the related data provided in Tables 14 and 15. According to a preferred embodiment, the computer may be programmed as follows:

(k) a sample of blood where the plasma is available, such as, for example, a sample of citrated blood, is obtained and placed in an appropriate container, the computer 30, as well as the recorder 28, sequentially records voltage values for a few seconds before injection of the reagent (thromboplastin calcium combined). As previously discussed, thromboplastin (tissue factor) is one of the factors in the human body that causes blood to clot. Prothrombin is another. Fibrinogen is yet another. Before injection of the thromboplastin, the output from the A/D converter 26 is relatively constant. When thromboplastin is injected into the plasma sample in the container, a significant and abrupt change occurs in the recorded voltage values of both the computer 30 and the recorder

28. This abrupt change is recognized by both the recorder 28 and, more importantly, by the computer 30 which uses such recognition to establish $T_o$. The computer 30 may be programmed so as to correlate the digital quantities of the A/D converter 26 to the analog output of the detector means photocell 10 which, in turn, is directly correlatable to the fibrinogen (FBG) concentration g/l of the sample of blood discussed herein and represented by the clotting curve shown in FIG. 6;

(l) the computer 30 may be programmed to look for a digital quantity representative of a critical quantity $F_1$, and when such occurs, record its instant time $T_1$. (The time span between $T_o$ and $T_1$ is the prothrombin time (PT), and has an normal duration of about 12 seconds, but may be greater than 30 seconds);

(m) following the detection of the quantity $c_1$, the computer 30 may be programmed to detect for the acceleration of fibrinogen (FBG) to fibrin conversion. The computer 30 is programmed to detect the maximum acceleration quantity $c_{MAP}$ or $c_{T2}$ as illustrated in FIG. 6, and its corresponding time of occurrence $t_{MAP}$, which is T2 in FIG. 6.

(d) The computer detects a quantity $c_{EOT}$ occurring at time $t_{EOT}$. Typically, it is important that the rate of fibrin formation increase for at least 1.5 seconds following the occurrence of ($T_1$); the computer determines a theoretical end of test (TEOT) based on the determination of the zero order kinetic rate. The computer may be programmed to determine the zero order rate, which is expressed as a Line (L) in FIG. 6. The TEOT may be determined by the corresponding time value (TEOT) along the line L which corresponds with the quantity $c_{EOT}$ (i.e., that corresponds with the value for T3);

(e) The computer 30 is programmed to ascertain the value for the time to start ($T_2S$) which corresponds with the time at which the simulated zero order kinetic rate begins.

(f) Following the detection of the acceleration of fibrinogen conversion to detect the start time $T_2S$, the computer 30 is programmed to detect for a deceleration of the fibrinogen conversion, wherein the fibrinogen concentration decreases from a predetermined quantity $c_{MAP}$ to a predetermined quantity $c_{EOT}$ having a value which is about equal but less than the first quantity $c_1$. The computer is programmed to ascertain a first delta (IUTz), by determining the difference between the quantity $c_{T2S}$ and the quantity $c_{EOT}$; and a second delta (IUXz) by determining the difference between the quantity $c_{T2S}$ and the quantity $c_{2\ (or\ CMAP)}$; the computer also determines the value ZTM by determining the difference between the time $T_2$ (which is Tmap) and the time $T_2S$;

(g) the computer 30 manipulates the collected data of (a); (b); (c); (d), (e) and (f) above, to determine the new fibrinogen transfer rate (nFTR). The nFTR may be arrived at based on the principle that if a required amount (e.g., 0.05 g/l) of fibrinogen concentration $c_1$ is first necessary to detect a clot point ($t_1$); then when the fibrinogen concentration ($c_{EOT}$) becomes less than the required amount $c_1$, which occurs at time ($t_{EOT}$), the fibrinogen end point has been reached. More particularly, the required fibrinogen concentration $c_1$ is the starting point of fibrinogen conversion of the clotting process and the less than required fibrinogen concentration $C_{EOT}$ is the end point of the fibrinogen conversion of the clotting process.

(h) the duration of the fibrinogen conversion of the clotting process of the present invention is defined by the zero order time period between TEOT and $T_2S$ and is generally indicated in FIG. 6 as IUTz. The difference between the corresponding concentrations $c_{T2S}$ and cT2 is used to define a delta IUXz. The computer now has the information needed to determine the TEOT, which is expressed by the following formula:

$$TEOT = T2S + (ZTM/IUX * IUT) \quad (12)$$

The TEOT is determined and the data collected is manipulated by the computer 30 to determine a new INR, referred to as INRn:

$$INRn = ((T_1 + TEot)/2) * 0.00535 * T_2S \quad (11)$$

Using the multiplier MUL (which in this example, as discussed herein and according to expression 10 above, preferably is 0.00535).

The computer 30 may be used to manipulate and derive the quantities of expression (11) to determine a new INR (INRn) utilizing known programming routines and techniques. The data collected by a computer 30 may be used to manipulate and derive INRn of expression (11). Similarly, one skilled in the art, using known mathematical techniques may derive the theoretical end of test TEOT of expression (5), and using the TEOT value in expression (11), in turn, may determine the new INR, INRn of expression (12). In the INRn determination, the determination is based on the patient's own sample, and does not rely on the determination of normal prothrombin times for the reagent used (e.g., thromboplastin, innovin or the like). With the INRn determination method, no longer does the accuracy of the quantities determined depend, in whole or part, on the number of specimens used, that is, the number of stable (or presumed stable) patients.

The new anticoagulation therapy value (INRn) does not require an ISI value, as was previously used to determine anticoagulation therapy factors. The new anticoagulation therapy value INRn uses for its ascertainment the values extracted from the clotting curve (see FIG. 6), in particular $T_2S$, Tmap, TEOT, $c_1$, $c_{T2S}$, ct2 and ceot. In determining the new INRn, the ISI is not required, nor is the MNPT, or the need to obtain and calculate the prothrombin times (PT's) for 20 presumed normal patients. In carrying out coagulation studies, the new anticoagulant therapy factor INRn may replace the INR traditionally used in anticoagulant therapy management (such as INR WHO and INRm). In addition, using the sample from the patient, the computer 30 has knowledge of the values obtained for the fibrinogen reaction, to ascertain the INRn.

Theoretical Clotting Area INRs Determination

An alternate embodiment for determining an anticoagulant therapy factor is provided and is based on determinations made during the clotting reaction of fibrinogen for a sample of a patient's blood. This alternate embodiment utilizes a theoretical clotting area. According to the illustration in FIG. 6, a clotting curve is shown where optical activity in instrument units is plotted against time (in seconds). Time values are indicated on the x axis, and optical activity values, such as absorbance values are indicated on the y axis. The optical activity values are measured with an instrument that detects changes in the optical activity (e.g., absorbance), and are recorded with their corresponding time values in order to derive a corresponding anticoagulant therapy factor value, ATFs or INRs. The INRs value is a value determined for the patient sample that generated the information represented by the clotting curve. The ATFs/INRs values obtained are useful in determining the treatment course for an individual, in particular where the individual has a blood disorder.

Figure 8:
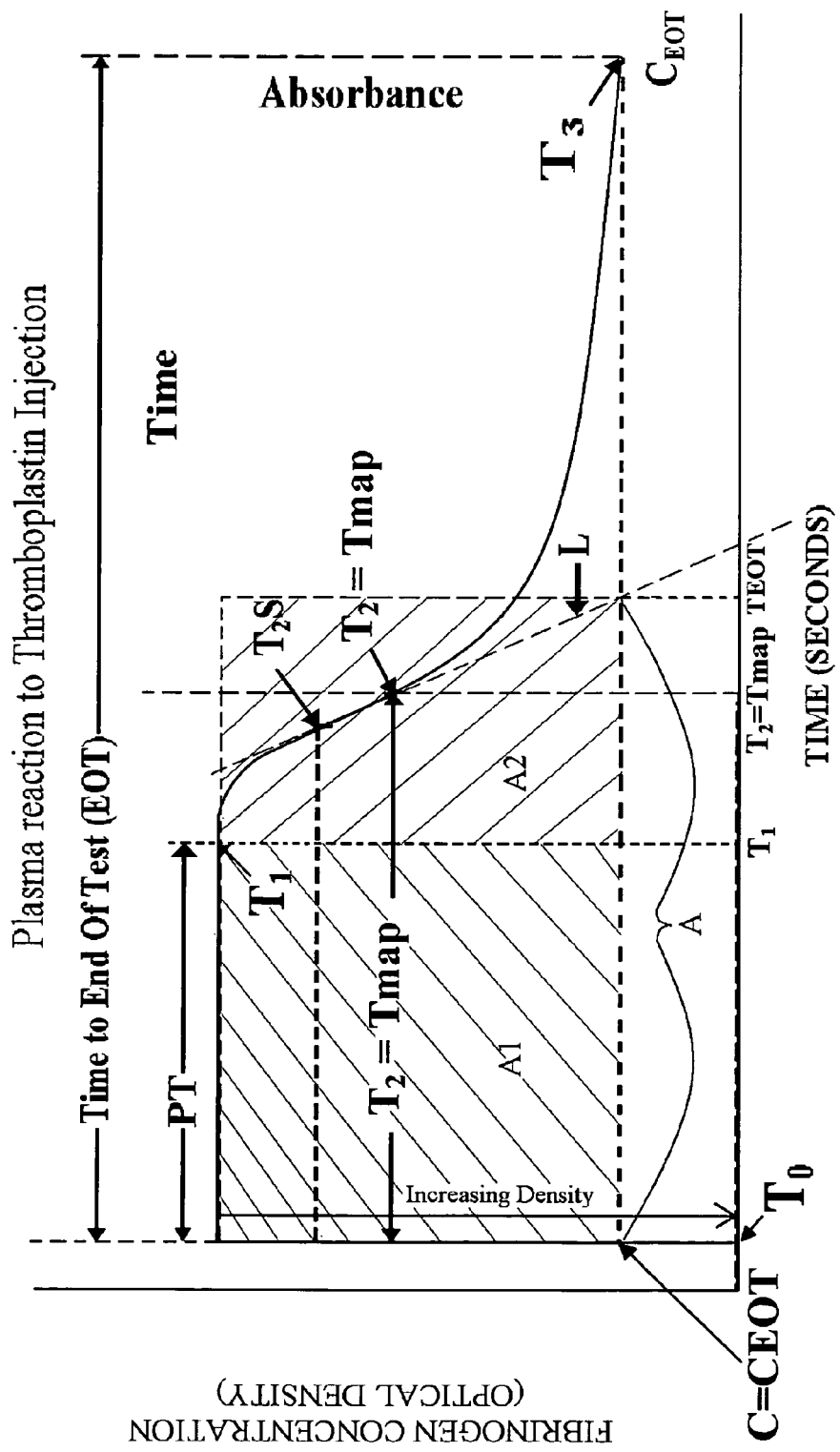
FIG. 8 is a figure depicting the clotting area of FIG. 7 with the clotting curve for a reaction of a blood sample containing fibrinogen with a thromboplastin reagent.

According to a preferred embodiment, the alternate embodiment determines an ATF value that utilizes the clotting curve information represented by the graph illustrated in FIG. 6. The clotting curve represents the optical activity for the coagulant reaction where the fibrinogen in the sample and a clotting agent are combined and the fibrinogen is transformed to fibrin. As illustrated in FIG. 8, the clotting curve defines an area below it and there also is a portion of the clotting area that is above the clotting curve. The alternate method is used for determining the INR for the sample, where the INR is an anticoagulant therapy factor and is represented by ATFs or INRs. The theoretical clotting area is derived to determine the INRs, and, according to the preferred alternate embodiment, utilizes an area defined by the time measurements at which certain functions of the clotting reaction occur. Preferably, an instrument is programmed with instructions for implementing processing of the signals based on the photodetection output of a photocell, such as, for example, the photocell of a spectrophotometer. The instrument described and shown in connection with FIG. 1 herein may be utilized to carry out the ATFs/INRs determination. Alternately, according to preferred embodiments, the spectrometric devices shown and described in connection with our copending application Ser. No. 12/932,824, filed on Mar. 7, 2011, may be used in connection with the method disclosed herein for determining the theoretical clotting area (A), shown in FIG. 7 being represented by area (A1) and area (A2), using the formulas set forth in expression (13), below.

Optical activity is determined for times corresponding with the time that the reagent is combined with the sample containing fibrinogen (To), and the time that represents the theoretical end of the test (TEOT). FIG. 6 illustrates a graph of the clotting curve and shows To, which is where the clotting agent, such as TPC or other clotting agent, is combined with the sample. The TEOT is also identified on FIG. 6. Preferably, the times T1 and TEOT are measured from the time To. The area (A) corresponds with the INRs. The INRs preferably is derived by utilizing a parity parameter to bring the time values in parity with the optical density measurements (such as absorbance values) that are recorded at the corresponding times. The TEOT may be determined as set forth herein in connection with the embodiments discussed herein, such as, for example, where the zero order kinetic line L is determined, and where the TEOT is derived. For example, in order to determine the TEOT, preferably, the slope of maximum acceleration on the clotting curve that corresponds with the maximum rate of formation of fibrin during the reaction of the fibrinogen in the sample with a clotting agent is determined. One preferred method for determining the slope is by determining the maximum acceleration point (identified as T2 or Tmap on FIG. 6). The determination of Tmap may be done as described herein in connection with the other embodiments. A preferred method involves sampling optical activity values (e.g., such as absorbance values) of the sample and clotting agent as the clotting reaction takes place to determine the last highest delta of an increasing rate of fibrinogen transformation. The slope is illustrated represented by the line L in FIG. 6, and the line L intersects c=Ceot, which provides a value for the TEOT.

According to a preferred embodiment, the ATFs or INRs may be expressed with the following formulae:

$$\text{Area} = T1 * TEOT \quad (13)$$

$$\text{ATFs} = \text{INRs} = T1 * TEOT * MUL \quad (14)$$

The MUL is a multiplier that is based on two relationships that are addressed by the multiplier. MUL relates the sampling rate of the instrument and the pixel parity of the x-y axis. The instrument used to measure the optical changes in the sample generates values, and preferably, the values, or signals are taken at a particular frequency. For example, a preferred sampling rate for the clotting curve reaction of a patient blood or blood component sample may be a number of optical absorbance values in a particular time interval. A preferred rate, for example, may be 100 optical absorbance values (or samples) per second, expressed 100/second. The sample rate preferably is used to derive a multiplier component, MUL. Also used to derive the multiplier component is the parity value, which is a multiplier utilized to create x-y pixel parity for the clotting curve information (that is shown expressed on the clotting curve graph, see FIG. 6). According to the example illustrated, the sampling rate used was 100 values per second. The pixel parity multiplier was 0.535. The multiplier, according to this example, is 0.535 (pixel parity value)/100 (the number of samples reflected in a second). The multiplier, or MUL, according to a preferred embodiment, was 0.00535.

In order to derive the ATFs, the clotting curve is considered, and the theoretical or hypothetical zero order kinetic line, or line L as it is referred to and appears on the Figures, provides an (x,y) coordinate of (TEOT, 0), where the time value at which the clotting reaction, if theorized from the slope or line taken between the point where the maximum acceleration of the conversion rate of fibrinogen transformation begins (T2S) and the end of the maximum conversion (which, according to preferred embodiments, may be determined as the last highest delta value of conversion rate), which is T2 or Tmap. The value, TEOT, is a time value, and generally, for example, may be expressed in seconds.

The INRs value preferably is determined using a clotting agent that reacts with the fibrinogen in the sample to provide a clotting reaction, such as the clotting reactions represented by the graph in FIG. 6. The clotting agents may be those discussed herein.

ATFs/INRs EXAMPLES

In accordance with the embodiment discussed above in connection with expression (14), the ATFs/INRs was determined for a number of patient samples. INRs/ATFs derivations were carried out using the data for the patient samples contained in Table 17. The INRs was determined as discussed herein by determining the PT for a sample, which is the value T1 (the time from the addition of the reagent to the time of the first clot, e.g., between T0 and T1 on FIG. 6). The clotting begins (at T1) and accelerates where the maximum conversion rate is determined at T2 (the maximum acceleration point or map). The coagulation reaction continues until reaching the end of test time, which is represented by time T3. The time T2S on the graph of FIG. 6 represents the beginning of the maximum acceleration of the clotting rate. The slope of the zero order kinetic reaction is represented by the line L. The theoretical end of the test TEOT may be determined by the point at which the line L crosses the line y=Ceot (see FIG. 6).

Based on carrying out the clotting reaction and detecting changes in the optical activity of the sample, the determination of the ATFs/INRs may be accomplished. Preferably, an instrument that has means for measuring the optical activity of the sample as the sample undergoes the coagulation reaction. According to preferred embodiments, a spectrophotometer such as, for example, the apparatus shown in FIG. 1 and described herein, may be used to provide optical activity data. According to alternate embodiments, a photocell and light source may be configured and arranged to provide information corresponding with the optical activity of a sample. For example, the light source, such as an LED light or other source, may be used to provide a beam that passes through the sample tube. According to a preferred embodiment, the light beam may be configurable by providing a variable power supply to operate the light source, as described in our copending patent application Ser. No. 12/932,824, filed on Mar. 7, 2011, the complete disclosure of which is herein incorporated by reference. The optical path output may be adjusted, e.g., increased or decreased, through the regulation of the light source power supply adjustment. A photocell preferably may be arranged to receive the light beam. The photocell preferably may be provided in an electric circuit that may be operated with a computer. The computer may be configured with a program that records the signals from the photocell over the time of the coagulation reaction. Preferably, the photocell output is part of a circuit. The circuit also may utilize a variable resistor and the variable resistor may be controlled though a computer. For example, if it is desirable to have the voltage from the voltage source varied, the computer may be operated with inputs from a keyboard or other input device to control the resistance. The negative output of the photocell also may be connected in the circuit though a variable resistor that may be controlled using the computer. According to one embodiment, the computer is programmed with software to implement the changes in the voltage so that the voltage is set to a level that will provide a baseline for the sample, and the computer may implement a routine that derives a voltage that will provide an appropriate scale for the optical activity measurements. The voltage setting may also be determined by blanking, where a blank of the sample container with water (or other material), or may be set to a baseline by determining the voltage corresponding to the optical activity of the sample itself, before the clotting agent addition. According to some embodiments, the reference voltage may be utilized by the computer, so that instructions are implemented to subtract the reference or baseline voltage from subsequent readings. In addition, the data from the photocell may be digitized so that the voltage readings may then be stored and manipulated.

Results for the coagulation studies on the data in Table 17, below, were carried out using Thromboplastin C as a reagent.

Table 17 shows data for samples corresponding to a sample ID A001 through A225, with some gaps in the sample numbers. Gaps in sample numbers indicate occurrences where a sample was not able to be tested because they were beyond three standard deviations. The INR values were determined based on the coagulation data for the sample. Each sample was reacted in a coagulation reaction with a clotting agent, which, for determination of the values in Table 17, was Thromboplastin C. The start of the recording of optical density values is represented by the start time (T0) (see FIG. 6) which corresponds with the time of the Thromboplastin C reagent addition to the sample. The prothrombin time (PT) or (T1), identified as (T1) in FIG. 6, was recorded, which is a time when the optical activity changes (after the addition of the reagent has been added at time To). The time to start (T2S) of the clotting reaction was determined and recorded, and the maximum acceleration point (MAP) was determined and the time corresponding therewith (Tmap) was recorded. The instrument unit value of the maximum acceleration point (Cmap) at the time of maximum acceleration (Tmap) was recorded. In Table 17, time value (T3) represents the end of test time where the fibrinogen transformation to fibrin in the sample has completed. The time (EtTm) represents the time of the end of the recording, which is later than the end of test time (T3), and which may be used to verify that the fibrinogen transformation has completed. Instrument unit value CT3 corresponding to the time T3, and the instrument unit value EtV1 corresponding with the time value EtTm, also are provided in Table 17. The instrument units corresponding with the time T1 (or prothrombin time PT) are provided in Table 17 as the value $C_{T1}$. The instrument unit value StV1 is a value determined using the MAP and by proceeding from the MAP and reverting to a point along the baseline of the clotting curve before the acceleration of the fibrinogen transformation takes place. The StV1 value may be used as a check for the PT, and corresponds with the time value StTm (which is a value that approximates the PT). The FTR is also reported in Table 17 and represents the fibrinogen transformation rate, which was derived using the expression TUX/IUT, which was determined for the reported INRz values in Table 17. The Area represents the area determined in accordance with expression T1*TEOT. The Area is multiplied by the multiplier MUL (which in this example was $\frac{1}{187}$ or 0.00535) in order to determine the INRs. The INRs values in Table 17 represent the Area*MUL. The values To, T1, Tmap and T2S preferably are determined as described herein and are recorded, and the corresponding associated instrument unit values $C_{T0}$, $C_{T1}$, $C_{MAP}$ and $C_{T2S}$, respectively are determined and recorded. A computer was provided with software containing instructions for obtaining the information from the coagulation reaction, including optical activity during the time of the coagulation reaction. The software also included instructions for recording and storing the data. Preferably, readings were taken every $\frac{1}{100}^{th}$ of a second, or 100 readings every second. The time values were recorded, and the corresponding optical activity values (in instrument units) at those respective times also were recorded. The data was stored and the software included instructions to manipulate the data to determine an anticoagulant therapy factor, which, using the data provided in Table 17, is identified as INRs, a new International Normalization Ratio (INR), based on the formula (14), INRs=T1*TEOT*MUL. According to one embodiment, the multiplier value (MUL) was utilized based on the pixel parity and sampling rate, which for the values in Table 17, was $\frac{1}{187}$, or 0.00535.

TABLE 17

SAMPLE DATA FOR ATF/INR DETERMINATIONS INCLUDING THE INRs DETERMINATION

| ID | INRm | INRz | INRs | PT (T1) | T2S | Tmap | T3 | StTm | EtTm |
|---|---|---|---|---|---|---|---|---|---|
| A001 | 2.97 | 2.98 | 2.91 | 18.49 | 22.38 | 23.58 | 49.55 | 18.88 | 49.64 |
| A002 | 3.17 | 3.02 | 2.85 | 19.19 | 23.33 | 24.43 | 37.75 | 18.30 | 37.84 |
| A003 | 3.36 | 3.03 | 3.06 | 19.84 | 23.48 | 25.27 | 37.55 | 19.70 | 37.64 |
| A004 | 2.05 | 2.36 | 2.00 | 14.94 | 20.11 | 21.62 | 37.55 | 14.61 | 37.64 |
| A005 | 2.87 | 2.66 | 2.60 | 18.11 | 21.95 | 23.92 | 37.55 | 18.35 | 37.64 |
| A007 | 2.04 | 2.05 | 1.79 | 14.89 | 18.64 | 19.38 | 33.95 | 14.67 | 34.04 |
| A008 | 2.61 | 2.82 | 2.56 | 17.16 | 21.95 | 23.23 | 41.95 | 17.21 | 42.04 |

TABLE 17-continued

SAMPLE DATA FOR ATF/INR DETERMINATIONS INCLUDING THE INRs DETERMINATION

| | | | | | | | | | |
|---|---|---|---|---|---|---|---|---|---|
| A009 | 3.16 | 3.27 | 3.02 | 19.17 | 24.26 | 25.55 | 37.95 | 19.90 | 38.04 |
| A010 | 1.78 | 1.84 | 1.55 | 13.78 | 17.55 | 18.73 | 30.15 | 14.21 | 30.24 |
| A011 | 2.09 | 1.98 | 1.81 | 15.10 | 18.19 | 19.36 | 33.75 | 14.88 | 33.84 |
| A012 | 3.19 | 2.86 | 2.84 | 19.26 | 22.55 | 24.01 | 36.95 | 19.25 | 37.04 |
| A013 | 3.47 | 3.46 | 3.41 | 20.21 | 24.55 | 26.05 | 50.15 | 19.86 | 50.24 |
| A014 | 1.78 | 1.79 | 1.52 | 13.76 | 17.28 | 18.41 | 30.15 | 13.75 | 30.24 |
| A015 | 1.86 | 1.86 | 1.62 | 14.11 | 17.64 | 18.79 | 30.15 | 14.22 | 30.24 |
| A016 | 3.04 | 2.93 | 2.82 | 18.73 | 22.43 | 23.36 | 45.75 | 18.67 | 45.84 |
| A017 | 1.80 | 1.88 | 1.62 | 13.85 | 17.55 | 18.77 | 31.35 | 13.87 | 31.44 |
| A018 | 2.07 | 2.18 | 1.95 | 15.02 | 19.07 | 21.01 | 34.55 | 14.86 | 34.64 |
| A019 | 1.84 | 1.97 | 1.72 | 14.05 | 17.90 | 19.09 | 36.75 | 13.76 | 36.84 |
| A020 | 3.55 | 3.74 | 3.43 | 20.49 | 25.69 | 26.49 | 42.75 | 20.26 | 42.84 |
| A021 | 2.85 | 2.78 | 2.70 | 18.07 | 21.87 | 23.38 | 37.35 | 17.52 | 37.44 |
| A022 | 2.11 | 2.24 | 1.99 | 15.20 | 19.28 | 20.62 | 36.75 | 15.45 | 36.84 |
| A023 | 3.09 | 2.96 | 2.85 | 18.92 | 22.72 | 23.92 | 43.35 | 18.32 | 43.44 |
| A024 | 3.33 | 3.58 | 3.34 | 19.75 | 25.57 | 27.26 | 45.35 | 19.93 | 45.44 |
| A025 | 1.84 | 1.80 | 1.53 | 14.03 | 17.39 | 17.81 | 27.45 | 13.61 | 30.24 |
| A026 | 1.56 | 1.67 | 1.42 | 12.78 | 16.34 | 17.30 | 31.75 | 12.93 | 31.84 |
| A027 | 1.48 | 1.54 | 1.33 | 12.41 | 15.50 | 16.58 | 33.35 | 12.40 | 33.44 |
| A028 | 1.91 | 1.99 | 1.78 | 14.34 | 18.03 | 19.04 | 39.15 | 14.40 | 39.24 |
| A029 | 2.05 | 2.14 | 1.92 | 14.92 | 18.70 | 20.26 | 40.55 | 14.67 | 40.64 |
| A030 | 2.57 | 2.63 | 2.56 | 17.00 | 20.76 | 21.99 | 48.75 | 17.16 | 48.84 |
| A031 | 2.60 | 2.65 | 2.45 | 17.14 | 21.51 | 22.95 | 39.55 | 17.68 | 39.64 |
| A032 | 3.85 | 3.89 | 3.72 | 21.46 | 26.04 | 26.82 | 48.15 | 21.39 | 48.24 |
| A033 | 2.94 | 2.97 | 2.82 | 18.39 | 22.75 | 24.33 | 41.95 | 16.58 | 42.04 |
| A034 | 2.21 | 2.28 | 2.06 | 15.58 | 19.48 | 20.80 | 38.95 | 14.71 | 39.04 |
| A035 | 4.87 | 4.53 | 5.04 | 24.58 | 30.42 | 33.72 | 47.75 | 23.26 | 47.84 |
| A036 | 3.11 | 2.96 | 2.89 | 18.99 | 22.41 | 23.18 | 43.55 | 19.25 | 43.64 |
| A037 | 2.41 | 2.79 | 2.36 | 16.38 | 21.97 | 23.02 | 36.95 | 16.40 | 37.04 |
| A038 | 1.59 | 1.54 | 1.32 | 12.91 | 15.72 | 16.63 | 29.75 | 12.59 | 31.24 |
| A039 | 1.46 | 1.59 | 1.30 | 12.27 | 15.92 | 17.25 | 30.15 | 11.79 | 30.24 |
| A040 | 2.36 | 2.38 | 2.24 | 16.21 | 19.86 | 21.29 | 39.75 | 16.33 | 39.84 |
| A041 | 2.32 | 2.48 | 2.35 | 16.03 | 20.04 | 21.48 | 45.15 | 15.94 | 45.24 |
| A042 | 4.07 | 4.33 | 3.99 | 22.17 | 27.49 | 28.09 | 49.35 | 22.16 | 49.44 |
| A044 | 4.34 | 3.88 | 3.96 | 22.99 | 27.07 | 28.46 | 41.15 | 21.20 | 41.24 |
| A045 | 2.70 | 2.83 | 2.64 | 17.52 | 22.01 | 23.58 | 45.75 | 17.51 | 45.84 |
| A047 | 2.82 | 2.93 | 2.73 | 17.95 | 22.50 | 23.94 | 41.55 | 17.89 | 41.64 |
| A048 | 3.84 | 3.78 | 3.81 | 21.44 | 26.02 | 27.87 | 46.15 | 21.47 | 46.24 |
| A049 | 2.70 | 2.50 | 2.50 | 17.51 | 20.34 | 22.01 | 39.55 | 17.10 | 39.64 |
| A050 | 2.74 | 2.87 | 2.68 | 17.66 | 22.31 | 24.13 | 40.75 | 17.08 | 40.84 |
| A051 | 1.92 | 1.92 | 1.75 | 14.37 | 17.72 | 18.46 | 35.55 | 14.28 | 35.64 |
| A052 | 2.77 | 2.65 | 2.59 | 17.76 | 21.28 | 22.94 | 40.35 | 17.32 | 40.44 |
| A053 | 3.09 | 2.87 | 2.72 | 18.91 | 22.60 | 23.56 | 38.75 | 18.53 | 38.84 |
| A054 | 2.10 | 2.06 | 1.88 | 15.13 | 18.40 | 20.12 | 33.15 | 14.39 | 33.24 |
| A055 | 5.39 | 6.00 | 6.30 | 26.05 | 32.30 | 34.28 | 70.15 | 26.51 | 70.24 |
| A056 | 3.52 | 3.79 | 3.63 | 20.40 | 25.80 | 27.34 | 53.15 | 19.89 | 53.24 |
| A057 | 2.87 | 2.66 | 2.50 | 18.14 | 21.61 | 22.66 | 35.15 | 17.79 | 35.24 |
| A058 | 8.49 | 9.07 | 10.19 | 33.82 | 41.85 | 45.34 | 81.95 | 30.69 | 82.04 |
| A059 | 2.72 | 2.77 | 2.51 | 17.57 | 21.95 | 22.95 | 34.15 | 17.56 | 34.24 |
| A060 | 3.12 | 3.04 | 2.82 | 19.02 | 23.49 | 24.54 | 36.55 | 19.11 | 36.64 |
| A061 | 2.49 | 2.47 | 2.38 | 16.70 | 20.20 | 21.50 | 38.35 | 16.45 | 38.44 |
| A062 | 6.14 | 7.67 | 7.45 | 28.07 | 37.69 | 39.90 | 78.95 | 27.67 | 79.04 |
| A063 | 3.05 | 3.17 | 3.10 | 18.78 | 23.35 | 25.84 | 42.15 | 17.95 | 42.24 |
| A064 | 2.23 | 2.26 | 2.04 | 15.68 | 19.48 | 20.73 | 32.55 | 15.37 | 32.64 |
| A065 | 2.68 | 2.89 | 2.68 | 17.41 | 22.34 | 24.26 | 39.75 | 17.10 | 39.84 |
| A066 | 1.99 | 1.93 | 1.70 | 14.69 | 18.11 | 19.28 | 30.15 | 14.68 | 30.24 |
| A067 | 1.65 | 1.84 | 1.57 | 13.19 | 17.29 | 18.12 | 36.75 | 13.66 | 36.84 |
| A068 | 2.51 | 2.44 | 2.36 | 16.78 | 20.05 | 21.86 | 37.35 | 17.29 | 37.44 |
| A069 | 2.41 | 2.24 | 2.08 | 16.39 | 19.46 | 20.21 | 31.95 | 16.40 | 32.04 |
| A070 | 2.39 | 2.28 | 2.12 | 16.31 | 19.58 | 20.66 | 37.55 | 15.39 | 37.64 |
| A071 | 1.89 | 2.02 | 1.79 | 14.28 | 18.01 | 19.61 | 39.55 | 13.49 | 39.64 |
| A072 | 1.82 | 1.96 | 1.78 | 13.94 | 17.61 | 18.83 | 43.55 | 13.22 | 43.64 |
| A073 | 1.41 | 1.71 | 1.39 | 12.06 | 16.39 | 17.72 | 37.75 | 12.45 | 37.84 |
| A074 | 1.63 | 1.83 | 1.51 | 13.11 | 17.32 | 18.89 | 33.35 | 13.43 | 33.44 |
| A075 | 1.53 | 1.39 | 1.17 | 12.64 | 15.17 | 15.71 | 26.34 | 12.93 | 30.24 |
| A076 | 1.44 | 1.57 | 1.38 | 12.18 | 15.54 | 16.73 | 37.55 | 12.17 | 37.64 |
| A077 | 4.64 | 4.85 | 5.01 | 23.88 | 29.00 | 30.64 | 68.15 | 23.18 | 68.24 |
| A078 | 2.12 | 2.18 | 1.99 | 15.23 | 18.93 | 20.51 | 37.15 | 15.40 | 37.24 |
| A080 | 7.27 | 7.76 | 9.23 | 30.92 | 36.28 | 38.50 | 86.95 | 31.11 | 87.04 |
| A081 | 3.61 | 4.27 | 3.95 | 20.69 | 27.25 | 28.59 | 57.95 | 21.17 | 58.04 |
| A082 | 1.54 | 1.73 | 1.51 | 12.68 | 16.57 | 17.53 | 43.55 | 12.68 | 43.64 |
| A083 | 1.60 | 1.59 | 1.36 | 12.97 | 16.00 | 17.04 | 30.15 | 12.42 | 30.24 |
| A084 | 6.70 | 6.86 | 8.06 | 29.52 | 34.53 | 37.73 | 76.55 | 29.27 | 76.64 |
| A085 | 3.29 | 3.59 | 3.59 | 19.62 | 25.14 | 28.43 | 48.15 | 19.66 | 48.24 |
| A086 | 2.69 | 2.73 | 2.61 | 17.47 | 21.37 | 22.39 | 46.95 | 17.59 | 47.04 |
| A087 | 1.84 | 1.93 | 1.72 | 14.06 | 17.60 | 18.99 | 40.75 | 13.75 | 40.84 |
| A088 | 1.71 | 1.88 | 1.62 | 13.44 | 17.39 | 18.49 | 37.95 | 13.43 | 38.04 |

TABLE 17-continued

SAMPLE DATA FOR ATF/INR DETERMINATIONS INCLUDING THE INRs DETERMINATION

| | | | | | | | | | |
|---|---|---|---|---|---|---|---|---|---|
| A089 | 2.19 | 2.12 | 1.92 | 15.52 | 18.89 | 20.02 | 33.95 | 15.29 | 34.04 |
| A090 | 6.13 | 6.70 | 7.51 | 28.05 | 34.40 | 37.78 | 84.35 | 27.31 | 84.44 |
| A091 | 7.71 | 8.68 | 9.20 | 31.99 | 39.58 | 41.64 | 74.75 | 31.38 | 74.84 |
| A092 | 1.91 | 2.33 | 1.99 | 14.36 | 19.42 | 21.08 | 50.15 | 14.35 | 50.24 |
| A093 | 4.80 | 5.00 | 5.01 | 24.37 | 29.39 | 30.21 | 53.15 | 22.78 | 53.24 |
| A094 | 3.13 | 3.39 | 2.98 | 19.07 | 24.84 | 25.77 | 42.95 | 18.28 | 43.04 |
| A095 | 1.50 | 1.62 | 1.41 | 12.48 | 15.95 | 17.00 | 39.55 | 12.47 | 39.64 |
| A096 | 2.12 | 1.93 | 1.80 | 15.22 | 17.92 | 19.14 | 30.95 | 15.21 | 31.04 |
| A097 | 1.33 | 1.27 | 1.11 | 11.67 | 13.92 | 14.89 | 27.63 | 11.58 | 30.24 |
| A098 | 1.41 | 1.46 | 1.27 | 12.07 | 15.00 | 16.05 | 34.95 | 11.71 | 35.04 |
| A099 | 1.76 | 1.78 | 1.53 | 13.67 | 17.04 | 18.11 | 30.15 | 13.92 | 30.24 |
| A100 | 1.40 | 1.61 | 1.37 | 12.02 | 15.71 | 17.08 | 41.95 | 11.28 | 42.04 |
| A101 | 2.76 | 2.82 | 2.73 | 17.71 | 21.79 | 23.55 | 44.75 | 17.13 | 44.84 |
| A102 | 3.63 | 3.64 | 3.61 | 20.75 | 24.96 | 25.99 | 57.95 | 21.27 | 58.04 |
| A103 | 1.96 | 2.27 | 2.00 | 14.58 | 19.13 | 20.70 | 45.75 | 14.83 | 45.84 |
| A104 | 3.14 | 3.37 | 3.47 | 19.10 | 23.49 | 27.37 | 51.95 | 19.31 | 52.04 |
| A105 | 3.69 | 3.76 | 3.98 | 20.93 | 24.99 | 26.57 | 63.15 | 20.92 | 63.24 |
| A107 | 2.81 | 2.81 | 2.76 | 17.90 | 21.63 | 23.09 | 50.20 | 18.00 | 52.04 |
| A108 | 2.05 | 2.16 | 1.91 | 14.93 | 18.93 | 20.43 | 33.55 | 15.05 | 33.64 |
| A109 | 2.26 | 2.35 | 2.23 | 15.82 | 19.44 | 21.64 | 42.15 | 15.85 | 42.24 |
| A110 | 3.90 | 4.43 | 4.64 | 21.61 | 27.03 | 29.19 | 67.75 | 21.64 | 67.84 |
| A111 | 2.55 | 2.79 | 2.69 | 16.92 | 21.24 | 24.12 | 45.75 | 16.61 | 45.84 |
| A112 | 2.27 | 2.55 | 2.41 | 15.85 | 20.28 | 21.63 | 56.43 | 16.32 | 58.04 |
| A113 | 1.85 | 1.89 | 1.75 | 14.10 | 17.12 | 18.76 | 38.35 | 13.67 | 38.44 |
| A114 | 1.96 | 2.18 | 1.92 | 14.58 | 18.82 | 20.19 | 43.35 | 15.12 | 43.44 |
| A115 | 2.29 | 2.72 | 2.36 | 15.93 | 21.39 | 22.90 | 47.35 | 16.25 | 47.44 |
| A116 | 1.73 | 1.61 | 1.49 | 13.53 | 15.90 | 17.10 | 29.98 | 13.14 | 31.84 |
| A117 | 1.59 | 1.85 | 1.61 | 12.93 | 17.12 | 18.16 | 49.15 | 13.03 | 49.24 |
| A118 | 2.18 | 2.08 | 1.94 | 15.49 | 18.54 | 19.71 | 35.35 | 15.03 | 35.44 |
| A119 | 2.98 | 2.82 | 2.92 | 18.53 | 21.48 | 23.28 | 50.95 | 18.52 | 51.04 |
| A120 | 2.11 | 2.11 | 1.88 | 15.18 | 18.76 | 19.62 | 34.35 | 15.17 | 34.44 |
| A121 | 2.05 | 2.15 | 1.94 | 14.95 | 18.74 | 20.36 | 36.55 | 15.59 | 36.64 |
| A122 | 1.76 | 1.89 | 1.68 | 13.70 | 17.19 | 18.82 | 42.35 | 13.28 | 42.44 |
| A123 | 1.79 | 1.80 | 1.63 | 13.80 | 16.78 | 18.26 | 31.54 | 13.15 | 33.04 |
| A124 | 1.77 | 1.68 | 1.51 | 13.73 | 16.44 | 17.50 | 29.07 | 13.84 | 29.64 |
| A125 | 1.39 | 1.46 | 1.33 | 11.93 | 15.07 | 15.92 | 37.95 | 11.92 | 38.04 |
| A126 | 3.63 | 3.59 | 3.66 | 20.75 | 25.11 | 27.37 | 41.35 | 20.98 | 41.44 |
| A127 | 2.36 | 2.35 | 2.28 | 16.20 | 19.63 | 20.54 | 51.15 | 16.27 | 51.24 |
| A128 | 3.89 | 3.62 | 3.57 | 21.59 | 25.16 | 26.03 | 49.55 | 20.87 | 49.64 |
| A129 | 5.13 | 5.86 | 6.00 | 25.32 | 32.20 | 34.47 | 66.15 | 25.65 | 66.24 |
| A130 | 4.66 | 5.39 | 4.95 | 23.94 | 31.73 | 33.07 | 60.35 | 21.93 | 60.44 |
| A131 | 1.72 | 1.93 | 1.68 | 13.49 | 17.47 | 19.10 | 35.95 | 13.48 | 36.04 |
| A132 | 2.56 | 3.27 | 2.86 | 16.97 | 24.01 | 26.61 | 47.95 | 17.32 | 48.04 |
| A133 | 2.64 | 3.08 | 2.90 | 17.27 | 22.41 | 24.52 | 50.65 | 17.26 | 53.04 |
| A134 | 6.30 | 7.84 | 7.59 | 28.48 | 37.77 | 39.63 | 64.95 | 27.67 | 65.04 |
| A135 | 1.48 | 1.49 | 1.30 | 12.40 | 15.36 | 16.23 | 31.15 | 12.41 | 31.24 |
| A136 | 4.20 | 4.28 | 4.38 | 22.57 | 27.22 | 28.75 | 63.10 | 22.95 | 64.24 |
| A137 | 1.96 | 1.99 | 1.74 | 14.56 | 18.25 | 19.56 | 36.95 | 13.58 | 37.04 |
| A138 | 2.00 | 2.36 | 2.04 | 14.73 | 19.67 | 21.19 | 46.15 | 14.74 | 46.24 |
| A139 | 2.07 | 2.31 | 2.11 | 15.03 | 19.36 | 20.51 | 48.75 | 15.23 | 48.84 |
| A140 | 1.29 | 1.48 | 1.22 | 11.44 | 14.99 | 16.28 | 38.35 | 11.71 | 38.44 |
| A141 | 2.17 | 2.20 | 2.02 | 15.45 | 19.06 | 20.07 | 36.35 | 15.64 | 36.44 |
| A142 | 3.32 | 3.24 | 2.97 | 19.71 | 24.36 | 25.31 | 37.79 | 18.26 | 39.04 |
| A143 | 2.56 | 2.56 | 2.48 | 16.97 | 20.91 | 23.81 | 37.75 | 16.96 | 37.84 |
| A144 | 2.44 | 2.46 | 2.23 | 16.53 | 20.45 | 21.49 | 42.81 | 16.73 | 43.04 |
| A145 | 1.38 | 1.46 | 1.25 | 11.91 | 15.09 | 16.05 | 37.55 | 11.90 | 37.64 |
| A146 | 2.16 | 2.27 | 2.18 | 15.38 | 19.19 | 20.18 | 49.55 | 15.80 | 49.64 |
| A147 | 1.59 | 1.67 | 1.43 | 12.92 | 16.29 | 17.43 | 34.55 | 13.13 | 34.64 |
| A148 | 2.40 | 2.39 | 2.27 | 16.37 | 19.88 | 20.88 | 46.95 | 16.03 | 47.04 |
| A149 | 1.53 | 1.60 | 1.36 | 12.61 | 16.04 | 16.93 | 34.35 | 12.78 | 34.44 |
| A150 | 1.55 | 1.60 | 1.43 | 12.72 | 15.86 | 16.84 | 39.95 | 12.71 | 40.04 |
| A151 | 2.80 | 2.90 | 2.82 | 17.89 | 21.97 | 23.44 | 58.75 | 17.88 | 58.84 |
| A152 | 2.19 | 2.13 | 1.91 | 15.51 | 19.02 | 20.16 | 33.45 | 14.86 | 33.84 |
| A153 | 1.71 | 1.90 | 1.69 | 13.46 | 17.34 | 18.52 | 47.55 | 13.74 | 47.64 |
| A154 | 2.28 | 2.26 | 2.17 | 15.88 | 19.06 | 20.58 | 44.75 | 15.41 | 44.84 |
| A155 | 4.59 | 4.84 | 5.08 | 23.75 | 30.13 | 33.35 | 53.55 | 23.45 | 53.64 |
| A156 | 2.79 | 2.80 | 2.55 | 17.85 | 22.10 | 23.06 | 40.95 | 17.43 | 41.04 |
| A157 | 2.24 | 2.20 | 2.03 | 15.72 | 19.16 | 19.88 | 37.15 | 15.16 | 37.24 |
| A158 | 3.56 | 3.42 | 3.35 | 20.52 | 24.45 | 25.53 | 46.55 | 18.40 | 46.64 |
| A159 | 3.94 | 4.21 | 4.31 | 21.74 | 27.09 | 29.76 | 61.35 | 21.51 | 61.44 |
| A160 | 2.67 | 2.89 | 2.69 | 17.39 | 22.14 | 24.02 | 44.35 | 16.75 | 44.44 |
| A161 | 1.66 | 1.82 | 1.58 | 13.24 | 16.83 | 18.59 | 35.95 | 13.23 | 36.04 |
| A162 | 6.47 | 7.15 | 7.82 | 28.92 | 35.32 | 37.56 | 79.75 | 27.09 | 79.84 |
| A163 | 3.83 | 3.67 | 3.80 | 21.40 | 25.31 | 27.09 | 49.55 | 20.91 | 49.64 |
| A164 | 3.65 | 3.82 | 3.59 | 20.81 | 25.84 | 26.79 | 49.35 | 21.27 | 49.44 |
| A165 | 2.62 | 2.60 | 2.43 | 17.20 | 20.99 | 21.95 | 43.75 | 17.57 | 43.84 |
| A166 | 2.19 | 2.23 | 2.06 | 15.52 | 19.13 | 20.18 | 43.03 | 14.58 | 43.84 |

TABLE 17-continued

SAMPLE DATA FOR ATF/INR DETERMINATIONS INCLUDING THE INRs DETERMINATION

| | | | | | | | | | |
|---|---|---|---|---|---|---|---|---|---|
| A167 | 2.78 | 2.90 | 2.55 | 17.80 | 22.39 | 22.99 | 38.15 | 17.95 | 38.24 |
| A168 | 3.64 | 3.53 | 3.73 | 20.77 | 24.33 | 25.44 | 51.55 | 21.00 | 51.64 |
| A169 | 4.13 | 3.91 | 4.13 | 22.35 | 25.76 | 26.76 | 62.15 | 22.34 | 62.24 |
| A170 | 1.39 | 1.41 | 1.18 | 11.93 | 14.85 | 15.90 | 31.79 | 11.60 | 32.44 |
| A171 | 3.35 | 3.54 | 3.40 | 19.81 | 25.06 | 26.96 | 47.95 | 20.00 | 48.04 |
| A172 | 2.46 | 2.33 | 2.24 | 16.58 | 19.67 | 20.50 | 39.75 | 17.05 | 39.84 |
| A173 | 1.51 | 1.47 | 1.32 | 12.55 | 15.25 | 16.08 | 30.75 | 12.73 | 30.84 |
| A174 | 1.84 | 1.81 | 1.67 | 14.04 | 17.00 | 18.10 | 36.75 | 14.03 | 36.84 |
| A175 | 1.77 | 1.76 | 1.51 | 13.71 | 17.05 | 17.83 | 34.84 | 13.32 | 36.24 |
| A176 | 3.33 | 3.38 | 3.31 | 19.75 | 24.04 | 25.23 | 50.35 | 19.28 | 50.44 |
| A177 | 1.74 | 1.64 | 1.48 | 13.59 | 16.19 | 17.28 | 31.35 | 13.34 | 31.44 |
| A178 | 2.37 | 2.55 | 2.36 | 16.22 | 20.52 | 21.78 | 43.11 | 15.39 | 43.64 |
| A179 | 2.45 | 2.51 | 2.28 | 16.56 | 20.69 | 21.85 | 39.95 | 16.07 | 40.04 |
| A180 | 2.17 | 2.21 | 2.03 | 15.43 | 19.03 | 20.41 | 37.55 | 15.78 | 37.64 |
| A181 | 3.41 | 3.78 | 3.76 | 20.01 | 26.08 | 29.59 | 52.35 | 20.28 | 52.44 |
| A182 | 2.10 | 2.09 | 1.95 | 15.15 | 18.53 | 19.35 | 39.18 | 14.47 | 41.04 |
| A183 | 1.56 | 1.50 | 1.28 | 12.79 | 15.54 | 16.46 | 28.95 | 12.54 | 29.04 |
| A184 | 2.58 | 2.59 | 2.51 | 17.06 | 20.69 | 21.95 | 47.68 | 16.69 | 48.04 |
| A185 | 3.26 | 3.45 | 3.35 | 19.52 | 24.32 | 25.97 | 54.15 | 18.41 | 54.24 |
| A186 | 3.12 | 3.52 | 3.80 | 19.01 | 22.67 | 29.11 | 65.55 | 18.00 | 65.64 |
| A187 | 1.81 | 1.72 | 1.54 | 13.91 | 16.79 | 17.57 | 35.55 | 13.22 | 35.64 |
| A188 | 3.01 | 3.09 | 2.95 | 18.64 | 22.95 | 24.40 | 36.72 | 19.00 | 38.64 |
| A189 | 2.98 | 3.13 | 3.02 | 18.53 | 23.48 | 25.90 | 45.95 | 18.52 | 46.04 |
| A190 | 3.38 | 3.69 | 3.46 | 19.91 | 25.18 | 26.54 | 44.68 | 20.61 | 45.44 |
| A191 | 2.04 | 2.00 | 1.82 | 14.91 | 18.05 | 19.10 | 34.53 | 14.33 | 36.24 |
| A192 | 2.43 | 2.62 | 2.23 | 16.46 | 21.45 | 22.35 | 39.47 | 17.58 | 40.44 |
| A193 | 2.13 | 2.08 | 1.97 | 15.26 | 18.27 | 19.60 | 39.35 | 15.16 | 39.44 |
| A194 | 2.29 | 2.33 | 2.16 | 15.92 | 19.61 | 21.10 | 38.55 | 15.27 | 40.04 |
| A195 | 1.39 | 1.64 | 1.35 | 11.95 | 16.03 | 17.12 | 35.10 | 11.80 | 36.84 |
| A196 | 1.99 | 2.09 | 1.89 | 14.68 | 18.44 | 19.71 | 43.95 | 14.67 | 44.04 |
| A197 | 1.78 | 1.88 | 1.59 | 13.76 | 17.64 | 18.37 | 42.35 | 12.74 | 42.44 |
| A198 | 1.93 | 1.89 | 1.79 | 14.44 | 17.62 | 18.13 | 31.95 | 14.30 | 32.04 |
| A199 | 1.42 | 1.49 | 1.25 | 12.11 | 15.28 | 16.33 | 29.55 | 12.41 | 29.64 |
| A200 | 1.40 | 1.39 | 1.23 | 12.01 | 14.60 | 15.62 | 31.95 | 11.84 | 32.04 |
| A201 | 2.58 | 2.58 | 2.48 | 17.06 | 20.72 | 21.83 | 42.55 | 16.56 | 42.64 |
| A202 | 2.27 | 2.31 | 2.15 | 15.86 | 19.48 | 20.57 | 37.28 | 16.30 | 38.44 |
| A203 | 2.01 | 1.95 | 1.77 | 14.76 | 17.89 | 18.82 | 37.23 | 15.04 | 37.44 |
| A204 | 1.81 | 1.66 | 1.49 | 13.91 | 16.54 | 17.20 | 30.75 | 13.52 | 30.84 |
| A205 | 1.87 | 2.11 | 1.78 | 14.19 | 18.71 | 19.73 | 39.55 | 14.18 | 39.64 |
| A207 | 2.73 | 2.84 | 2.68 | 17.60 | 21.88 | 23.14 | 46.15 | 16.83 | 46.24 |
| A208 | 3.05 | 3.12 | 3.12 | 18.76 | 22.85 | 24.53 | 50.15 | 18.16 | 50.24 |
| A209 | 1.85 | 1.91 | 1.70 | 14.09 | 17.71 | 18.33 | 37.35 | 13.70 | 37.44 |
| A210 | 2.29 | 2.27 | 2.14 | 15.92 | 19.31 | 20.63 | 40.95 | 14.20 | 41.04 |
| A211 | 2.68 | 2.81 | 2.59 | 17.41 | 21.86 | 23.03 | 47.55 | 17.43 | 47.64 |
| A212 | 2.80 | 2.95 | 2.75 | 17.87 | 22.38 | 23.51 | 45.15 | 17.50 | 45.24 |
| A213 | 2.67 | 2.73 | 2.82 | 17.38 | 20.91 | 22.53 | 56.75 | 17.64 | 56.84 |
| A214 | 2.70 | 2.80 | 2.77 | 17.51 | 21.33 | 23.66 | 44.75 | 17.85 | 44.84 |
| A215 | 2.47 | 2.40 | 2.29 | 16.63 | 19.96 | 21.23 | 42.55 | 16.62 | 42.64 |
| A216 | 4.15 | 4.64 | 4.61 | 22.42 | 28.51 | 30.54 | 61.15 | 21.19 | 61.24 |
| A217 | 2.33 | 2.66 | 2.52 | 16.10 | 20.76 | 22.01 | 65.15 | 16.09 | 65.24 |
| A218 | 2.82 | 3.30 | 3.06 | 17.96 | 23.54 | 25.10 | 59.95 | 18.37 | 60.04 |
| A219 | 2.74 | 2.60 | 2.53 | 17.64 | 21.10 | 22.86 | 38.75 | 17.21 | 38.84 |
| A220 | 1.93 | 2.01 | 1.75 | 14.43 | 18.21 | 19.42 | 34.75 | 14.91 | 34.84 |
| A222 | 1.89 | 1.87 | 1.73 | 14.27 | 17.25 | 18.42 | 33.95 | 13.97 | 34.04 |
| A223 | 1.74 | 1.65 | 1.52 | 13.60 | 16.25 | 17.09 | 33.55 | 13.59 | 33.64 |
| A224 | 1.64 | 1.76 | 1.49 | 13.12 | 16.79 | 18.12 | 32.95 | 12.71 | 33.04 |
| A225 | 1.82 | 1.72 | 1.55 | 13.94 | 16.85 | 17.40 | 33.15 | 13.93 | 33.24 |

| ID | TSOT | TEOT | CT1 | CT2S | CTmap = EtZo | CT3 | StV1 | EtV1 | FTR | AREA |
|---|---|---|---|---|---|---|---|---|---|---|
| A001 | 19.58 | 29.45 | 3738 | 3717 | 3708 | 3664 | 3739 | 3663 | 0.167 | 544.53 |
| A002 | 20.76 | 27.73 | 3724 | 3710 | 3704 | 3686 | 3726 | 3686 | 0.250 | 532.14 |
| A003 | 20.80 | 28.85 | 3740 | 3728 | 3720 | 3704 | 3741 | 3704 | 0.333 | 572.38 |
| A004 | 16.86 | 24.99 | 3733 | 3705 | 3692 | 3663 | 3734 | 3664 | 0.317 | 373.35 |
| A005 | 19.39 | 26.88 | 3738 | 3725 | 3715 | 3700 | 3739 | 3700 | 0.400 | 486.80 |
| A007 | 16.27 | 22.49 | 3739 | 3723 | 3718 | 3697 | 3741 | 3698 | 0.200 | 334.88 |
| A008 | 19.21 | 27.89 | 3741 | 3711 | 3697 | 3646 | 3742 | 3646 | 0.215 | 478.59 |
| A009 | 21.31 | 29.42 | 3741 | 3725 | 3718 | 3697 | 3742 | 3697 | 0.250 | 563.98 |
| A010 | 15.04 | 21.09 | 3742 | 3725 | 3717 | 3701 | 3743 | 3701 | 0.333 | 290.62 |
| A011 | 15.42 | 22.44 | 3713 | 3687 | 3676 | 3647 | 3715 | 3648 | 0.282 | 338.84 |
| A012 | 19.79 | 27.58 | 3743 | 3726 | 3717 | 3695 | 3744 | 3695 | 0.290 | 531.19 |
| A013 | 21.85 | 31.55 | 3738 | 3711 | 3696 | 3641 | 3740 | 3641 | 0.214 | 637.63 |
| A014 | 14.54 | 20.67 | 3732 | 3715 | 3708 | 3694 | 3733 | 3694 | 0.333 | 284.42 |
| A015 | 14.96 | 21.47 | 3738 | 3724 | 3718 | 3704 | 3739 | 3705 | 0.316 | 302.94 |
| A016 | 19.77 | 28.14 | 3741 | 3721 | 3714 | 3678 | 3742 | 3679 | 0.167 | 527.06 |
| A017 | 14.50 | 21.94 | 3742 | 3717 | 3707 | 3681 | 3742 | 3681 | 0.278 | 303.87 |

TABLE 17-continued

SAMPLE DATA FOR ATF/INR DETERMINATIONS INCLUDING THE INRs DETERMINATION

| | | | | | | | | | | |
|---|---|---|---|---|---|---|---|---|---|---|
| A018 | 16.27 | 24.24 | 3734 | 3721 | 3712 | 3697 | 3735 | 3697 | 0.375 | 364.08 |
| A019 | 15.18 | 22.92 | 3744 | 3712 | 3698 | 3653 | 3745 | 3654 | 0.241 | 322.03 |
| A020 | 22.49 | 31.29 | 3741 | 3725 | 3721 | 3697 | 3742 | 3698 | 0.148 | 641.13 |
| A021 | 18.85 | 27.91 | 3741 | 3725 | 3717 | 3693 | 3742 | 3694 | 0.258 | 504.33 |
| A022 | 16.38 | 24.53 | 3740 | 3714 | 3702 | 3667 | 3741 | 3667 | 0.255 | 372.86 |
| A023 | 20.12 | 28.12 | 3743 | 3717 | 3705 | 3663 | 3745 | 3663 | 0.222 | 532.03 |
| A024 | 22.64 | 31.65 | 3740 | 3714 | 3699 | 3660 | 3741 | 3660 | 0.278 | 625.09 |
| A025 | 14.45 | 20.33 | 3743 | 3729 | 3727 | 3715 | 3745 | 3715 | 0.143 | 285.23 |
| A026 | 13.35 | 20.82 | 3742 | 3714 | 3705 | 3672 | 3743 | 3672 | 0.214 | 266.08 |
| A027 | 12.95 | 20.02 | 3739 | 3713 | 3702 | 3667 | 3740 | 3667 | 0.239 | 248.45 |
| A028 | 15.42 | 23.16 | 3742 | 3711 | 3699 | 3650 | 3743 | 3651 | 0.200 | 332.11 |
| A029 | 16.01 | 24.07 | 3740 | 3709 | 3691 | 3647 | 3742 | 3647 | 0.290 | 359.12 |
| A030 | 17.92 | 28.14 | 3743 | 3713 | 3700 | 3635 | 3744 | 3635 | 0.167 | 478.38 |
| A031 | 18.81 | 26.73 | 3728 | 3713 | 3705 | 3684 | 3729 | 3685 | 0.286 | 458.15 |
| A032 | 23.39 | 32.44 | 3732 | 3715 | 3710 | 3674 | 3733 | 3675 | 0.125 | 696.16 |
| A033 | 19.59 | 28.68 | 3739 | 3715 | 3703 | 3670 | 3741 | 3670 | 0.267 | 527.43 |
| A034 | 16.84 | 24.76 | 3740 | 3718 | 3707 | 3674 | 3742 | 3674 | 0.250 | 385.76 |
| A035 | 26.79 | 38.34 | 3734 | 3723 | 3713 | 3699 | 3736 | 3699 | 0.417 | 942.40 |
| A036 | 20.10 | 28.42 | 3735 | 3720 | 3715 | 3681 | 3736 | 3681 | 0.128 | 539.70 |
| A037 | 18.70 | 26.99 | 3740 | 3712 | 3703 | 3669 | 3741 | 3669 | 0.209 | 442.10 |
| A038 | 13.39 | 19.06 | 3742 | 3719 | 3710 | 3686 | 3743 | 3685 | 0.265 | 246.06 |
| A039 | 12.93 | 19.74 | 3738 | 3720 | 3712 | 3697 | 3740 | 3698 | 0.364 | 242.21 |
| A040 | 17.33 | 25.80 | 3741 | 3718 | 3705 | 3664 | 3742 | 3664 | 0.241 | 418.22 |
| A041 | 16.95 | 27.45 | 3739 | 3709 | 3695 | 3637 | 3740 | 3638 | 0.197 | 440.02 |
| A042 | 23.89 | 33.69 | 3735 | 3717 | 3714 | 3686 | 3736 | 3687 | 0.100 | 746.91 |
| A044 | 24.15 | 32.21 | 3741 | 3720 | 3710 | 3683 | 3743 | 3683 | 0.270 | 740.51 |
| A045 | 19.16 | 28.19 | 3739 | 3710 | 3694 | 3647 | 3740 | 3647 | 0.254 | 493.89 |
| A047 | 19.49 | 28.39 | 3735 | 3712 | 3701 | 3667 | 3736 | 3667 | 0.244 | 509.60 |
| A048 | 22.73 | 33.21 | 3733 | 3717 | 3708 | 3682 | 3733 | 3682 | 0.257 | 712.02 |
| A049 | 17.74 | 26.65 | 3737 | 3723 | 3714 | 3689 | 3738 | 3689 | 0.265 | 466.64 |
| A050 | 19.50 | 28.43 | 3739 | 3722 | 3711 | 3685 | 3741 | 3685 | 0.297 | 502.07 |
| A051 | 14.98 | 22.75 | 3738 | 3701 | 3691 | 3633 | 3740 | 3634 | 0.149 | 326.92 |
| A052 | 18.79 | 27.26 | 3737 | 3722 | 3712 | 3686 | 3739 | 3687 | 0.286 | 484.14 |
| A053 | 20.20 | 26.92 | 3738 | 3723 | 3717 | 3696 | 3739 | 3697 | 0.231 | 509.06 |
| A054 | 15.53 | 23.27 | 3733 | 3713 | 3701 | 3679 | 3734 | 3679 | 0.353 | 352.08 |
| A055 | 28.64 | 45.25 | 3736 | 3712 | 3699 | 3627 | 3737 | 3627 | 0.153 | 1178.76 |
| A056 | 22.72 | 33.23 | 3740 | 3706 | 3689 | 3624 | 3741 | 3625 | 0.210 | 677.89 |
| A057 | 18.81 | 25.81 | 3723 | 3707 | 3701 | 3683 | 3724 | 3682 | 0.240 | 468.19 |
| A058 | 37.55 | 56.35 | 3738 | 3722 | 3709 | 3668 | 3740 | 3667 | 0.236 | 1905.76 |
| A059 | 18.75 | 26.75 | 3736 | 3720 | 3715 | 3696 | 3737 | 3696 | 0.208 | 470.00 |
| A060 | 20.97 | 27.69 | 3730 | 3718 | 3713 | 3698 | 3731 | 3698 | 0.250 | 526.66 |
| A061 | 17.76 | 26.70 | 3734 | 3719 | 3711 | 3679 | 3736 | 3680 | 0.205 | 445.89 |
| A062 | 33.45 | 49.66 | 3739 | 3716 | 3704 | 3651 | 3740 | 3651 | 0.185 | 1393.96 |
| A063 | 19.75 | 30.82 | 3737 | 3724 | 3715 | 3697 | 3739 | 3696 | 0.321 | 578.80 |
| A064 | 16.20 | 24.32 | 3737 | 3716 | 3708 | 3685 | 3738 | 3685 | 0.258 | 381.34 |
| A065 | 19.14 | 28.74 | 3740 | 3720 | 3708 | 3680 | 3741 | 3680 | 0.300 | 500.36 |
| A066 | 15.57 | 21.62 | 3738 | 3725 | 3719 | 3707 | 3739 | 3707 | 0.333 | 317.60 |
| A067 | 14.72 | 22.19 | 3739 | 3705 | 3694 | 3640 | 3740 | 3640 | 0.169 | 292.69 |
| A068 | 17.58 | 26.30 | 3739 | 3724 | 3713 | 3686 | 3740 | 3686 | 0.289 | 441.31 |
| A069 | 16.46 | 23.77 | 3734 | 3718 | 3714 | 3695 | 3735 | 3695 | 0.174 | 389.59 |
| A070 | 16.99 | 24.33 | 3738 | 3714 | 3704 | 3670 | 3740 | 3670 | 0.227 | 396.82 |
| A071 | 15.13 | 23.45 | 3737 | 3710 | 3695 | 3659 | 3739 | 3659 | 0.294 | 334.87 |
| A072 | 14.56 | 23.91 | 3738 | 3708 | 3696 | 3646 | 3740 | 3646 | 0.194 | 333.31 |
| A073 | 13.65 | 21.48 | 3738 | 3703 | 3686 | 3638 | 3739 | 3639 | 0.266 | 259.05 |
| A074 | 14.44 | 21.51 | 3718 | 3696 | 3684 | 3664 | 3719 | 3665 | 0.387 | 282.00 |
| A075 | 13.01 | 17.33 | 3741 | 3733 | 3731 | 3725 | 3742 | 3725 | 0.250 | 219.05 |
| A076 | 12.73 | 21.17 | 3742 | 3716 | 3705 | 3664 | 3743 | 3665 | 0.216 | 257.85 |
| A077 | 25.72 | 39.22 | 3740 | 3714 | 3701 | 3633 | 3742 | 3633 | 0.160 | 936.57 |
| A078 | 16.20 | 24.39 | 3740 | 3721 | 3710 | 3683 | 3741 | 3683 | 0.289 | 371.46 |
| A080 | 32.73 | 55.82 | 3741 | 3725 | 3715 | 3637 | 3742 | 3637 | 0.114 | 1725.95 |
| A081 | 23.64 | 35.70 | 3742 | 3707 | 3694 | 3625 | 3743 | 3626 | 0.160 | 738.63 |
| A082 | 13.69 | 22.23 | 3742 | 3712 | 3702 | 3653 | 3743 | 3654 | 0.172 | 281.88 |
| A083 | 13.61 | 19.54 | 3742 | 3719 | 3709 | 3685 | 3744 | 3685 | 0.294 | 253.43 |
| A084 | 31.06 | 51.06 | 3742 | 3729 | 3717 | 3667 | 3743 | 3667 | 0.194 | 1507.29 |
| A085 | 21.27 | 34.24 | 3742 | 3722 | 3705 | 3675 | 3743 | 3676 | 0.370 | 671.79 |
| A086 | 18.51 | 27.90 | 3742 | 3714 | 3704 | 3650 | 3743 | 3650 | 0.156 | 487.41 |
| A087 | 15.08 | 22.90 | 3742 | 3713 | 3697 | 3652 | 3744 | 3652 | 0.262 | 321.97 |
| A088 | 14.68 | 22.52 | 3737 | 3700 | 3685 | 3630 | 3738 | 3630 | 0.214 | 302.67 |
| A089 | 16.25 | 23.16 | 3742 | 3721 | 3712 | 3687 | 3744 | 3687 | 0.265 | 359.44 |
| A090 | 30.77 | 50.05 | 3741 | 3712 | 3685 | 3587 | 3743 | 3588 | 0.218 | 1403.90 |
| A091 | 35.00 | 53.77 | 3741 | 3721 | 3712 | 3659 | 3742 | 3659 | 0.145 | 1720.10 |
| A092 | 16.52 | 25.88 | 3740 | 3691 | 3663 | 3582 | 3741 | 3582 | 0.257 | 371.64 |
| A093 | 25.56 | 38.41 | 3739 | 3725 | 3722 | 3692 | 3741 | 3693 | 0.094 | 936.05 |
| A094 | 22.46 | 29.18 | 3741 | 3718 | 3709 | 3676 | 3743 | 3677 | 0.220 | 556.46 |
| A095 | 13.25 | 21.13 | 3743 | 3707 | 3693 | 3638 | 3744 | 3637 | 0.200 | 263.70 |
| A096 | 15.31 | 22.10 | 3739 | 3724 | 3717 | 3700 | 3740 | 3701 | 0.304 | 336.36 |
| A097 | 10.87 | 17.80 | 3741 | 3719 | 3712 | 3691 | 3742 | 3691 | 0.250 | 207.73 |

TABLE 17-continued

SAMPLE DATA FOR ATF/INR DETERMINATIONS INCLUDING THE INRs DETERMINATION

| | | | | | | | | | | |
|---|---|---|---|---|---|---|---|---|---|---|
| A098 | 12.46 | 19.72 | 3742 | 3713 | 3701 | 3659 | 3743 | 3659 | 0.222 | 238.02 |
| A099 | 14.19 | 20.96 | 3742 | 3718 | 3709 | 3685 | 3743 | 3685 | 0.273 | 286.52 |
| A100 | 13.18 | 21.26 | 3741 | 3704 | 3684 | 3623 | 3743 | 3624 | 0.250 | 255.55 |
| A101 | 18.66 | 28.83 | 3740 | 3724 | 3715 | 3688 | 3742 | 3689 | 0.257 | 510.58 |
| A102 | 22.38 | 32.56 | 3740 | 3720 | 3712 | 3661 | 3741 | 3661 | 0.136 | 675.62 |
| A103 | 16.27 | 25.59 | 3741 | 3710 | 3693 | 3640 | 3742 | 3640 | 0.243 | 373.10 |
| A104 | 20.44 | 34.02 | 3730 | 3719 | 3705 | 3681 | 3731 | 3681 | 0.368 | 649.78 |
| A105 | 21.83 | 35.52 | 3738 | 3720 | 3711 | 3660 | 3739 | 3660 | 0.150 | 743.43 |
| A107 | 19.07 | 28.81 | 3740 | 3719 | 3707 | 3660 | 3741 | 3660 | 0.203 | 515.70 |
| A108 | 15.43 | 23.93 | 3743 | 3729 | 3723 | 3709 | 3744 | 3709 | 0.300 | 357.27 |
| A109 | 16.69 | 26.41 | 3740 | 3725 | 3713 | 3687 | 3741 | 3688 | 0.324 | 417.81 |
| A110 | 23.21 | 40.16 | 3737 | 3714 | 3701 | 3635 | 3738 | 3634 | 0.163 | 867.86 |
| A111 | 18.04 | 29.72 | 3739 | 3719 | 3701 | 3666 | 3740 | 3666 | 0.340 | 502.86 |
| A112 | 17.66 | 28.46 | 3742 | 3711 | 3695 | 3614 | 3743 | 3614 | 0.165 | 451.09 |
| A113 | 14.66 | 23.21 | 3737 | 3716 | 3702 | 3664 | 3739 | 3664 | 0.269 | 327.26 |
| A114 | 15.85 | 24.64 | 3732 | 3706 | 3694 | 3655 | 3733 | 3655 | 0.235 | 359.25 |
| A115 | 18.05 | 27.75 | 3742 | 3711 | 3697 | 3652 | 3743 | 3652 | 0.237 | 442.06 |
| A116 | 12.81 | 20.53 | 3742 | 3724 | 3717 | 3697 | 3744 | 3697 | 0.259 | 277.77 |
| A117 | 14.56 | 23.28 | 3739 | 3707 | 3694 | 3630 | 3740 | 3630 | 0.169 | 301.01 |
| A118 | 16.20 | 23.39 | 3742 | 3728 | 3721 | 3699 | 3744 | 3699 | 0.241 | 362.31 |
| A119 | 19.03 | 29.50 | 3742 | 3727 | 3716 | 3678 | 3743 | 3678 | 0.224 | 546.64 |
| A120 | 16.18 | 23.20 | 3737 | 3719 | 3713 | 3688 | 3738 | 3688 | 0.194 | 352.18 |
| A121 | 15.73 | 24.29 | 3740 | 3727 | 3720 | 3703 | 3741 | 3703 | 0.292 | 363.14 |
| A122 | 14.60 | 22.94 | 3736 | 3709 | 3692 | 3649 | 3738 | 3650 | 0.288 | 314.28 |
| A123 | 13.82 | 22.07 | 3742 | 3728 | 3721 | 3703 | 3744 | 3703 | 0.280 | 304.57 |
| A124 | 13.44 | 20.50 | 3736 | 3719 | 3713 | 3696 | 3737 | 3696 | 0.261 | 281.47 |
| A125 | 12.31 | 20.81 | 3719 | 3680 | 3668 | 3599 | 3720 | 3599 | 0.148 | 248.26 |
| A126 | 22.10 | 33.02 | 3743 | 3735 | 3729 | 3714 | 3744 | 3714 | 0.286 | 685.17 |
| A127 | 16.99 | 26.27 | 3741 | 3712 | 3702 | 3639 | 3742 | 3639 | 0.137 | 425.57 |
| A128 | 22.55 | 30.96 | 3739 | 3721 | 3715 | 3681 | 3741 | 3681 | 0.150 | 668.43 |
| A129 | 26.90 | 44.31 | 3743 | 3722 | 3713 | 3674 | 3744 | 3674 | 0.188 | 1121.93 |
| A130 | 28.32 | 38.67 | 3740 | 3712 | 3701 | 3655 | 3742 | 3656 | 0.196 | 925.76 |
| A131 | 14.39 | 23.27 | 3738 | 3721 | 3712 | 3689 | 3739 | 3690 | 0.290 | 313.91 |
| A132 | 19.73 | 31.50 | 3742 | 3714 | 3697 | 3665 | 3743 | 3665 | 0.347 | 534.56 |
| A133 | 18.89 | 31.38 | 3742 | 3722 | 3710 | 3671 | 3743 | 3670 | 0.231 | 541.93 |
| A134 | 31.96 | 49.86 | 3743 | 3718 | 3710 | 3666 | 3744 | 3666 | 0.154 | 1420.01 |
| A135 | 12.42 | 19.60 | 3741 | 3714 | 3706 | 3675 | 3742 | 3676 | 0.211 | 243.04 |
| A136 | 24.30 | 36.26 | 3744 | 3723 | 3712 | 3658 | 3745 | 3658 | 0.169 | 818.39 |
| A137 | 15.54 | 22.35 | 3739 | 3708 | 3693 | 3661 | 3741 | 3661 | 0.319 | 325.42 |
| A138 | 16.81 | 25.84 | 3742 | 3710 | 3693 | 3641 | 3743 | 3641 | 0.246 | 380.62 |
| A139 | 16.68 | 26.26 | 3742 | 3714 | 3702 | 3642 | 3743 | 3642 | 0.167 | 394.69 |
| A140 | 12.26 | 19.92 | 3743 | 3707 | 3690 | 3642 | 3744 | 3642 | 0.262 | 227.88 |
| A141 | 16.23 | 24.41 | 3739 | 3711 | 3701 | 3658 | 3740 | 3658 | 0.189 | 377.13 |
| A142 | 21.32 | 28.16 | 3742 | 3726 | 3721 | 3706 | 3744 | 3705 | 0.238 | 555.03 |
| A143 | 17.80 | 27.33 | 3739 | 3724 | 3710 | 3693 | 3740 | 3693 | 0.452 | 463.79 |
| A144 | 17.92 | 25.28 | 3740 | 3706 | 3692 | 3641 | 3741 | 3641 | 0.215 | 417.88 |
| A145 | 12.28 | 19.67 | 3739 | 3701 | 3688 | 3639 | 3740 | 3639 | 0.210 | 234.27 |
| A146 | 16.36 | 26.54 | 3736 | 3716 | 3709 | 3664 | 3737 | 3664 | 0.135 | 408.19 |
| A147 | 13.57 | 20.67 | 3742 | 3711 | 3698 | 3661 | 3743 | 3661 | 0.260 | 267.06 |
| A148 | 17.15 | 25.88 | 3742 | 3712 | 3701 | 3646 | 3743 | 3646 | 0.167 | 423.66 |
| A149 | 13.37 | 20.12 | 3743 | 3707 | 3695 | 3652 | 3744 | 3653 | 0.222 | 253.71 |
| A150 | 13.21 | 20.99 | 3742 | 3696 | 3679 | 3607 | 3743 | 3607 | 0.191 | 266.99 |
| A151 | 19.36 | 29.45 | 3737 | 3698 | 3676 | 3586 | 3738 | 3586 | 0.196 | 526.86 |
| A152 | 16.11 | 23.07 | 3737 | 3714 | 3705 | 3682 | 3739 | 3682 | 0.281 | 357.82 |
| A153 | 14.65 | 23.44 | 3729 | 3688 | 3670 | 3595 | 3730 | 3595 | 0.194 | 315.50 |
| A154 | 16.56 | 25.57 | 3727 | 3704 | 3690 | 3644 | 3729 | 3643 | 0.230 | 406.05 |
| A155 | 26.34 | 39.98 | 3739 | 3719 | 3702 | 3667 | 3741 | 3667 | 0.327 | 949.53 |
| A156 | 19.38 | 26.74 | 3733 | 3716 | 3710 | 3687 | 3734 | 3687 | 0.207 | 477.31 |
| A157 | 15.85 | 24.20 | 3736 | 3713 | 3708 | 3678 | 3738 | 3678 | 0.143 | 380.42 |
| A158 | 21.57 | 30.57 | 3737 | 3721 | 3715 | 3687 | 3739 | 3688 | 0.182 | 627.30 |
| A159 | 23.59 | 37.10 | 3733 | 3712 | 3696 | 3652 | 3735 | 3652 | 0.267 | 806.55 |
| A160 | 19.20 | 28.96 | 3738 | 3713 | 3697 | 3655 | 3740 | 3655 | 0.276 | 503.61 |
| A161 | 14.32 | 22.36 | 3740 | 3720 | 3706 | 3676 | 3741 | 3677 | 0.326 | 296.05 |
| A162 | 30.84 | 50.55 | 3739 | 3719 | 3709 | 3651 | 3740 | 3651 | 0.147 | 1461.91 |
| A163 | 22.34 | 33.22 | 3738 | 3723 | 3714 | 3683 | 3740 | 3684 | 0.231 | 710.91 |
| A164 | 22.80 | 32.30 | 3734 | 3718 | 3713 | 3684 | 3735 | 3684 | 0.147 | 672.16 |
| A165 | 18.51 | 26.43 | 3735 | 3704 | 3692 | 3636 | 3736 | 3636 | 0.176 | 454.60 |
| A166 | 16.46 | 24.78 | 3733 | 3700 | 3687 | 3630 | 3735 | 3629 | 0.183 | 384.59 |
| A167 | 19.69 | 26.74 | 3735 | 3717 | 3713 | 3688 | 3736 | 3688 | 0.138 | 475.97 |
| A168 | 22.11 | 33.58 | 3731 | 3719 | 3713 | 3669 | 3733 | 3670 | 0.122 | 697.46 |
| A169 | 23.09 | 34.54 | 3726 | 3702 | 3693 | 3623 | 3727 | 3623 | 0.114 | 771.97 |
| A170 | 12.12 | 18.53 | 3740 | 3714 | 3704 | 3679 | 3741 | 3679 | 0.286 | 221.06 |
| A171 | 22.07 | 32.12 | 3740 | 3718 | 3704 | 3666 | 3741 | 3666 | 0.269 | 636.30 |
| A172 | 17.01 | 25.31 | 3741 | 3725 | 3720 | 3691 | 3742 | 3691 | 0.147 | 419.64 |
| A173 | 12.29 | 19.64 | 3740 | 3715 | 3708 | 3678 | 3741 | 3679 | 0.194 | 246.48 |
| A174 | 14.43 | 22.23 | 3733 | 3705 | 3693 | 3648 | 3734 | 3648 | 0.211 | 312.11 |
| A175 | 14.48 | 20.64 | 3719 | 3686 | 3676 | 3640 | 3721 | 3640 | 0.217 | 282.97 |

TABLE 17-continued

SAMPLE DATA FOR ATF/INR DETERMINATIONS INCLUDING THE INRs DETERMINATION

| | | | | | | | | | | |
|---|---|---|---|---|---|---|---|---|---|---|
| A176 | 21.21 | 31.33 | 3739 | 3720 | 3712 | 3671 | 3741 | 3671 | 0.163 | 618.77 |
| A177 | 13.47 | 20.41 | 3739 | 3719 | 3711 | 3688 | 3741 | 3689 | 0.267 | 277.37 |
| A178 | 17.31 | 27.16 | 3740 | 3712 | 3701 | 3654 | 3741 | 3653 | 0.186 | 440.54 |
| A179 | 18.02 | 25.79 | 3739 | 3716 | 3706 | 3672 | 3740 | 3673 | 0.233 | 427.08 |
| A180 | 16.27 | 24.55 | 3733 | 3717 | 3709 | 3685 | 3734 | 3685 | 0.250 | 378.81 |
| A181 | 22.16 | 35.16 | 3739 | 3720 | 3703 | 3676 | 3740 | 3676 | 0.386 | 703.55 |
| A182 | 15.48 | 24.04 | 3739 | 3713 | 3706 | 3666 | 3741 | 3666 | 0.149 | 364.21 |
| A183 | 12.93 | 18.76 | 3726 | 3709 | 3703 | 3688 | 3727 | 3688 | 0.286 | 239.94 |
| A184 | 17.79 | 27.49 | 3738 | 3715 | 3705 | 3661 | 3740 | 3661 | 0.185 | 468.98 |
| A185 | 21.46 | 32.13 | 3736 | 3710 | 3695 | 3639 | 3738 | 3639 | 0.211 | 627.18 |
| A186 | 19.67 | 37.35 | 3738 | 3718 | 3675 | 3620 | 3740 | 3620 | 0.439 | 710.02 |
| A187 | 14.45 | 20.69 | 3739 | 3712 | 3703 | 3667 | 3741 | 3667 | 0.200 | 287.80 |
| A188 | 20.05 | 29.56 | 3731 | 3713 | 3704 | 3672 | 3732 | 3670 | 0.209 | 551.00 |
| A189 | 20.06 | 30.46 | 3730 | 3706 | 3689 | 3657 | 3731 | 3657 | 0.347 | 564.42 |
| A190 | 21.10 | 32.52 | 3730 | 3715 | 3710 | 3688 | 3731 | 3686 | 0.172 | 647.47 |
| A191 | 15.43 | 22.77 | 3738 | 3723 | 3717 | 3696 | 3740 | 3694 | 0.207 | 339.50 |
| A192 | 19.14 | 25.31 | 3739 | 3721 | 3714 | 3691 | 3740 | 3690 | 0.226 | 416.60 |
| A193 | 15.91 | 24.18 | 3741 | 3725 | 3716 | 3685 | 3743 | 3685 | 0.225 | 368.99 |
| A194 | 16.44 | 25.38 | 3735 | 3718 | 3710 | 3687 | 3736 | 3687 | 0.258 | 404.05 |
| A195 | 13.38 | 21.17 | 3739 | 3688 | 3667 | 3589 | 3740 | 3590 | 0.214 | 252.98 |
| A196 | 15.65 | 24.03 | 3738 | 3716 | 3706 | 3672 | 3739 | 3673 | 0.233 | 352.76 |
| A197 | 15.45 | 21.66 | 3739 | 3703 | 3691 | 3637 | 3741 | 3638 | 0.185 | 298.04 |
| A198 | 14.30 | 23.23 | 3727 | 3714 | 3712 | 3692 | 3729 | 3692 | 0.091 | 335.44 |
| A199 | 12.48 | 19.25 | 3741 | 3717 | 3708 | 3683 | 3742 | 3683 | 0.265 | 233.12 |
| A200 | 11.54 | 19.12 | 3737 | 3716 | 3709 | 3685 | 3738 | 3686 | 0.233 | 229.63 |
| A201 | 17.87 | 27.22 | 3740 | 3722 | 3715 | 3681 | 3742 | 3681 | 0.171 | 464.37 |
| A202 | 15.77 | 25.37 | 3737 | 3720 | 3715 | 3693 | 3738 | 3692 | 0.179 | 402.37 |
| A203 | 15.20 | 22.44 | 3739 | 3713 | 3704 | 3669 | 3740 | 3669 | 0.205 | 331.21 |
| A204 | 14.56 | 19.97 | 3738 | 3723 | 3718 | 3697 | 3740 | 3697 | 0.192 | 277.78 |
| A205 | 15.88 | 23.47 | 3740 | 3715 | 3706 | 3673 | 3741 | 3673 | 0.214 | 333.04 |
| A207 | 18.89 | 28.50 | 3728 | 3709 | 3701 | 3667 | 3730 | 3667 | 0.190 | 501.60 |
| A208 | 20.05 | 31.06 | 3736 | 3721 | 3712 | 3677 | 3738 | 3678 | 0.209 | 582.69 |
| A209 | 15.23 | 22.55 | 3741 | 3721 | 3716 | 3682 | 3743 | 3682 | 0.128 | 317.73 |
| A210 | 16.17 | 25.09 | 3741 | 3722 | 3714 | 3687 | 3742 | 3687 | 0.229 | 399.43 |
| A211 | 19.10 | 27.79 | 3741 | 3708 | 3694 | 3637 | 3742 | 3637 | 0.197 | 483.82 |
| A212 | 18.99 | 28.78 | 3740 | 3722 | 3716 | 3688 | 3741 | 3688 | 0.176 | 514.30 |
| A213 | 18.35 | 30.36 | 3741 | 3722 | 3710 | 3652 | 3742 | 3653 | 0.174 | 527.66 |
| A214 | 18.58 | 29.59 | 3739 | 3726 | 3715 | 3687 | 3740 | 3687 | 0.282 | 518.12 |
| A215 | 16.91 | 25.80 | 3737 | 3713 | 3703 | 3667 | 3738 | 3667 | 0.217 | 429.05 |
| A216 | 24.63 | 38.48 | 3740 | 3719 | 3708 | 3665 | 3742 | 3665 | 0.204 | 862.72 |
| A217 | 17.63 | 29.30 | 3740 | 3710 | 3698 | 3628 | 3741 | 3628 | 0.146 | 471.73 |
| A218 | 20.27 | 31.86 | 3738 | 3694 | 3673 | 3582 | 3739 | 3583 | 0.189 | 572.21 |
| A219 | 18.17 | 26.77 | 3741 | 3726 | 3717 | 3697 | 3742 | 3697 | 0.310 | 472.22 |
| A220 | 15.35 | 22.72 | 3741 | 3715 | 3704 | 3674 | 3742 | 3674 | 0.268 | 327.85 |
| A222 | 14.71 | 22.71 | 3725 | 3712 | 3706 | 3684 | 3727 | 3684 | 0.214 | 324.07 |
| A223 | 13.06 | 20.95 | 3741 | 3722 | 3717 | 3694 | 3742 | 3695 | 0.185 | 284.92 |
| A224 | 13.80 | 21.22 | 3742 | 3715 | 3703 | 3675 | 3743 | 3675 | 0.300 | 278.41 |
| A225 | 14.43 | 20.81 | 3740 | 3718 | 3713 | 3682 | 3741 | 3682 | 0.139 | 290.09 |

By determining the prothrombin time (T1) and the theoretical end of the test (TEOT), the INRs may be determined. The instrument pixel parity and sampling rate multiplier preferably is applied to the product of T1 and TEOT to provide the resultant INRs.

INRs A001 ID Example

An example of the determination of the INRs is provided using expression (14) and the reported data in Table 17. The TPC derived values of Table 17 for the sample ID A001, included the value PT or T1, where T1 or PT=18.49. The value of TEOT was determined and reported in Table 17, and for A001, is TEOT=29.45. Taking the product of T1 and TEOT, the value is 544.53, which is reported in Table 17 as the Area, which is a theoretical area determined according to the expression (13) above. Referring to FIG. 7, the theoretical area A is shown corresponding to a first area portion A1, representing the square of the value T1, (i.e., $T1^2$), and a second area portion A2 representing the rectangular area of the product of T1 and (TEOT−T1). Since the expression A1 plus A2, which is represented by $T1^2+T1*(TEOT-T1)$ is simplified to T1*TEOT, the Area (A) represented by the combined areas A1 and A2, may be determined by the expression A=T1*TEOT. From the determination of the Area, the INRs may be obtained. According to one embodiment, the INRs is determined using the formula of expression (14) above. The time values and instrument unit values were taken into account for the pixel parity and sampling rate. A multiplier (MUL) (1/187 or 0.00535) that takes into account the pixel parity was applied to the area by multiplying the multiplier (MUL) and the area to obtain the INRs. As shown in relation to the clotting curve in FIG. 8, the area included in the preferred INR determination, where INRs is derived, includes area portions above and below the clotting curve.

Comparative Results

Comparative INR values also were determined using the values obtained in Table 17. Table 17, in addition to reporting the INRs values (using expression (14)), also includes the reporting of INRm and INRz values, for comparative purposes. The comparative results between the INR values derived from the data reported in Table 17 are presented in Table 18.

TABLE 18

COMPARATIVE RESULTS FOR INRs VERSUS INRm and INRz

| TPC | | Ng | | | Lassen 1 = Pass 2 = Fail | | | Poller | | |
|---|---|---|---|---|---|---|---|---|---|---|
| | | MisMatch | <=0.4 | <=0.7 | MisMatch | <=0.4 | <=0.7 | ±10% | Total | Pcnt |
| INRs | INRm | 10.60% | 87.20% | 94.00% | 1 | 1 | 1 | 9 | 218 | 4.10% |
| INRs | INRz | 10.60% | 87.20% | 94.00% | 1 | 1 | 1 | 9 | 218 | 4.10% |

The above data represented in Table 18 shows comparisons for INR/ATF determinations made to compare INRs (obtained using the formula in expression (14) above) with: (1) INR values obtained using the World Health Organization method which is represented by INRm, uses the ISI of the manufacturer and is determined by $INRm = (PT/Mnpt)^{ISI}$ and (2) INRz which is determined by: $INRz = (Map/Mnxt)^{\wedge 2-FTR}$. In each comparison case in Table 18, the reagent used to obtain the data was Thromboplastin C.

As a result of the comparisons set forth in Table 18, the hereinbefore description of the new anticoagulant therapy factor (ATFs/INRs) does correlate at least as well as, and preferably better than, studies carried out using the International Normalized Ratio (INR) and International Sensitivity Index (ISI) for the INR values obtained using the World Health Organization (WHO) values, represented in Table 18 as INRm, and studies carried out using INR/ATF determinations using methods where the mean normal prothrombin time of a number of individuals having presumed normal coagulation functions must be determined, as with INRz. The inventive method represented by the formula in expression (14) and expressed herein as INRs and/or ATFs is an improvement over the prior methods.

Power Regression Determination and Comparisons

According to an alternate embodiment, the Area is determined as discussed herein using expression (13), and a multiplier is applied with the use of a power regression. The results in Table 17 include values for an Area for each respective sample. The PT or T1 is the prothrombin time, which is the point where the conversion of fibrinogen to fibrin begins to decay after achieving the maximum rate. This, as discussed herein, is referred to as the maximum acceleration point (MAP). As described herein, the MAP is used to determine the mean normal maximum time (MNXT) (or MNPT as it is sometimes also referred to). The MNXT is used to derive the INRm, which is the WHO INR determination, where the mean of a number of presumed normal coagulation patients is used. According to the following expression, the INRm, the WHO INR, is:

$$INRm = (XT/MNXT)^{ISI}$$

According to preferred embodiments, the present invention provides an area determination which represents a hypothetical or theoretical clotting area. The clotting area has two sides, as shown in FIG. 7. Using each sample's maximum fibrinogen conversion rate, the time to convert all of the fibrinogen to fibrin in a sample using this rate is determined. This time to convert the fibrinogen to fibrin in the sample defines a hypothetical or theoretical end of test (TEOT) (or HEOT as it also may be referred to). The TEOT is designated as the height of the area. The other side of the area is the time required to convert sufficient prothrombin to thrombin, thus beginning the conversion of fibrinogen to fibrin. The time required for the conversion of prothrombin to thrombin is represented by the value T1 (or PT) and is designated as the length of the area. In this area determination, the two sides are not parallel. The value TEOT and the value T1 are defining two sides of an event creating the hypothetical clotting area. The one side represents the length (T1) and the other side represents the height (TEOT). This relationship is illustrated in FIG. 7. This is expressed by the equation of expression (13): Area=T1*TEOT.

According to further embodiments of the invention, an expression is derived to enable the use of a power progression expression to determine the INRs for a sample. The INRs may be related to the INRm (WHO determined INR value) by utilization of a power regression that relates the clotting area (A) with the INRs of the sample. The relationship of the INRm values determined for fibrinogen standards may be used to provide an expression or formula from which determinations of an INRs for patient samples may be done by determining the clotting area for the patient sample. Preferably, the patient sample clotting area determination is made using the same thromboplastin, and more preferably, the same batch of thromboplastin, and the same instrument, so that the patient samples may be reacted in a coagulation reaction with a coagulation reagent, and the clotting area (A) determined, and an INRs for the patient sample determined using the power regression obtained with the fibrinogen standard samples (for the thromboplastin reagent and the instrument).

According to a preferred method, a number of fibrinogen standards are run and the respective area for each fibrinogen standard is determined. From these determinations, an expression was derived for determining the INRs value using the thromboplastin for which the fibrinogen standard determinations were made. One preferred method involves utilizing five fibrinogen standards, a high fibrinogen standard, a low fibrinogen standard and three fibrinogen/INR control levels 1, 2 and 3. For each of the five samples, an Area value and an INR value are calculated and plotted. According to exemplary embodiments, three thromboplastins (e.g., TPC, BPT and Innovin) were used to provide three power regressions.

Each level has an INR value, and replacing the prothrombin time ratio (PR) with the values for an INR based on the following relationship in expression (15):

$$INR = (MAP/MNXT)^{ISI} \qquad (15)$$

where MAP is the point in time that is where maximum rate of conversion of fibrinogen to fibrin occurs, where MNXT is the mean normal maximum time, and where ISI is an exponent that is the ISI (international sensitivity index) of the manufacturer for the clotting reagent used (e.g., thromboplastin).

A solution curve for each thromboplastin using the five levels of standards and controls was created. The Area is plotted on the "x" axis and the INR is plotted on the "y" axis. To solve for "y", and because the INR value uses an exponent, the solution should solve for an exponent. The power regression is implemented to provide a result that relates the INRs to an INRm for a particular thromboplastin, such as, for example, TPC thromboplastin (and for a particular batch of thromboplastin. The use of "y"=INR and "x"=Area provides relationships for determining INRs based on the INR(standard) for coagulation determinations carried out with a clotting reagent (e.g., thromboplastin), where according to a preferred embodiment, the INR(standard) (which is an INR obtained for the fibrinogen standard samples) is determined in accordance with expression (15). For example, according to one example, five levels were obtained, and, for TPC, the INR was $y=0.0174x^{0.8117}$, for INN the INR was $y=0.1333x^{0.4329}$, and for BTP was $y=0.005x^{1.0179}$. Using these expressions, the INRm or "y" as it is designated in the previous expressions, may be determined based on the area determined for the sample according to expression (14), where Area=T1*TEOT*MUL. The INRs may therefore be substituted in the expression as "x", and a corresponding INRm may be determined by solving for "y". The use of this method provides a way to determine the correlation of the INRs with the WHO determined INRm.

A linear regression and Pearson's R results were determined, and for TPC was y=0.9688 and R2=0.9834, for INN was y=0.9332 and R2=0.984, and for BTP was y=0.911 and R2=0.99.

As discussed herein, the INR is calculated by a standard method, where the INR is the international normalized ratio and the ISI is the international sensitivity index. The prothrombin ratio (PR) is a sample's prothrombin time divided by a mean normal prothrombin time (MNPT) created by using 20-plus presumed normal samples. INR=Prothrombin Ratio$^{ISI}$. The method for determining an INRs value for a patient blood sample was carried out as follows. A standard curve was created with fibrinogen standards, and, preferably, as in this example, using FDA-cleared high and low fibrinogen standards and three fibrinogen/INR controls of levels 1, 2 and 3. For each of these 5 samples, a hypothetical or theoretical clotting AREA value (A) and an INR value were calculated and plotted for each of the tested thromboplastins. The clotting area (A) was determined by obtaining values for the time and optical activity as discussed herein. A spectrophotometric device was used, and the output of the spectrophotometric device was provided to a computer. The computer was programmed with software, and the software included instructions to record, store and manipulate the time and absorbance data to provide the INR, area and INRs values.

Figure 9:
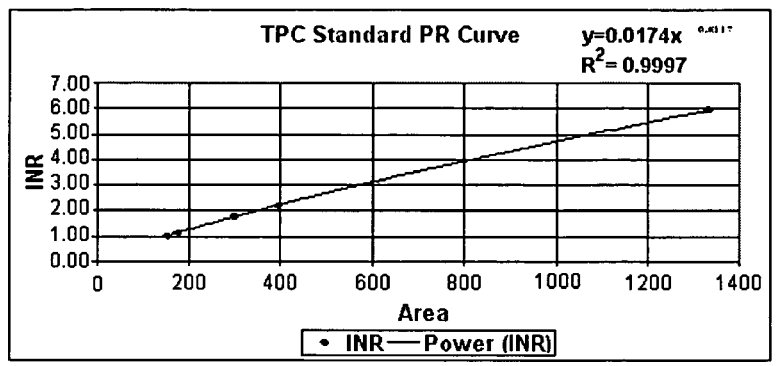
FIGS. 9, 10 and 11 illustrate solution curves for clotting reagents, TPC, Innovin and BPT, respectively, based on a power regression.
Figure 10:
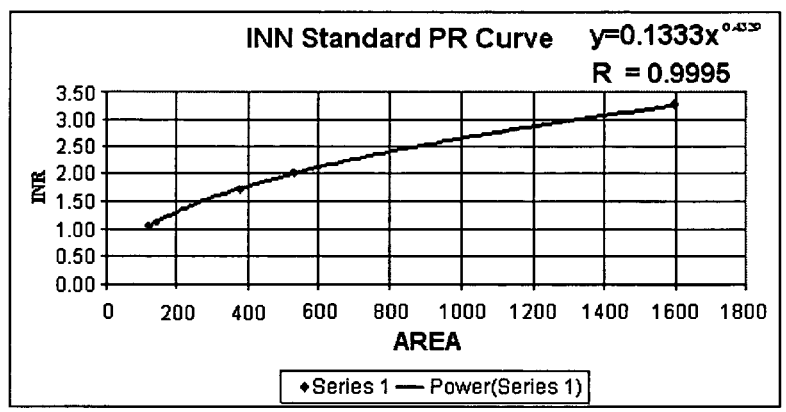
Figure 11:
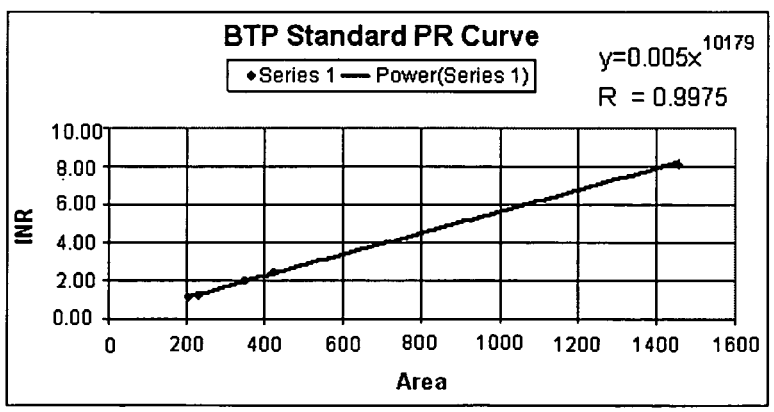
Figure 12:
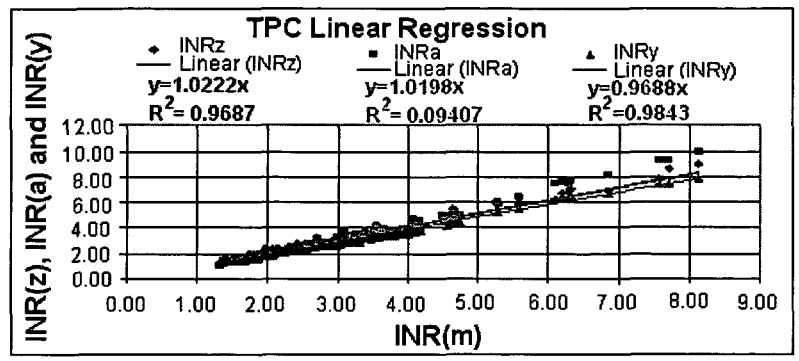
FIGS. 12, 13 and 14 illustrate curves for clotting reagents, TPC, Innovin and BPT, respectively, for INR determinations, based on a linear regression.
Figure 13:
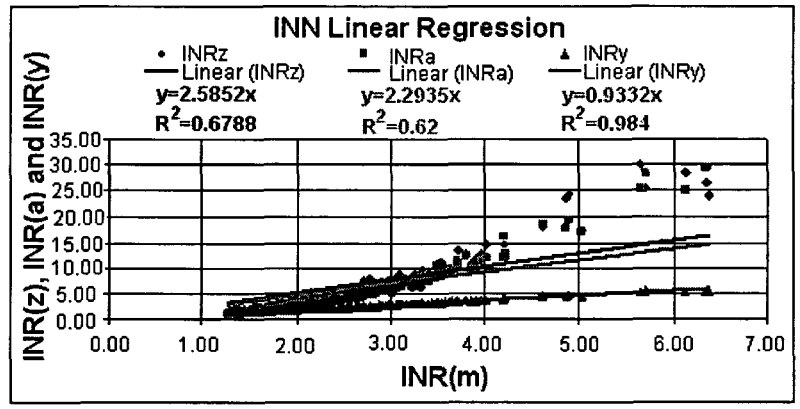
Figure 14:
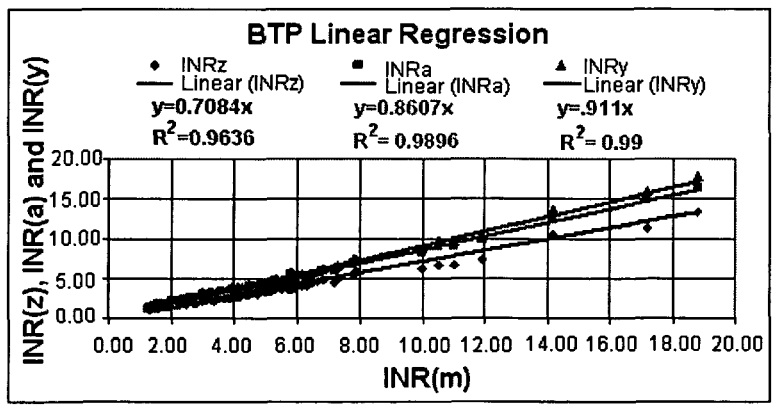

First, the fibrinogen sample was reacted by introducing by injection a clotting reagent into the sample, while the sample was in position on the spectrophotometer device so that time and optical dentisy values could be obtained for the sample and recorded, as the fibrinogen transformation to fibrin was occurring. A determination was made to record the occurrence of the prothrombin time (T1). The time and absorbance values continued to be recorded. A maximum acceleration point (MAP) was determined for the rate of fibrinogen conversion. This is the point where the conversion of fibrinogen to fibrin begins to decay after achieving a maximum rate. This is called the maximum acceleration point (MAP) and is used to determine a mean normal maximum time (MNXT). Next was to define the hypothetical or theoretical clotting area (A). By using each fibrinogen standard sample's maximum fibrinogen conversion rate, we determined the conversion time by calculating the time to convert all of the fibrinogen to fibrin in a sample using this rate. This time defines a hypothetical or theoretical end of test (TEOT) and is designated as the height of the clotting area (A). The other side is the time required to convert sufficient prothrombin to thrombin (which is represented as the time value T1 in FIGS. 6, 7 and 8), thus beginning the conversion of fibrinogen to fibrin. This time is represented and referred to as the prothrombin time (T1) and is designated the length of the area (A). According to a preferred embodiment, these two sides are not parallel lines, but rather, are defining two sides of an event creating a hypothetical or theoretical clotting area (A). The clotting area is expressed by the equation: AREA=T1*HEOT. Each of the abovementioned fibrinogen standard levels has an INR value, and replacing the standard prothrombin time ratio (PR) element in the original INR expression with values relating to the time to convert the fibrinogen in the sample to fibrin using the rate of maximum acceleration and the mean normal maximum time, the equation ISI becomes expression (15): INR=(MAP/MNXT)$^{ISI}$ The method illustrated according to this example utilizes the Area of the fibrinogen standard samples and the INR (standard) values determined for the fibrinogen standard samples to derive an equation, which comprises a power regression. The INR area method was compared and related to the reference INR(standard) values obtained using the method of expression (15). A solution curve for each thromboplastin (which in this example included TPC, BPT and Innovin) using the 5 levels of fibrinogen standards and controls was created. The AREA is plotted on the 'x' axis and the INR area method is plotted on the 'y' axis. To solve for 'y', and because the INR value uses an exponent, the solution is to solve for an exponent. A solution that related the INRs derivation to the standards and controls was developed in the form of a power regression. The solution curve, where INR on the 'y' axis and AREA on the 'x' axis, was as follows: for TPC: $y=0.0174 \times 0.8117$, for INN: $y=0.1333x^{0.4329}$ and for BTP: $y=0.005x^{1.0179}$. Examples of plots illustrating the solution curves for these clotting reagents are shown in FIGS. 9-11.

Applying these solutions to the three thromboplastins tested using the same 218 samples (which were used to provide the data in Table 17, above) gave a linear regression and Pearson's R results of: TPC: y=0.9688 and $R^2$=0.9834, INN: y=0.9332 and $R^2$=0.984 and BTP: y=0.911 with $R^2$=0.99.

According to preferred embodiments, the INRs determination made using the power regression embodiments may be implemented utilizing the computer in the manner described herein in connection with determinations made of the zero order kinetic reactions and determinations of the time and optical activity values. According to one embodiment, the method includes determining an INR value for known fibrinogen standard samples by conducting a clotting reaction for the reaction of each known fibrinogen standard sample and a clotting reagent, and, for each known fibrinogen sample, determining the time to maximum acceleration (XT) for each standard fibrinogen sample, determining the maximum rate of acceleration (MNXT) by determining a slope corresponding with the maximum acceleration rate of transformation of fibrinogen to fibrin during the clotting reaction of the standard fibrinogen sample, and determining the INR value for the fibrinogen standard sample by the expression INR(standard)=(XT/MNXT)$^{ISI}$, wherein ISI is an exponent and is the manufacturer's ISI value for the clotting reagent used to carry out the clotting reaction. The method preferably includes deriving the INRs for a patient sample by determining an expression based on the INR values obtained for each fibrinogen standard sample, including determining, from said clotting area (A) for each standard fibrinogen sample and the INR value for each standard fibrinogen sample, a power regression expression, wherein y=m*A^e, where y is the INRs, m is a constant, A is the clotting area, and e is another constant which is an exponent, and wherein obtaining the INRs for a patient sample comprises determining the clotting area A for the patient sample, raising the area A to the exponent e, and multiplying the value (the e power of A) by the constant m to obtain the INRs. The power regression constants m and e are obtained using the INR(standard) value and the clotting area A determined for each fibrinogen standard sample according to the expression INR(standard)=m*A^e. In this manner, the INRs of a patient sample may be derived using the power regression expression, and substituting for the A value the clotting area of the patient sample (from conducting a clotting reaction with the thromboplastin) and solving the expression for the INRs.

The present methods, including, in particular, the INRs determination, provide resultant INR values (INRs value) for a patient blood sample (or blood component sample) which may be used to determine treatments for a patient, such as, for example, blood therapy treatments. The methods herein may include administering to a living being, such as, for example, a patient, a course of treatment. The course of treatment, for example, may involve a treatment agent for regulating the clotting activity of blood and administering that blood treatment agent to the patient. The INR value, (INRs), corresponds with the clotting activity of the blood of the living being and therefore provides a reference for the amount of treatment agent to be administered. The INRs may be determined for the patient at intervals, and administering the treatement may be done at intervals. For example, the treatment agent may comprise an anticoagulant, such as, coumadin or warfarin.

The present invention provides apparatus and methods for obtaining an new anticoagulant therapy value, INRs, without encountering the complications involved with obtaining the prior art quantities International Normalized Ratio (INR) and International Sensitivity Index (ISI). Preferred embodiments utilize a determination based on the time of commencement of the fibrinogen transformation, which is the prothrombin time (T1 or PT) and a time of the hypothetical or theoretical end of test (TEOT). These values are used to derive a hypothetical clotting area. The hypothetical clotting area determinations, when compared with WHO determined INR values are consistent.

The new International Normalized Ratio (INRs) preferably is a replacement for the International Normalized Ratio (INR) such as that of the WHO, or the manufacturers of the clotting reagent that may provide an ISI for use with their particular clotting reagent. Embodiments of the invention may determine an INRs value, which preferably is derived by determining a clotting area. According to one embodiment, the clotting area is adjusted with a multiplier to provide an INRs value. Another embodiment utilizes fibrinogen standard solutions, and provides a power regression obtained from the standards that relates the clotting area of the standard samples, so that an expression may be used to determine patient INRs values based on the clotting area determined for those patient samples.

Existing medical literature, instrumentation and methodologies are closely linked to the International Normalized Ratio (INR). The new INRs was compared for correlation with the INR by comparative testing, to INR quantities of INRm and INRz, even with the understanding that the INR determination may have an error of about +/−15%, at a 95% confidence interval, which needs to be taken into account to explain certain inconsistencies. The hereinbefore description of the new INRs does correlate at least as well as, and preferably better than, studies carried out using the traditional methods and determinations involving International Normalized Ratio (INR).

While the invention has been described with reference to specific embodiments, the description is illustrative and is not to be construed as limiting the scope of the invention. The sample container used to contain the sample may comprise a vial, or cuvette, including, for example, the sample container disclosed in our U.S. Pat. No. 6,706,536. For example, although described in connection with body fluids of a human, the present invention has applicability to veterinary procedures, as well, where fluids are to be measured or analyzed. Various modifications and changes may occur to those skilled in the art without departing from the spirit and scope of the invention described herein and as defined by the appended claims

What is claimed is:

1. A method for determining a coagulation parameter for a blood or blood component of a living being, comprising:

reacting a sample of blood or a blood component containing fibrinogen with a clotting agent that transforms fibrinogen to fibrin by combining said blood sample with said clotting agent;

recording, with recording means for making optical measurements, time and optical density values for the sample that correspond with the optical activity of fibrinogen activity during the reaction with the clotting agent, wherein optical density values plotted at their respective corresponding times over the course of the reaction represent a clotting curve;

determining the time at which the sample and the clotting agent combined therewith begin to form a change in clotting activity, wherein (T1) represents the time at which the sample and the clotting agent combined therewith begin to form a change in clotting activity, and wherein (c1) represents an optical density value of the sample at the time (T1) where the sample and the clotting agent combined therewith begin to form a change in clotting activity;

determining a slope corresponding with a maximum acceleration rate of transformation of fibrinogen to fibrin during the clotting reaction;

determining an end of test time (TEOT) corresponding with an optical density value (cEOT) that is indicative of a substantial completion of the reaction of the fibrinogen of the sample and the clotting agent to transform the fibrinogen in the sample to fibrin, wherein said time (TEOT) corresponds with the time at which a line of said slope that represents the rate of maximum acceleration of the clotting activity based on the optical activity of the clotting reaction intersects said optical density value at c=(cEOT);

determining a value for an anticoagulant therapy factor (INRs) for the sample, wherein INRs corresponds with a clotting area (A) represented by the time (T1) at which the sample and the clotting agent combined therewith begin to form a change in clotting activity and the time corresponding with the end of test time (TEOT);

wherein the clotting area (A) is defined by two sides wherein one side defining said clotting area (A) is represented by the value (T1) and wherein the other side defining said clotting area is represented by the value (TEOT), and wherein the determination of the INRs value is based on the correspondence of a clotting area defined by taking the product of (T1) and (TEOT), and multiplying the said product by a multiplier (MUL), wherein said multiplier (MUL) represents a value based on a sampling rate and a pixel parity value, and wherein said multiplier (MUL) is expressed by the pixel parity value divided by the sampling rate, and wherein said INRs value is expressed by the following relationship: INRs= (T1*TEOT)*MUL, where (MUL) is a multiplier that relates the sampling rate at which time and optical activity measurements are recorded with the pixel parity of the x-y-axis of the clotting curve.

2. The method of claim 1, wherein said clotting area (A) comprises at least a portion that is beneath said clotting curve for said reaction, and at least a portion that is above said clotting curve for said reaction.

3. The method of claim 1, wherein said slope that represents the maximum acceleration of the clotting activity based on the optical activity of the clotting reaction and that intersects said optical density value (cEOT) is defined by a slope of the line between points along the clotting curve, (T2S) and (Tmap), where T2S is the time the maximum acceleration of the conversion rate of fibrinogen transformation begins and Tmap is a time to maximum acceleration of the clotting reaction.

4. The method of claim 1, wherein recording, with recording means for making optical measurements, time and optical density values for the sample during the reaction with the clotting agent includes developing a series of analog electrical voltage signals having voltage amplitudes proportional to an optical density of a clotting component of said sample.

5. The method of claim 4, wherein the clotting component comprises fibrinogen.

6. The method of claim 4, wherein the recording means comprises an instrument, and wherein the multiplier (MUL) relates the sampling rate of the instrument and a pixel parity of the x-y axis of the clotting curve, wherein they axis represents optical density and wherein the x axis represents time.

7. The method of claim 6, wherein the multiplier (MUL) is $1/187$ or about 0.00535.

8. The method of claim 1, wherein determining the INRs includes determining a pixel parity value for said recording means for making optical measurements and converting said optical density values and said time values to a scale based on the pixel parity for the said recording means.

9. The method of claim 8, wherein converting said optical density values and said time values to a scale based on the pixel parity for the said recording means comprises converting one or more of the group of said optical density values and the group of time values to a scale based on the pixel parity for the said recording means.

10. The method of claim 1, including recording an optical activity value ($C_{TMAP}$) at a time of maximum acceleration (Tmap) of the clotting reaction and at a time T2S, wherein (T2S) represents the time at which the maximum acceleration of the conversion rate of fibrinogen transformation begins, and wherein said slope that represents the maximum acceleration of the clotting activity based on the optical activity of the clotting reaction and that intersects said optical density value at c=cEOT is defined by a slope of the line between points along the clotting curve, (T2S) and (Tmap).

11. The method of claim 1, wherein a sampling rate at which time and optical density values are recorded is about 100 values per second.

12. The method of claim 1, further comprising determining a time to maximum acceleration (Tmap) of the clotting reaction for the transformation from fibrinogen to fibrin in the sample, and wherein said determining of Tmap comprises determining a last highest delta value of conversion rate from the time the maximum acceleration of the conversion rate of fibrinogen transformation begins at a time value (T2S).

13. The method of claim 12, wherein the last highest delta value of the conversion rate is obtained by measuring the delta value of two points at a fixed interval and recording said measurements, wherein each conversion rate comprises one value corresponding to time and a second value corresponding to optical density.

14. The method of claim 1, wherein a rate of optical activity increases for at least about 1.5 seconds following the commencement of the reaction between the fibrinogen in the sample and the clotting agent.

15. The method of claim 1, wherein said clotting area (A) is defined by a first area portion (A1) represented by a square of (T1) and a second area portion (A2) represented by a rectangular area portion defined by the product of (T1) and (TEOT), said clotting area comprising the first portion in a location represented under the clotting curve and between the optical density c=cEOT, and the second portion above the clotting curve.

16. The method of claim 1, wherein the value (T1) represents the time differential between (i) the time at which the sample and the clotting agent are combined (To) and (ii) the time the clotting agent and sample begin to form a change in clotting activity (T1); and wherein the time value (TEOT) represents the time differential between (i) a time (To) at which the sample and clotting agent are combined and (ii) a time value corresponding with the intersection of (a) a line having the aforesaid slope that represents the rate of maximum acceleration of the clotting activity and (b) an optical activity value representing the end of the reaction, wherein the optical activity value representing the end of the reaction is defined by the line $y=C_{EOT}$.

17. An apparatus for determining an anticoagulant therapy factor (INRs) according to the method of claim 1, said apparatus having a processor and a computer chip preprogrammed with a set of instructions for cooperating with an output of a photodetection device which provides electrical data to said processor as a function of the optical density for a sample being analyzed, said apparatus having input means and storage means for storing data, said set of instructions including instructions for implementing steps to obtain time and optical activity data from the clotting activity of the sample based on the optical activity of the sample during a reaction period, the instructions including implementing the steps of claim 1 to record values for optical measurements, time and optical activity during the clotting reaction and to determine one or more anticoagulant therapy factors (INRs) for the sample.

18. The method of claim 1, wherein the method includes adjusting the clotting area (A) according to a power regression that relates the clotting area (A) to a known standard to determine an INRs for the sample.

19. The method of claim 18, including determining the clotting area (A) for a plurality of fibrinogen standard samples whose fibrinogen concentrations are known.

20. The method of claim 19, wherein said fibrinogen standard samples include at least one high fibrinogen standard and at least one low fibrinogen standard.

21. The method of claim 20, wherein said fibrinogen standards include at least a plurality of fibrinogen standards between said high fibrinogen standard and said low fibrinogen standard.

22. The method of claim 19, wherein the method includes determining an INR value for said known fibrinogen standard samples by conducting a clotting reaction using each fibrinogen standard sample and a clotting reagent, and, for each fibrinogen sample, determining a time to maximum acceleration (XT) for each standard fibrinogen sample, determining a maximum rate of acceleration (MNXT) by determining a slope corresponding with a maximum acceleration rate of transformation of fibrinogen to fibrin during the clotting reaction of the standard fibrinogen sample, and determining the INR value for the fibrinogen standard sample by the expression INR(standard)=$(XT/MNXT)^{ISI}$, wherein ISI is an exponent and is a manufacturer's ISI value for the clotting reagent used to carry out the clotting reaction.

23. The method of claim 22, including deriving the INRs for a patient sample by determining an expression based on the INR values obtained for each fibrinogen standard sample, including determining, from said clotting area (A) for each standard fibrinogen sample and the INR value for each standard fibrinogen sample, a power regression expression wherein y=m*A^e, where y is the INRs, m is a constant, A is the clotting area, and e is another constant which is an exponent, and wherein obtaining the INRs for a patient sample comprises determining the clotting area A for the patient sample, raising the area A to the exponent e, and multiplying the value by the constant m to obtain the INRs.

24. The method of claim 23, wherein the power regression constants m and e are obtained using the INR(standard) value and the clotting area A determined for each fibrinogen standard sample according to the expression INR(standard) =m*A^e.

25. A method for determining a coagulation parameter for a blood or blood component of a living being, comprising:
reacting a sample of blood or a blood component containing fibrinogen with a clotting agent that transforms fibrinogen to fibrin by combining said blood sample with said clotting agent;
recording, with recording means for making optical measurements, time and optical density values for the sample that correspond with the optical activity of fibrinogen activity during the reaction with the clotting agent, wherein optical density values plotted at their respective corresponding times over the course of the reaction represent a clotting curve;
determining the time at which the sample and the clotting agent combined therewith begin to form a change in clotting activity, wherein (T1) represents the time at which the sample and the clotting agent combined therewith begin to form a change in clotting activity, and wherein (c1) represents an optical density value of the sample at the time (T1) where the sample and the clotting agent combined therewith begin to form a change in clotting activity;
determining a slope corresponding with a maximum acceleration rate of transformation of fibrinogen to fibrin during the clotting reaction;
determining an end of test time (TEOT) corresponding with an optical density value (cEOT) that is indicative of a substantial completion of the reaction of the fibrinogen of the sample and the clotting agent to transform the fibrinogen in the sample to fibrin, wherein said time (TEOT) corresponds with the time at which a line of said slope that represents the rate of maximum acceleration of the clotting activity based on the optical activity of the clotting reaction intersects said optical density value at c=(cEOT);
determining a value for an anticoagulant therapy factor (INRs) for the sample, wherein INRs corresponds with a clotting area (A) represented by the time (T1) at which the sample and the clotting agent combined therewith begin to form a change in clotting activity and the time corresponding with the end of test time (TEOT);
wherein the clotting area (A) is defined by two sides wherein one side defining said clotting area (A) is represented by the value (T1) and wherein the other side defining said clotting area is represented by the value (TEOT),
wherein said clotting area is a scaled area, and wherein said scaled area defining said INRs is derived by determining a pixel parity value for said recording means for making optical measurements and converting said optical density values and said time values to a scale based on the pixel parity for the said recording means.

26. The method of claim 25, wherein said pixel parity value is a multiplier (MUL), and wherein said multiplier (MUL) is a multiplier that relates the sampling rate at which time and optical activity measurements are recorded with the pixel parity of the x-y axis of the clotting curve.

27. The method of claim 26, wherein said multiplier (MUL) represents a value based on the sampling rate and the pixel parity values, and is expressed by the pixel parity value divided by the sampling rate.

28. The method of claim 27, wherein the multiplier (MUL) is $\frac{1}{187}$ or about 0.00535 and is defined by a pixel parity value of 0.535 and a sampling rate of 100 samples per second, using the expression pixel parity/sampling rate.

29. The method of claim 25, wherein said determination of an INRs value is expressed by the following relationship: INRs=(T1*TEOT)*MUL, wherein (MUL) represents a scaling value.

30. The method of claim 29, wherein the scaling value (MUL) is based on a value that corresponds with a parity of fibrinogen transformation per unit of time.

31. The method of claim 25, wherein said determination of an INRs value is expressed by the following relationship: INRs=T1*TEOT*MUL, and wherein the INRs is determined by scaling the clotting area (A), wherein scaling includes adjusting the product of (T1) and (TEOT) by a multiplier, (MUL), wherein the multiplier (MUL) is a value that relates a sampling rate at which time and optical activity measurements are recorded with a pixel parity of the x-y axis of the clotting curve.

32. The method of claim 25, wherein the method includes adjusting the clotting area (A) according to a power regression that relates the clotting area (A) to a known standard to determine an INRs for the sample.

33. The method of claim 32, including determining the clotting area (A) for a plurality of fibrinogen standard samples whose fibrinogen concentrations are known.

34. The method of claim 33, wherein said fibrinogen standard samples include at least one high fibrinogen standard and at least one low fibrinogen standard.

35. The method of claim 34, wherein said fibrinogen standards include at least a plurality of fibrinogen standards between said high fibrinogen standard and said low fibrinogen standard.

36. The method of claim 33, wherein the method includes determining an INR value for said known fibrinogen standard samples by conducting a clotting reaction using each fibrinogen standard sample and a clotting reagent, and, for each fibrinogen sample, determining a time to maximum acceleration (XT) for each standard fibrinogen sample, determining a maximum rate of acceleration (MNXT) by determining a slope corresponding with a maximum acceleration rate of transformation of fibrinogen to fibrin during the clotting reaction of the standard fibrinogen sample, and determining the INR value for the fibrinogen standard sample by the expression INR(standard)=$(XT/MNXT)^{ISI}$, wherein ISI is an exponent and is a manufacturer's ISI value for the clotting reagent used to carry out the clotting reaction.

37. The method of claim 36, including deriving the INRs for a patient sample by determining an expression based on the INR values obtained for each fibrinogen standard sample, including determining, from said clotting area (A) for each standard fibrinogen sample and the INR value for each standard fibrinogen sample, a power regression expression wherein y=m*A^e, where y is the INRs, m is a constant, A is the clotting area, and e is another constant which is an exponent, and wherein obtaining the INRs for a patient sample comprises determining the clotting are A for the patient sample, raising the area A to the exponent e, and multiplying the value by the constant m to obtain the INRs.

38. The method of claim 37, wherein the power regression constants m and e are obtained using the INR(standard) value and the clotting area A determined for each fibrinogen standard sample according to the expression INR(standard) =m*A^e.

39. A method of treating a living being who has a blood disorder by determining a coagulation parameter for a blood or blood component of a living being and administering a treatment based on the coagulation parameter, wherein the method includes:
monitoring anticoagulant therapy for said living being, comprising determining an anticoagulant therapy factor (INRs) for the patient by:
reacting a sample of blood or a blood component containing fibrinogen with a clotting agent that transforms fibrinogen to fibrin by combining said blood sample with said clotting agent;
recording, with recording means for making optical measurements, time and optical density values for the sample that correspond with the optical activity of fibrinogen activity during the reaction with the clotting agent, wherein optical density values plotted at their respective corresponding times over the course of the reaction represent a clotting curve;
determining the time at which the sample and the clotting agent combined therewith begin to form a change in clotting activity, wherein (T1) represents the time at which the sample and the clotting agent combined therewith begin to form a change in clotting activity, and wherein (c1) represents an optical density value of the sample at the time (T1) where the sample and the clotting agent combined therewith begin to form a change in clotting activity;
determining a slope corresponding with a maximum acceleration rate of transformation of fibrinogen to fibrin during the clotting reaction;
determining an end of test time (TEOT) corresponding with an optical density value (cEOT) that is indicative of a substantial completion of the reaction of the fibrinogen of the sample and the clotting agent to transform the fibrinogen in the sample to fibrin, wherein said time (TEOT) corresponds with the time at which a line of said slope that represents the rate of maximum acceleration of the clotting activity based on the optical activity of the clotting reaction intersects said optical density value at c=(cEOT);
determining a value for an anticoagulant therapy factor (INRs) for the sample, wherein INRs corresponds with a clotting area (A) represented by the time (T1) at which the sample and the clotting agent combined therewith begin to form a change in clotting activity and the time corresponding with the end of test time (TEOT);
wherein the clotting area (A) is defined by two sides wherein one side defining said clotting area (A) is represented by the value (T1) and wherein the other side defining said clotting area is represented by the value (TEOT); and wherein the determination of the INRs value is based on the correspondence of a clotting area defined by taking the product of (T1) and (TEOT), and multiplying the said product by a multiplier (MUL), wherein said multiplier (MUL) represents a value based on a sampling rate and a pixel parity value, and wherein said multiplier (MUL) is expressed by the pixel parity value divided by the sampling rate, and wherein said INRs value is expressed by the following relationship: INRs=(T1*TEOT)*MUL, where (MUL) is a multiplier that relates the sampling rate at which time and optical activity measurements are recorded with the pixel parity of the x-y-axis of the clotting curve; and
administering to the living being a course of treatment, wherein said course of treatment involves at least one treatment agent for regulating the clotting activity of blood that is administered to said living being, wherein said INR value, (INRs), corresponds with the clotting activity of said blood of said living being and comprises a reference for the amount of treatment agent to be administered to said living being.

40. The method of claim 39, wherein said steps of monitoring and administering are done at intervals over the course of treatment.

41. The method of claim 39, wherein the treatment agent comprises an anticoagulant.

42. The method of claim 39, wherein the treatment agent comprises coumadin.

43. The method of claim 39, wherein the treatment agent comprises warfarin.

44. An apparatus for determining a new anticoagulant therapy factor (INRs) comprising:
a. means including a light source, a test tube, a photocell, a battery, and a variable resistor all for developing an analog electric voltage signal having an amplitude proportional to an optical density of a liquid sample containing fibrinogen;
b. means including an A/D converter and a computer both cooperating for converting and recording the developed analog signal into a series of digital voltage signal values;
c. means for injecting a coagulant into a body fluid sample, thereby producing an abrupt change in the optical density of the body fluid sample, said abrupt change producing a change in the amplitude of the electrical analog signals, which, in turn, produces an abrupt change in the value of said digital voltage signals, the value of said digital voltage signals being directly indicative of fibrinogen concentration in the body fluid sample;
d. means, including a computer, with computer readable media that is programmed with instructions for implementing monitoring of said voltage digital signal values corresponding with the optical density of the body fluid sample and representing the coagulant activity and for processing the digital signal values;
e. means, including said computer, for recording an instant time (T1) at a start of a zero order kinetic rate of conversion of fibrinogen to fibrin for a reaction of a reagent which reacts with fibrinogen present in the body fluid sample to convert the fibrinogen to fibrin, and a value corresponding to the start time (T1);
f. means, including said computer, for recording a time to maximum acceleration (Tmap) for the rate of conversion of fibrinogen to fibrin for the body fluid sample;
g. means, including said computer, for monitoring voltage digital signal values at times (T1) and the time to maximum acceleration (Tmap) for respective fibrinogen concentration quantities (CT1) and (CTmap) based on the respective optical densities of the sample at those times and the corresponding digital voltage signals;

h. means, including said computer, for determining a slope that represents a rate of maximum acceleration of the clotting activity based on the optical activity of the clotting reaction and for determining an end of test time (TEOT) corresponding with an optical density value (cEOT) that is indicative of a substantial completion of the reaction of the fibrinogen of the sample and the clotting agent, wherein said time (TEOT) corresponds with the time at which a line of said slope that represents the rate of maximum acceleration of the clotting activity based on the optical activity of the clotting reaction intersects said optical density value at c=(cEOT);

i. means, including said computer, for determining an anticoagulant therapy factor value (INRn) for the sample, based on the correspondence of a clotting area defined by taking the product of (T1) and (TEOT), and multiplying the said product by a multiplier (MUL), wherein said multiplier (MUL) represents a value based on a sampling rate and a pixel parity value, and wherein said multiplier (MUL) is expressed by the pixel parity value divided by the sampling rate, and wherein said INRs value is expressed by the following relationship: INRs= (T1*TEOT)*MUL, where (MUL) is a multiplier that relates the sampling rate at which time and optical activity measurements are recorded with the pixel parity of the x-y axis of the clotting curve.

45. The apparatus of claim 44, wherein said (INRs) is determined by assigning the (MUL) a value of $1/187$ or about 0.00535.

* * * * *